United States Patent
Gardinier et al.

(10) Patent No.: US 9,469,632 B2
(45) Date of Patent: Oct. 18, 2016

(54) 6-SUBSTITUTED-3H-1,3-BENZOTHIAZOL-2-ONE COMPOUNDS AS TARP-GAMMA 8 DEPENDENT AMPA RECEPTOR ANTAGONISTS

(71) Applicant: Eli Lilly and Company, Indianapolis, IN (US)

(72) Inventors: Kevin Matthew Gardinier, Fishers, IN (US); Douglas Linn Gernert, Indianapolis, IN (US); Patric James Hahn, Indianapolis, IN (US); Sean Patrick Hollinshead, Indianapolis, IN (US); Albert Khilevich, Westfield, IN (US); Daniel Ray Mayhugh, Carmel, IN (US); Paul Leslie Ornstein, Northbrook, IL (US); Warren Jaye Porter, Indianapolis, IN (US); Jon Kevin Reel, Carmel, IN (US); Jeffrey Michael Schkeryantz, Fishers, IN (US); Patrick Gianpietro Spinazze, Avon, IN (US); Freddie Craig Stevens, Indianapolis, IN (US); Jeffrey Michael Witkin, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/718,129

(22) Filed: May 21, 2015

(65) Prior Publication Data
US 2015/0344468 A1   Dec. 3, 2015

Related U.S. Application Data

(60) Provisional application No. 62/004,005, filed on May 28, 2014.

(51) Int. Cl.
C07D 417/14 (2006.01)
A61K 31/41 (2006.01)

(52) U.S. Cl.
CPC ............. C07D 417/14 (2013.01); A61K 31/41 (2013.01)

(58) Field of Classification Search
None
See application file for complete search history.

(56) References Cited

U.S. PATENT DOCUMENTS

| 8,765,960 B2 | 7/2014 | Reel et al. |
| 2008/0255086 A1 | 10/2008 | Gillen et al. |
| 2014/0148441 A1* | 5/2014 | Reel ............... C07D 417/14 514/217 |

FOREIGN PATENT DOCUMENTS

| EP | 1300396 A1 | 9/2003 |
| WO | 98/15542 A1 | 4/1998 |
| WO | 2007/076161 A2 | 7/2007 |
| WO | 2010/041162 A1 | 4/2010 |
| WO | 2013/036224 A1 | 3/2013 |

OTHER PUBLICATIONS

Michael A. Rogawski, "Revisiting AMPA Receptors as an Antiepileptic Drug Target", Epilepsy Currents, vol. 11, No. 2 Mar./Apr. 2011 pp. 56-63.
Martin B Gill and David S Bredt, "An Emerging Role for TARPs in Neuropsychiatric Disorders", Neuropsychopharmacology Reviews (2011) 36, pp. 362-363.

(Continued)

Primary Examiner — Timothy R Rozof
(74) Attorney, Agent, or Firm — R. Craig Tucker

(57) ABSTRACT

A TARP γ8 dependant AMPA receptor antagonist of the formula:

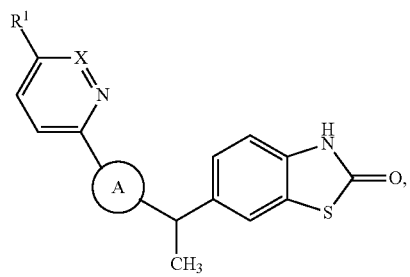

wherein X is CH or N;
A is

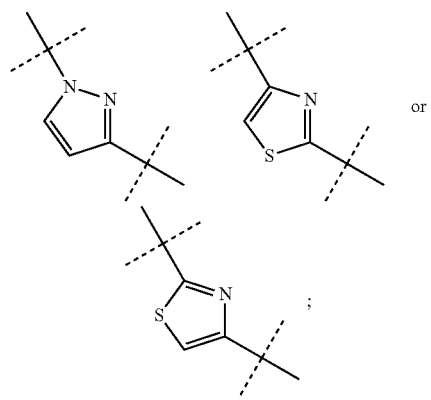

and
$R^1$ is as defined herein;
its pharmaceutically acceptable salts, uses, and methods for its preparation are described.

26 Claims, No Drawings

(56) References Cited

OTHER PUBLICATIONS

Timothy Gross, Shine Chou, Alan Dyke, Beatriz Dominguez, Michelle Groarke, Jonathan Medlock, Michael Ouellette, Jayachandra P. Reddy, Andreas Seger, Scott Zook, Antonio Zanotti-Gerosa, "Application of [BoPhoz Fh] catalysts in the asymmetric hydrogenation of a pyridyl benzothiophene alkene" Tetrahedron Letters (2012) 53, pp. 1025-1028.

Xiang Wang, Anil Guram, Seb Caille, Jack Hu, J P. Preston, Michael Ronk and Shawn Walker, "Highly Enantioselective Hydrogenation of Styrenes Directed by 2'-Hydroxyl Groups" Organic Letters (2011) vol. 13, No. 7, pp. 1881-1883.

Borut Zupancic, Barbara Mohar and Michel Stephan, "Heavyweight "R-SMS-Phos" Ligands in the Olefins' Hydrogenation Arena" Organic Letters (2010) vol. 12, No. 6, pp. 1296-1299.

Daniela Catarzi, et al., "Competitive AMPA Receptor Antagonists", Medicinal Research Reviews, New York, NY, (Mar. 2007),vol. 27, No. 2., pp. 239-278.

Chimirri A. et al., "AMPA Receptor Antagonists", Expert Opinion on Therapeutic Patents, Informa Healthcare, GB (Jan. 1999), vol. 9, No. 5, pp. 557-570.

* cited by examiner

6-SUBSTITUTED-3H-1,3-BENZOTHIAZOL-2-ONE COMPOUNDS AS TARP-GAMMA 8 DEPENDENT AMPA RECEPTOR ANTAGONISTS

This U.S. regular application claims priority to U.S. provisional application Ser. No. 62/004,005, filed May 28, 2014.

Epilepsy affects over 50 million people world-wide, with 30-40% of treated patients being resistant to current pharmacotherapies and only about 8% of treated patients being maintained seizure free. Epilepsy is often defined as when a person has two or more unprovoked epileptic seizures. The International League Against Epilepsy (ILAE) defines an epileptic seizure as "a transient occurrence of signs and/or symptoms due to abnormal excessive or synchronous neuronal activity in the brain." Seizures are thought to have a number of underlying causalities which adds to the difficulty in treating epilepsy. Seizures have been divided according to their clinical presentation including generalized seizures (absence, atonic, tonic-clonic (grand mal), and myoclonic), simple and complex partial onset seizures, gelastic seizures, dacrystic seizures, and status epilepticus. Current therapies target a variety of mechanisms including GABA (γ-aminobutyric acid) receptor agonism, T-type calcium channel blockers, sodium channel modulators, synaptic vesicle protein SV2A modulation, and inhibition of GABA transaminase. More recently, AMPA (α-amino-3-hydroxyl-5-methyl-4-isoxazole-propionic acid) receptor antagonists have been investigated for treatment of seizures as well.

AMPA receptors are glutamate sensitive ion channels on postsynaptic membranes of excitatory synapses in the central nervous system and are largely responsible for mediating fast neurotransmission across synaptic gaps. AMPA receptor antagonists are known anticonvulsant agents and their ability to down modulate excitatory neurotransmission is key to their anti-epileptic therapeutic potential. However, since AMPA receptor activity is so ubiquitous in the CNS, general antagonism affects most areas of the CNS resulting in undesired effects, such as ataxia, sedation, and/or dizziness, which are shared by all known general AMPA receptor antagonists. Typically these general antagonists have very narrow therapeutic dosing windows, meaning that typically the doses needed to obtain anti-convulsant activity are close to or overlap with doses at which undesired effects are observed. (Michael A. Rogawski. "Revisiting AMPA Receptors as an Antiepileptic Drug Target" *Epilepsy Currents* 11.2 (2011).)

Transmembrane AMPA Receptor Regulatory Proteins (TARPs) are a fairly recently discovered family of proteins that have been found to associate with and modulate the activity of AMPA receptors. Several TARPs are fairly regiospecific in the brain, leading to physiological differentiation of the AMPA receptor activity. As for example, TARP γ2 (stargazin) dependent AMPA receptors are primarily localized in the cerebellum and cerebral cortex and TARP γ8 dependent AMPA receptors are localized primarily in the hippocampus, which region is particularly relevant to seizure origination and/or propagation. It has been theorized that targeting individual TARPs may enable selective modulation of specific brain circuits without globally affecting synaptic transmission. (Gill, Martin B. and Bredt, David S., Neuropsychopharmacology 36(1): 362-363 (2011).)

Levetiracetam ((S)-2-(2-oxopyrrolidin-1-yl)butanamide), gabapentin (2-[1-(aminomethyl)cyclohexyl]acetic acid), topiramate (2,3:4,5-Bis-O-(1-methylethylidene)-beta-D-fructopyranose sulfamate), and carbamazepine (5H-dibenzo[b,f]azepine-5-carboxamide) are current leading therapeutic drugs for epileptic seizures. None of the currently approved drugs appear to act entirely through modulation of AMPA receptors.

Talampanel ((8R)-7-Acetyl-5-(4-aminophenyl)-8,9-dihydro-8-methyl-7H-1,3-dioxolo[4,5-h][2,3]benzodiazepine), selurampanel (BGG492) (N-[7-isopropyl-6-(2-methyl-2H-pyrazol-3-yl)-2,4-dioxo-1,4-dihydro-2H-quinazolin-3-yl]methanesulfonamide), and parampanel (5'-(2-cyanophenyl)-1'-phenyl-2,3'-bipyridinyl-6'(1H)-one) are general (non-TARP dependent/non-selective) AMPA receptor antagonists being tested as anti-epileptics.

It is here suggested that a selective TARP γ8 dependent AMPA receptor antagonist could be an effective anti-seizure/anti-epileptic therapeutic without the undesired effects (e.g. sedation, ataxis, and/or dizziness) of general (non-TARP dependent/non-selective) AMPA antagonists or TARP γ2 dependent AMPA antagonists, the later of which are more associated with AMPA receptor antagonism in the cerebellum.

The present invention provides a family of compounds as described herein. The exemplified compounds demonstrate selective TARP γ8-dependent AMPA receptor antagonist activity in vitro. The exemplified compounds demonstrate efficacy in animal models of seizure. Certain of the compounds demonstrate efficacy in animal models of pain. As a result of these in vitro and in vivo observations, the compounds of the invention are believed to be useful for the treatment of seizures in patients with epilepsy, as for example simple and/or complex partial onset seizures, and/or primary and/or secondary generalized seizures. As a result of these data, the compounds are alternatively believed to be useful in the treatment of pain.

The present invention provides a compound of Formula I

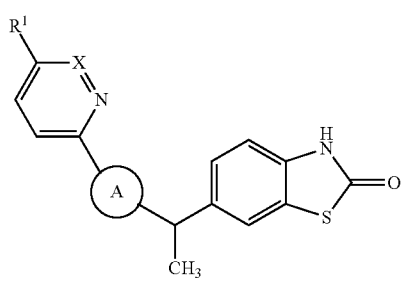

or a pharmaceutically acceptable salt thereof,
wherein X is CH or N;
A is

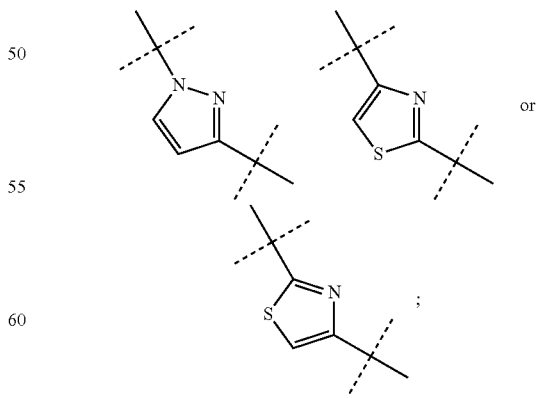

and
$R^1$ is selected from the group consisting of
hydrogen,
deuterium, fluoro,
methyl,
HO—($C_1$-$C_4$)-alkyl, optionally substituted with with one or two methyl or deuterium groups,
HO—($C_1$-$C_3$)-alkoxy, optionally substituted with one or two methyl or deuterium groups,
fluoro-($C_1$-$C_3$)-alkyl,
HO—($C_1$-$C_3$)-alkoxy-methyl, optionally substituted with with one or two methyl groups,
cyano-($C_1$-$C_3$)-alkoxy,
HO—($C_1$-$C_3$)-alkylthio, optionally substituted with with one or two methyl groups,
HO—($C_1$-$C_3$)-alkyl-NH—,
HO—($C_1$-$C_3$)-alkyl-N($CH_3$)—,
methylsulfinyl,
acyl,
aminocarbonyl,
methylcarbonylmethoxymethyl,
aminomethylcarbonyloxyethoxy,
triazolylmethyl,
1-methyl-imidizol-2-ylthio,
5-hydroxymethyl-tetrahydrofuran-2-yl,
3-hydroxy-3-methylazetidin-1-yl,
3-methoxy-azetidin-1-yl
3-methoxy-3-methylazetidin-1-yl
4-hydroxypiperidin-1-yl,
4-hydroxy-4-methyl-piperidin-1-yl,
4-hydroxy-4-vinyl-piperidin-1-yl,
4-hydroxymethyl-piperidin-1-yl,
4-(2-hydroxyethyl)-piperindin-1-yl,
morpholin-4-yl,
2-hydroxymethyl-morpholin-4-yl,
morpholin-4-yl-ethoxy, and
tetrahydropyran-4-yl,
provided that when A is

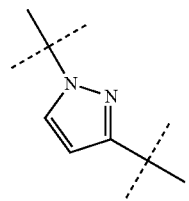

then $R^1$ is not unsubstituted HO—($C_1$-$C_3$)-alkoxy, deuterium substituted HO—($C_1$-$C_3$)-alkoxy, or HO—($C_1$-$C_3$)-alkylthio.

In another aspect of the invention there is provided a pharmaceutical composition comprising a compound of Formula I, or a pharmaceutically acceptable salt thereof, and one or more pharmaceutically acceptable carriers, diluents, or excipients. Furthermore, this aspect of the invention provides a pharmaceutical composition for treating seizures, as for example simple and/or complex partial onset seizures, and/or primary and/or secondary generalized seizures, in patients with epilepsy, comprising a compound of Formula I, or a pharmaceutically acceptable salt thereof, and one or more pharmaceutically acceptable excipients, carriers, or diluents. Further, this aspect of the invention provides a pharmaceutical composition comprising a compound of Formula I, or a pharmaceutically acceptable salt thereof, a second therapeutic agent which is an antiepileptic drug, as for example levetiracetam, gabapentin, topiramate, or carbamazepine, and one or more pharmaceutically acceptable carriers, diluents, or excipients.

The present invention also provides a method of treating seizures, as for example simple and/or complex partial onset seizures, and/or primary and/or secondary generalized seizures, in a mammal with epilepsy, comprising administering to a mammal in need of such treatment an effective amount of a compound of Formula I, or a pharmaceutically acceptable salt thereof. In another embodiment of this aspect of the invention, the method further comprises administering in simultaneous, separate or sequential combination, a second therapeutic agent which is an antiepileptic drug, as for example levetiracetam, gabapentin, topiramate, or carbamazepine. In one particular embodiment of these methods of treatment, the mammal is a human.

This invention also provides a compound of Formula I, or a pharmaceutically acceptable salt thereof for use in therapy. Within this aspect, the invention provides a compound of Formula I, or a pharmaceutically acceptable salt thereof, for use in the treatment of seizures, as for example simple and/or complex partial onset seizures, and/or primary and/or secondary generalized seizures, in a mammal, particularly a human, with epilepsy. Further, this aspect of the invention provides the compound of Formula I, or a pharmaceutically acceptable salt thereof, for use in simultaneous, separate or sequential combination with an antiepileptic drug, as for example levetiracetam, gabapentin, topiramate, or carbamazepine, in the treatment of seizures in a mammal, particularly a human, with epilepsy.

Another aspect of this invention provides the use of a compound of Formula I, or a pharmaceutically acceptable salt thereof, in the manufacture of a medicament for the treatment of seizures, as for example simple and/or complex partial onset seizures, and/or primary and/or secondary generalized seizures, in a mammal, particularly a human, with epilepsy. Further, the invention provides the use of a compound of Formula I, or a pharmaceutically acceptable salt thereof, in the manufacture of a medicament for the treatment of seizures, as for example simple and/or complex partial onset seizures, and/or primary and/or secondary generalized seizures, in a mammal, particularly a human, with epilepsy, wherein said medicament is to be adminstered in simultaneous, seperate or sequential combination with a second therapeutic agent which is an antiepileptic drug, as for example levetiracetam, gabapentin, topiramate, or carbamazepine.

Yet another aspect of the invention provides for a pharmaceutical composition for treating pain, comprising a compound of Formula I, or a pharmaceutically acceptable salt thereof, and one or more pharmaceutically acceptable excipients, carriers, or diluents.

Another aspect of the invention provides a method of treating pain, particularly nociceptive pain, in a mammal comprising administering to a mammal in need of such treatment an effective amount of a compound of Formula I, or a pharmaceutically acceptable salt thereof. In one particular embodiment of this method of treatment, the mammal is a human.

Another aspect of the invention provides a compound of Formula I, or a pharmaceutically acceptable salt thereof, for use in the treatment of pain, particularly nociceptive pain, particularly in a human.

Another aspect of this invention provides the use of a compound of Formula I, or a pharmaceutically acceptable salt thereof, in the manufacture of a medicament for the treatment of pain, particularly nociceptive pain.

Compounds of this invention have basic and acidic moieties, and accordingly react with a number of organic and inorganic acids and bases to form pharmaceutically acceptable salts. Pharmaceutically acceptable salts of the compound of the present invention are contemplated within the scope of the present application. The term "pharmaceutically acceptable salt" as used herein, refers to any salt of the compound of the invention that is substantially non-toxic to living organisms. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008); and S. M. Berge, et al., "Pharmaceutical Salts", *Journal of Pharmaceutical Sciences*, Vol 66, No. 1, January 1977.

As used herein, the designations "isomer 1", "isomer 2", "isomer 3", and "isomer 4" refer to the separated stereoisomers that elute from chiral chromatography separations under the stated conditions as specified in the preparations and examples.

Abbreviations used herein are defined as follows:
"AMPA" means α-amino-3-hydroxyl-5-methyl-4-isoxazole-propionic acid.
"ACN" means acetonitrile
"Brine" means saturated NaCl.
"CHO" means Chinese hamster ovary.
"CTZ" means cyclothiazide.
"DCM" means dichloromethane.
"DMEM means Dulbecco's Minimum Eagle's Medium.
"DMSO" means dimethyl sulfoxide (perdeuterated [d6] if for NMR).
"$ED_{50}$" means the dose that produces the 50% of the maximum effect observed.
"Eq" means molar equivalent.
"EtOAc" means ethyl acetate.
"EtOH" means ethanol.
"FLIPR" means fluorescence imaging plate reader.
"HBSS" means Hank's Buffered Salt Solution.
"HEPES" means 4-(2-hydroxyethyl)-1-piperazine ethanesulfonic acid.
"HPLC" means high pressure liquid chromatography.
"hr." or "h" means hour or hours.
"$IC_{50}$" means the concentration at which 50% of the maximum inhibition is achieved.
"IPAm" means isopropylamine.
"LCMS" means liquid chromatography mass spectrometry.
"MeOH" means methanol.
"min" or "m" means minutes.
"MS" means mass spectroscopy or mass spectrum.
"p.o." means per os, by mouth.
"PEPPSI™" means dichloro-(3-chloro-1-pyridyl)-(1,3-diphenyl-2H-imidazol-2-yl)palladium
"PEPPSI-ipr™" means [1,3-Bis(2,6-Diisopropylphenyl) imidazol-2-ylidene](3-chloropyridyl)palladium(II) dichloride
"PTZ" means pentylenetetrazole.
"RT" or "rt" means retention time.
"S.C." means subcutaneous.
"SEM" means standard error of the mean.
"TARP" means Transmembrane AMPA Receptor Regulatory Protein.
"THF" means tetrahydrofuran.

Separately preferred groups of compounds of the present invention are as follows:

1) In that the compounds of the invention have a chiral center at the carbon linker between the benzothiazolone moiety and the "A" moiety, and as it is well known in the biological arts that one isomer of a chiral pair is sometimes more active than the other with regard to various properties, with respect to the present invention, one enantiomer is more active in the FLIPR antagonist functional assay described herein, as for example having about 4-50× lower $IC_{50}$ compared to the opposite enantiomer at this chiral center. Furthermore, this more active isomer with regard to the in vitro antagonist assay also demonstrates greater protective activity against induced seizures in the rat pentylenetetrazole (PTZ) induced seizure model described herein. It is within the skill of the art to separate the isomers, as for example by the techniques described in the preparations and examples herein, and to determine which is the more active in either or both of the in vitro antagonist functional assay and PTZ induced seizure model. These more active isomers are particularly preferred compounds of the invention.

2) The compounds designated as examples herein are separated stereoisomers showing the greater activities in the in vitro antagonist assay as compared to other stereoisomers. The compounds designated as examples and their pharmaceutically acceptable salts are particularly preferred compounds of the invention.

3) It is believed that the more active isomers of the compounds of the invention generally have the (S) configuration at the chiral center at the carbon linker between the benzothiazolone moiety and the "A" moiety. Therefore the compounds of the invention having the (S) configuration at this chiral center are generally preferred over the compounds having the (R) configuration. (i.e. compounds having the following stereochemistry:

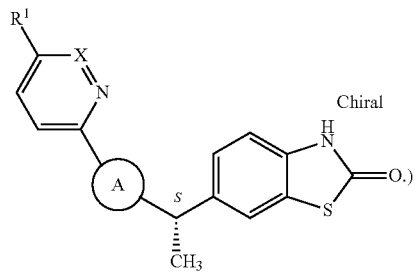

4) Compounds wherein X is CH; A is

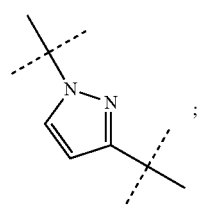

and
$R^1$ is selected from the group consisting of
deuterium,
fluoro,
2-hydroxyethyl,
1-hydroxyethyl,
2-hydroxy-2,2-dideutero-ethyl,
1-hydroxy-1-methylethyl,
2-hydroxy-propyl,
2-hydroxy-2-methylpropyl,
3-hydroxy-3-methylbutyl,
2-hydroxy-2-methyl-propoxy,
3-hydroxy-2,2-dimethyl-propoxy, 2-fluoroethyl,
2-hydroxyethoxymethyl,
2-hydroxy-2-methylpropoxymethyl,
2-hydroxypropoxymethyl,
1-(2-hydroxyethoxy)-ethyl,
1-(2-hydroxypropoxy)-ethyl,
cyanomethoxy,
2-hydroxy-1-methyl-ethylthio,
2-hydroxyethylamino,
N-(2-hydroxyethyl)-N-(methyl)amino,
methylsulfinyl,
methylcarbonylmethoxymethyl,
aminomethylcarbonyloxyethoxy,
1,2,3-triazol-1-ylmethyl,
1-methyl-imidizol-2-ylthio,
5-hydroxymethyl-tetrahydrofuran-2-yl,
3-hydroxy-3-methylazetidin-1-yl,
3-methoxy-azetidin-1-yl
3-methoxy-3-methylazetidin-1-yl
4-hydroxypiperidin-1-yl,
4-hydroxy-4-methyl-piperidin-1-yl,
4-hydroxy-4-vinyl-piperidin-1-yl,
4-(2-hydroxyethyl)-piperindin-1-yl,
morpholin-4-yl,
2-hydroxymethyl-morpholin-4-yl,
morpholin-4-yl-ethoxy, and
tetrahydropyran-4-yl.

5) Compounds wherein X is N; A is

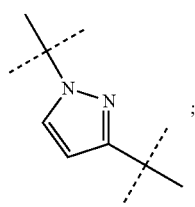

and
$R^1$ is selected from the group consisting of
hydrogen,
methyl,
hydroxymethyl, and
aminocarbonyl.

6) Compounds wherein X is CH; A is

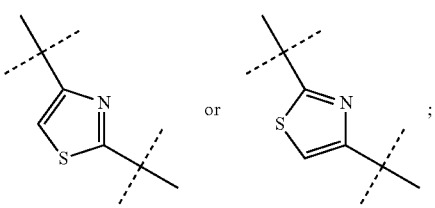

and
$R^1$ is selected from the group consisting of
hydrogen,
2-hydroxyethyl,
3-hydroxy-3-methylbutyl,
2-hydroxyethoxy, and
acyl.

One particularly preferred compound of the present invention is 6-[1-[1-[5-(2-hydroxyethyl)-2-pyridyl]pyrazol-3-yl]ethyl]-3H-1,3-benzothiazol-2-one, isomer 2 ((S) isomer), or a pharmaceutically acceptable salt thereof, with the freebase thereof being especially preferred.

General Chemistry

The compounds of the present invention can be prepared by general methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical.

Generally, a compound of formula I may be prepared from a compound of formula II where $Pg^1$ is a suitable protecting group (Scheme 1). More specifically, a compound of formula II where $Pg^1$ is a protecting group such as methoxymethyl or trimethylsilylethoxymethyl is reacted with an acid such as trifluoroacetic acid in a suitable solvent to provide a compound of formula I. Suitable solvents include tetrahydrofuran, dichloromethane and acetonitrile.

Alternatively, a compound of formula II where $Pg^1$ is a protecting group such as trimethylsilylethoxymethyl is reacted with a fluoride source such as tetra-butyl ammonium fluoride in a suitable solvent to provide a compound of formula I. Suitable solvents include dichloromethane and acetonitrile.

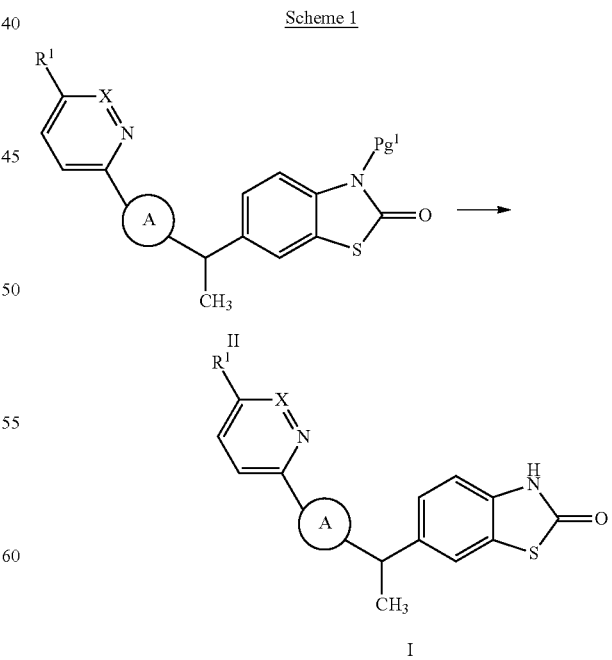

Scheme 1

Generally, a compound of formula II where A is pyrazolyl (formula IIa) may be prepared from a compound of formula IV where PO is a suitable protecting group (Scheme 2). More specifically, a compound of formula IV where $Pg^1$ is methoxymethyl or trimethylsilylethoxymethyl is reacted with a compound of formula III where L is a suitable leaving group in the presence of a suitable base in a suitable solvent to provide a compound of formula IIa. Suitable leaving groups include fluoro, chloro or bromo. Suitable bases include potassium carbonate, cesium carbonate, lithium t-butoxide, sodium t-butoxide, sodium hydride and lithium hexamethyldisilylamide. Suitable solvents include dimethylformamide and tetrahydrofuran.

Alternatively, a compound of formula IIa may be prepared from a compound of formula IV via a compound of formula Va (Scheme 2). More specifically, a compound of formula IV is reacted with a compound of formula VI where L is a suitable leaving group such as fluoro, chloro or bromo and R is an appropriate precursor group to the group $R^1$ to provide a compound of formula Va. The reaction is carried out in the presence of a suitable base such as potassium carbonate, cesium carbonate, lithium t-butoxide, sodium t-butoxide, sodium hydride and lithium hexamethyldisilylamide in solvent such as dimethylformamide and tetrahydrofuran. A compound of formula Va is reacted under conditions including those described in the preparations and examples to convert the precursor group R to the corresponding group $R^1$ of a compound of formula IIa where $Pg^1$ is a suitable protecting group.

Generally, a compound of formula II where A is thiazolyl (formula IIb) may be prepared from a compound of formula VII where PO is a suitable protecting group (Scheme 3). More specifically, a compound of formula VII where $Pg^1$ is methoxymethyl is coupled with a compound of formula IIIa in the presence of a suitable catalyst in a suitable solvent to provide a compound of formula IIb. Suitable catalysts include zinc chloride and palladium catalysts such as $Pd_2(dba)_3$ and PEPPSI-iPr ([1,3-Bis(2,6-Diisopropylphenyl)-imidazol-2-ylidene](3-chloropyridyl)palladium(II) dichloride). Suitable solvents include dioxane and tetrahydrofuran.

Alternatively, a compound of formula IIb may be prepared from a compound of formula VII via a compound of formula Vb (Scheme 3). More specifically, a compound of formula VII is coupled with a compound of formula VIa where R is an appropriate precursor group to the group $R^1$ to provide a compound of formula Vb. The coupling may be carried out as essentially described above as well as described in the preparations and examples. A compound of formula Vb is reacted under conditions including those described in the preparations and examples to convert the precursor group R to the corresponding group $R^1$ of a compound of formula IIb where $Pg^1$ is a suitable protecting group.

Scheme 2

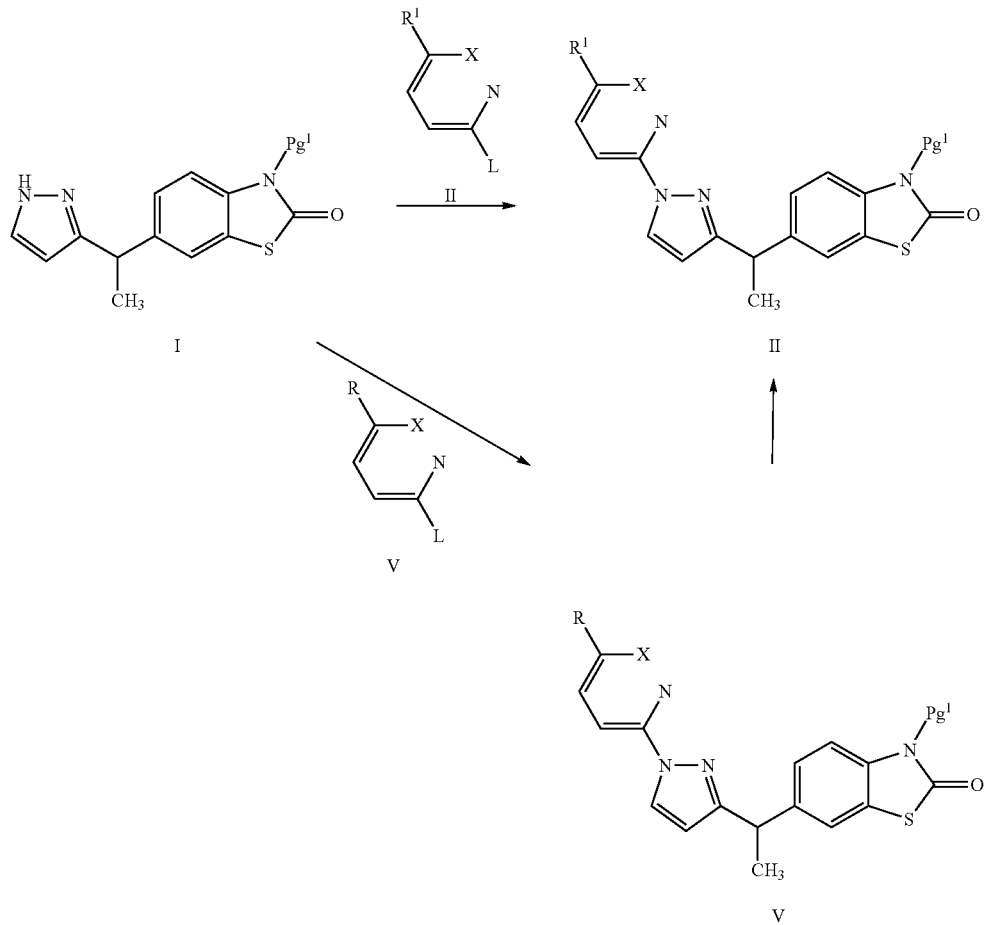

Scheme 3

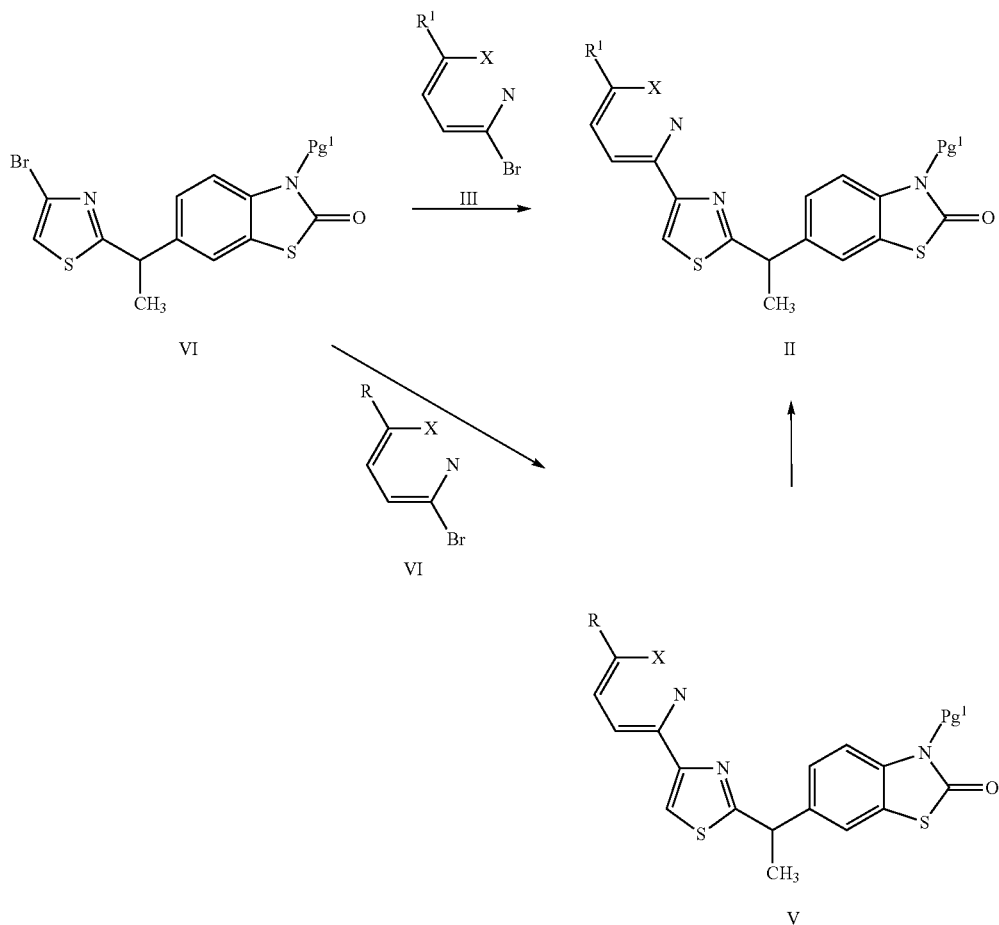

Generally, a compound of formula II where A is thiazolyl (formula IIc) may be prepared from a compound of formula VIII (Scheme 4). More specifically, a compound of formula VIII is reacted with a compound of formula IX in the presence of a base such as potassium carbonate in a solvent such as dioxane to provide a compound of formula IIc.

Alternatively, a compound of formula IIc may be prepared from a compound of formula VIIIa via a compound of formula Vc (Scheme 4). More specifically, a compound of formula VIIIa where R is an appropriate precursor group to the group $R^1$ is reacted with a compound of formula IX to provide a compound of formula Vc. The reaction may be carried out as essentially described above as well as described in the preparations and examples. A compound of formula Vc is reacted under conditions including those described in the preparations and examples to convert the precursor group R to the corresponding group $R^1$ of a compound of formula IIc where $Pg^1$ is a suitable protecting group.

Scheme 4

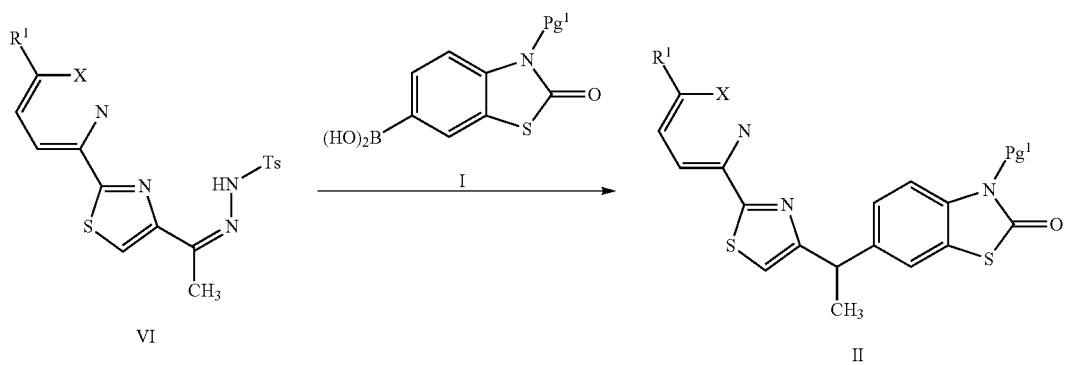

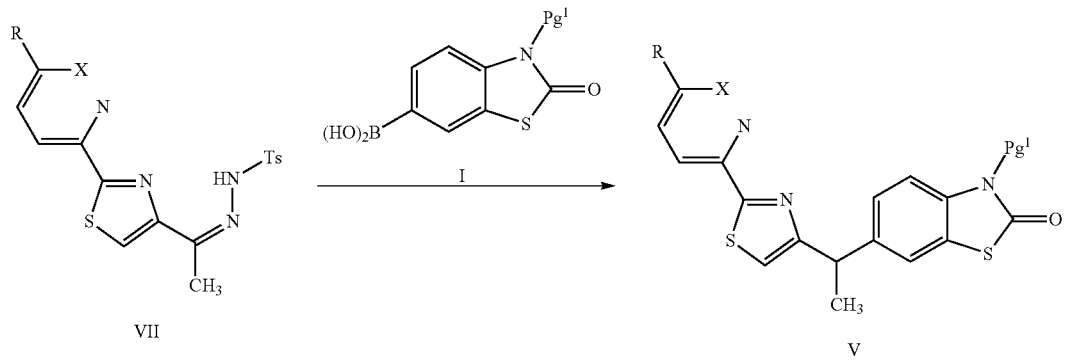

In the following illustrative preparations and examples, solvents are generally removed under reduced pressure (evaporated). In some procedures indicated yields are representative crude yields for products which are isolated by evaporation or filtration and used directly without further purification.

Preparation 1: 6-Acetyl-3-(methoxymethyl)-3H-1,3-benzothiazol-2-one

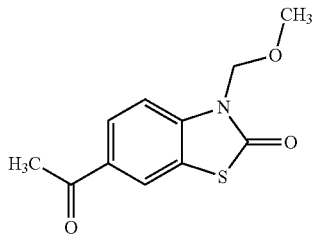 [SMILES: COCn1c(=O)sc2cc(C(C)=O)ccc21]

Add cesium carbonate (1.5 Eq; 310.5 mmoles; 101.1 g) to a solution of 6-acetyl-3H-1,3-benzothiazol-2-one (40.0 g, 207 mmoles) in dimethylformamide (690 mL). Add chloromethyl methyl ether (1.3 Eq, 269 mmoles, 20.4 mL) dropwise and stir at room temperature for 18 hr. Transfer to a separatory funnel, add EtOAc (1 L), wash with water (2×200 mL), and then brine (200 mL). Back extract with DCM (300 mL). Dry the combined organic layers over Na$_2$SO$_4$, filter and concentrate. Slurry the concentrate in 200 ml hexanes/EtOAc (75:25), and filter to give 6-acetyl-3-(methoxymethyl)-3H-1,3-benzothiazol-2-one as a white solid (37.0 g, 156 mmoles, 75% yield). LCMS (low) rt=1.68 min., M+1=238.

Preparation 2: 6-[1-Hydroxy-1-(1-tetrahydropyran-2-yl-1H-pyrazol-5-yl)ethyl]-3-(methoxymethyl)-3H-1,3-benzothiazol-2-one (mixture of diasteromers)

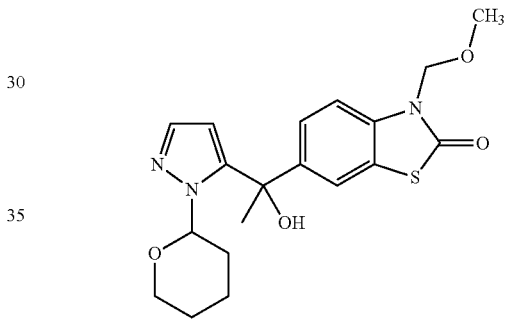

Add 1-tetrahydropyran-2-yl-pyrazole (1.5 Eq, 202 mmoles, 30.8 g)(Aldrich) and THF (900 mL) to a flame dried 2 L 3 neck round bottom flask and cool to −78° C. (dry ice/acetone bath). Add t-butyl lithium (2.5 M in THF) (1.5 Eq, 202 mmoles; 81.0 mL) dropwise, maintaining at least −68° C., and stir for 60 min at −78° C. Add a solution of 6-acetyl-3-(methoxymethyl)-3H-1,3-benzothiazol-2-one (32.0 g, 134 mmoles) in THF (450 mL) dropwise over 45 min, and stir at −78 for 30 min Remove the dry ice bath and allow to warm to −50° C. and stir for 1 hr. (do not let temp. rise above −45° C.). Quench the reaction with MeOH (80 mL). Transfer to a separatory funnel, add EtOAc (2000 mL), and wash with water (500 mL) and then brine (500 mL). The organic layer is dried over Na$_2$SO$_4$, filter and concentrate to give a crude yellow oil. Purify the material by HPLC, eluting with hexanes/EtOAc (6:4) to yield 6-[1-hydroxy-1-(1-tetrahydropyran-2-yl-1H-pyrazol-5-yl)ethyl]-3-(methoxymethyl)-3H-1,3-benzothiazol-2-one as a white foam (44 g, 113 mmoles, 84% yield) (mixture of diasteromers). LCMS (Low) rt=1.76 min., M+1=288, and rt=1.86 min, M+1=288

Preparation 3: 3-(Methoxymethyl)-6-[1-(1H-pyrazol-5-yl)ethenyl]-3H-1,3-benzothiazol-2-one

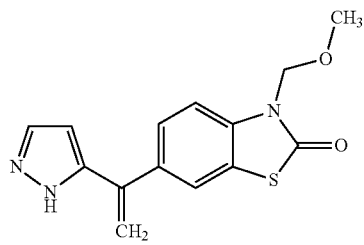 [SMILES: C=C(c1ccc2c(c1)sc(=O)n2COC)c1ccn[nH]1]

Add trifluoroacetic acid (20 Eq (molar), 2.26 moles, 170 mL) to a solution of 6-[1-hydroxy-1-(1-tetrahydropyran-2-yl-1H-pyrazol-5-yl)ethyl]-3-(methoxymethyl)-3H-1,3-benzothiazol-2-one (44 g, 113 mmoles) in DCM (0.2 M, 8.81 moles, 565 mL) and stir at room temperature over night (16 hr.). Concentrate the resulting dark purple reaction mixture, dissolve it in EtOAc (2 L) and neutralize the solution by slowly adding saturated aqueous sodium bicarbonate. Transfer to a separatory funnel and extract into EtOAc, wash with water (300 mL) and then brine (300 mL). Dry over $Na_2SO_4$, filter, and concentrate. Purify the material by HPLC, eluting with EtOAc/Hexanes (1:1) to give 3-(methoxymethyl)-6-[1-(1H-pyrazol-5-yl)ethenyl]-3H-1,3-benzothiazol-2-one (30 g, 104 mmoles, 92% yield) as a thick yellow oil. LCMS (Low) desired product peak at rt=1.82 min, M+1=288.

Preparation 4: 3-(Methoxymethyl)-6-[1-(1H-pyrazol-5-yl)ethyl]-3H-1,3-benzothiazol-2-one

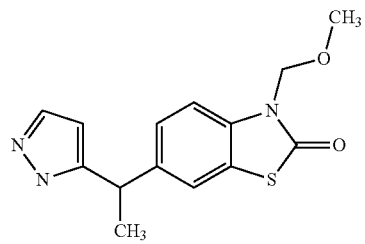 [SMILES: COCn1c(=O)sc2cc(C(C)c3ccn[nH]3)ccc21]

Add 5% palladium/carbon (15 g; 7.0 mmoles) to a $N_2$ purged flask and add EtOAc (250 mL). Add 3-(methoxymethyl)-6-[1-(1H-pyrazol-5-yl)ethenyl]-3H-1,3-benzothiazol-2-one (29 g, 101 mmoles) as a solution in EtOAc (250 mL). Degas under vacuum and charge with hydrogen via balloon. Stir overnight, evacuate excess hydrogen under pressure and flush with $N_2$. Filter through diatomaceous earth and concentrate to give 3-(methoxymethyl)-6-[1-(1H-pyrazol-5-yl)ethyl]-3H-1,3-benzothiazol-2-one as a thick yellow oil (27 g, 93 mmoles; 92% yield). Material may be carried into the next step without further purification. LCMS (Low) rt=1.73 min, M+1=290.

Preparation 5: Synthesis of trimethyl-[2-(pyrazol-1-ylmethoxy)ethyl]silane

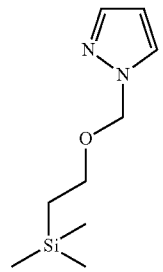

A solution of 1H-Pyrazol (320.0 g, 4.70 mol) in THF (0.96 L) is added to a solution of sodium hydride (206.8 g, 5.17 mol) in THF (2.24 L) at 0° C. under nitrogen atmosphere. The mixture is stirred for 1 hr at 5° C. 2-(trimethylsilyl) ethoxy methyl chloride (752.2 g, 4.51 mol) is added to the mixture dropwise at 10° C. for a period of 30 min and the whole mixture is then stirred for 1 hr at 10° C. and 4 hr at 25° C. The reaction is quenched by addition of ice cold water (1.0 L) slowly at 10° C. and stirred for 30 min. Extract with diethyl ether (3×1.5 L), wash organic layer with water (2×2.5 L) and brine solution (1.5 L). Dry organic layer over sodium sulphate and evaporate solvent to obtain a crude oil. The material is purified by silica gel chromatography (5% hexanes in EtOAc) to afford desired compound as a clear oil (980 g, 105%). M+1=199.

Preparation 6: Synthesis of 2-oxo-3H-1,3-benzothiazole-6-carbaldehyde

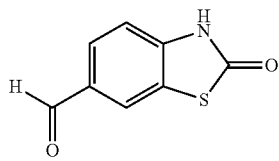

A solution of 6-bromobenzo[d]thiazol-2(3H)-one (345.0 g, 1.49 mol) in THF (6.9 L) is cooled at −50° C. and methylmagnesiumbromide solution (1 L, 1.5 M in THF, 1.49 mol) is added dropwise over a period of 30 min at −50° C. Stir for 15 min and add n-ButylLithium (2.1 L, 2.5 M in hexane, 5.24 mol) dropwise over 45 minutes at −50° C. Stir suspension for 1 hr at below −50° C. and add dimethylformamide (0.75 L, 9.74 mol) dropwise over of 30 min Stir the mixture 1 additional hour at −50° C. and 1 hr at 25° C. Quench the reaction by addition of 2.5 M citric acid solution (4.0 L) at −10° C. Extract the mixture with EtOAc (2×5 L) and wash organic phase with brine (3 L). Dry over sodium sulphate and evaporate solvent. The crude material is suspended in diethyl ether (4 L) and stir for 2 h. Filter the solid, wash with more diethyl ether (1 L) and dry under vacuum to afford desired compound as a white solid (228 g, 85%). M+1=180.

Preparation 7: Synthesis of 6-[hydroxy-[2-(2-trimethylsilylethoxymethyl)pyrazol-3-yl]methyl]-3H-1,3-benzothiazol-2-one

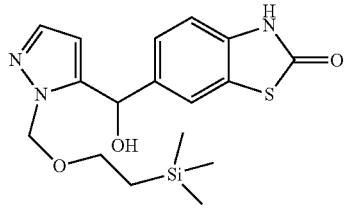 [SMILES: C[Si](C)(C)CCOCn1nccc1C(O)c1ccc2[nH]c(=O)sc2c1]

Add 2,2-6,6 tetramethylpiperidinylmagnesium lithium chloride complex (2.26 L, 1M solution in toluene/THF, 2.26 mol) to a solution of 1-((2-(trimethylsilyl)ethoxy)methyl)-1H-pyrazole (415.5, 2.096 mol) in THF (1.03 L) at 0° C. under inert atmosphere and stir for 15 min at same temperature and 2 hrs at 20° C. In another flask add portionwise 2-oxo-2,3-dihydrobenzo[d]thiazole-6-carbaldehyde (300.0 g, 1.67 mol) to the solution of NaH (60% suspension in mineral oil, 73.65 g, 1.84 mol) in THF (3 L) at 0° C. and stir for 15 min at 0° C. and 1 hr at 20° C. Then add the contents of the first flask into the second flask at 10° C. over a period of 30 min Let the whole mixture warm to 23° C. and stir for 16 h at that temperature. Quench the reaction by addition of 2 M citric acid solution (3.0 L) at 5° C. Extract with EtOAc (3×3.0 L). Combine organic extracts and wash with water (8×3.0 L) and brine solution (3.0 L). Dry the organic layer with sodium sulphate and evaporate to give a crude brown viscous oil. The crude material is dissolved in acetonitrile (10 L), hexane (15.0 L) is added and the mixture stirred vigorously for 20 min Separate both layers and evaporate bottom layer to afford desired compound (643 g, 101%) as a solid. M+1=378.

Preparation 8: Synthesis of 6-[2-(2-trimethylsilylethoxymethyl)pyrazole-3-carbonyl]-3H-1,3-benzothiazol-2-one

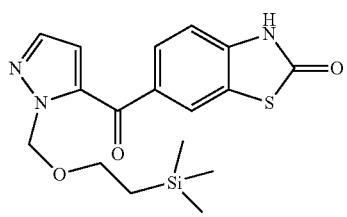 [SMILES: C[Si](C)(C)CCOCn1nccc1C(=O)c1ccc2[nH]c(=O)sc2c1]

Add activated manganese(IV) oxide (921.0 g, 5.0 eq) to a solution of 6-(hydroxy(1-((2-(trimethylsilyl)ethoxy)methyl)-1H-pyrazol-5-yl)methyl)benzo[d]thiazol-2(3H)-one (800.0 g, 2.12 mol) in 1,4-dioxane (4.0 L). Stir with a mechanical stirrer at 60° C. for 5 h. Filter the mixture through a diatomaceous earth bed and wash with hot 1,4-dioxane (10 L) and evaporate solvent to give a crude solid. Suspend the solid in Et$_2$O (5 L) and stir for 30 min at 25° C. Filter the mixture and dry under vacuum to afford desired compound (590 g, 74%). M+1=376.

Preparation 9: Synthesis of 6-(1H-pyrazole-5-carbonyl)-3H-1,3-benzothiazol-2-one hydrochloride

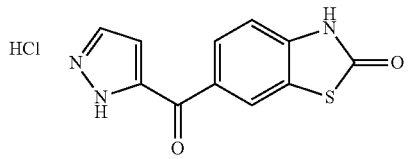 [SMILES: Cl ; O=C(c1ccc2[nH]c(=O)sc2c1)c1ccn[nH]1]

Add portionwise 6-(1-((2-(trimethylsilyl)ethoxy)methyl)-1H-pyrazole-5-carbonyl) benzo[d]thiazol-2(3H)-one (100 g; 0.27 mol) to a solution of hydrogen chloride (4M in dioxane, 1.5 L) at 22° C. Stir for 3 h, filter the solid, wash with 1,4-dioxane (100 mL) and dry under vacuum to afford desired compound (75 g, 100%). M+1=246.

Preparation 10: Synthesis of 3-(methoxymethyl)-6-[2-(2-trimethylsilylethoxymethyl)pyrazole-3-carbonyl]-1,3-benzothiazol-2-one

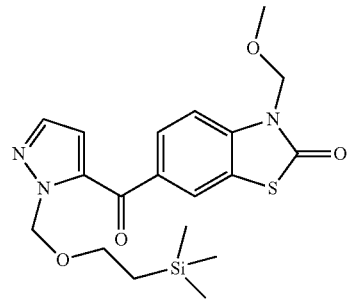 [SMILES: COCn1c(=O)sc2cc(C(=O)c3ccnn3COCC[Si](C)(C)C)ccc21]

Add a solution of 6-(1-((2-(trimethylsilyl)ethoxy)methyl)-1H-pyrazole-5-carbonyl)benzo[d]thiazol-2(3H)-one (150.0 g, 0.40 mol) in DMF (0.5 L) to a stirred solution of sodium hydride (60% suspension in mineral oil, 20.76 g, 0.52 mol) in DMF (1.0 L) dropwise at 0° C. over 25 min Stir 30 min at that temperature and add methylchloromethyl ether (39.43 ml, 0.519 mol) dropwise at 0° C. over a period of 30 min. Stir the mixture for 2 h while warming to 25° C. Quench the reaction by addition of cold water (1 L) at 10° C. and stir for 10 min Extract with EtOAc (3×1.5 L) and wash the organic layer with brine (1.5 L) and water (2×2.5 L). Dry over sodium sulphate and evaporate the solvent to afford the desired crude compound as a solid (185 g, 110%) without further purification. M+1=420.

Preparation 11: Synthesis of 6-[1-hydroxy-1-[2-(2-trimethylsilylethoxymethyl)pyrazol-3-yl]ethyl]-3-(methoxymethyl)-1,3-benzothiazol-2-one

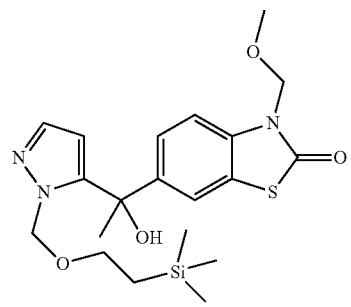 [SMILES: COCn1c(=O)sc2cc(C(C)(O)c3ccnn3COCC[Si](C)(C)C)ccc21]

Add methylmagnesium bromide (882 ml, 1.5 M in THF, 1.32 mol) to a solution of 3-(methoxymethyl)-6-(1-((2-(trimethylsilyl)ethoxy)methyl)-1H-pyrazole-5-carbonyl)benzo[d]thiazol-2(3H)-one (185.0 g, 0.44 mol) in THF (2 L) dropwise at 0° C. over 30 min Stir the mixture for 4 h while warming to 25° C. The reaction is quenched by slow addition of water (1.0 L) and a saturated aqueous ammonium chloride solution (1 L). Extract with EtOAc (2×2.5 L and wash organic layer with brine (3 L) and water (3 L). Dry over sodium sulphate and evaporate solvent to give the desired crude compound as a solid (190 g, 99%) without further purification. M+1=436.

Preparation 12: Synthesis of 3-(methoxymethyl)-6-[1-(1H-pyrazol-5-yl)vinyl]-1,3-benzothiazol-2-one

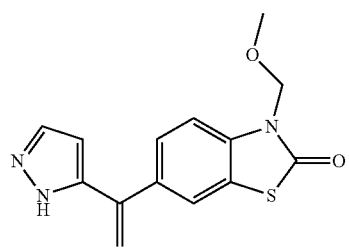 [SMILES: C=C(c1ccc2c(c1)sc(=O)n2COC)c1ccn[nH]1]

To a solution of 6-(1-hydroxy-1-(1-((2-(trimethylsilyl)ethoxy)methyl)-1H-pyrazol-5-yl)ethyl)-3-(methoxymethyl)benzo[d]thiazol-2(3H)-one (150 g, 0.34 mol) in dichloromethane (500 mL) is added trifluroacetic acid (280 mL, 3.72 mol) dropwise at 0° C. over a period of 30 min Stir first 1 h at 0° C. and then 16 h while warming to 25° C. Quench by very slow addition of an aqueous saturated solution of NaHCO$_3$ solution. Extract with DCM (2×2 L) and wash the organic layer with brine (2 L) and water (3×2 L). Dry with sodium sulphate and evaporate to give crude solid (ca. 100 g). Purify by column chromatography (60-90% EtOAc in hexanes) to give desired compound as a white solid (75 g, 76%). M+1=288.

Preparation 13: Synthesis of 3-(methoxymethyl)-6-[1-(1H-pyrazol-5-yl)ethyl]-1,3-benzothiazol-2-one

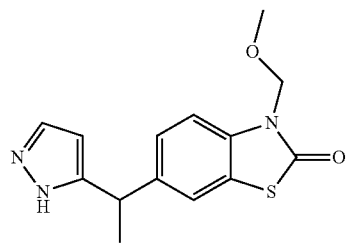 [SMILES: COCn1c(=O)sc2cc(C(C)c3ccn[nH]3)ccc21]

Add Pd/C (10% wt/wt, 50% moisture, 29.0 g) to a solution of 6-(1-(1H-pyrazol-5-yl) vinyl)-3-(methoxymethyl)benzo[d]thiazol-2(3H)-one (125.0 g, 0.44 mol) in MeOH (2.5 L). Place the mixture in a Parr reactor under a hydrogen atmosphere (50 psi) and stir at 30° C. for 5 h. Filter the mixture through diatomaceous earth and evaporate the solvent to give a pale yellow viscous oil. Purify by silica gel chromatography (eluent 40 to 50% EtOAc in hexanes) to afford desired compound as a solid (88.3 g, 71%). M+1=290.

Preparation 14: Isolation of 3-(methoxymethyl)-6-[1-(1H-pyrazol-3-yl)ethyl]-1,3-benzothiazol-2-one, Isomer 1 and Isomer 2

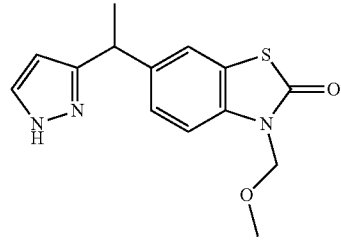 [SMILES: COCn1c(=O)sc2cc(C(C)c3cc[nH]n3)ccc21]

Resolve 3-(methoxymethyl)-6-[1-(1H-pyrazol-3-yl)ethyl]-1,3-benzothiazol-2-one into its enantiomers by chiral chromatography using (R,R) Whelk-O 1, 20% EtOH/CO$_2$, 5 mL/min, 225 nm Isomer 1 has retention time of 2.0 min and Isomer 2 has retention time of 2.7 min.

Preparation 15: Isolation of [5-(6-fluoro-3-pyridyl)tetrahydrofuran-2-yl]methanol, isomers 1, 2, 3 and 4

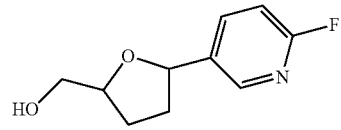

Resolve [5-(6-Fluoro-3-pyridyl)tetrahydrofuran-2-yl]methanol into its diasteriomers by chiral chromatography using two separations. In the first separation use Chiralpak® AD-H, 20% IPA/CO2, 5 mL/min, 270 nm. Isomer 1 and Isomer 2 are a mixture with a retention time of 1 min, Isomer 3 has a retention time of 1.16 min and Isomer 4 is 1.52 min Isomer 1 and 2 are separated using Chiralcel® OJ-H, 40/60 IPA/hexane, 1 mL/min, 270 nm Isomer 1 has a retention time of 5.12 min and Isomer 2 is 5.48 min NOE experimentation indicates that Isomer 1 and 2 are cis diasteriomers and Isomer 3 and 4 are trans diasteriomers. LCMS (low) Isomer 1 rt=0.614 min, M+1=198, Isomer 2 rt=0.615 min, M+1=198, Isomer 3 rt=0.611 min, M+1=198, Isomer 4 rt=0.611 min, M+1=198.

Preparation 16: Synthesis of 2-fluoro-5-[5-(tetrahydropyran-2-yloxymethyl)tetrahydrofuran-2-yl]pyridine, Isomer 1

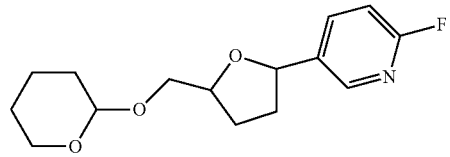 [SMILES: Fc1ccc(C2CCC(COC3CCCCO3)O2)cn1]

Dissolve the [5-(6-Fluoro-3-pyridyl)tetrahydrofuran-2-yl]methanol (0.9 g, 4.6 mmol) in dichloromethane (5 mL) then add the dihydropyran (500 uL, 5.5 mmoL) and the p-toluenesulphonic acid (39 mg, 0.23 mmol). Stir the mixture at room temperature for 3 days then dilute the mixture with saturated sodium bicarbonate and extract twice using dichloromethane. Dry the organics using sodium sulfate then filter and evaporate. Chromatograph the residue using a gradient from hexane to 60% ethyl acetate in hexane to give 2-fluoro-5-[5-(tetrahydropyran-2-yloxymethyl)tetrahydrofuran-2-yl]pyridine as a clear oil (816 mg, 2.8 mmol, 60%). LCMS (low) Isomer 1 rt=1.073 min Mass was not observed.

Preparation 17: Synthesis of 2-fluoro-5-[5-(tetrahydropyran-2-yloxymethyl)tetrahydrofuran-2-yl]pyridine, Isomer 2

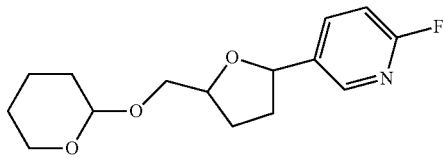 [SMILES: Fc1ccc(C2CCC(COC3CCCCO3)O2)cn1]

Dissolve the [5-(6-Fluoro-3-pyridyl)tetrahydrofuran-2-yl]methanol (1.12 g, 5.7 mmol) in dichloromethane (6 mL) then add the dihydropyran (623 uL, 6.8 mmoL) and the p-toluenesulphonic acid (49 mg, 0.28 mmol). Stir the mixture at room temperature for 3 days then dilute the mixture with saturated sodium bicarbonate and extract twice using dichloromethane. Dry the organics using sodium sulfate then filter and evaporate. Chromatograph the residue using a gradient from hexane to 60% ethyl acetate in hexane to give 2-fluoro-5-[5-(tetrahydropyran-2-yloxymethyl)tetrahydrofuran-2-yl]pyridine as a clear oil (1.1 g, 3.9 mmol, 69%). LCMS (low) Isomer 2 rt=1.079 min Mass was not observed.

Preparation 18: Synthesis of 2-fluoro-5-[5-(tetrahydropyran-2-yloxymethyl)tetrahydrofuran-2-yl]pyridine, Isomer 3

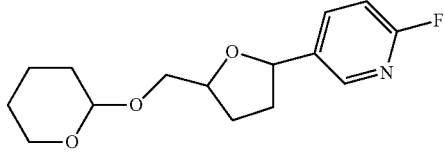 [SMILES: Fc1ccc(C2CCC(COC3CCCCO3)O2)cn1]

Dissolve the [5-(6-Fluoro-3-pyridyl)tetrahydrofuran-2-yl]methanol (0.88 g, 4.5 mmol) in dichloromethane (5 mL) then add the dihydropyran (489 uL, 5.4 mmoL) and the p-toluenesulphonic acid (38 mg, 0.22 mmol). Stir the mixture at room temperature for 3 days then dilute the mixture with saturated sodium bicarbonate and extract twice using dichloromethane. Dry the organics using sodium sulfate then filter and evaporate. Chromatograph the residue using a gradient from hexane to 60% ethyl acetate in hexane to give 2-fluoro-5-[5-(tetrahydropyran-2-yloxymethyl)tetrahydrofuran-2-yl]pyridine as a clear oil (880 mg, 3.0 mmol, 67%). LCMS (low) Isomer 3 rt=1.057 min Mass was not observed.

Preparation 19: Synthesis of 6-[1-[1-[5-[5-(hydroxymethyl)tetrahydrofuran-2-yl]-2-pyridyl]pyrazol-3-yl]ethyl]-3H-1,3-benzothiazol-2-one, Isomer 4 (trans)

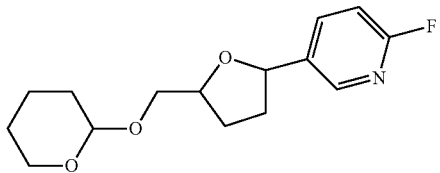 [SMILES: Fc1ccc(C2CCC(COC3CCCCO3)O2)cn1]

Dissolve the [5-(6-Fluoro-3-pyridyl)tetrahydrofuran-2-yl]methanol (0.82 g, 4.2 mmol) in dichloromethane (4 mL) then add the dihydropyran (456 uL, 5.0 mmoL) and the p-toluenesulphonic acid (36 mg, 0.21 mmol). Stir the mixture at room temperature for 3 days then dilute the mixture with saturated sodium bicarbonate and extract twice using dichloromethane. Dry the organics using sodium sulfate then filter and evaporate. Chromatograph the residue using a gradient from hexane to 60% ethyl acetate in hexane to give 2-fluoro-5-[5-(tetrahydropyran-2-yloxymethyl)tetrahydrofuran-2-yl]pyridine as a clear oil (0.87 g, 3.1 mmol, 74%). LCMS (low) Isomer 4 rt=1.061 min Mass was not observed.

Preparation 20: Synthesis of 2-fluoro-5-methanesulfinyl-pyridine

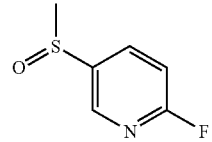

Compound m-chloroperoxybenzoic acid (6.0 g, 26.8 mmoles) is added to 2-fluoro-5-methylsulfanyl-pyridine (3.49 g, 24.4 mmoles) in dichloromethane (50 mL; 50.000 mL) at ~0° C. After complete consumption of starting material, the mixture is diluted with dichloromethane to 80 mL total volume and the solids filtered off. The solution is washed with 1N sodium hydroxide and saturated aqueous sodium chloride, dried over sodium sulfate, filtered and concentrated to a colorless oil. Purification on 80 grams silica gel (50%, then 100% ethyl acetate in hexanes, 65 mL/min) gives 2.79 g of 2-fluoro-5-methylsulfinyl-pyridine as a waxy white solid. LCMS (low) rt=0.427, M+1=160.0.

Preparation 21: Synthesis of 5-(bromomethyl)-2-fluoro-pyridine

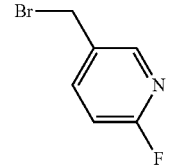

Add N-bromo succinimide (98.9 mmol, 17.6 g), benzoyl peroxide (4.49 mmol, 1.10 g) to a solution of 2-fluoro-5-methyl-pyridine (90 mmol; 10 g) in CCl$_4$ (100 mL). Heat to reflux for 2 h, cool, filter, and concentrate. Purify by LC (330 g silica): dissolve crude mixture in minimum volume of DCM, add to column and elute with a gradient of EtOAc/Hexanes (1:9) to 1:1 over 50 minutes to afford the title intermediate (9.2 g, 54%) as a pale yellow oil. Mass spectrum (m/z): 190 (M+1).

Preparation 22: Synthesis of 2-Fluoro-5-(triazol-1-ylmethyl)pyridine

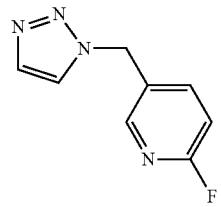 [SMILES: Fc1ccc(Cn2ccnn2)cn1]

Add K$_2$CO$_3$ (5.78 mmol, 800 mg) and 5-(bromomethyl)-2-fluoro-pyridine (5.3 mmol, 1.0 g) to a solution of 1H-1,2,3-triazole (6.4 mmol, 0.38 mL) in acetonitrile (16 mL). Stir at room temperature for 72 h. Pour into a separatory funnel and dilute with EtOAc (200 mL) and water (50 mL). Wash organic layer with water (50 mL) then brine (50 mL). Dry organic layer over Na$_2$SO$_4$, filter, and concentrate. Purify by LC (40 g silica): dissolve crude mixture in minimum volume of DCM, add to column and elute with Hexanes/EtOAc (1:1) to EtOAc over 45 minutes to afford 2-fluoro-5-(triazol-2-ylmethyl)pyridine (300 mg, 32%) as a white solid (first eluting, Mass spectrum (m/z): 179 (M+1)) and the title intermediate (second eluting, 600 mg, 64%) as a white solid. Mass spectrum (m/z): 179 (M+1).

Preparation 23: Synthesis of 6-[1-(5-bromo-2-pyridyl)pyrazole-3-carbonyl]-3H-1,3-benzothiazol-2-one

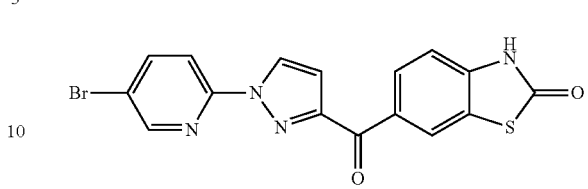

Add potassium carbonate (1.15 kg, 8.35 mol) portionwise to a solution of 6-(1H-pyrazole-5-carbonyl)-3H-1,3-benzothiazol-2-one hydrochloride (600 g, 2.09 mol) in DMF (4.80 L) at 40° C. Stir the mixture for 45 minutes and add a solution of 5-bromo-2-fluoropyridine (404.05 g, 2.30 mol) in DMF (600 mL). Then stir the reaction at 130° C. for 10 hr. Cool the reaction to 10° C. and add water (12 L). Stir the mixture at 20° C. for 3.5 h, filter, wash with water (3 L) and dry under vacuum for 16 h. Slurry the material with ethanol (3.9 L) first and then with hexanes (3 L). Dry the material under vacuum for 24 h to afford desired compound (824 g, 98%). M+1=402.

The following compounds are prepared essentially by the method of Preparation 23.

| Preparation | Name | Structure | Mass (M + 1) |
|---|---|---|---|
| 24 | Methyl 6-[3-[1-[3-(methoxymethyl)-2-oxo-1,3-benzothiazol-6-yl]ethyl]pyrazol-1-yl]pyridine-3-carboxylate | 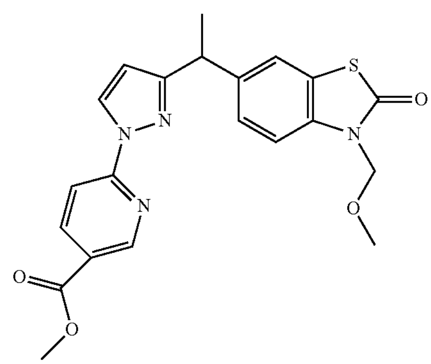 [SMILES: COCn1c(=O)sc2cc(C(C)c3ccn(-c4ccc(C(=O)OC)cn4)n3)ccc21] | 425 |
| 25 | 3-(Methoxymethyl)-6-[1-[1-[5-[5-(tetrahydropyran-2-yloxymethyl)tetrahydrofuran-2-yl]-2-pyridyl]pyrazol-3-yl]ethyl]-1,3-benzothiazol-2-one, isomer 1 | 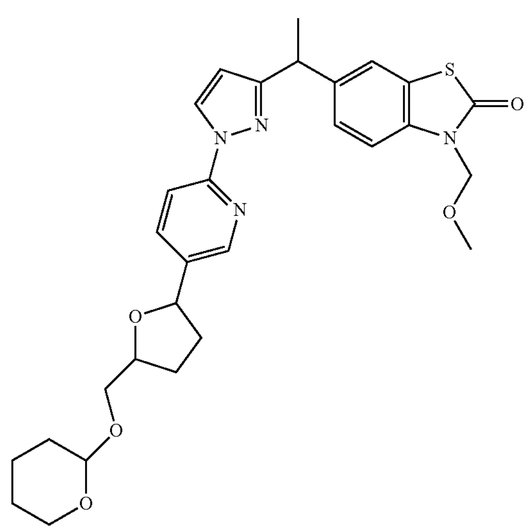 [SMILES: COCn1c(=O)sc2cc(C(C)c3ccn(-c4ccc(C5CCC(COC6CCCCO6)O5)cn4)n3)ccc21] | 551 |

| Preparation | Name | Structure | Mass (M + 1) |
|---|---|---|---|
| 26 | 3-(Methoxymethyl)-6-[1-[1-[5-[5-(tetrahydropyran-2-yloxymethyl) tetrahydrofuran-2-yl]-2-pyridyl]pyrazol-3-yl]ethyl]-1,3-benzothiazol-2-one | 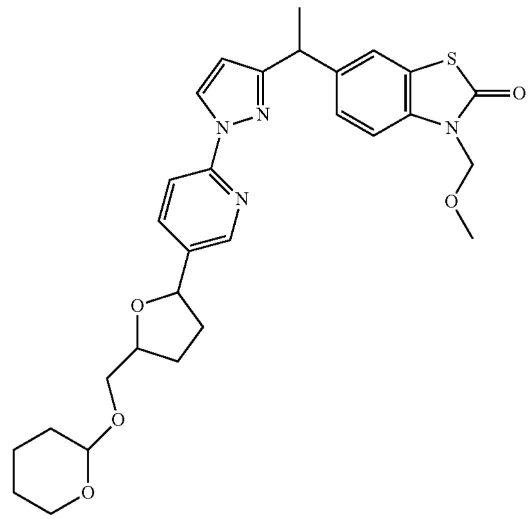 [SMILES: COCn1c(=O)sc2cc(C(C)c3ccn(-c4ccc(C5CCC(COC6CCCCO6)O5)cn4)n3)ccc21] | 551 |
| 27 | 3-(Methoxymethyl)-6-[1-[1-[5-[5-(tetrahydropyran-2-yloxymethyl) tetrahydrofuran-2-yl]-2-pyridyl]pyrazol-3-yl]ethyl]-1,3-benzothiazol-2-one | 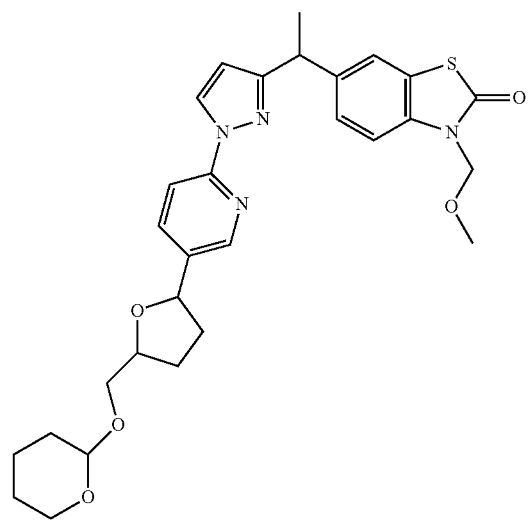 [SMILES: COCn1c(=O)sc2cc(C(C)c3ccn(-c4ccc(C5CCC(COC6CCCCO6)O5)cn4)n3)ccc21] | 551 |
| 28 | 3-(Methoxymethyl)-6-[1-[1-[5-[5-(tetrahydropyran-2-yloxymethyl) tetrahydrofuran-2-yl]-2-pyridyl]pyrazol-3-yl]ethyl]-1,3-benzothiazol-2-one | 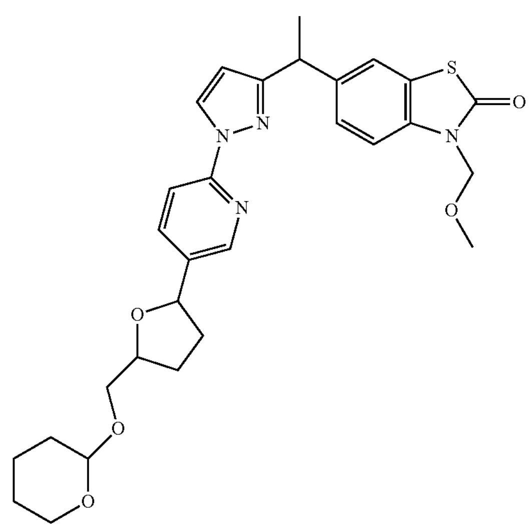 [SMILES: COCn1c(=O)sc2cc(C(C)c3ccn(-c4ccc(C5CCC(COC6CCCCO6)O5)cn4)n3)ccc21] | 551 |

-continued

| Preparation | Name | Structure | Mass (M + 1) |
|---|---|---|---|
| 29 | 6-(1-(1-(5-iodopyridin-2-yl)-1H-pyrazol-3-yl)ethyl)-3-(methoxymethyl)benzo[d]thiazol-2(3H)-one | 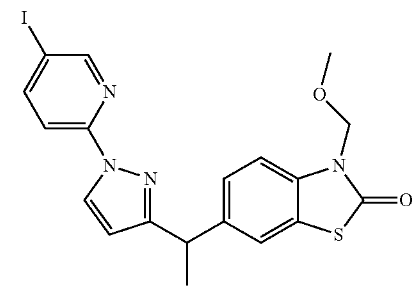 [SMILES: COCn1c(=O)sc2cc(C(C)c3ccn(-c4ccc(I)cn4)n3)ccc21] | 493 |
| 30 | 6-[1-[1-(5-bromo-2-pyridyl)pyrazol-3-yl]ethyl]-3-(methoxymethyl)-1,3-benzothiazol-2-one | 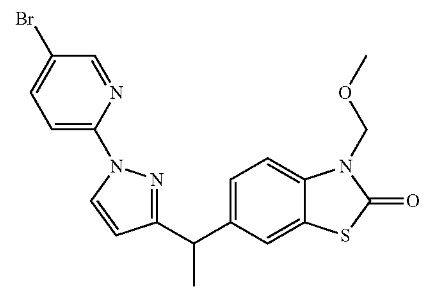 [SMILES: COCn1c(=O)sc2cc(C(C)c3ccn(-c4ccc(Br)cn4)n3)ccc21] | 447 |
| 31 | 6-[1-[1-(5-bromo-2-pyridyl)pyrazol-3-yl]ethyl]-3-(methoxymethyl)-1,3-benzothiazol-2-one | 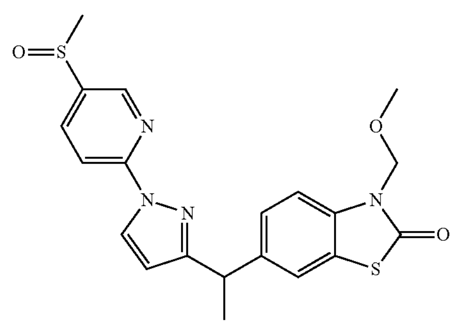 [SMILES: COCn1c(=O)sc2cc(C(C)c3ccn(-c4ccc(S(C)=O)cn4)n3)ccc21] | 429 |
| 32 | 6-[1-[1-[5-(2-tetrahydropyran-2-yloxyethyl)-2-pyridyl]pyrazol-3-yl]ethyl]-3H-1,3-benzothiazol-2-one | 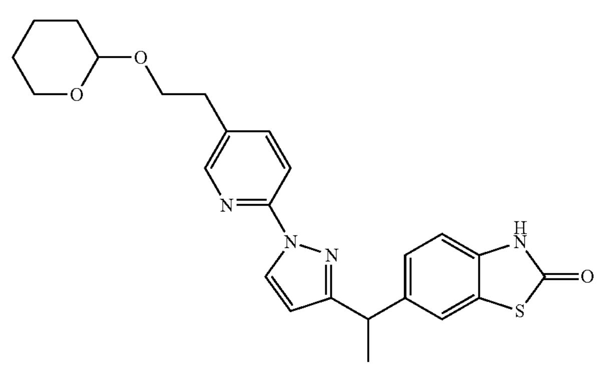 [SMILES: CC(c1ccc2[nH]c(=O)sc2c1)c1ccn(-c2ccc(CCOC3CCCCO3)cn2)n1] | 451 |
| 33 | methyl 6-[3-[1-[3-(methoxymethyl)-2-oxo-1,3-benzothiazol-6-yl]ethyl]pyrazol-1-yl]pyridine-3-carboxylate | 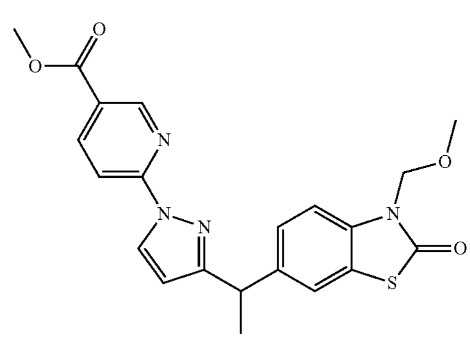 [SMILES: COCn1c(=O)sc2cc(C(C)c3ccn(-c4ccc(C(=O)OC)cn4)n3)ccc21] | 425 |

| Preparation | Name | Structure | Mass (M + 1) |
|---|---|---|---|
| 34 | Methyl 6-[3-[1-[3-(methoxymethyl)-2-oxo-1,3-benzothiazol-6-yl]ethyl]pyrazol-1-yl]pyridine-3-carboxylate | 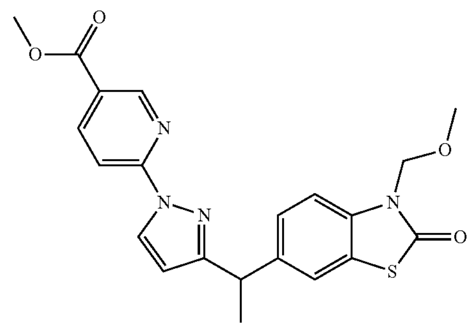 [SMILES: COCn1c(=O)sc2cc(C(C)c3ccn(-c4ccc(C(=O)OC)cn4)n3)ccc21] | 425 |
| 35 | 3-(methoxymethyl)-6-[1-[1-(6-methylpyridazin-3-yl)pyrazol-3-yl]ethyl]-1,3-benzothiazol-2-one | 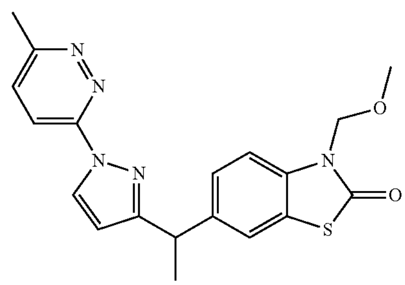 [SMILES: COCn1c(=O)sc2cc(C(C)c3ccn(-c4ccc(C)nn4)n3)ccc21] | 382 |
| 36 | 3-(Methoxymethyl)-6-[1-[1-(5-nitro-2-pyridyl)pyrazol-3-yl]ethyl]-1,3-benzothiazol-2-one | 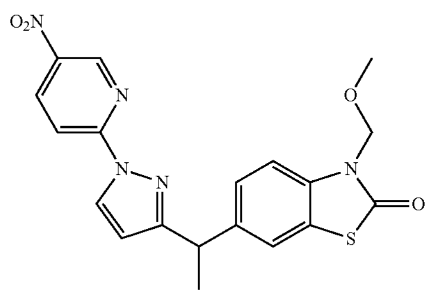 [SMILES: COCn1c(=O)sc2cc(C(C)c3ccn(-c4ccc([N+](=O)[O-])cn4)n3)ccc21] | 412 |
| 37 | 3-(Methoxymethyl)-6-[1-[1-[5-(triazol-1-ylmethyl)-pyridyl)pyrazol-3-yl]ethyl]-1,3-benzothiazol-2-one | 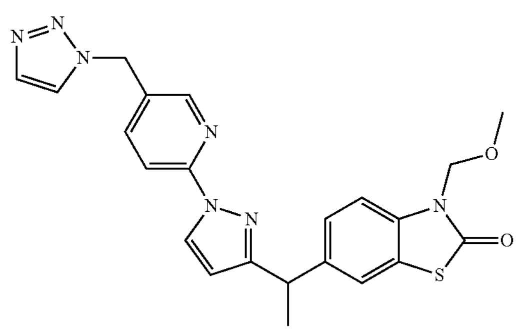 [SMILES: COCn1c(=O)sc2cc(C(C)c3ccn(-c4ccc(Cn5ccnn5)cn4)n3)ccc21] | 448 |

Preparation 38: Synthesis of 6-[1-[1-[5-(hydroxymethyl)-5-methyl-2-pyridyl]pyrazol-3-yl]ethyl]-3-(methoxymethyl)-1,3-benzothiazol-2-one

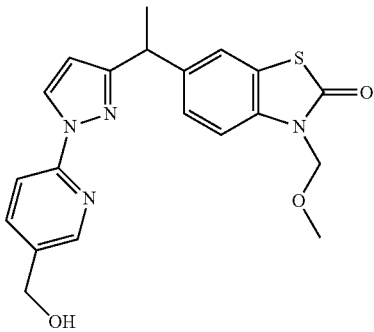 [SMILES: COCn1c(=O)sc2cc(C(C)c3ccn(-c4ccc(CO)cn4)n3)ccc21]

Dissolve 6-[3-[1-[3-(methoxymethyl)-2-oxo-1,3-benzothiazol-6-yl]ethyl]pyrazol-1-yl]pyridine-3-carboxylate (5.8 g, 13.66 mmol) in tetrahydrofuran (74 mL) and add lithium borohydride (470 mg, 20.5 mmol) at room temperature. Heat the mixture to 50° C. overnight. Cool the mixture to 0° C. and carefully add aqueous saturated ammonium chloride solution. Partition between ethyl acetate and water then extract twice with ethyl acetate. Dry the organics with sodium sulfate then filter and evaporate. Chromatograph the mixture using a gradient from hexane up to 100% ethyl acetate to give 6-[1-[1-[5-(hydroxymethyl)-5-methyl-2-pyridyl]pyrazol-3-yl]ethyl]-3-(methoxymethyl)-1,3-benzothiazol-2-one as a white solid (3.2 g, 8.1 mmol, 59%). LCMS (low) rt=2.07 min, M+1=397.

Preparation 39: Synthesis of ethyl 2-[[6-[3-[1-[3-(methoxymethyl)-2-oxo-1,3-benzothiazol-6-yl]ethyl]pyrazol-1-yl]-3-pyridyl]methoxy]acetate

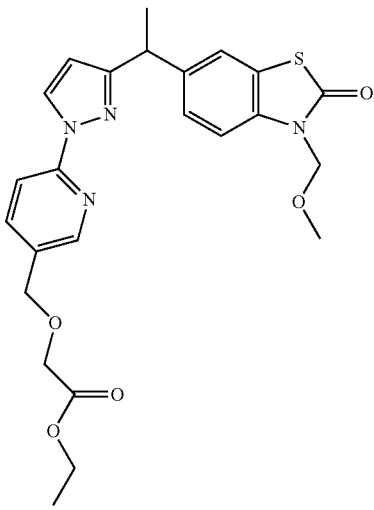 [SMILES: CCOC(=O)COCc1ccc(-n2ccc(C(C)c3ccc4c(c3)sc(=O)n4COC)n2)nc1]

Dissolve 6-[1-[1-[5-(hydroxymethyl)-5-methyl-2-pyridyl]pyrazol-3-yl]ethyl]-3-(methoxymethyl)-1,3-benzothiazol-2-one (3.2 g, 8.1 mmol) in tetrahydrofuran (81 mL) and cool the mixture to 0° C. Add lithium bis(trimethylsilyl)amide (9.7 mL, 9.7 mmol, 1M solution in tetrahydrofuran) and warm the mixture to room temperature for one hour. Cool the mixture to 0° C. and add ethylbromoacetate (2.24 mL, 20.2 mmol) then allow the mixture to come to room temperature overnight. Dilute the mixture with saturated ammonium chloride and extract the mixture with ethyl acetate three times. Dry the organics with sodium sulfate then filter and evaporate. Chromatograph the residue using a gradient from hexane to 40% ethyl acetate in hexane to give ethyl 2-[[6-[3-[1-[3-(methoxymethyl)-2-oxo-1,3-benzothiazol-6-yl]ethyl]pyrazol-1-yl]-3-pyridyl]methoxy]acetate as a light yellow oil (1.64 g, 3.4 mmol, 41%). LCMS (low) rt=2.50 min, M+1=483.

Preparation 40: Synthesis of 6-[1-[1-[5-(2-hydroxyethoxymethyl)-2-pyridyl]pyrazol-3-yl]ethyl]-3-(methoxymethyl)-1,3-benzothiazol-2-one

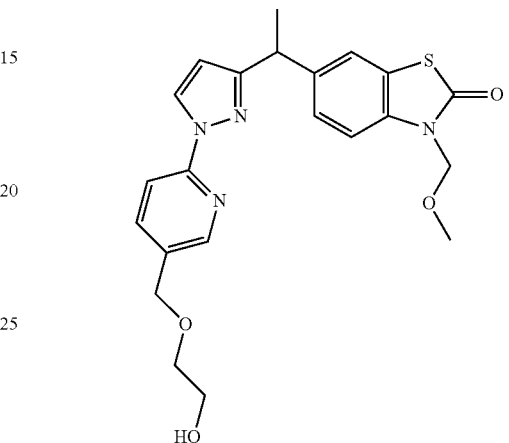

Dissolve ethyl 2-[[6-[3-[1-[3-(methoxymethyl)-2-oxo-1,3-benzothiazol-6-yl]ethyl]pyrazol-1-yl]-3-pyridyl]methoxy]acetate (1.64 g, 3.4 mmol) in tetrahydrofuran (35 mL) and add lithium borohydride (222 mg, 10.2 mmol) at room temperature. Heat the mixture to 50° C. for four hours. Cool the mixture to 0° C. and carefully add aqueous saturated ammonium chloride solution then extract twice with ethyl acetate. Dry the organics with sodium sulfate then filter and evaporate. Chromatograph the mixture using a gradient from 50% ethyl acetate/hexane up to 100% ethyl acetate to give 6-[1-[1-[5-(2-hydroxyethoxymethyl)-2-pyridyl]pyrazol-3-yl]ethyl]-3-(methoxymethyl)-1,3-benzothiazol-2-one as a clear oil (1.36 g, 3.1 mmol, 91%). LCMS (low) rt=2.10 min, M+1=441.

Preparation 41: Synthesis of 2-[[6-[3-[1-[3-(Methoxymethyl)-2-oxo-1,3-benzothiazol-6-yl]ethyl]pyrazol-1-yl]-3-pyridyl]methoxy]acetic acid

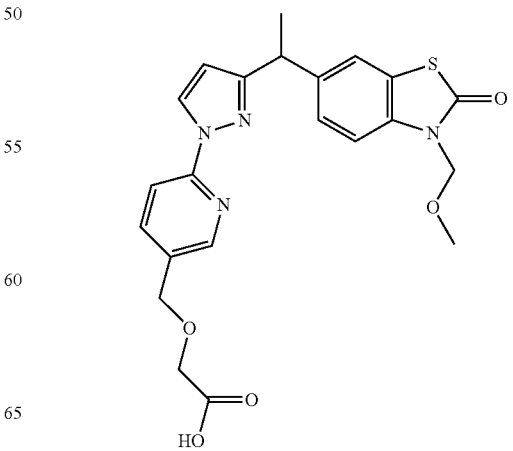

Dissolve ethyl 2-[[6-[3-[1-[3-(methoxymethyl)-2-oxo-1,3-benzothiazol-6-yl]ethyl]pyrazol-1-yl]-3-pyridyl]methoxy]acetate (2.3 g, 4.77 mmol) in tetrahydrofuran (38 mL) and add lithium hydroxide (2 g, 47.66 mmol) and water (9 mL). Stir the mixture overnight at room temperature. Make the solution basic with 1N sodium hydroxide and extract with diethyl ether. Make the aqueous acidic with 1N hydrochloric acid and extract twice with ethyl acetate. Dry the ethyl acetate extracts with sodium sulfate then filter and evaporate to give 2-[[6-[3-[1-[3-(methoxymethyl)-2-oxo-1,3-benzothiazol-6-yl]ethyl]pyrazol-1-yl]-3-pyridyl]methoxy]acetic acid as a white solid (2.25 g, 4.95 mmol, 104%). LCMS (low) rt=1.14 min, M+1=455.

Preparation 42: Synthesis of N-methoxy-2-[[6-[3-[1-[3-(methoxymethyl)-2-oxo-1,3-benzothiazol-6-yl]ethyl]pyrazol-1-yl]-3-pyridyl]methoxy]-N-methyl-acetamide

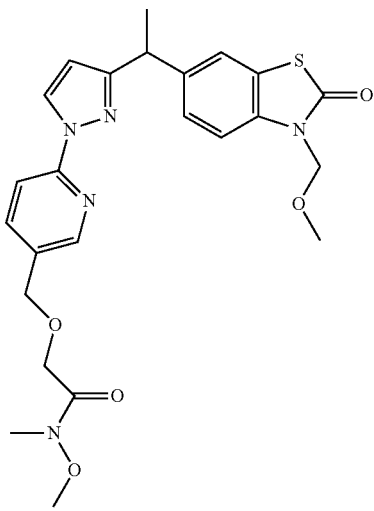 [SMILES: COCn1c(=O)sc2cc(C(C)c3ccn(-c4ccc(COCC(=O)N(C)OC)cn4)n3)ccc21]

Dissolve 2-[[6-[3-[1-[3-(methoxymethyl)-2-oxo-1,3-benzothiazol-6-yl]ethyl]pyrazol-1-yl]-3-pyridyl]methoxy]acetic acid (2.25 g, 4.95 mmol) in dichloromethane (15 mL) and add 1-(3-dimethylaminopropyl)-3-ethylcarbodiimide hydrochloride (1.13 g, 5.89 mmol), N,O-dimethylhydroxylamine hydrochloride (0.52 g, 5.33 mmol) and pyridine (2.7 mL, 33.4 mmol). Stir the mixture for three days. Dilute the mixture with saturated sodium bicarbonate and brine and extract twice with ethyl acetate. Dry the organic fractions with sodium sulfate, filter and evaporate. Chromatograph the residue using a gradient from 30% ethyl acetate/hexane to 100% ethyl acetate to give N-methoxy-2-[[6-[3-[1-[3-(methoxymethyl)-2-oxo-1,3-benzothiazol-6-yl]ethyl]pyrazol-1-yl]-3-pyridyl]methoxy]-N-methyl-acetamide as a white solid (1.27 g, 2.50 mmol). LCMS (low) rt=1.20 min, M+1=498.

Preparation 43: Synthesis of 6-[1-[1-[5-(Acetonyloxymethyl)-2-pyridyl]pyrazol-3-yl]ethyl]-3-(methoxymethyl)-1,3-benzothiazol-2-one

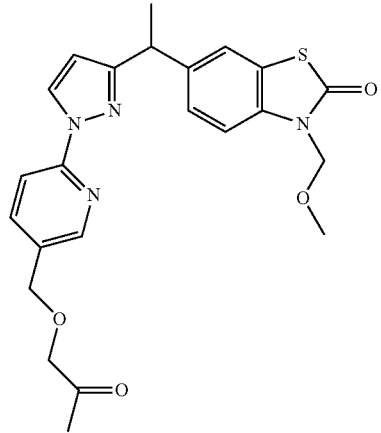 [SMILES: COCn1c(=O)sc2cc(C(C)c3ccn(-c4ccc(COCC(C)=O)cn4)n3)ccc21]

Dissolve N-methoxy-2-[[6-[3-[1-[3-(methoxymethyl)-2-oxo-1,3-benzothiazol-6-yl]ethyl]pyrazol-1-yl]-3-pyridyl]methoxy]-N-methyl-acetamide (1.27 g, 2.55 mmol) in tetrahydrofuran (20 mL) and cool the mixture to −20° C. Slowly add methylmagnesiumbromide (2.5 mL, 7.5 mmol, 3M solution in diethyl ether) and allow the mixture to warm to room temperature. Stir for an additional 20 minutes then dilute the mixture with saturated ammonium chloride. Extract the mixture 3 times with ethyl acetate. Dry the organics with sodium sulfate then filter and evaporate. Chromatograph the residue using a gradient from hexane to 80% ethyl acetate/hexane to give 6-[1-[1-[5-(acetonyloxymethyl)-2-pyridyl]pyrazol-3-yl]ethyl]-3-(methoxymethyl)-1,3-benzothiazol-2-one as a white solid (0.8 g, 69%). LCMS (low) rt=1.22 min, M+1=453.

Preparation 44: Synthesis of 6-(1-(1-(5-(4-hydroxypiperidin-1-yl)pyridin-2-yl)-1H-pyrazol-3-yl)ethyl)-3-(methoxymethyl)benzo[d]thiazol-2(3H)-one

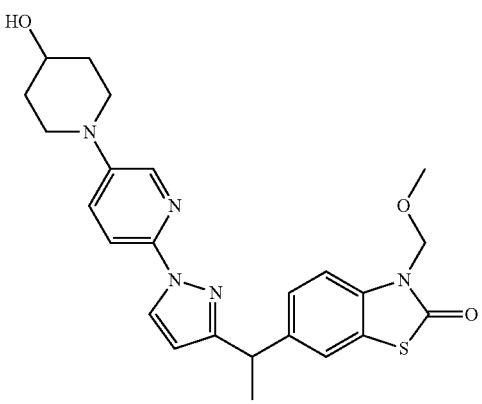 [SMILES: COCn1c(=O)sc2cc(C(C)c3ccn(-c4ccc(N5CCC(O)CC5)cn4)n3)ccc21]

A pressure vial is charged with 6-(1-(1-(5-iodopyridin-2-yl)-1H-pyrazol-3-yl)ethyl)-3-(methoxymethyl)benzo[d]thiazol-2(3H)-one (1.98 g, 4.0 mmoles), potassium phosphate (1.7 g, 8.0 mmoles), 1,1'-bi-2-naphthol (230.3 mg, 804.3 µmoles), copper(I) bromide (115.4 mg, 804.3 µmoles), and 4-hydroxypiperidine (610.2 mg, 6.0 mmoles). Then anhydrous Dimethylformamide (4.0 mL) is added. Ar gas is bubbled through the vial for 1 min. The vial is sealed and heated at 85° C. for 24 h. The reaction mixture is diluted with THF and filtered. The filtrate is concentrated to a dark oil. The oil is purified using 50-100% EtOAc/hexane. Obtained the title compound as a yellowish oil 3141358 (1.44 g, 3.1 mmoles, 76.91% yield). M+1=466.

Preparation 45: Synthesis of 6-(1-(1-(5-(4-hydroxy-4-methylpiperidin-1-yl)pyridin-2-yl)-1H-pyrazol-3-yl)ethyl)-3-((2-(trimethylsilyl)ethoxy)methyl)benzo[d]thiazol-2(3H)-one

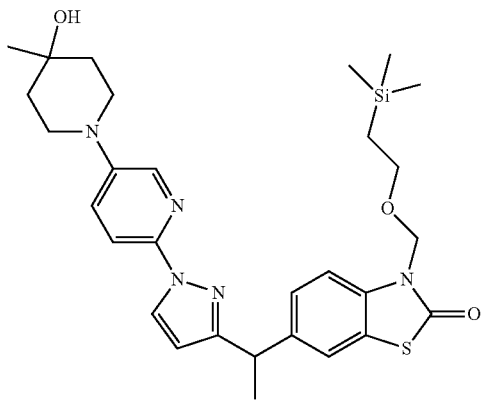 [SMILES: CC(c1ccc2c(c1)sc(=O)n2COCC[Si](C)(C)C)c1ccn(-c2ccc(N3CCC(C)(O)CC3)cn2)n1]

The title compound is prepared essentially by the method of Preparation 44 using 6-(1-(1-(5-iodopyridin-2-yl)-1H-pyrazol-3-yl)ethyl)-3-((2-(trimethylsilyl)ethoxy)methyl)benzo[d]thiazol-2(3H)-one and 4-methylpiperidin-4-ol as starting materials. M+1=566.

Preparation 46: Synthesis of 6-(1-(1-(5-(4-(2-hydroxyethyl)piperidin-1-yl)pyridin-2-yl)-1H-pyrazol-3-yl)ethyl)-3-((2-(trimethylsilyl)ethoxy)methyl)benzo[d]thiazol-2(3H)-one

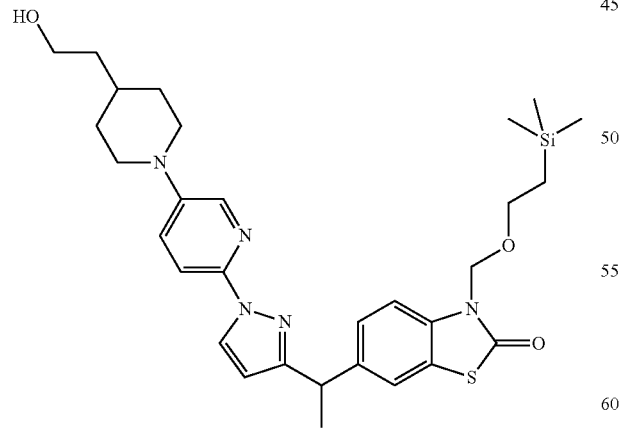

The title compound is prepared essentially by the method of Preparation 44 using 6-(1-(1-(5-iodopyridin-2-yl)-1H-pyrazol-3-yl)ethyl)-3-((2-(trimethylsilyl)ethoxy)methyl)benzo[d]thiazol-2(3H)-one and 4-ethanolpiperidine as the starting materials. M+1=580.

Preparation 47: Synthesis of 6-(1-(1-(5-((2-hydroxypropyl)thio)pyridin-2-yl)-1H-pyrazol-3-yl)ethyl)-3-((2-(trimethylsilyl)ethoxy)methyl)benzo[d]thiazol-2(3H)-one

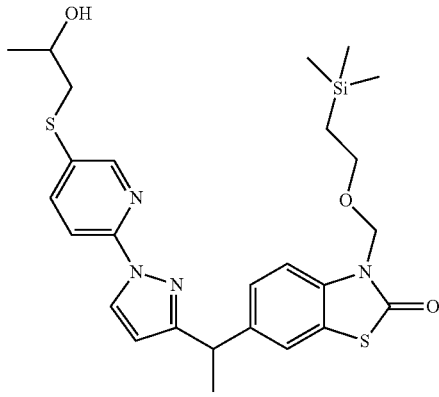 [SMILES: CC(O)CSc1ccc(-n2ccc(C(C)c3ccc4c(c3)sc(=O)n4COCC[Si](C)(C)C)n2)nc1]

The title compound is prepared essentially by the method of Preparation 44 using 6-(1-(1-(5-iodopyridin-2-yl)-1H-pyrazol-3-yl)ethyl)-3-((2-(trimethylsilyl)ethoxy)methyl)benzo[d]thiazol-2(3H)-one and 1-mercapto-2-propanol as the appropriate starting materials. M+1=543.

Preparation 48: Synthesis of ethyl 2-((6-(3-(1-(2-oxo-3-((2-(trimethylsilyl)ethoxy)methyl)-2,3-dihydrobenzo[d]thiazol-6-yl)ethyl)-1H-pyrazol-1-yl)pyridin-3-yl)thio)propanoate

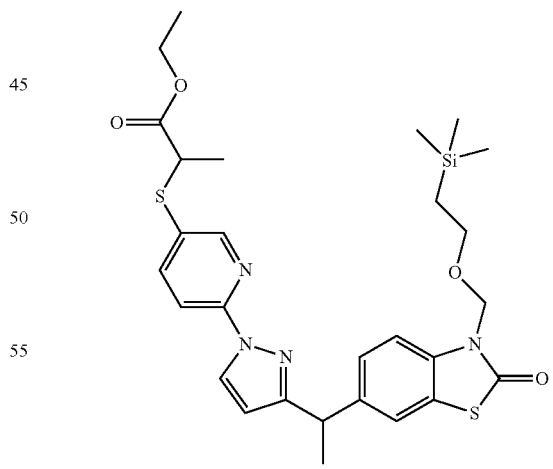

The title compound is prepared essentially by the method of Preparation 44 using 6-(1-(1-(5-iodopyridin-2-yl)-1H-pyrazol-3-yl)ethyl)-3-((2-(trimethylsilyl)ethoxy)methyl)benzo[d]thiazol-2(3H)-one and ethyl 2-mercaptopropionate as the appropriate starting materials. M+1=585.

Preparation 49: Synthesis of 6-{1-[1-(6-Chloro-pyridazin-3-yl)-1H-pyrazol-3-yl]-ethyl}-3-methoxymethyl-3H-benzothiazol-2-one

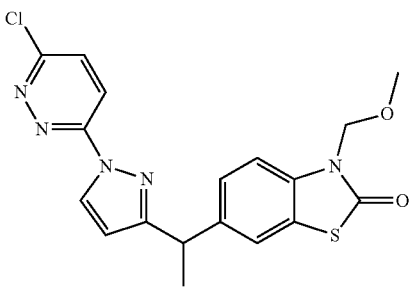 [SMILES: COCn1c(=O)sc2cc(C(C)c3ccn(-c4ccc(Cl)nn4)n3)ccc21]

To 3-(methoxymethyl)-6-[1-(1H-pyrazol-5-yl)ethyl]-1,3-benzothiazol-2(3H)-one (6.5 g, 22.5 mmoles) in dimethylformamide (110 mL) is added sodium hydride (95%, 851 mg, 33.7 mmoles) and the mixture is stirred at room temperature 10 minutes. 3,6-dichloropyridazine (6.69 g, 44.9 mmoles) is added and the mixture stirred at room temperature. After 30 minutes, the reaction is diluted with ethyl acetate (~400 mL), washed with water, 1N lithium chloride and saturated aqueous sodium chloride and dried over sodium sulfate. The mixture is filtered, concentrated and purified on 2 220 g silica gel columns, 0 to 30% ethyl acetate in hexanes to give 6-{1-[1-(6-chloro-pyridazin-3-yl)-1H-pyrazol-3-yl]-ethyl}-3-methoxymethyl-3H-benzothiazol-2-one (6.1 g, 67.57% yield) as a white solid. LCMS (low) rt=1.27 min, M+1 402.0

Preparation 50: Synthesis of 6-(1-{1-[6-(2-hydroxy-ethylsulfanyl)-pyridazin-3-yl]-1H-pyrazol-3-yl}-ethyl)-3-methoxymethyl-3H-benzothiazol-2-one

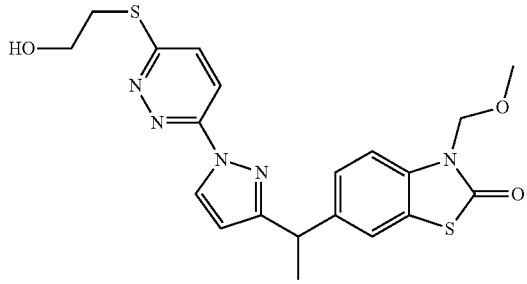 [SMILES: COCn1c(=O)sc2cc(C(C)c3ccn(-c4ccc(SCCO)nn4)n3)ccc21]

2-Mercaptoethanol (0.18 mL, 2.57 mL) is added to a mixture of 6-{1-[1-(6-chloro-pyridazin-3-yl)-1H-pyrazol-3-yl]-ethyl}-3-methoxymethyl-3H-benzothiazol-2-one (860 mg, 2.14 mmoles) and cesium carbonate (1.55 g, 4.71 mmoles) in Dimethylformamide (8 mL). After stirring ~1 hour, the liquid is decanted from the solids. The solids are washed with more ethyl acetate. The combined organics are washed with 1N lithium chloride and saturated aqueous sodium chloride and concentrated to provide a clear oil. Purification on 64 g silica gel (15 to 70% ethyl acetate in hexanes, 65 mL/min) gives 6-(1-{1-[6-(2-hydroxy-ethylsulfanyl)-pyridazin-3-yl]-1H-pyrazol-3-yl}-ethyl)-3-methoxymethyl-3H-benzothiazol-2-one (744 mg, 78.38% yield) as a sticky white solid. LCMS (low) rt=1.11 min, M+1 444.0.

Preparation 51: Isolation of 3-(methoxymethyl)-6-[1-(1H-pyrazol-5-yl)ethyl]-1,3-benzothiazol-2-one, Isomer 1

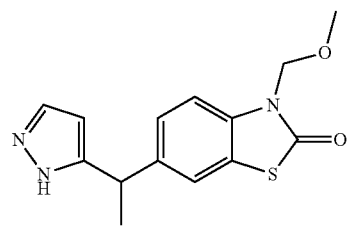 [SMILES: COCn1c(=O)sc2cc(C(C)c3ccn[nH]3)ccc21]

Racemic 3-(methoxymethyl)-6-[1-(1H-pyrazol-5-yl)ethyl]-1,3-benzothiazol-2-one is resolved into its enantiomers by chiral chromatography using (R,R) Whelk-O, 4.6× 150 mm, 20% EtOH/80% $CO_2$, 5 mL/min, 225 nm Isomer 1 retention time is 2.0 min. and Isomer 2 is 2.6 min Isomer 1 is carried forward.

Preparation 52: Synthesis of 6-[1-[1-[5-(hydroxymethyl)-2-pyridyl]pyrazol-3-yl]ethyl]-3-(methoxymethyl)-1,3-benzothiazol-2-one

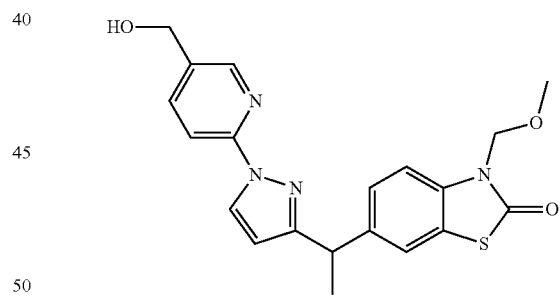

To a mixture of methyl 6-[3-[1-[3-(methoxymethyl)-2-oxo-1,3-benzothiazol-6-yl]ethyl]pyrazol-1-yl]pyridine-3-carboxylate (3.4 g, 8 mmoles) in Tetrahydrofuran (40 mL) is added a 2 M solution of Lithium Borohydride in Tetrahydrofuran (6 mL, 12 mmoles). The mixture is heated at 50° C. for 6 h. The reaction is quenched with the slow addition of saturated NH4Cl. The mixture is partitioned between EtOAc and water. The aqueous phase is extracted with EtOAc (2×). The combined organic phase is washed with brine, dried ($Na_2SO_4$) and concentrated to obtain 6-[1-[1-[5-(hydroxymethyl)-2-pyridyl]pyrazol-3-yl]ethyl]-3-(methoxymethyl)-1,3-benzothiazol-2-one (2.8 g; 88%). LCMS approx. 85% purity (+) 397.

Preparation 53: Synthesis of 6-[3-[1-[3-(methoxymethyl)-2-oxo-1,3-benzothiazol-6-yl]ethyl]pyrazol-1-yl]pyridine-3-carbaldehyde

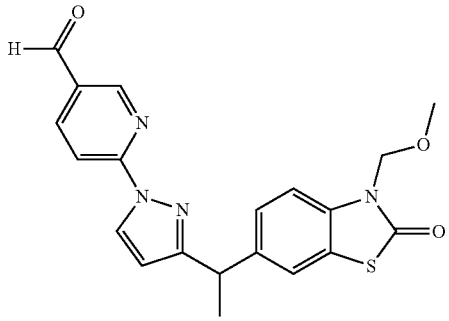 [SMILES: COCn1c(=O)sc2cc(C(C)c3ccn(-c4ccc(C=O)cn4)n3)ccc21]

To a solution of 6-[1-[1-[5-(hydroxymethyl)-2-pyridyl]pyrazol-3-yl]ethyl]-3-(methoxymethyl)-1,3-benzothiazol-2-one (2.8 g, 7 mmoles) in chloroform (75 mL) is added manganese(IV) oxide (6.2 g, 71 mmoles). The mixture is heated at reflux for 2 hours. The mixture is cooled to room temperature, filtered through a pad of filter cel, and concentrated to obtain 6-[3-[1-[3-(methoxymethyl)-2-oxo-1,3-benzothiazol-6-yl]ethyl]pyrazol-1-yl]pyridine-3-carbaldehyde (2.55 g, 91%). LCMS (+) 395.0.

Preparation 54: Synthesis of 6-[1-[1-[5-(1-hydroxyethyl)-2-pyridyl]pyrazol-3-yl]ethyl]-3-(methoxymethyl)-1,3-benzothiazol-2-one

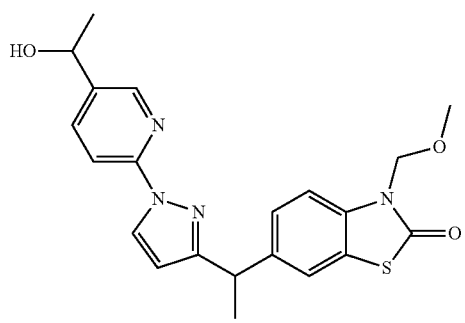 [SMILES: COCn1c(=O)sc2cc(C(C)c3ccn(-c4ccc(C(C)O)cn4)n3)ccc21]

A mixture of 6-[3-[1-[3-(methoxymethyl)-2-oxo-1,3-benzothiazol-6-yl]ethyl]pyrazol-1-yl]pyridine-3-carbaldehyde (2.55 g, 6.5 mmoles) and tetrahydrofuran (0.2 M, 30.mL) is cooled to 0° C., and a 3 M solution of methylmagnesium bromide (4.3 mL, 13 mmoles). The cooling bath is removed, and the mixture is warmed to room temperature. After approximately 1 h, the reaction mixture is quenched with sat. NH$_4$Cl solution and the mixture is partitioned between EtOAc and water. The aqueous phase is extracted with EtOAc (2×). The combined organic phase is washed with brine, dried (Na$_2$SO$_4$) and concentrated to yield 6-[1-[1-[5-(1-hydroxyethyl)-2-pyridyl]pyrazol-3-yl]ethyl]-3-(methoxymethyl)-1,3-benzothiazol-2-one (2.6 g, 99%). LCMS (+) 411.0.

Preparation 55: Synthesis of methyl 6-[3-[1-[3-(methoxymethyl)-2-oxo-1,3-benzothiazol-6-yl]ethyl]pyrazol-1-yl]pyridazine-3-carboxylate

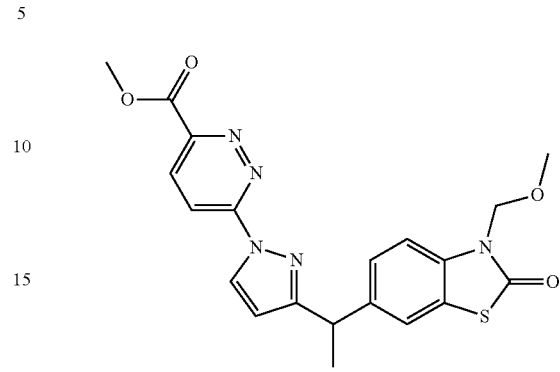

To a mixture of 3-(methoxymethyl)-6-[1-(1H-pyrazol-5-yl)ethyl]-1,3-benzothiazol-2(3H)-one (1.47 g, 5.1 mmoles) in dimethylformamide (25 mL) is added sodium hydride (406 mg, 10.2 mmoles, 60% dispersion) and stirred at room temperature for 10 minutes. Ethyl 6-chloropyridazine-3-carboxylate (2.4 g, 12.7 mmoles) is added, and the mixture is stirred at room temperature for 40 min. The reaction mixture is quenched with saturated NH$_4$Cl solution and partitioned between ethyl acetate and water. The organic layer is washed with saturated aqueous sodium chloride and concentrated. The material is purified by flash chromatography (220 g silica gel, 0 to 60% ethyl acetate/hexane) to yield ethyl 6-[3-[1-[3-(methoxymethyl)-2-oxo-1,3-benzothiazol-6-yl]ethyl]pyrazol-1-yl]pyridazine-3-carboxylate (895 mg; 40%). LCMS (+) 440.0

Preparation 56: Synthesis of 6-[1-[1-[6-(hydroxymethyl)pyridazin-3-yl]pyrazol-3-yl]ethyl]-3-(methoxymethyl)-1,3-benzothiazol-2-one

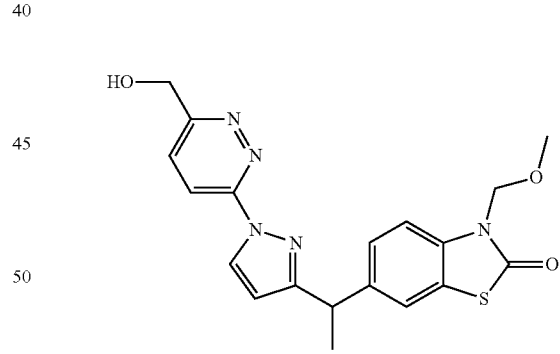

A mixture of ethyl 6-[3-[1-[3-(methoxymethyl)-2-oxo-1,3-benzothiazol-6-yl]ethyl]pyrazol-1-yl]pyridazine-3-carboxylate (1.18 g, 2.7 mmoles) and tetrahydrofuran is cooled to 0° C. Sodium borohydride (113 mg, 3 mmoles) is added and the cooling bath is removed. After a couple hours, additional sodium borohydride (113 mg, 3 mmoles) is added, and the mixture is stirred for another couple hours. The reaction is quenched with water and saturated NH$_4$Cl solution, and partitioned between EtOAc and water. The aqueous phase is extracted with EtOAc (2×). The combined organic phase is washed with brine, dried (Na$_2$SO$_4$) and concentrated. The material is purified by flash chromatography (silica gel, 120 g, eluted 60% EtOAc/hexane to 100%

EtOAc) to obtain 6-[1-[1-[6-(hydroxymethyl)pyridazin-3-yl]pyrazol-3-yl]ethyl]-3-(methoxymethyl)-1,3-benzothiazol-2-one (485 mg, 45%). LCMS (+) 398.0.

Preparation 57: Synthesis of 6-[1-[1-(5-fluoro-2-pyridyl)pyrazol-3-yl]ethyl]-3-(methoxymethyl)-1,3-benzothiazol-2-one

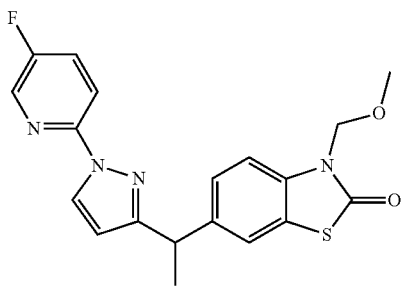 [SMILES: COCn1c(=O)sc2cc(C(C)c3ccn(-c4ccc(F)cn4)n3)ccc21]

A mixture of 3-(methoxymethyl)-6-[1-(1H-pyrazol-5-yl)ethyl]-1,3-benzothiazol-2-one (1 g, 3.5 mmoles), 2,5-difluoropyridine (2.2 mL; 21 mmoles), and cesium carbonate (1.24 g, 3.80 mmoles) is heated at 180° C. in a vial for approx. 4 h. The mixture is partitioned between EtOAc and water. The aqueous phase is extracted with EtOAc (2×). The combined organic phase is washed with brine, dried ($Na_2SO_4$), and concentrated. The crude material is purified by flash chromatography (80 g silica gel, eluted hexane to 50% EtOAc/hexane) to yield 6-[1-[1-(5-fluoro-2-pyridyl)pyrazol-3-yl]ethyl]-3-(methoxymethyl)-1,3-benzothiazol-2-one (614 mg; 46%) LCMS (+) 385.0

Preparation 58: Synthesis of 3-(methoxymethyl)-6-[1-[1-(5-morpholino-2-pyridyl)pyrazol-3-yl]ethyl]-1,3-benzothiazol-2-one

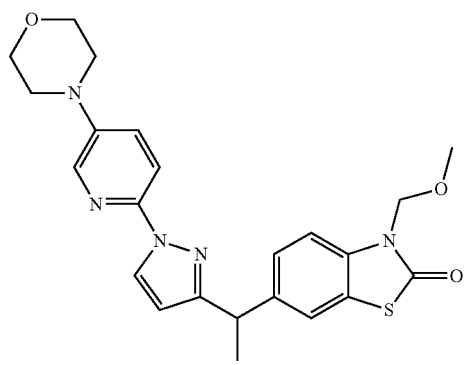 [SMILES: COCn1c(=O)sc2cc(C(C)c3ccn(-c4ccc(N5CCOCC5)cn4)n3)ccc21]

To a microwave Vial is added 6-[1-[1-(5-bromo-2-pyridyl)pyrazol-3-yl]ethyl]-3-(methoxymethyl)-1,3-benzothiazol-2-one (1 g, 2.2 mmoles), tris(dibenzylideneacetone)dipalladium(0) (514 mg, 0.25 equiv (molar); 561µmoles), X-phos (0.5 equiv (molar); 1.12 mmoles; 535.24 mg), sodium t-butoxide (445 mg, 4.5 mmoles), toluene (9 mL, 0.25 M), and morpholine (587 mg, 6.7 mmoles). The vial is evacuated under vacuum and flushed with nitrogen (3×). The mixture is heated to 100° C. in a microwave with stirring on and held for 30 min EtOAc is added, and the mixture is filtered. The material is purified by flash chromatography (40 g silica gel, eluted with hexane to 50% acetone/hexane) to yield 3-(methoxymethyl)-6-[1-[1-(5-morpholino-2-pyridyl)pyrazol-3-yl]ethyl]-1,3-benzothiazol-2-one (300 mg; 29%). LCMS (+) 452.

Preparation 59: Synthesis of tert-butyl 2-[6-[3-[1-[3-(methoxymethyl)-2-oxo-1,3-benzothiazol-6-yl]ethyl]pyrazol-1-yl]-3-pyridyl]acetate

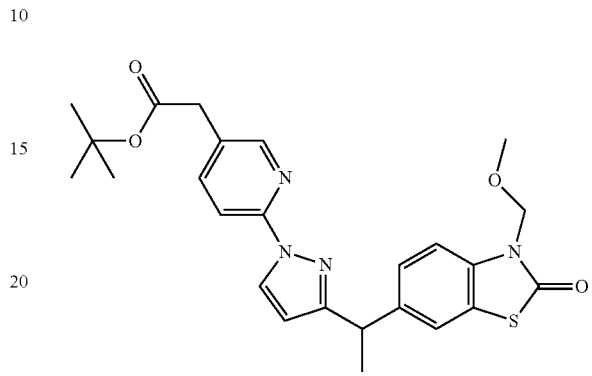

6-[1-[1-(5-bromo-2-pyridyl)pyrazol-3-yl]ethyl]-3-(methoxymethyl)-1,3-benzothiazol-2-one (8.23 g, 18.5 mmol) is dissolved in tetrahydrofuran (110 mL, 0.2M). Add PEPPSI-ipr (376 mg, 0.55 mmol) then purge this solution with nitrogen for 20 min. before adding a solution of chloro(2,2-dimethylpropanoyloxymethyl)zinc in ether (110.88 mL of a 0.5M solution, 55.4 mmol). Heat this mixture to 80° C. under nitrogen with stirring. After 3 hrs, cool the reaction to ambient temperature and partition between ethyl acetate and an aqueous saturated solution of ammonium chloride. Extract the aqueous layer with ethyl acetate and dry the combined organics with magnesium sulfate. Filter the organics and evaporate the liquid. Purify this residue with silica gel (330 g, 25% EtOAc in hexanes) to give tert-butyl 2-[6-[3-[1-[3-(methoxymethyl)-2-oxo-1,3-benzothiazol-6-yl]ethyl]pyrazol-1-yl]-3-pyridyl]acetate as a pale yellow foam (2.8 g, 32%). M+1=481.

Preparation 60: Synthesis of 6-[1-[1-[5-(2,2-dideuterio-2-hydroxy-ethyl)-2-pyridyl]pyrazol-3-yl]ethyl]-3-(methoxymethyl)-1,3-benzothiazol-2-one

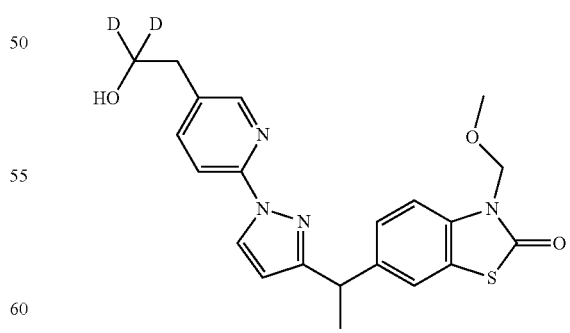

Dissolve tert-butyl 2-[6-3-[1-[3-(methoxymethyl)-2-oxo-1,3-benzothiazol-6-yl]ethyl]pyrazol-1-yl]-3-pyridyl]acetate (2.8 g, 5.96 mmol) in tetrahydrofuran (60 mL) and cool this to 0° C. under an atmosphere of nitrogen with stirring. Add lithium aluminum deuteride (250 mg, 5.96 mmol) to this mixture and stir for 30 min Add Rochelle's salt (as a 2N soln) to the reaction and remove the ice bath and stir for another 30 min Extract this mixture with ethyl acetate and dry the combined organics with magnesium sulfate, filter, and evaporate to dryness. Purify this residue with silica gel (330 g, 40% EtOAc in hexanes) to give 6-[1-[1-[5-(2,2-dideuterio-2-hydroxy-ethyl)-2-pyridyl]pyrazol-3-yl]ethyl]-3-(methoxymethyl)-1,3-benzothiazol-2-one as a yellow solid (1.8 g, 73%) M+1=413.

Preparation 59: Synthesis of ethyl 2-[(6-bromo-3-pyridyl)oxy]acetate

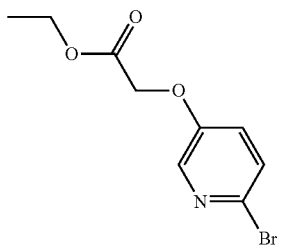

Add ethyl 2-bromoacetate (94.8 mmoles; 15.8 g) dropwise to a solution of 2-bromo-5-hydroxypyridine (86.2 mmoles, 15.0 g), acetonitrile (150 mL), cesium carbonate (259 mmoles, 84.2 g) with stirring at 0° C. The mixture is stirred at 25° C. for 4 h. Quench with ice Water and extract into EtOAc (200 mL×3). Dry the organic layer over Na$_2$SO$_4$, filter, and concentrate. The product is crystallized from diethyl ether and petroleum ether to give the titled intermediate (20.0 g, 89%) as a brown solid. Mass spectrum (m/z): 261.74 (M+1).

Preparation 60: Synthesis of ethyl 2-[[6-[3-[1-[3-(methoxymethyl)-2-oxo-1,3-benzothiazol-6-yl]ethyl]pyrazol-1-yl]-3-pyridyl]oxy]acetate

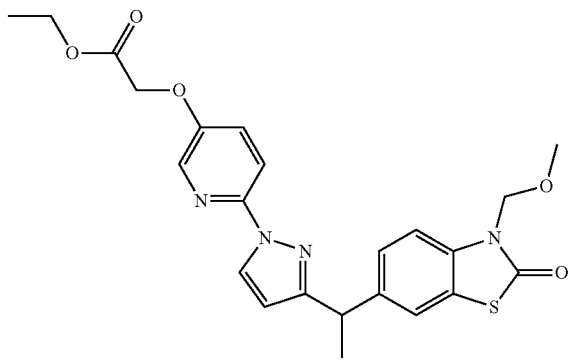 [SMILES: CCOC(=O)COc1ccc(-n2ccc(C(C)c3ccc4c(c3)sc(=O)n4COC)n2)nc1]

Reaction was performed in 10 batches of 1.0 g (3-(methoxymethyl)-6-[1-(1H-pyrazol-3-yl)ethyl]-1,3-benzothiazol-2-one (total: 34.5 mmoles, 10 g) each.

To a 20 mL screw-cap vial add 3-(methoxymethyl)-6-[1-(1H-pyrazol-3-yl)ethyl]-1,3-benzothiazol-2-one (3.45 mmoles, 1 g), ethyl 2-[(6-bromo-3-pyridyl)oxy]acetate (6.9 mmoles, 1.79 g), Dimethyl Sulfoxide (14 mL) and Potassium Carbonate (8.6 mmoles, 1.2 g). The reaction vessel is purged 3 times with nitrogen. Add L-Proline (0.69 mmoles, 80 mg) and Copper(I) Iodide (0.35 mmoles, 66 mg). Heat to 140° C. and stir overnight. The separate batches were combined during work. Add reaction mixture to ice water (1.5 L) and extract with Ethyl Acetate (5×500 mL). Dry the organic layer over Na$_2$SO$_4$, filter, and concentrate.

Purify by flash chromatography on silica with ethyl acetate/hexane (18:82) to afford the titled intermediate (7.1 g, 44%) as light brown solid. Mass spectrum (m/z): 469 (M+1).

Preparation 61: Synthesis of 6-[1-[1-[5-(2-hydroxy-2-methyl-propoxy)-2-pyridyl]pyrazol-3-yl]ethyl]-3-(methoxymethyl)-1,3-benzothiazol-2-one

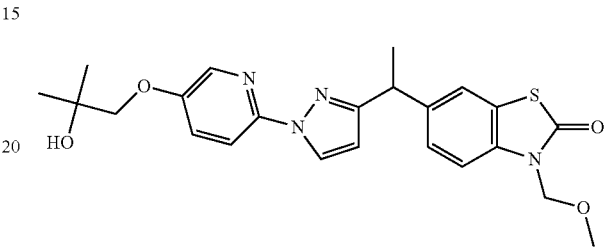

To a 2-neck flask under nitrogen add tetrahydrofuran (40 mL) and ethyl 2-[[6-[3-[1-[3-(methoxymethyl)-2-oxo-1,3-benzothiazol-6-yl]ethyl]pyrazol-1-yl]-3-pyridyl]oxy]acetate (4.4 g, 9.39 mmoles). Cool the mixture to −30° C. and hold for 10 min. with stirring. Add a solution of MeMgBr (37.5 mmoles, 12.5 mL) drop-wise to the reaction mixture under nitrogen. Stir reaction mixture at −30° C. for 1 h. Quench with saturated aq. NH$_4$Cl and extract into ethyl acetate. Dry organic layer over Na$_2$SO$_4$, filter, and concentrate. Purify by LC (silica, 40 g) eluting with 28% ethyl acetate in hexane to give the title intermediate (2.6 g, 60%) as a colorless oil. Mass spectrum (m/z): 455.0 (M+1).

Preparation 62: Synthesis of 6-[1-[1-(5-Amino-2-pyridyl)pyrazol-3-yl]ethyl]-3-(methoxymethyl)-1,3-benzothiazol-2-one

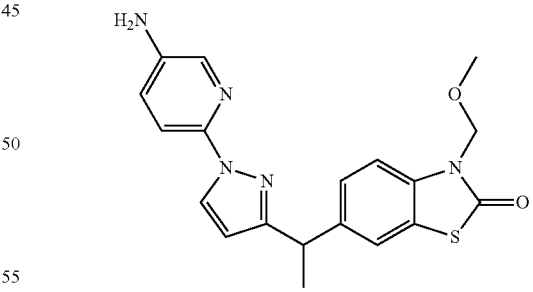

Add 3-(methoxymethyl)-6-[1-[1-(5-nitro-2-pyridyl)pyrazol-3-yl]ethyl]-1,3-benzothiazol-2-one (5.6 mmoles, 2.3 g) as a slurry in EtOAc (20 mL) to a suspension of 5% Palladium on Carbon (0.559 mmoles, 1.2 g) in Ethyl Acetate (70 mL). Place under an atmosphere of hydrogen and stir at ambient temperature overnight. Remove hydrogen by vacuum and purge with nitrogen and filter through diatomaceous earth. Concentrate to give the titled intermediate (1.8 g, 86%) as a white foam. Mass spectrum (m/z):382 (M+1).

Preparation 63: Synthesis of ethyl 2-[[6-[3-[1-[3-(methoxymethyl)-2-oxo-1,3-benzothiazol-6-yl]ethyl]pyrazol-1-yl]-3-pyridyl]amino]acetate

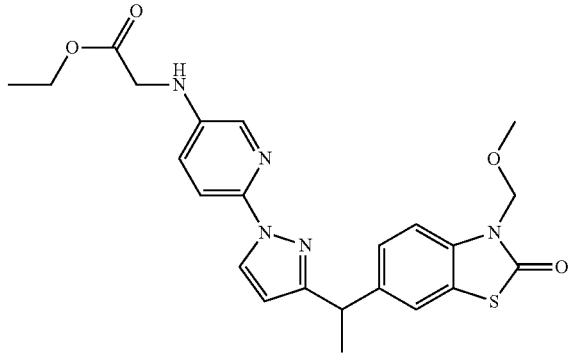 [SMILES: CCOC(=O)CNc1ccc(-n2ccc(C(C)c3ccc4c(c3)sc(=O)n4COC)n2)nc1]

Add sodium hydride (4.70 mmoles, 188 mg) to a solution of 6-[1-[1-(5-amino-2-pyridyl)pyrazol-3-yl]ethyl]-3-(methoxymethyl)-1,3-benzothiazol-2-one (4.2 mmoles, 1.6 g) in dimethylformamide (0.73 mL) and stir at room temperature for 20 min Add ethyl bromoacetate (4.70 mmoles; 521 µL) and heat to 100° C. for 6 h. Pour over ice and extract into EtOAc (200 mL), then wash with water (50 mL) and brine (50 mL). Dry over Na₂SO₄, filter, and concentrate. Purify by LC (silica) eluting with Hexanes/EtOAc (6:4) to give the titled intermediate (900 mg, 45%) as a yellow oil. Mass spectrum (m/z):468 (M+1).

Preparation 64: Synthesis of 6-[1-[1-[5-(2-Hydroxy-ethylamino)-2-pyridyl]pyrazol-3-yl]ethyl]-3-(methoxymethyl)-1,3-benzothiazol-2-one

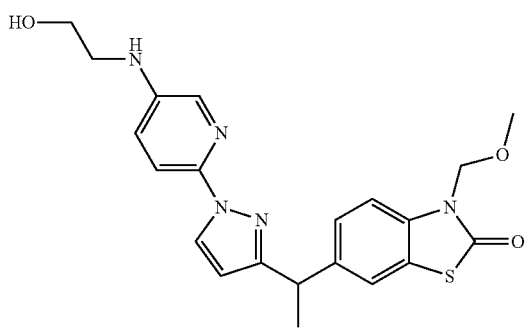 [SMILES: COCn1c(=O)sc2cc(C(C)c3ccn(-c4ccc(NCCO)cn4)n3)ccc21]

Add lithium aluminum hydride (1.0 mmole, 1.0 mL of 1M in THF) drop-wise to a solution of ethyl 2-[[6-[3-[1-[3-(methoxymethyl)-2-oxo-1,3-benzothiazol-6-yl]ethyl]pyrazol-1-yl]-3-pyridyl]amino]acetate (1.7 mmoles, 800 mg) in tetrahydrofuran (8.5 mL) cooled to 0° C. and stir for 15 minutes. Quench with NaK tartrate 10%/H₂O (Rochelles salt, 5 mL) and stir 30 min Extract into EtOAc (150 mL), wash with water (60 mL) and brine (60 mL). Dry over Na₂SO₄, filter, and concentrate. Purify by LC (80 g silica) and elute with 85% DCM/MeOH to10% DCM/MeOH to give the titled intermediate (500 mg, 68%) as yellow oil. Mass spectrum (m/z): 426 (M+1).

Preparation 65: Synthesis of ethyl 2-[[6-[3-[1-[3-(methoxymethyl)-2-oxo-1,3-benzothiazol-6-yl]ethyl]pyrazol-1-yl]-3-pyridyl]-methyl-amino]acetate

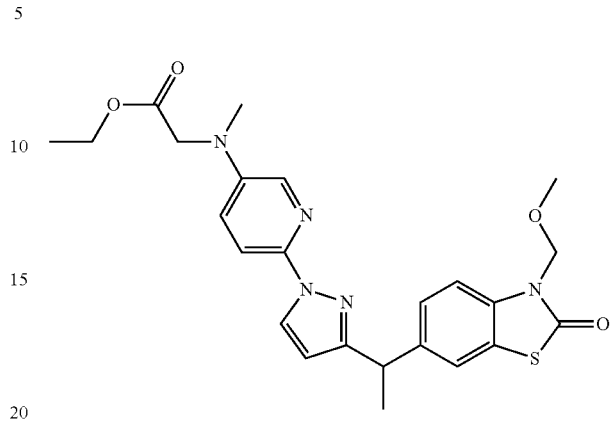

To a screw cap vial add ethyl 2-[[6-[3-[1-[3-(methoxymethyl)-2-oxo-1,3-benzothiazol-6-yl]ethyl]pyrazol-1-yl]-3-pyridyl]amino]acetate (1.58 mmoles, 740 mg) dimethylformamide (15.8 mL) and sodium hydride portion wise (3.1 mmoles, 127 mg). Stir at room temperature for 20 minutes and add methyl iodide (4.75 mmoles, 296 µL). Heat to 50° C. for 6 h, concentrate, and purify by LC (40 g silica) eluting with hexane/EtOAc (6:4) to give the title intermediate (300 mg, 39%) as a pale yellow oil. Mass spectrum (m/z): 482 (M+1).

Preparation 66: Synthesis of 6-[1-[1-[5-[2-hydroxy-ethyl(methyl)amino]-2-pyridyl]pyrazol-3-yl]ethyl]-3-(methoxymethyl)-1,3-benzothiazol-2-one

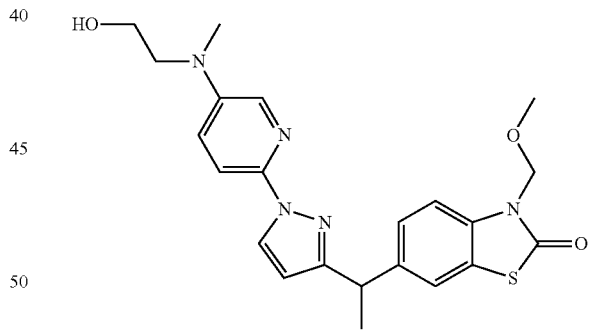

Add lithium aluminum hydride (449 µmoles; 449 µL of 1M in THF) drop-wise to a solution of ethyl 2-[[6-[3-[1-[3-(methoxymethyl)-2-oxo-1,3-benzothiazol-6-yl]ethyl]pyrazol-1-yl]-3-pyridyl]-methyl-amino]acetate (747 µmoles, 360 mg) in tetrahydrofuran (7.5 mL) cooled to −15° C. Remove ice bath and allow to warm to −10° C. and stir for 10 minutes. Quench with NaK tartrate 10%/H₂O (3 mL). Stir 30 minutes then extract into EtOAc (50 mL), and wash with water (20 mL) and Brine (20 mL). Dry organic layer over Na₂SO₄, filter, and concentrate. Purify by LC (12 g silica) eluting with 20% EtOAc/Hexanes to 60% EtOAc/Hexanes to afford the title intermediate (220 mg, 67%) as clear oil. Mass spectrum (m/z):440 (M+1).

Preparation 67: Synthesis of 6-[1-[1-[5-(2-Hydroxy-ethoxymethyl)-2-pyridyl]pyrazol-3-yl]ethyl]-3H-1,3-benzothiazol-2-one

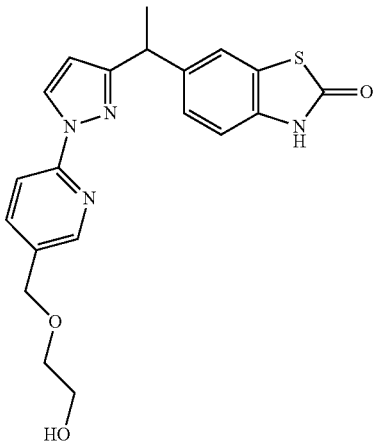 [SMILES: CC(c1ccc2[nH]c(=O)sc2c1)c1ccn(-c2ccc(COCCO)cn2)n1]

Dissolve 6-[1-[1-[5-(2-hydroxyethoxymethyl)-2-pyridyl]pyrazol-3-yl]ethyl]-3-(methoxymethyl)-1,3-benzothiazol-2-one (1.36 g, 3.1 mmol) in trifluoroacetic acid (20 mL) and heat the mixture at 55° C. overnight. Evaporate the mixture and then reconstitute in tetrahydrofuran (20 mL) and add ammonium hydroxide (20 mL). Stir the mixture at room temperature for three hours then evaporate the tetrahydrofuran and dilute the mixture with saturated sodium bicarbonate. Extract the solution three times with ethyl acetate and then dry the organics using sodium sulfate. Filter the mixture then chromatograph using a gradient from 50% ethyl acetate/hexane to 100% ethyl acetate to obtain 6-[1-[1-[5-(2-hydroxyethoxymethyl)-2-pyridyl]pyrazol-3-yl]ethyl]-3H-1,3-benzothiazol-2-one as a white solid (0.96 g, 2.43 mmol, 79%). LCMS (low) rt=1.88 min, M+1=397.

The following compounds are prepared essentially by the method of Preparation 67.

| Preparation | Name | Structure | Mass (M + 1) |
|---|---|---|---|
| 68 | 6-[1-[1-[5-(acetonyloxymethyl)-2-pyridyl]pyrazol-3-yl]ethyl]-3H-1,3-benzothiazol-2-one | 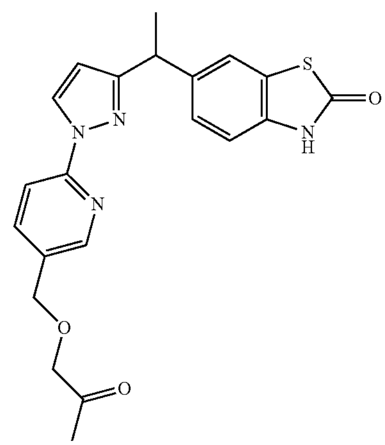 [SMILES: CC(=O)COCc1ccc(-n2ccc(C(C)c3ccc4[nH]c(=O)sc4c3)n2)nc1] | 409 |
| 69 | Methyl 6-[3-[1-(2-oxo-3H-1,3-benzothiazol-6-yl)ethyl]pyrazol-1-yl]pyridine-3-carboxylate | 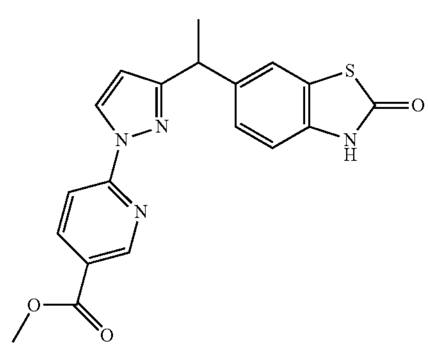 [SMILES: COC(=O)c1ccc(-n2ccc(C(C)c3ccc4[nH]c(=O)sc4c3)n2)nc1] | 381 |

| Preparation | Name | Structure | Mass (M + 1) |
|---|---|---|---|
| 70 | 6-(1-(1-(5-(4-hydroxypiperidin-1-yl)pyridin-2-yl)-1H-pyrazol-3-yl)ethyl)benzo[d]thiazol-2(3H)-one | 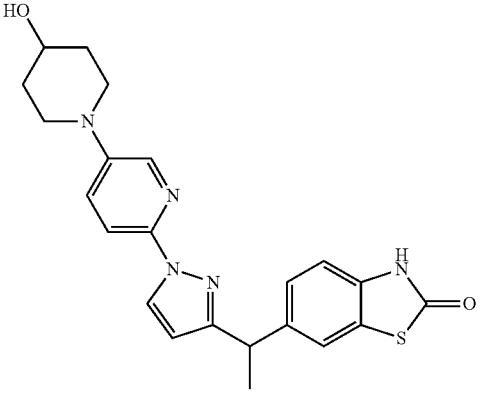 [SMILES: CC(c1ccc2[nH]c(=O)sc2c1)c1ccn(-c2ccc(N3CCC(O)CC3)cn2)n1] | 422 |
| 71 | 6-(1-{1-[6-(2-Hydroxy-ethylsulfanyl)-pyridazin-3-yl]-1H-pyrazol-3-yl}-ethyl)-3H-benzothiazol-2-one | 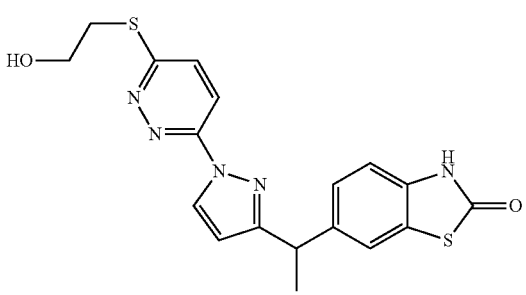 [SMILES: CC(c1ccc2[nH]c(=O)sc2c1)c1ccn(-c2ccc(SCCO)nn2)n1] | 400 |
| 72 | 6-[1-(1-Pyridazin-3-yl-1H-pyrazol-3-yl)-ethyl]-3H-benzothiazol-2-one | 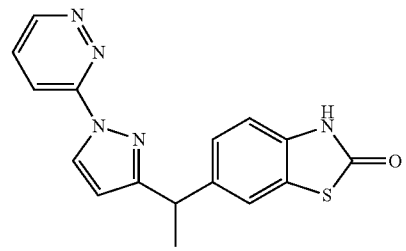 [SMILES: CC(c1ccc2[nH]c(=O)sc2c1)c1ccn(-c2cccnn2)n1] | 324 |
| 73 | 6-{1-[1-(5-Methanesulfinyl-pyridin-2-yl)-1H-pyrazol-3-yl]-ethyl}-3H-benzothiazol-2-one | 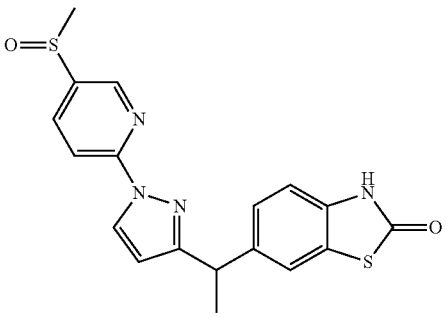 [SMILES: CC(c1ccc2[nH]c(=O)sc2c1)c1ccn(-c2ccc(S(C)=O)cn2)n1] | 385 |

-continued
| Preparation | Name | Structure | Mass (M + 1) |
|---|---|---|---|
| 74 | 6-[1-[1-(5-tetrahydropyran-4-yl-2-pyridyl)pyrazol-3-yl]ethyl]-3H-1,3-benzothiazol-2-one | 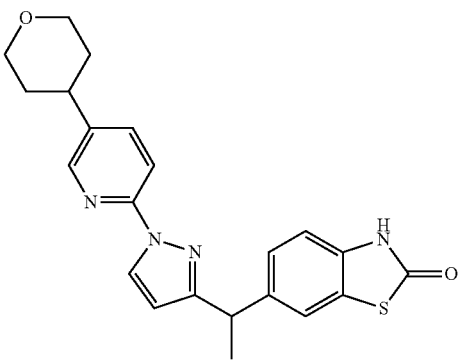 [SMILES: CC(c1ccc2[nH]c(=O)sc2c1)c1ccn(-c2ccc(C3CCOCC3)cn2)n1] | 407 |
| 75 | 6-[1-[1-(5-fluoro-2-pyridyl)pyrazol-3-yl]ethyl]-3H-1,3-benzothiazol-2-one | 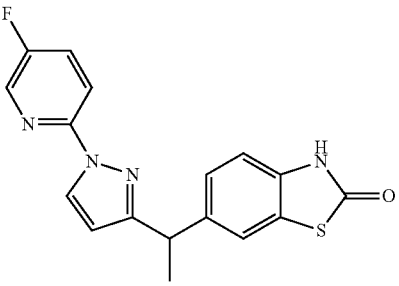 [SMILES: CC(c1ccc2[nH]c(=O)sc2c1)c1ccn(-c2ccc(F)cn2)n1] | 412 |
| 76 | 6-[1-[1-(5-morpholino-2-pyridyl)pyrazol-3-yl]ethyl]-3H-1,3-benzothiazol-2-one | 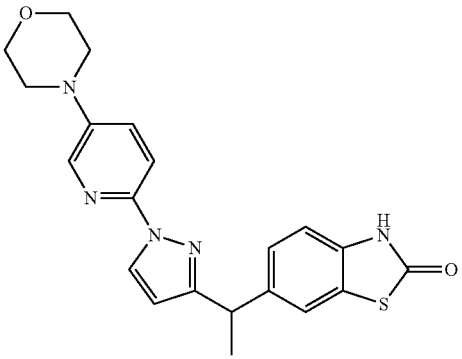 [SMILES: CC(c1ccc2[nH]c(=O)sc2c1)c1ccn(-c2ccc(N3CCOCC3)cn2)n1] | 408 |
| 77 | 6-[1-[1-(5-deuterio-2-pyridyl)pyrazol-3-yl]ethyl]-3H-1,3-benzothiazol-2-one | 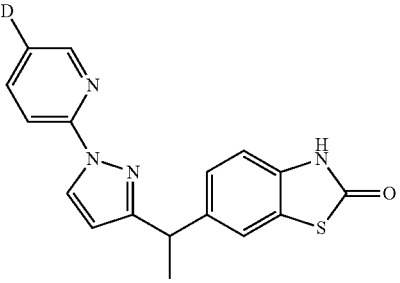 | 324 |

-continued

| Preparation | Name | Structure | Mass (M + 1) |
|---|---|---|---|
| 78 | 6-[1-[1-(5-hydroxyethyl-2-pyridyl)pyrazol-3-yl]ethyl]-3H-1,3-benzothiazol-2-one | 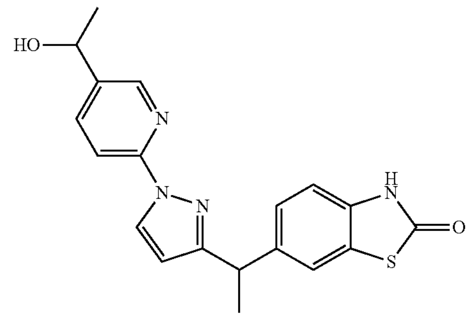 [SMILES: CC(O)c1ccc(-n2ccc(C(C)c3ccc4[nH]c(=O)sc4c3)n2)nc1] | 367 |
| 79 | 6-[1-[1-(6-methylpyridazin-3-yl)pyrazol-3-yl]ethyl]-3H-1,3-benzothiazol-2-one | 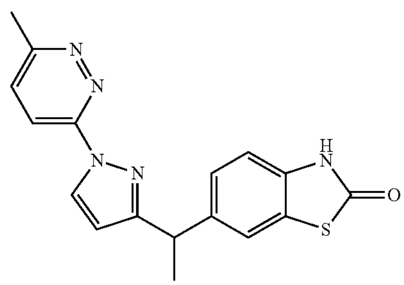 [SMILES: Cc1ccc(-n2ccc(C(C)c3ccc4[nH]c(=O)sc4c3)n2)nn1] | 338 |
| 80 | 6-[1-[1-[6-(hydroxymethyl)pyridazin-3-yl]pyrazol-3-yl]ethyl]-3H-1,3-benzothiazol-2-one | 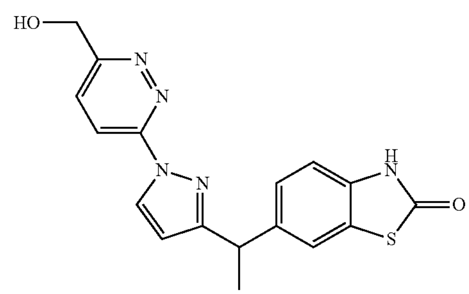 [SMILES: CC(c1ccc2[nH]c(=O)sc2c1)c1ccn(-c2ccc(CO)nn2)n1] | 354 |
| 81 | 6-[1-[1-[5-(2,2-dideuterio-2-hydroxy-ethyl)-2-pyridyl]pyrazol-3-yl]ethyl]-3H-1,3-benzothiazol-2-one | 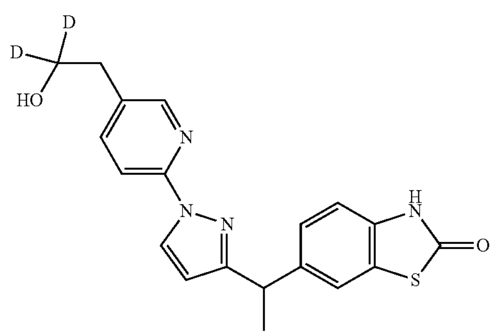 [SMILES: [2H]C([2H])(O)Cc1ccc(-n2ccc(C(C)c3ccc4[nH]c(=O)sc4c3)n2)nc1] | 369 |

-continued

| Preparation | Name | Structure | Mass (M + 1) |
|---|---|---|---|
| 82 | 6-[1-[1-[5-(2-hydroxy-2-methyl-propoxy)-2-pyridyl]pyrazol-3-yl]ethyl]-3H-1,3-benzothiazol-2-one | 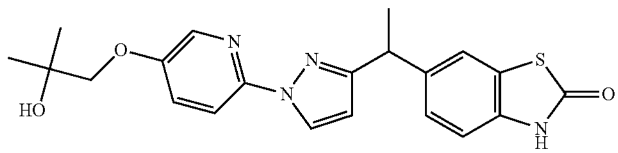 [SMILES: CC(c1ccc2[nH]c(=O)sc2c1)c1ccn(-c2ccc(OCC(C)(C)O)cn2)n1] | 411 |
| 83 | 6-[1-[1-[5-(2-Hydroxyethylamino)-2-pyridyl]pyrazol-3-yl]ethyl]-3H-1,3-benzothiazol-2-one | 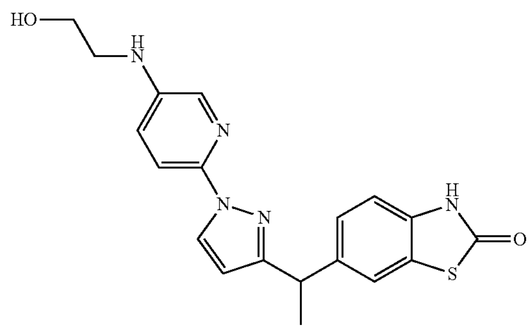 [SMILES: CC(c1ccc2[nH]c(=O)sc2c1)c1ccn(-c2ccc(NCCO)cn2)n1] | 382 |
| 84 | 6-[1-[1-[5-[2-Hydroxyethyl(methyl)amino]-2-pyridyl]pyrazol-3-yl]ethyl]-3H-1,3-benzothiazol-2-one | 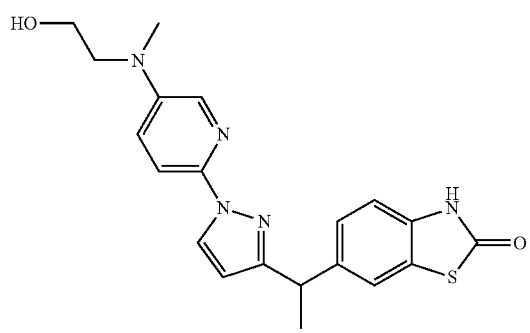 [SMILES: CC(c1ccc2[nH]c(=O)sc2c1)c1ccn(-c2ccc(N(C)CCO)cn2)n1] | 396 |
| 85 | 6-[1-[1-[5-(Triazol-1-ylmethyl)-2-pyridyl]pyrazol-3-yl]ethyl]-3H-1,3-benzothiazol-2-one hydrochloride | 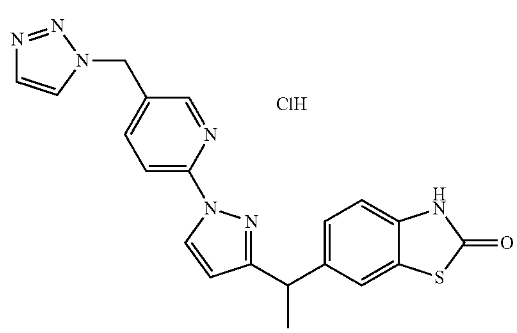 [SMILES: CC(c1ccc2[nH]c(=O)sc2c1)c1ccn(-c2ccc(Cn3ccnn3)cn2)n1 ; Cl] | 404 |

Preparation 86: Synthesis of 6-[1-[1-[5-(2-hydroxy-propoxymethyl)-2-pyridyl]pyrazol-3-yl]ethyl]-3H-1,3-benzothiazol-2-one

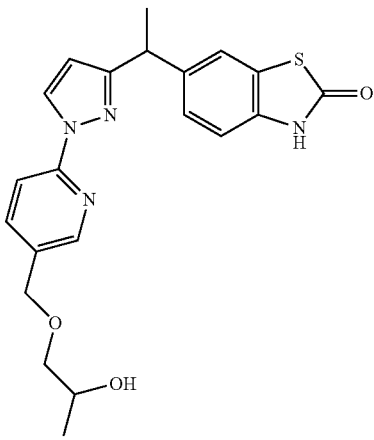 [SMILES: CC(O)COCc1ccc(-n2ccc(C(C)c3ccc4[nH]c(=O)sc4c3)n2)nc1]

Dissolve 6-[1-[1-[5-(acetonyloxymethyl)-2-pyridyl]pyrazol-3-yl]ethyl]-3H-1,3-benzothiazol-2-one (0.60 g, 1.47 mmol) in tetrahydrofuran (20 mL) and add lithium borohydride (96 mg, 4.41 mmol) at room temperature. Stir the mixture at room temperature for ten minutes. Cool the mixture to 0° C. and carefully add aqueous saturated ammonium chloride solution then extract twice with ethyl acetate. Dry the organics with sodium sulfate then filter and evaporate to give 6-[1-[1-[5-(2-hydroxypropoxymethyl)-2-pyridyl]pyrazol-3-yl]ethyl]-3H-1,3-benzothiazol-2-one as a clear oil (0.53 g, 1.3 mmol, 87%). LCMS (low) rt=1.04 min, M+1=411.

Preparation 87: Synthesis of ethyl 2-[[6-[3-[1-(2-oxo-3H-1,3-benzothiazol-6-yl)ethyl]pyrazol-1-yl]-3-pyridyl]methoxy]acetate

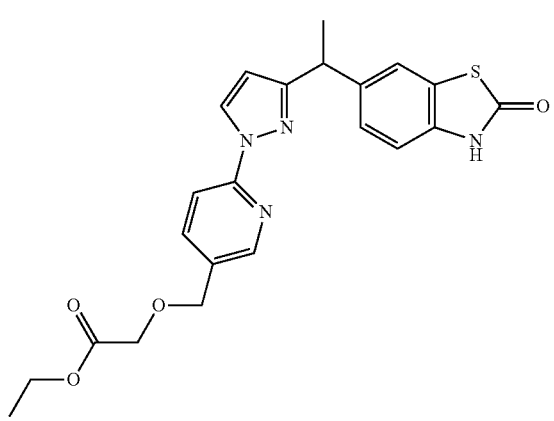 [SMILES: CCOC(=O)COCc1ccc(-n2ccc(C(C)c3ccc4[nH]c(=O)sc4c3)n2)nc1]

Dissolve ethyl 2-[[6-[3-[1-[3-(methoxymethyl)-2-oxo-1,3-benzothiazol-6-yl]ethyl]pyrazol-1-yl]-3-pyridyl]methoxy]acetate (2 g, 4.1 mmol) in trifluoroacetic acid (50 mL) and heat to 50° C. overnight. Cool the mixture to room temperature then evaporate the mixture and then reconstitute in tetrahydrofuran (50 mL) and add ammonium hydroxide (50 mL). Stir the mixture at room temperature for two hours then evaporate the tetrahydrofuran and dilute the mixture with saturate sodium bicarbonate. Extract the solution three times with ethyl acetate and then dry the organics using sodium sulfate. Filter the mixture then chromatograph using a gradient from hexane to 70% ethyl acetate/hexane to obtain ethyl 2-[[6-[3-[1-(2-oxo-3H-1,3-benzothiazol-6-yl)ethyl]pyrazol-1-yl]-3-pyridyl]methoxy]acetate as a white solid (1.1 g, 2.5 mmol, 60%). LCMS (low) rt=2.27 min, M+1=439.

Preparation 88: Synthesis of 6-[1-[1-[5-[(2-hydroxy-2-methyl-propoxy)methyl]-2-pyridyl]pyrazol-3-yl]ethyl]-3H-1,3-benzothiazol-2-one

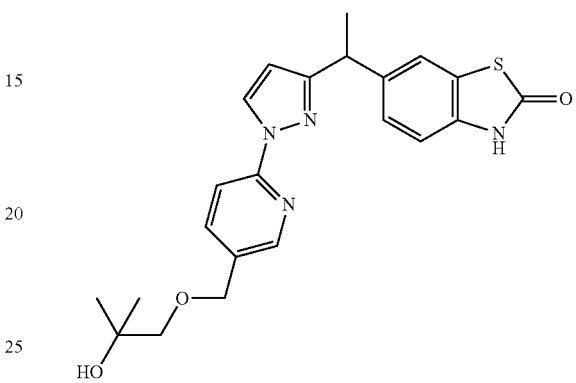

Dissolve ethyl 2-[[6-[3-[1-(2-oxo-3H-1,3-benzothiazol-6-yl)ethyl]pyrazol-1-yl]-3-pyridyl]methoxy]acetate (0.52 g, 1.15 mmol) in tetrahydrofuran (10 mL), cool to 0° C. and slowly add the methylmagnesiumbromide (1.92 mL, 5.8 mmol, 3M solution in diethyl ether). Stir at 0° C. for 20 minutes then warm to room temperature for one hour. Dilute the mixture with saturated ammonium chloride and extract three times with ethyl acetate. Dry the organics using sodium sulfate then filter and evaporate. Chromatograph the residue using a gradient from hexane to 80% ethyl acetate/hexane to give 6-[1-[1-[5-[(2-Hydroxy-2-methyl-propoxy)methyl]-2-pyridyl]pyrazol-3-yl]ethyl]-3H-1,3-benzothiazol-2-one as a white solid (382 mg, 0.81 mmol, 70%). LCMS (low) rt=2.13 min, M+1=425.

Preparation 89: Synthesis of 6-(1-(1-(5-iodopyridin-2-yl)-1H-pyrazol-3-yl)ethyl)benzo[d]thiazol-2(3H)-one

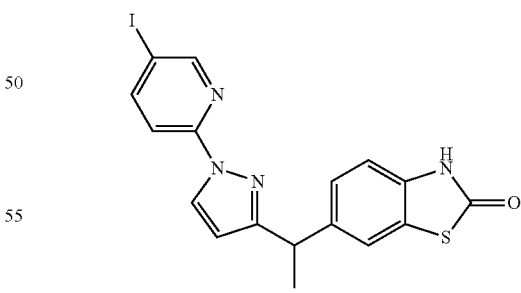

To 6-(1-(1-(5-iodopyridin-2-yl)-1H-pyrazol-3-yl)ethyl)-3-(methoxymethyl)benzo[d]thiazol-2(3H)-one (700 mg, 1.4 mmoles) is added Trifluoroacetic Acid (14 mL; 185.2 mmoles). The reaction is heated at 70° C. overnight. The reaction mixture is concentrated and Tetrahydrofuran (14 mL) and 28% Ammonium Hydroxide (14 mL) are added. The reaction mixture is stirred at room temperature for 3 h. The reaction mixture is concentrated to remove the organic.

The remaining aqueous is diluted with a small amount of water (10 mL) and extracted with EtOAc (3×). The organic layers are combined, washed with brine, dried over Na₂SO₄, and concentrated to give the title compound as a yellow solid (594 mg, 1.3 mmoles, 93.20% yield). M+1=449.

Preparation 90: Synthesis of 6-(1-(1-(5-iodopyridin-2-yl)-1H-pyrazol-3-yl)ethyl)-3-((2-(trimethylsilyl)ethoxy)methyl)benzo[d]thiazol-2(3H)-one

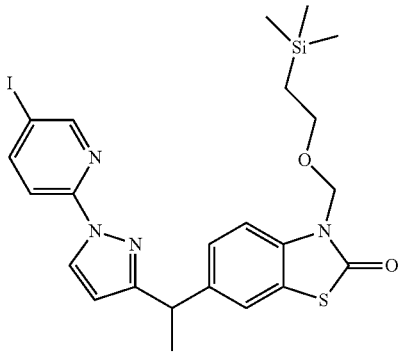 [SMILES: CC(c1ccc2c(c1)sc(=O)n2COCC[Si](C)(C)C)c1ccn(-c2ccc(I)cn2)n1]

To 6-(1-(1-(5-iodopyridin-2-yl)-1H-pyrazol-3-yl)ethyl)benzo[d]thiazol-2(3H)-one (397 mg, 885.59 μmoles) in anhydrous Dimethylformamide (7 mL) at 0° C. under Ar gas is added in portions Sodium Hydride (60% dispersion, 42.50 mg, 1.06 mmoles). The reaction mixture is stirred at 0° C. for 20 min and (2-(chloromethoxy)ethyl)trimethylsilane (177.18 mg, 1.06 mmoles) is slowly added. The ice bath is removed and the reaction stirred at room temperature for 2 h. The reaction mixture is quenched into sat. aq. NH₄Cl and extracted with EtOAc (3×). The organic layers are combined, washed with brine, dried over Na₂SO₄, and concentrated. The residue is purified using 5% EtOAc/hexane to give the title compound as a clear oil (275 mg, 475.33 μmoles, 53.67% yield). M+1=579.

Preparation 91: Synthesis of 6-(1-(1-(5-((1-hydroxypropan-2-yl)thio)pyridin-2-yl)-1H-pyrazol-3-yl)ethyl)-3-((2-(trimethylsilyl)ethoxy)methyl)benzo[d]thiazol-2(3H)-one

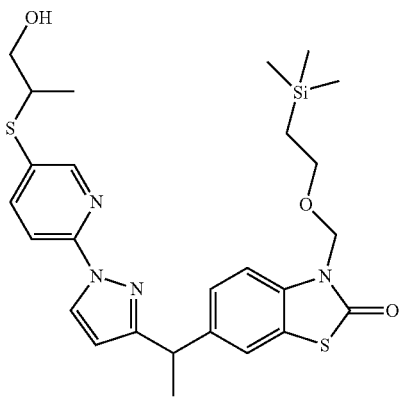 [SMILES: CC(CO)Sc1ccc(-n2ccc(C(C)c3ccc4c(c3)sc(=O)n4COCC[Si](C)(C)C)n2)nc1]

To ethyl 2-((6-(3-(1-(2-oxo-3-((2-(trimethylsilyl)ethoxy)methyl)-2,3-dihydrobenzo[d]thiazol-6-yl)ethyl)-1H-pyrazol-1-yl)pyridin-3-yl)thio)propanoate (926 mg, 1.58 mmoles) in anhydrous Tetrahydrofuran (7.92 mL) at 0° C. is added in portions via syringe over a 7 min period Diisobutylaluminum Hydride (1M in toluene, 6.33 mL, 6.33 mmoles). The reaction mixture is stirred at 0° C. for 1 h. The reaction is quenched with sat. aq. NH₄Cl and transferred to a separatory funnel, diluted with a small amount of water and extracted with EtOAc (3×). The organic layers are combined. An emulsion forms in the organic layer. The organic layer is filtered through diatomaceous earth and the diatomaceous earth washed with EtOAc. The filtrate is dried over Na₂SO₄ and concentrated. The residue is purified using 30% EtOAc/hexane. Obtained is the title compound as a clear oil (232 mg, 427.41 μmoles, 26.99% yield). M+1=543.

Preparation 92: Synthesis of 6-(1-(1-(5-(4-oxopiperidin-1-yl)pyridin-2-yl)-1H-pyrazol-3-yl)ethyl)-3-((2-(trimethylsilyl)ethoxy)methyl)benzo[d]thiazol-2(3H)-one

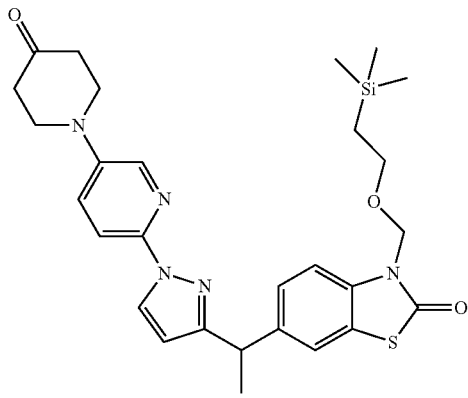 [SMILES: CC(c1ccc2c(c1)sc(=O)n2COCC[Si](C)(C)C)c1ccn(-c2ccc(N3CCC(=O)CC3)cn2)n1]

To 6-(1-(1-(5-(4-hydroxypiperidin-1-yl)pyridin-2-yl)-1H-pyrazol-3-yl)ethyl)-3-((2-(trimethylsilyl)ethoxy)methyl)benzo[d]thiazol-2(3H)-one (3 g, 5.44 mmoles) in anhydrous Dichloromethane (77 mL) at 0° C. is added Sodium Bicarbonate (2.06 g, 24.47 mmoles), followed by the addition of dess-martin (2.77 g, 6.52 mmoles) in 4 portions over a 7 min period. The ice bath is removed and the reaction mixture is allowed to warm up to room temperature. After stirring at room temperature for 1 h, the reaction mixture is quenched with sat. aq. Na₂S₂O₃ (70 mL) and stirred for 10 min. The mixture is diluted with water (50 mL) and CH₂Cl₂ (50 mL) and is transferred to a separatory funnel. The organic layer is separated and the aqueous extracted with CH₂Cl₂ (2×). Emulsions form. The organic layers are combined and filtered through diatomaceous earth to get rid of emulsions. The filtrate is washed with brine, dried over Na₂SO₄ and concentrated. The residue is purified using 65% EtOAc/hexane to give the title compound (2.11 g, 3.84 mmoles, 70.59% yield). M+1=550.

EXAMPLE 1

Isolation of 6-[1-[1-[5-(2-hydroxyethoxymethyl)-2-pyridyl]pyrazol-3-yl]ethyl]-3H-1,3-benzothiazol-2-one, Isomer 2

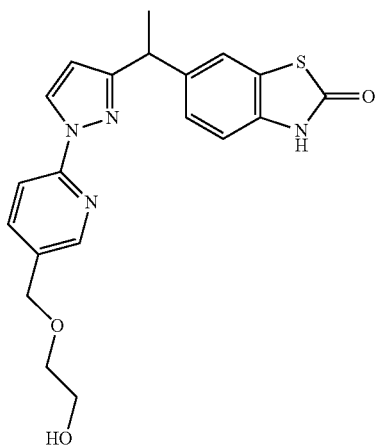 [SMILES: CC(c1ccc2[nH]c(=O)sc2c1)c1ccn(-c2ccc(COCCO)cn2)n1]

6-[1-[1-[5-(2-hydroxyethoxymethyl)-2-pyridyl]pyrazol-3-yl]ethyl]-3H-1,3-benzothiazol-2-one was resolved into its enantiomer by chiral chromatography using Chiralpak® IA, 60/40 EtOH/ACN (0.2% IPA), 1 mL/min., 225 nm. Isomer 1 retention time is 3.22 min and Isomer 2 is 5.54 min.

EXAMPLE 2

Isolation of 6-[1-[1-[5-(acetonyloxymethyl)-2-pyridyl]pyrazol-3-yl]ethyl]-3H-1,3-benzothiazol-2-one, Isomer 2

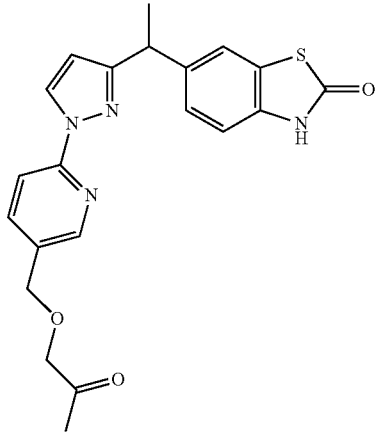 [SMILES: CC(=O)COCc1ccc(-n2ccc(C(C)c3ccc4[nH]c(=O)sc4c3)n2)nc1]

Racemic 6-[1-[1-[5-(acetonyloxymethyl)-2-pyridyl]pyrazol-3-yl]ethyl]-3H-1,3-benzothiazol-2-one is resolved into its enantiomers by chiral chromatography using Chiralpak® IA, 60/40 EtOH/ACN (0.2% IPA), 1 mL/min, 225 nm. Isomer 1 retention time is 3.22 min and isomer 2 is 4.71 min.

EXAMPLE 3

Isolation of 6-(1-(1-(5-(4-hydroxypiperidin-1-yl)pyridin-2-yl)-1H-pyrazol-3-yl)ethyl)benzo[d]thiazol-2(3H)-one, Isomer 1

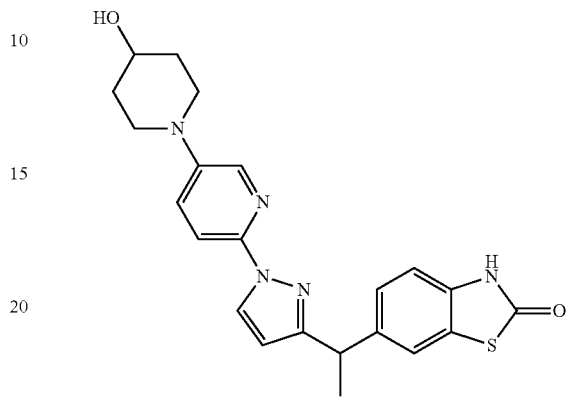

The compound 6-(1-(1-(5-(4-hydroxypiperidin-1-yl)pyridin-2-yl)-1H-pyrazol-3-yl)ethyl)benzo[d]thiazol-2(3H)-one (960 mg, 2.3 mmoles) is resolved into its enantiomers using 45% MeOH (w/0.2% isopropyl amine):55% $CO_2$ on Lux Su Amylose-2, 5 mL/min, 290 nm. Isomer 1 retention time is 2.6 min and isomer 2 is 3.7 min.

EXAMPLE 4

Isolation of 6-{1-[1-(5-Methanesulfinyl-pyridin-2-yl)-1H-pyrazol-3-yl]-ethyl}-3H-benzothiazol-2-one, Isomer 4

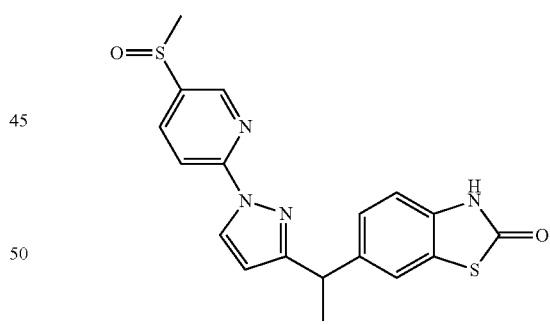

6-{1-[1-(5-Methanesulfinyl-pyridin-2-yl)-1H-pyrazol-3-yl]-ethyl}-3H-benzothiazol-2-one isomer 4 is isolated from the mixture of isomers by 2 sequential chiral chromatography operations. Purification on Chiralpak® AD-H (3×25 cm, 5 um, 60/40 ethanol/acetonitrile, 30 mL/min) gives 2 fractions. The first eluting fraction contains 3 isomers, including isomer 4. This mixture of 3 isomers is then separated on Chiralpak® AS-H (3×25 cm, 5 um, 60/40 ethanol/acetonitrile, 25 mL/min) Isomer 4, the last eluting isomer, has a retention time of 6.06 minutes on a Chiralpak® AS-H column (4.6×150 mm) eluting with 60/40 ethanol/acetonitrile containing 0.2% isopropyl amine, 1.0 mL/min LCMS (low) rt=1.804 min, M+1=385.0.

EXAMPLE 5

Isolation of 6-[1-[1-[5-[2-(hydroxymethyl)morpholin-4-yl]-2-pyridyl]pyrazol-3-yl]ethyl]-3H-1,3-benzothiazol-2-one, Isomer 2

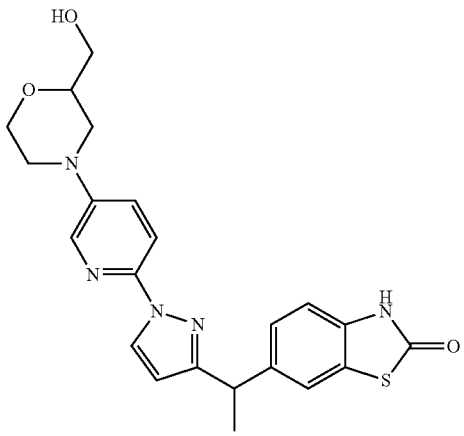 [SMILES: CC(c1ccc2[nH]c(=O)sc2c1)c1ccn(-c2ccc(N3CCOC(CO)C3)cn2)n1]

Compound 6-[1-[1-[5-[2-(hydroxymethyl)morpholin-4-yl]-2-pyridyl]pyrazol-3-yl]ethyl]-3H-1,3-benzothiazol-2-one was resolved into its stereoisomers by chiral chromatography using Chiralcel® OD-H, 40% methanol/$CO_2$, 5 ml/min, 225 nm, r.t. (isomer 2)=4.22 min.

EXAMPLE 6 & 7

Isolation of 6-[1-[1-[5-(1-hydroxyethyl)-2-pyridyl]pyrazol-3-yl]ethyl]-3H-1,3-benzothiazol-2-one, Isomer 1 and Isomer 2

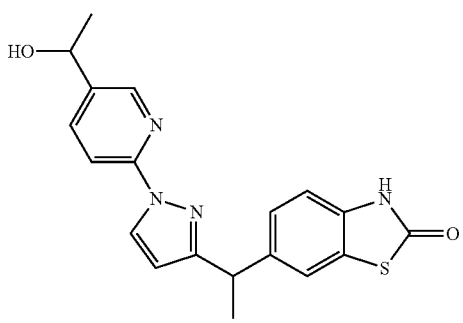

The two active diastereomers of 6-[1-[1-[5-(1-hydroxyethyl)-2-pyridyl]pyrazol-3-yl]ethyl]-3H-1,3-benzothiazol-2-one are separated by chiral chromatography using Chiralpak® AD-H, 4.6×150 mm, 40% ACN/60% MeOH, 0.6 mL/min, 250 nm. Isomer 1 retention time is 7.6 min and isomer 2 is 10.6 min.

EXAMPLE 8

Isolation of 6-[1-[1-(6-methylpyridazin-3-yl)pyrazol-3-yl]ethyl]-3H-1,3-benzothiazol-2-one, Isomer 2

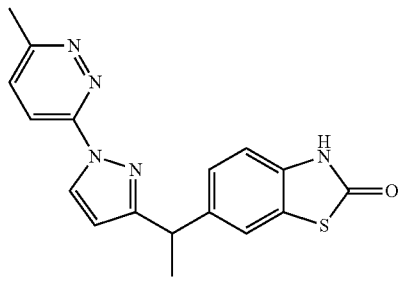 [SMILES: Cc1ccc(-n2ccc(C(C)c3ccc4[nH]c(=O)sc4c3)n2)nn1]

Racemic 6-[1-[1-(6-methylpyridazin-3-yl)pyrazol-3-yl]ethyl]-3H-1,3-benzothiazol-2-one is resolved into its enantiomers by chiral chromatography using Chiralpak® AD-H, 4.6×150 mm, 40% CAN/60% EtOH with 0.2% IPAm, 0.6 mL/min, 250 nm. Isomer 1 retention time is 6.0 min and isomer 2 is 11.0 min.

EXAMPLE 9

Isolation of 6-[1-[1-[6-(hydroxymethyl)pyridazin-3-yl]pyrazol-3-yl]ethyl]-3H-1,3-benzothiazol-2-one, Isomer 2

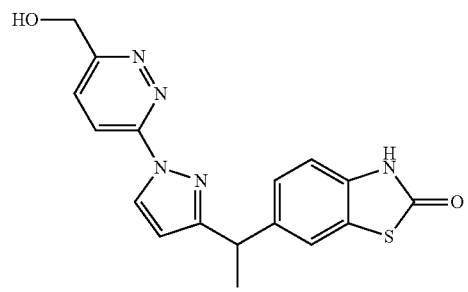 [SMILES: CC(c1ccc2[nH]c(=O)sc2c1)c1ccn(-c2ccc(CO)nn2)n1]

Racemic 6-[1-[1-[6-(hydroxymethyl)pyridazin-3-yl]pyrazol-3-yl]ethyl]-3H-1,3-benzothiazol-2-one is resolved into its enantiomers by chiral chromatography using Chiralpak® AD-H, 4.6×150 mm, 3/2 EtOH/ACN 0.2% IPAm, 1 mL/min, 225 nm. Isomer 1 retention time is 3.26 min and isomer 2 is 4.29 min.

EXAMPLE 10

Isolation of 6-[1-[1-(5-fluoro-2-pyridyl)pyrazol-3-yl]ethyl]-3H-1,3-benzothiazol-2-one, Isomer 1

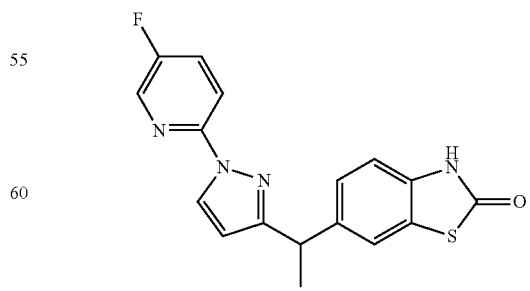

Compound 6-[1-[1-(5-fluoro-2-pyridyl)pyrazol-3-yl]ethyl]-3H-1,3-benzothiazol-2-one is resolved into its enantiomers by chiral chromatography using Chiralcel®

OJ-H, 30% MeOH/CO$_2$, 5 mL/min, 225 nm. Isomer 1 retention time is 2.21 min and isomer 2 is 2.75 min.

EXAMPLE 11

Isolation of 6-[1-[1-[5-(2,2-dideuterio-2-hydroxy-ethyl)-2-pyridyl]pyrazol-3-yl]ethyl]-3H-1,3-benzothiazol-2-one, Isomer 2

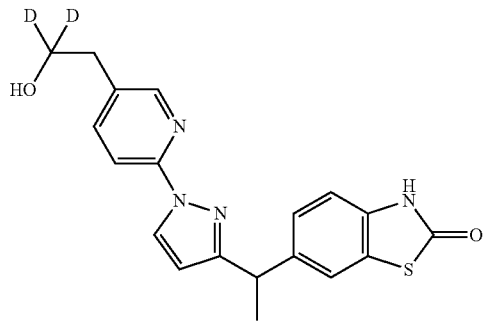 [SMILES: [2H]C([2H])(O)Cc1ccc(-n2ccc(C(C)c3ccc4[nH]c(=O)sc4c3)n2)nc1]

Racemic 6-[1-[1-[5-(2,2-dideuterio-2-hydroxy-ethyl)-2-pyridyl]pyrazol-3-yl]ethyl]-3-(methoxymethyl)-1,3-benzothiazol-2-one is resolved into its enantiomers by chiral chromatography using Chiralpak® AD-H, 4.6×150 mm, 50% ACN/50% MeOH, 0.6 mL/min, 280 nm. Isomer 1 retention time is 8.1 min and isomer 2 is 14.7 min.

EXAMPLE 12

6-[1-[1-(5-morpholino-2-pyridyl)pyrazol-3-yl]ethyl]-3H-1,3-benzothiazol-2-one, Isomer 1

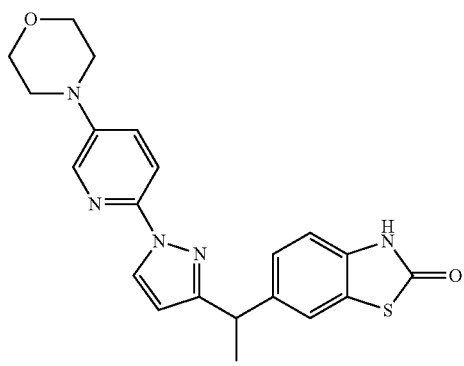

A mixture of 3-(methoxymethyl)-6-[1-[1-(5-morpholino-2-pyridyl)pyrazol-3-yl]ethyl]-1,3-benzothiazol-2-one (300 mg, 0.7 mmoles) and Trifluoroacetic Acid (5 mL) is heated at 90° C. for 3 h. The mixture is conc. to dryness. Tetrahydrofuran (5 mL) and 28% Ammonium Hydroxide (3 mL) are added, and stirred for 30 min. The mixture is partitioned between EtOAc and water. The aqueous phase is extracted with EtOAc (2×). The combined organic phase is washed with brine, dried (Na2SO4) and concentrated. The material is purified by flash chromatography (silica gel, 24 g, eluted 20% EtOAc/hexane to 100% EtOAc) to yield 6-[1-[1-(5-morpholino-2-pyridyl)pyrazol-3-yl]ethyl]-3H-1,3-benzothiazol-2-one (136 mg, 50%) LCMS (+) 408.0

6-[1-[1-(5-morpholino-2-pyridyl)pyrazol-3-yl]ethyl]-3H-1,3-benzothiazol-2-one is resolved into its enantiomers by chiral chromatography using Chiralcel® OJ-H 4.6×150 mm, 95/5 MeOH/CAN 0.2% IPAm, 1 mL/min, 225 nm. Isomer 1 retention time is 4.9 min and isomer 2 is 7.1 min.

EXAMPLE 13

Isolation of 6-[1-[1-[5-(2-hydroxy-2-methyl-propoxy)-2-pyridyl]pyrazol-3-yl]ethyl]-3H-1,3-benzothiazol-2-one, Isomer 1

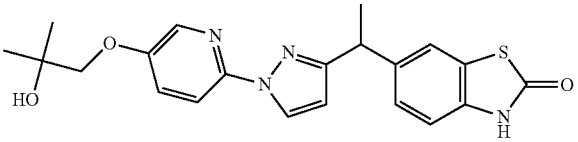 [SMILES: CC(c1ccc2[nH]c(=O)sc2c1)c1ccn(-c2ccc(OCC(C)(C)O)cn2)n1]

The two enantiomers of 6-[1-[1-[5-(2-hydroxy-2-methyl-propoxy)-2-pyridyl]pyrazol-3-yl]ethyl]-3H-1,3-benzothiazol-2-one are separated by chiral chromatography using Chiralpak® AD, 8×40.5 cm, 40% EtOH/10% IPA/50% ACN, 450 mL/min, 260 nm. Isomer 1 retention time is 8.3 min., (492 mg, 49%) and Isomer 2 is 18.2 min, (468 mg, 47%).

EXAMPLE 14

Isolation of 6-[1-[1-[5-(2-Hydroxyethylamino)-2-pyridyl]pyrazol-3-yl]ethyl]-3H-1,3-benzothiazol-2-one, Isomer 2

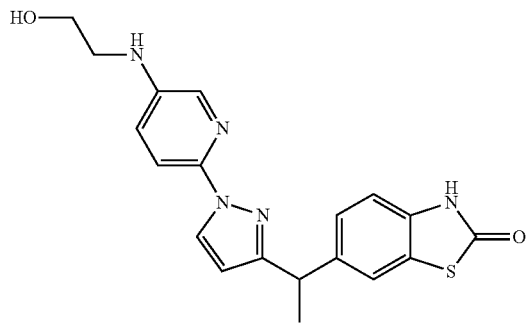 [SMILES: CC(c1ccc2[nH]c(=O)sc2c1)c1ccn(-c2ccc(NCCO)cn2)n1]

The two enantiomers of 6-[1-[1-[5-(2-hydroxyethyl-amino)-2-pyridyl]pyrazol-3-yl]ethyl]-3H-1,3-benzothiazol-2-one are separated by chiral chromatography using Chiralpak® AS-H, 2.1×15 cm, 40% MeOH (0.2% IPAm)/CO2, 70 mL/min, 225 nm. Isomer 1 retention time is 3.2 min, (110 mg, 25%), Mass spectrum (m/z): 382 (M+1). Isomer 2 is 4.5 min, (137 mg, 31%), Mass spectrum (m/z): 382 (M+1).

EXAMPLE 15

Isolation of 6-[1-[1-[5-[2-Hydroxyethyl(methyl)amino]-2-pyridyl]pyrazol-3-yl]ethyl]-3H-1,3-benzothiazol-2-one, Isomer 2

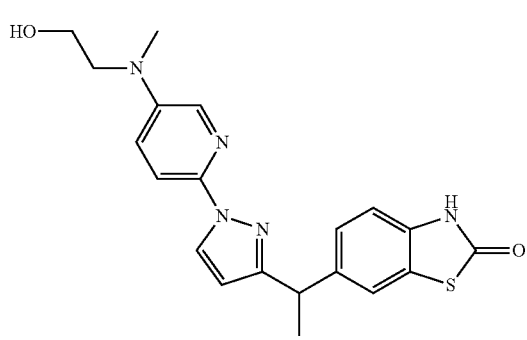 [SMILES: CC(c1ccc2[nH]c(=O)sc2c1)c1ccn(-c2ccc(N(C)CCO)cn2)n1]

The two enantiomers of 6-[1-[1-[5-[2-hydroxyethyl(methyl)amino]-2-pyridyl]pyrazol-3-yl]ethyl]-3H-1,3-benzothiazol-2-one are separated by chiral chromatography using Chiralpak® AD-H, 3×25 cm, 80% EtOH/20% ACN, 22 mL/min, 225 nm. Isomer 1 retention time is 11.3 min, (53 mg, 28%) as a pale yellow solid and Isomer 2 is 15.6 min, (52 mg, 27%) as a pale yellow solid.

EXAMPLE 16

Isolation of 6-(1-{1-[6-(2-Hydroxy-ethylsulfanyl)-pyridazin-3-yl]-1H-pyrazol-3-yl}-ethyl)-3H-benzothiazol-2-one, Isomer 2

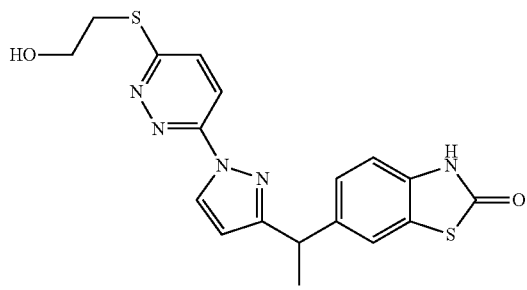 [SMILES: CC(c1ccc2[nH]c(=O)sc2c1)c1ccn(-c2ccc(SCCO)nn2)n1]

Compound 6-(1-{1-[6-(2-hydroxy-ethylsulfanyl)-pyridazin-3-yl]-1H-pyrazol-3-yl}-ethyl)-3H-benzothiazol-2-one is resolved into its enantiomers by chiral chromatography (Chiralpak® AD (20 uM), 8×40.5 cm, 9:1 ethanol:acetonitrile, 450 mL/min) Isomer 2 is obtained as a white solid. Retention time is 8.31 min on a Chiralpak® AD-H 4.6×150 mm column eluting with 9:1 ethanol:acetonitrile, 0.6 mL/min LCMS (low) rt=0.980 min, M+1 400.0.

EXAMPLE 17

Isolation of 6-[1-[1-[5-[(2-hydroxy-2-methyl-propoxy)methyl]-2-pyridyl]pyrazol-3-yl]ethyl]-3H-1,3-benzothiazol-2-one, Isomer 1

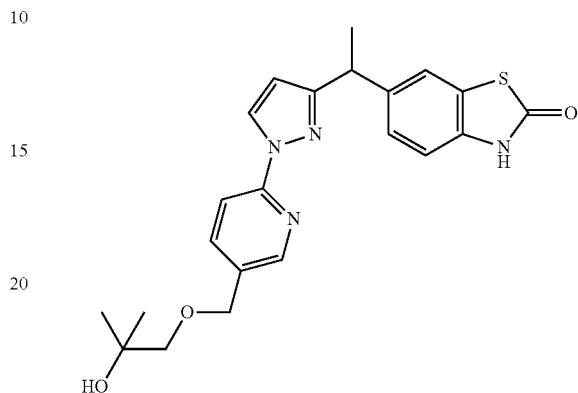

Resolve 6-[1-[1-[5-[(2-Hydroxy-2-methyl-propoxy)methyl]-2-pyridyl]pyrazol-3-yl]ethyl]-3H-1,3-benzothiazol-2-one into its enantiomers by chiral chromatography using Chiralcel® OJ-H, 35% iPrOH/CO$_2$, 5 mL/min, 225 nm Isomer 1 retention time is 1.77 min and isomer 2 is 2.36 min.

EXAMPLE 18 & 19

Isolation of 6-(1-(1-(5-((1-hydroxypropan-2-yl)thio)pyridin-2-yl)-1H-pyrazol-3-yl)ethyl)benzo[d]thiazol-2(3H)-one, isomers 1 and 2

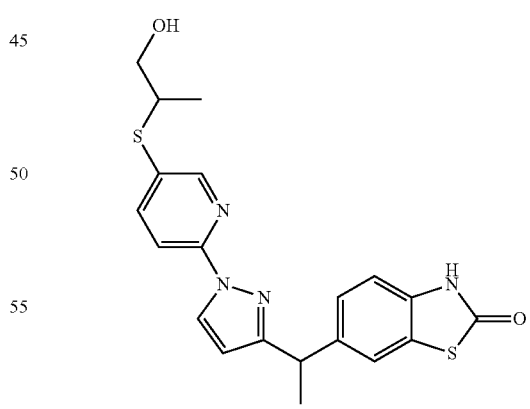

Compound 6-(1-(1-(5-((1-hydroxypropan-2-yl)thio)pyridin-2-yl)-1H-pyrazol-3-yl)ethyl)benzo[d]thiazol-2(3H)-one is resolved into its enantiomers using Chiralpak® AD-H, 3/2 MeOH/ACN 0.2% IPAm 1.0 mL/min, 225 nm. Isomer 1 retention time is 3.3 min, isomer 2 is 4.1 min, isomer 3 is 6.4 min, and isomer 4 is 19.1 min.

Preparation 93: Synthesis of 6-(1-(1-(5-(4-hydroxy-4-vinylpiperidin-1-yl)pyridin-2-yl)-1H-pyrazol-3-yl)ethyl)-3-((2-(trimethylsilyl)ethoxy)methyl)benzo[d]thiazol-2(3H)-one

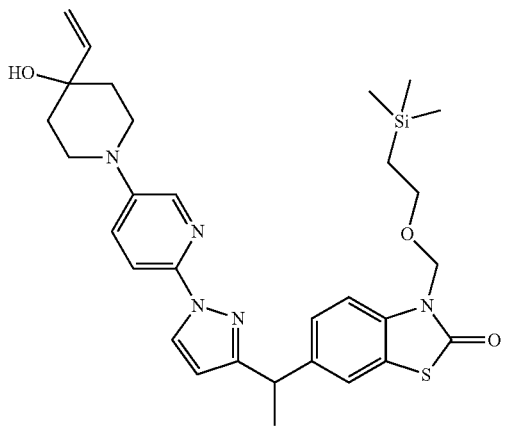 [SMILES: C=CC1(O)CCN(c2ccc(-n3ccc(C(C)c4ccc5c(c4)sc(=O)n5COCC[Si](C)(C)C)n3)nc2)CC1]

To vinylmagnesium bromide (1M in THF, 1.66 mL, 1.66 mmoles) at room temperature is added Zinc Dichloride (17.53 mg, 127.33 μmoles) under Ar gas. The reaction mixture is stirred at room temperature for 1 h and then the temp is lowered to 0° C. and a solution of 6-(1-(1-(5-(4-oxopiperidin-1-yl)pyridin-2-yl)-1H-pyrazol-3-yl)ethyl)-3-((2-(trimethylsilyl)ethoxy)methyl)benzo[d]thiazol-2(3H)-one (700 mg, 1.27 mmoles) in anhydrous tetrahydrofuran (1.7 mL) is added slowly over a 2 min period. After 5 min at room temperature the reaction mixture is quenched with sat. aq. NH$_4$Cl and is stirred for 5 min. The mixture is transferred to a separatory funnel and extracted with EtOAc (3×). The organic layers are combined, washed with brine, dried over Na$_2$SO$_4$, and concentrated. The residue is purified using 35% EtOAc/hexane. Obtained is the title compound (323 mg, 558.99 μmoles, 43.90% yield). M+1=578.

Preparation 94: Synthesis of 6-(1-(1-(5-(4-hydroxy-4-vinylpiperidin-1-yl)pyridin-2-yl)-1H-pyrazol-3-yl)ethyl)benzo[d]thiazol-2(3H)-one

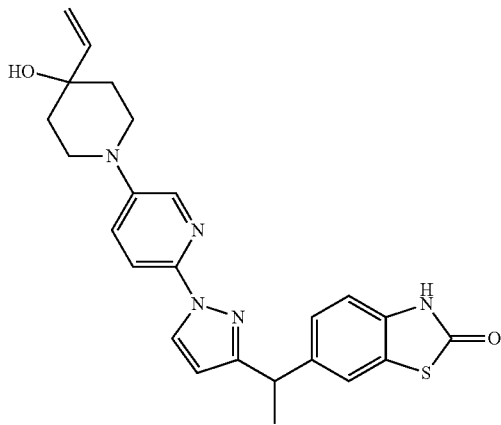 [SMILES: C=CC1(O)CCN(c2ccc(-n3ccc(C(C)c4ccc5[nH]c(=O)sc5c4)n3)nc2)CC1]

To a solution of 6-(1-(1-(5-(4-hydroxy-4-vinylpiperidin-1-yl)pyridin-2-yl)-1H-pyrazol-3-yl)ethyl)-3-((2-(trimethyl-silyl)ethoxy)methyl)benzo[d]thiazol-2(3H)-one (320 mg, 553.8 μmoles) in anhydrous acetonitrile (11 mL) is added Bu$_4$NF (1M THF, 1.7 mL, 1.7 mmoles). The reaction mixture is refluxed overnight. The reaction mixture is diluted with EtOAc (3×), filtered through diatomaceous earth and the filtrate concentrated. The residue is purified using 65% EtOAc/hexane to give the title compound (76 mg, 169.8 μmoles, 30.66% yield). M+1=448

EXAMPLE 20

Isolation of 6-(1-(1-(5-(4-hydroxy-4-vinylpiperidin-1-yl)pyridin-2-yl)-1H-pyrazol-3-yl)ethyl)benzo[d]thiazol-2(3H)-one, Isomer 1

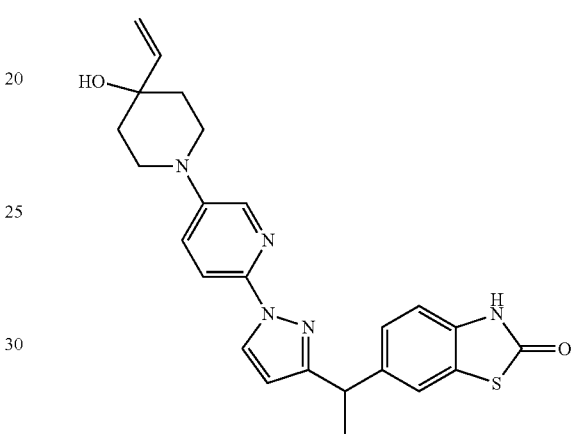

Racemic 6-(1-(1-(5-(4-hydroxy-4-vinylpiperidin-1-yl)pyridin-2-yl)-1H-pyrazol-3-yl)ethyl)benzo[d]thiazol-2(3H)-one is resolved into its enantiomers using Chiralcel® OJ-H, 40% MeOH/CO$_2$, 5 ml/min, 225 nm. Isomer 1 retention time is 3.5 min and isomer 2 is 4.0 min.

Preparation 95: Synthesis of 6-(1-(1-(5-(3-hydroxy-3-methylazetidin-1-yl)pyridin-2-yl)-1H-pyrazol-3-yl)ethyl)-3-((2-(trimethylsilyl)ethoxy)methyl)benzo[d]thiazol-2(3H)-one

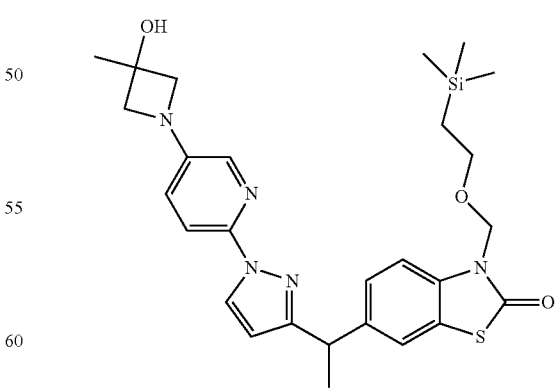

A pressure vial is charged with 6-(1-(1-(5-iodopyridin-2-yl)-1H-pyrazol-3-yl)ethyl)-3-((2-(trimethylsilyl)ethoxy)methyl)benzo[d]thiazol-2(3H)-one (1.55 g, 2.7 mmoles), 3-methylazetidin-3-ol hydrochloride (496.6 mg, 4.0 mmoles) and cesium carbonate (2.8 g, 8.6 mmoles). To the vial is added dimethylformamide (4.5 mL) and the mixture stirred for 5 min under Ar gas. To the vial is then added 1,1'-Bi-2-naphthol (153.4 mg, 535.8 μmoles) and Copper(I) Bromide (76.9 mg, 535.8 μmoles). Argon gas is bubbled through the vial for 4 min. The vial is sealed and heated at 85° C. overnight. The reaction mixture is diluted with THF and filtered. The filtrate is concentrated to a dark oil. The oil is purified using 40% EtOAc/hexane to give the title compound (685 mg, 1.3 mmoles, 48% yield). M+1=538.

EXAMPLE 21

Isolation of 6-(1-(1-(5-(3-hydroxy-3-methylazetidin-1-yl)pyridin-2-yl)-1H-pyrazol-3-yl)ethyl)benzo[d]thiazol-2(3H)-one, isomer 1

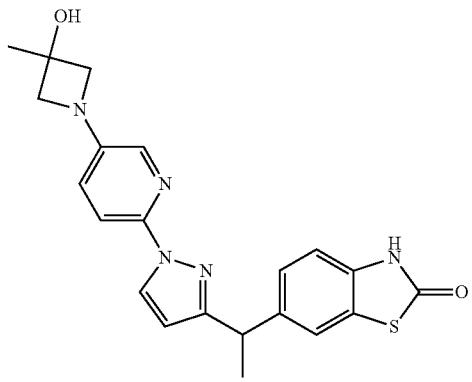 [SMILES: CC(c1ccc2[nH]c(=O)sc2c1)c1ccn(-c2ccc(N3CC(C)(O)C3)cn2)n1]

Racemic 6-(1-(1-(5-(3-hydroxy-3-methylazetidin-1-yl)pyridin-2-yl)-1H-pyrazol-3-yl)ethyl)benzo[d]thiazol-2(3H)-one is resolved into its enantiomers using Chiralcel® OJ-H, 40% MeOH/CO$_2$, 5 ml/min, 225 nm. Isomer 1 retention time is 3.5 min and isomer 2 retention time is 4.6 min.

Preparation 96: Synthesis of 6-(1-(1-(5-(3-methoxyazetidin-1-yl)pyridin-2-yl)-1H-pyrazol-3-yl)ethyl)-3-((2-(trimethylsilyl)ethoxy)methyl)benzo[d]thiazol-2(3H)-one

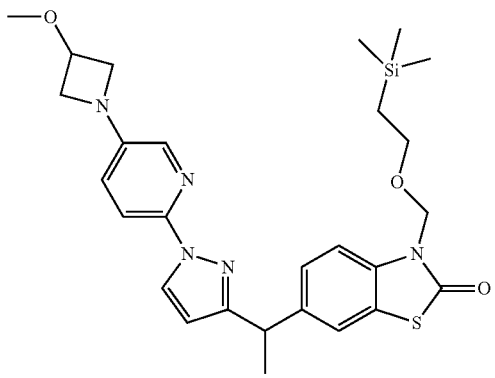 [SMILES: COC1CN(c2ccc(-n3ccc(C(C)c4ccc5c(c4)sc(=O)n5COCC[Si](C)(C)C)n3)nc2)C1]

The title compound is prepared essentially by the method of Preparation 74 using 3-methoxy-azetidine hydrochloride as starting material. M+1=538.

EXAMPLE 22

Isolation of 6-(1-(1-(5-(3-methoxyazetidin-1-yl)pyridin-2-yl)-1H-pyrazol-3-yl)ethyl)benzo[d]thiazol-2(3H)-one, Isomer 2

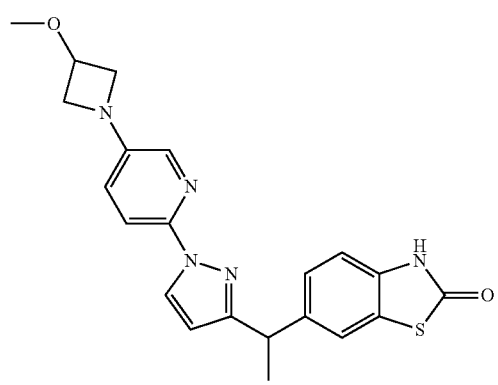 [SMILES: COC1CN(c2ccc(-n3ccc(C(C)c4ccc5[nH]c(=O)sc5c4)n3)nc2)C1]

Compound 6-(1-(1-(5-(3-methoxyazetidin-1-yl)pyridin-2-yl)-1H-pyrazol-3-yl)ethyl)benzo[d]thiazol-2(3H)-one is resolved into its enantiomers using Chiralpak® IA, 3/2 EtOH/ACN 0.2% IPAm, 1.0 mL/min, 225 nm. Isomer 1 retention time is 4.1 min and isomer 2 is 5.9 min.

Preparation 97: Synthesis of 6-(1-(1-(5-(3-methoxy-3-methylazetidin-1-yl)pyridin-2-yl)-1H-pyrazol-3-yl)ethyl)-3-((2-(trimethylsilyl)ethoxy)methyl)benzo[d]thiazol-2(3H)-one

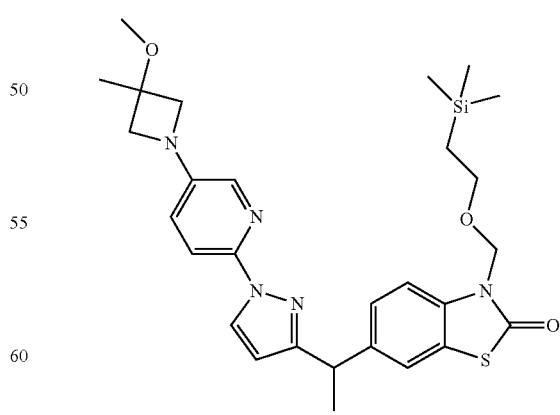

The title compound is prepared essentially by the method of Preparation 74 using 3-methoxy-3-methylazetidine hydrochloride as the starting material. M+1=552.

EXAMPLE 23

Isolation of 6-(1-(1-(5-(3-methoxy-3-methylazetidin-1-yl)pyridin-2-yl)-1H-pyrazol-3-yl)ethyl)benzo[d]thiazol-2(3H)-one isomer 2

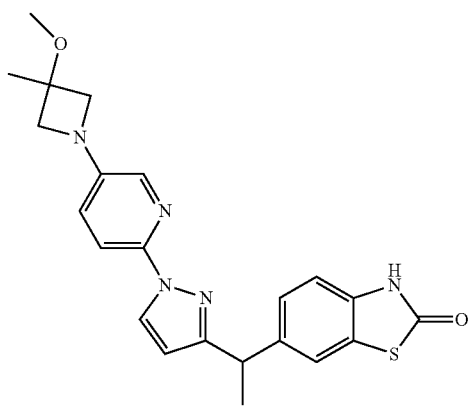 [SMILES: COC1(C)CN(c2ccc(-n3ccc(C(C)c4ccc5[nH]c(=O)sc5c4)n3)nc2)C1]

Compound 6-(1-(1-(5-(3-methoxy-3-methylazetidin-1-yl)pyridin-2-yl)-1H-pyrazol-3-yl)ethyl)benzo[d]thiazol-2(3H)-one is resolved into its enantiomers using Chiralpak® IA, 3/2 EtOH/ACN 0.2% IPAm 1.0 mL/min, 225 nm Isomer 1 retention time is 4.0 min and isomer 2 is 4.8 min.

Preparation 98: Synthesis of 3-methoxymethyl-6-[1-(1-pyridazin-3-yl-1H-pyrazol-3-yl)-ethyl]-3H-benzothiazol-2-one

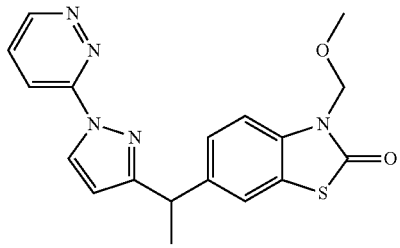 [SMILES: COCn1c(=O)sc2cc(C(C)c3ccn(-c4cccnn4)n3)ccc21]

A mixture of 6-{1-[1-(6-chloro-pyridazin-3-yl)-1H-pyrazol-3-yl]-ethyl}-3-methoxymethyl-3H-benzothiazol-2-one (250 mg, 0.62 mmoles) and 10% Pd/C (250 mg) in Methanol (6 mL), Tetrahydrofuran (6 mL) and Triethylamine (1 mL) is stirred at room temperature under 1 atm of hydrogen at room temperature for 30 minutes. The catalyst is filtered off and the filtrate concentrated. The residue is dissolved in ethyl acetate, washed with water, 0.1N hydrochloric acid and saturated aqueous sodium chloride, then dried over sodium sulfate, filtered and concentrated. Purification on 24 g silica gel (15 to 60% ethyl acetate in hexanes, 65 mL/min) gives 156 mg of 3-(methoxymethyl)-6-[1-(1-pyridazin-3-ylpyrazol-3-yl)ethyl]-1,3-benzothiazol-2-one as a clear oil. LCMS (low) rt=2.03 min, M+1=368.0.

EXAMPLE 24

Isolation of 6-[1-(1-Pyridazin-3-yl-1H-pyrazol-3-yl)-ethyl]-3H-benzothiazol-2-one, Isomer 2

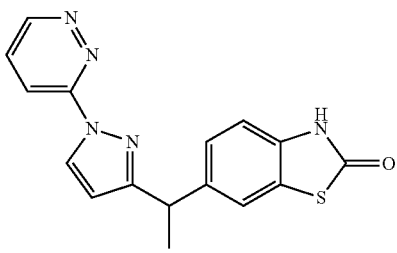 [SMILES: CC(c1ccc2[nH]c(=O)sc2c1)c1ccn(-c2cccnn2)n1]

Compound 6-[1-(1-pyridazin-3-yl-1H-pyrazol-3-yl)-ethyl]-3H-benzothiazol-2-one is resolved into its enantiomers by chiral chromatography. Chiralpak® AD 8×40.5 cm, 40% acetonitrile/60% methanol, 450 mL/min Isomer 2 has retention time of 14.3 min on a Chiralpak® AD-H 4.6×150 mm column, eluting with 40% acetonitrile/60% methanol, 0.6 mL/min LCMS (low) rt=1.807 min, M+1=324.0.

Preparation 99: Synthesis of 3-methoxymethyl-6-(1-{1-[5-(2-oxo-propyl)-pyridin-2-yl]-1H-pyrazol-3-yl}-ethyl)-3H-benzothiazol-2-one

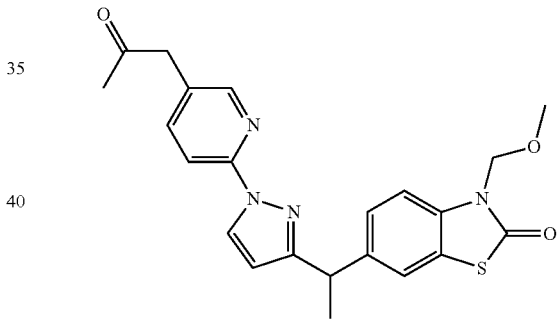

A flame dried vial is charged with tris(dibenzylideneacetone)dipalladium (0) (54 mg, 0.06 mmoles), 2-(dicyclohexylphosphino)-2'-methylbiphenyl (52 mg, 0.12 mmoles) and tetrahydrofuran (2 mL). The vial is flushed with argon for 2 minutes and heated to ~45° C. in a heating block for 20 minutes. A separate flame dried vial is charged with 6-[1-[1-(5-bromo-2-pyridyl)pyrazol-3-yl]ethyl]-3-(methoxymethyl)-1,3-benzothiazol-2-one (530 mg, 1.19 mmoles), Potassium phosphate tribasic (631 mg, 2.98 mmoles) and acetone (5 mL) and flushed with argon for 5 minutes. The catalyst solution is added to this mixture and heated to 70° C. in a heating block. When no starting material remains, the mixture is cooled to room temperature. The mixture is partitioned between water and tetrahydrofuran. The organic layer is washed with saturated aqueous sodium chloride, dried over sodium sulfate, filtered and concentrated to give a dark orange oil. Purification on 40 g silica gel (0 to 40% ethyl acetate in hexanes, 65 mL/min) to give 158 mg of 6-[1-[1-(5-acetonyl-2-pyridyl)pyrazol-3-yl]ethyl]-3-(methoxymethyl)-1,3-benzothiazol-2-one as a light yellow gum. LCMS (low) rt=2.255 min, M+1=423.2.

Preparation 100: Synthesis of 6-(1-{1-[5-(2-oxo-propyl)-pyridin-2-yl]-1H-pyrazol-3-yl}-ethyl)-3H-benzothiazol-2-one

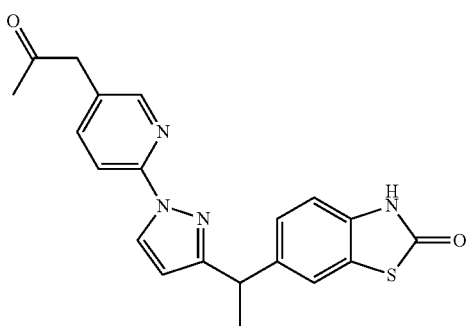 [SMILES: CC(=O)Cc1ccc(-n2ccc(C(C)c3ccc4[nH]c(=O)sc4c3)n2)nc1]

A solution of 6-[1-[1-(5-acetonyl-2-pyridyl)pyrazol-3-yl]ethyl]-3-(methoxymethyl)-1,3-benzothiazol-2-one (150 mg, 0.36 mmoles) in trifluoroacetic acid (8 mL) is boiled overnight under nitrogen. The mixture is concentrated, dissolved in tetrahydrofuran (6 mL) and 30% ammonium hydroxide (0.75 mL) and stirred at room temperature 30 minutes. Silica gel (~12 g) is added and the solvent removed. Purification on 40 g silica gel (0 to 6% methanol in dichloromethane, 65 mL/min) gives 100 mg of 6-[1-[1-(5-acetonyl-2-pyridyl)pyrazol-3-yl]ethyl]-3H-1,3-benzothiazol-2-one as a white foam. LCMS (low) rt=2.016 minutes, M+1=379.2.

Preparation 100a: Isolation of 6-[1-[1-(5-acetonyl-2-pyridyl)pyrazol-3-yl]ethyl]-3H-1,3-benzothiazol-2-one, Isomer 2

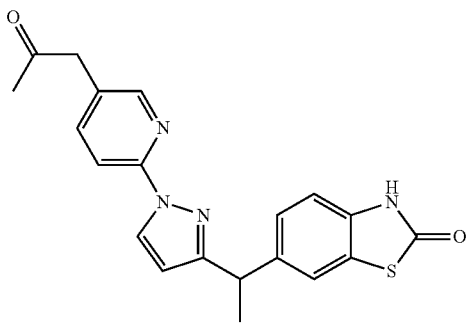 [SMILES: CC(=O)Cc1ccc(-n2ccc(C(C)c3ccc4[nH]c(=O)sc4c3)n2)nc1]

Compound 6-[1-[1-(5-acetonyl-2-pyridyl)pyrazol-3-yl]ethyl]-3H-1,3-benzothiazol-2-one is separated into its isomers by chiral chromatography on a Chiralpak® AD-H column (3×25 cm, 5 um, 9:1 methanol:acetonitrile with 0.2% isopropylamine, 40 mL/min) Isomer 2 has retention time of 6.065 min on a Chiralpak® AD-H 4.6×150 mm column eluting with 9:1 methanol:acetonitrile with 0.2% isopropylamine, at 1.0 mL/min LCMS (low) rt=2.058 min, M+1=379.0.

Preparation 101: Synthesis of 6-((S)-1-{1-[5-(2-Hydroxy-propyl)-pyridin-2-yl]-1H-pyrazol-3-yl}-ethyl)-3H-benzothiazol-2-one

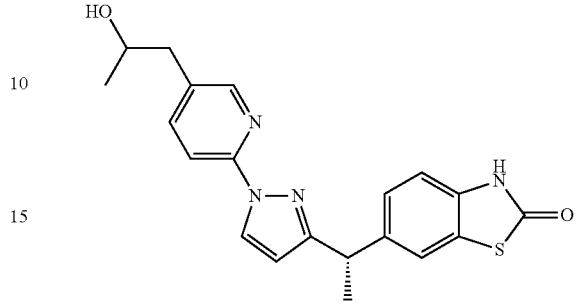

Sodium borohydride (0.011 g, 0.27 mmol) is added to a solution of 6-[(1S)-1-[1-(5-acetonyl-2-pyridyl)pyrazol-3-yl]ethyl]-3H-1,3-benzothiazol-2-one, Isomer 2 (0.104 g, 0.27 mmol) in methanol (3 mL) and tetrahydrofuran (1 mL). After stirring ~25 minutes, the reaction is quenched with saturated ammonium chloride and diluted with ethyl acetate. The organic layer is washed with saturated sodium chloride, dried over sodium sulfate, filtered and concentrated. Purification on 40 g silica gel eluting with 0 to 100% ethyl acetate in hexanes gives 85 mg of 6-[1-[1-[5-(2-hydroxypropyl)-2-pyridyl]pyrazol-3-yl]ethyl]-3H-1,3-benzothiazol-2-one as a white solid. LCMS (low) rt=1.956 min, M+1=381.0.

EXAMPLE 25

Isolation of 6-((S)-1-{1-[5-(2-Hydroxy-propyl)-pyridin-2-yl]-1H-pyrazol-3-yl}-ethyl)-3H-benzothiazol-2-one, Isomer 2

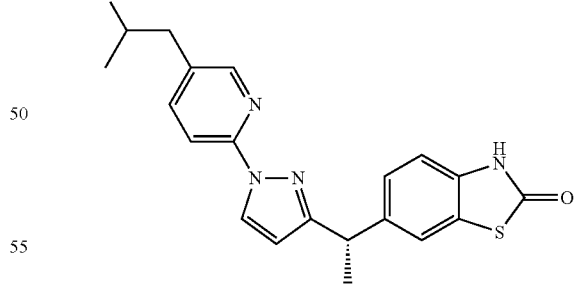

Compound 6-(1-{1-[5-(2-hydroxy-propyl)-pyridin-2-yl]-1H-pyrazol-3-yl}-ethyl)-3H-benzothiazol-2-one is separated into its isomers on a 2.0×25 cm Lux Amylose-2, 5 micron column eluting with 25% ethanol in carbon dioxide at 70 mL/min Isomer 2 has a retention time of 4.93 min on a Lux Amylose-2 column eluting with 25% ethanol in carbon dioxide, 5 mL/min LCMS (QC_T0) rt=1.492 min, M+1=381.0.

Preparation 102: Synthesis of 5-(3,6-dihydro-2H-pyran-4-yl)-2-fluoro-pyridine

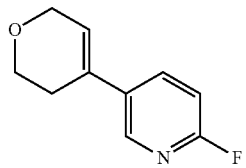 [SMILES: Fc1ccc(C2=CCOCC2)cn1]

To a solution of 5-bromo-2-fluoro-pyridine (4.0 g, 22.5 mmol, 1 equiv.) and tetrahydropyran-4-one (2.28 g, 22.5 mmol, 1 equiv.) in 1,4-dioxane (26 ml) is added p-toluenesulfonylhydrazide (4.32 g, 22.5 mmol, 1 equiv.), 2-(dicyclohexylphosphino)-2',4',6'-tri-i-propyl-1,1'-biphenyl (X-Phos) (442 mg, 900 umol, 0.04 equiv.), tris(dibenzylideneacetone)dipalladium(0) (309 mg, 337 umol, 0.015 equiv.), and lithium t-butoxide (4.14 g, 51.75 mmol, 2.3 equiv.). After the mixture is heated at 110° C. overnight, it is cooled to room temperature, filtered through diatomaceous earth, and the filtered solids washed with dichloromethane. The filtrate is concentrated to an oil and purified by silica chromatography eluting with 0-10% ethyl acetate in dichloromethane to give 5-(3,6-dihydro-2H-pyran-4-yl)-2-fluoro-pyridine (838 mg, 4.63 mmol, 21%) as an oil. LCMS (low pH): 180, M+H, r.t.=1.53 min.

Preparation 103: Synthesis of 6-[1-[1-[5-(3,6-dihydro-2H-pyran-4-yl)-2-pyridyl]pyrazol-3-yl]ethyl]-3-(methoxymethyl)-1,3-benzothiazol-2-one

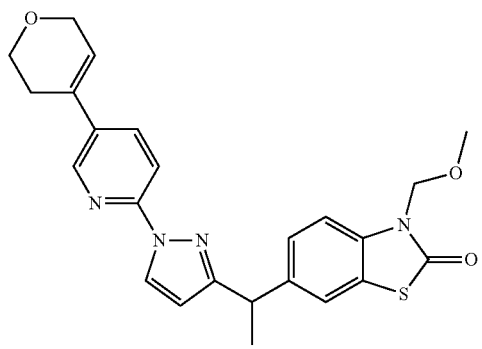 [SMILES: COCn1c(=O)sc2cc(C(C)c3ccn(-c4ccc(C5=CCOCC5)cn4)n3)ccc21]

To a solution of 3-(methoxymethyl)-6-[1-(1H-pyrazol-3-yl)ethyl]-1,3-benzothiazol-2-one (680 mg, 2.35 mmol, 1 equiv.) in N,N-dimethylformamide (7 ml) is added lithium t-butoxide (285 mg, 3.53 mmol, 1.5 equiv.). The mixture is stirred for 15 minutes, then a solution of 5-(3,6-dihydro-2H-pyran-4-yl)-2-fluoro-pyridine (631 mg, 3.53 mmol, 1.5 equiv.) in N,N-dimethylformamide (1.5 ml) is added. This mixture is heated in a microwave reactor at 180° C. for 2 hours, then cooled to ambient temperature and partitioned between ethyl acetate and water. After the aqueous layer is extracted with ethyl acetate (3×), the combined extracts are washed with water, brine, and dried over sodium sulfate. This is filtered and the filtrate concentrated to an oil which is purified by silica chromatography eluting with 0-10% ethyl acetate in dichloromethane to give 6-[1-[1-[5-(3,6-dihydro-2H-pyran-4-yl)-2-pyridyl]pyrazol-3-yl]ethyl]-3-(methoxymethyl)-1,3-benzothiazol-2-one (286 mg, 0.64 mmol, 27%) as a foam. LCMS (low pH): 449, M+H, r.t.=2.59 min.

Preparation 104: Synthesis of 3-(methoxymethyl)-6-[1-[1-(5-tetrahydropyran-4-yl-2-pyridyl)pyrazol-3-yl]ethyl]-1,3-benzothiazol-2-one

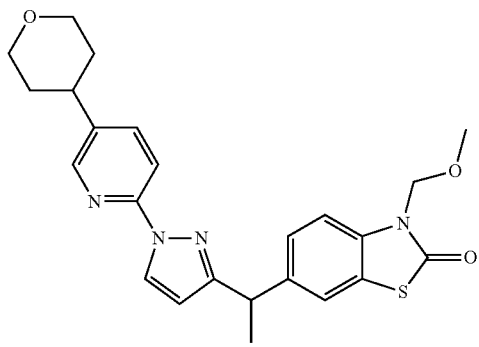 [SMILES: COCn1c(=O)sc2cc(C(C)c3ccn(-c4ccc(C5CCOCC5)cn4)n3)ccc21]

To a solution of 6-[1-[1-[5-(3,6-dihydro-2H-pyran-4-yl)-2-pyridyl]pyrazol-3-yl]ethyl]-3-(methoxymethyl)-1,3-benzothiazol-2-one (280 mg, 624 umol, 1 equiv.) in ethyl acetate (30 ml) is added 10% palladium/carbon (195 mg). A hydrogen-filled balloon is connected and the mixture is stirred at ambient temperature for 20 hours. The mixture is filtered through filter cell and the filtered solids are washed with ethyl acetate. The filtrate is concentrated to yield 3-(methoxymethyl)-6-[1-[1-(5-tetrahydropyran-4-yl-2-pyridyl)pyrazol-3-yl]ethyl]-1,3-benzothiazol-2-one (260 mg, 0.58 mmol, 93%) as a solid. LCMS (low pH): 451, M+H, r.t.=2.44 min.

EXAMPLE 26

Isolation of 6-[1-[1-(5-tetrahydropyran-4-yl-2-pyridyl)pyrazol-3-yl]ethyl]-3H-1,3-benzothiazol-2-one, Isomer 1

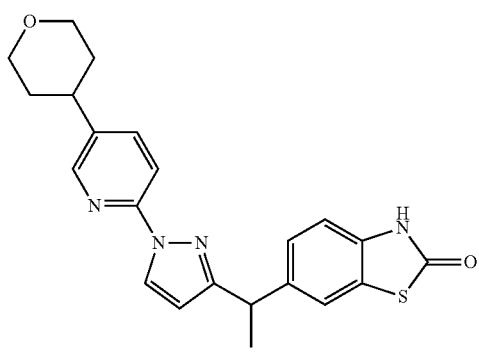 [SMILES: CC(c1ccc2[nH]c(=O)sc2c1)c1ccn(-c2ccc(C3CCOCC3)cn2)n1]

Compound of 6-[1-[1-(5-tetrahydropyran-4-yl-2-pyridyl)pyrazol-3-yl]ethyl]-3H-1,3-benzothiazol-2-one is resolved into its stereoisomers by chiral chromatography using Chiralcel® OJ-H, 40% methanol/CO2, 5 ml/min, 225 nm, (isomer 1)=2.71 min.

Preparation 105: Synthesis of 2-oxo-3H-1,3-benzothiazole-6-carbaldehyde

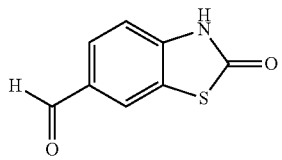 [SMILES: O=Cc1ccc2[nH]c(=O)sc2c1]

To a cooled (−78° C.) solution of 6-bromo-3H-1,3-benzothiazol-2-one (9.91 g, 43 mmol, 1 equiv.) in tetrahydrofuran (100 ml) is added methylmagnesium bromide (3M in diethyl ether) (16.51 ml, 49.5 mmol, 1.15 equiv.). After 30 minutes, tetrahydrofuran (200 ml) is added at a rate which maintains the internal temperature below −50° C. The mixture is cooled to −78° C. and tert-butyllithium (1.7M in pentane) (96.2 ml, 163.6 mmol, 3.8 equiv.) is added dropwise. N,N-Dimethylformamide (19.98 ml, 258 mmol, 6 equiv.) is added and the mixture is removed from the cooling bath and stirred for 2 hours. The mixture is dilute with water and the aqueous layer is adjusted to pH 3 with 1N HCl. The aqueous layer is extracted with ethyl acetate (5×) and the combined organic extracts are dried over sodium sulfate, filtered, and concentrated to a solid. The crude solid is slurried and stirred in 1:1 diethyl ether/hexanes for 30 minutes, then filtered and dried to give 2-oxo-3H-1,3-benzothiazole-6-carbaldehyde (7.37 g, 41.1 mmol, 95%) as a solid. LCMS (low pH): r.t.=1.32 min.

Preparation 106: Synthesis of 2-oxo-3-(2-trimethylsilylethoxymethyl)-1,3-benzothiazole-6-carbaldehyde

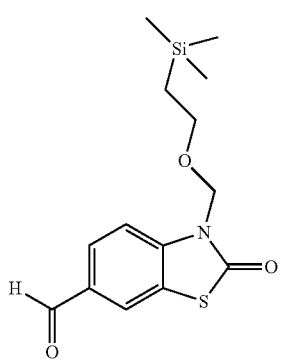 [SMILES: C[Si](C)(C)CCOCn1c(=O)sc2cc(C=O)ccc21]

Sodium hydride (2.44 g, 61.1 mmol, 1.5 equiv.) is added to a cooled (0° C.) solution of 2-oxo-3H-1,3-benzothiazole-6-carbaldehyde (7.3 g, 40.74 mmol, 1 equiv.) in N,N-dimethylformamide (125 ml). The mixture is stirred for 20 minutes and 2-(trimethylsilyl)ethoxymethyl chloride (9.39 ml, 52.9 mmol, 1.3 equiv.) is added dropwise. The mixture is stirred overnight at ambient temperature, quenched with saturated aqueous ammonium chloride and diluted with ethyl acetate. The organic layer is washed with brine (5×), dried over sodium sulfate, filtered, and concentrated to an oil. It is purified by silica chromatography eluting with 0%-20% ethyl acetate in hexanes to yield 2-oxo-3-(2-trimethylsilylethoxymethyl)-1,3-benzothiazole-6-carbaldehyde as a solid (9.5 g, 30.7 mmol, 75%). LCMS (low pH): r.t.=2.52 min.

Preparation 107: Synthesis of 6-[hydroxy-(1-tetrahydropyran-2-ylpyrazol-3-yl)methyl]-3-(2-trimethylsilylethoxymethyl)-1,3-benzothiazol-2-one

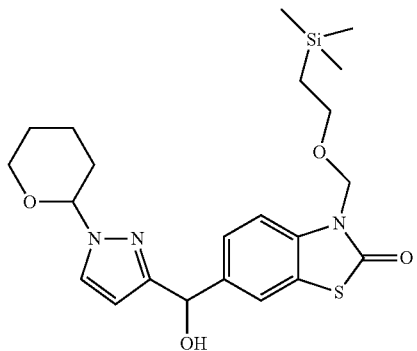 [SMILES: C[Si](C)(C)CCOCn1c(=O)sc2cc(C(O)c3ccn(C4CCCCO4)n3)ccc21]

To a solution of 1-tetrahydropyran-2-ylpyrazole (762 mg, 5 mmol, 1 equiv.) in tetrahydrofuran (35 ml) cooled at −78° C. is added n-butyllithium (2.5M in hexanes) (2.2 ml, 5.5 mmol, 1.1 equiv.) dropwise. The mixture is warmed to 0° C. for 10 minutes and then is warmed to ambient temperature for 10 minutes. It is cooled to −78° C. and a solution of 2-oxo-3-(2-trimethylsilylethoxymethyl)-1,3-benzothiazole-6-carbaldehyde (1.55 g, 5 mmol, 1 equiv.) in tetrahydrofuran (7 ml) is added. The mixture is stirred at −78° C. for one hour, quenched with aqueous saturated ammonium chloride, and extracted with ethyl acetate. The extracts are dried over sodium sulfate, filtered, and concentrated to an oil which is purified by silica chromatography eluting with 0-45% ethyl acetate in hexanes to afford 6-[hydroxy-(1-tetrahydropyran-2-ylpyrazol-3-yl)methyl]-3-(2-trimethylsilylethoxymethyl)-1,3-benzothiazol-2-one (1.99 g, 4.31 mmol, 86%) as a mixture of diastereomers. LCMS (low pH): r.t.=2.27 min.

Preparation 108: Synthesis of 6-(1-tetrahydropyran-2-ylpyrazole-3-carbonyl)-3-(2-trimethylsilylethoxymethyl)-1,3-benzothiazol-2-one

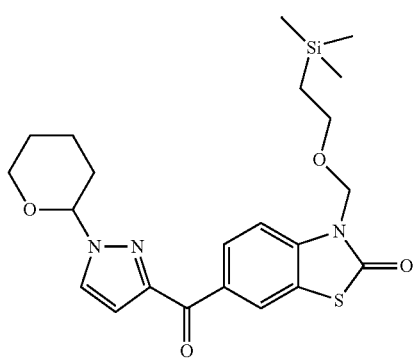 [SMILES: C[Si](C)(C)CCOCn1c(=O)sc2cc(C(=O)c3ccn(C4CCCCO4)n3)ccc21]

Manganese (IV) oxide (2.17 g, 21.23 mmol, 5 equiv.) is added to a solution of 6-[hydroxy-(1-tetrahydropyran-2-ylpyrazol-3-yl)methyl]-3-(2-trimethylsilylethoxymethyl)-1,3-benzothiazol-2-one (1.96 g, 4.25 mmol, 1 equiv.) in chloroform (20 ml) and the mixture is heated at 75° C. for 90 minutes. The mixture is cooled, filtered through diatomaceous earth, and the filtrate concentrated to give 6-(1-tetrahydropyran-2-ylpyrazole-3-carbonyl)-3-(2-trimethylsilylethoxymethyl)-1,3-benzothiazol-2-one (2 g, 4.25 mmol, 100%). LCMS (low pH): 376, M-THP+H, r.t.=2.82 min.

Preparation 109: Synthesis of 6-[1-(1-tetrahydropyran-2-ylpyrazol-3-yl)vinyl]-3-(2-trimethylsilylethoxymethyl)-1,3-benzothiazol-2-one

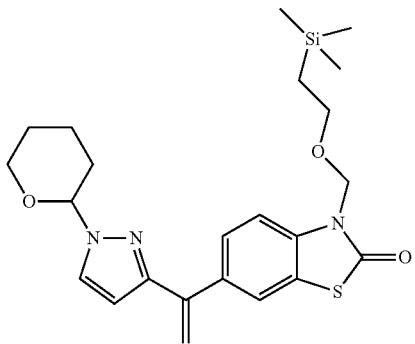 [SMILES: C=C(c1ccc2c(c1)sc(=O)n2COCC[Si](C)(C)C)c1ccn(C2CCCCO2)n1]

To a cooled (−78° C.) suspension of (methyl)triphenylphosphonium bromide (515 mg, 1.44 mmol, 1.3 equiv.) in tetrahydrofuran (15 ml) is added 1M lithium bis(trimethylsilyl)amide (solution in tetrahydrofuran) (1.44 ml, 1.44 mmol, 1.3 equiv.) and the mixture is warmed to 0° C. for 30 minutes. A solution of 6-(1-tetrahydropyran-2-ylpyrazole-3-carbonyl)-3-(2-trimethylsilylethoxymethyl)-1,3-benzothiazol-2-one (510 mg, 1.11 mmol, 1 equiv.) in tetrahydrofuran (15 ml) is added dropwise and the mixture is stirred at room temperature for 3 hours. The solution is diluted with aqueous saturated ammonium chloride and extracted with ethyl acetate (2×). The combined extracts are dried over sodium sulfate, filtered, and concentrated to an oil which is purified by silica chromatography eluting with 0-35% ethyl acetate in hexanes to yield 6-[1-(1-tetrahydropyran-2-ylpyrazol-3-yl)vinyl]-3-(2-trimethylsilylethoxymethyl)-1,3-benzothiazol-2-one (420 mg, 0.92 mmol, 83%). LCMS (low pH): 373, M-THP+H, r.t.=2.86 min.

Preparation 110: Synthesis of 6-[1-(1-tetrahydropyran-2-ylpyrazol-3-yl)ethyl]-3-(2-trimethylsilylethoxymethyl)-1,3-benzothiazol-2-one

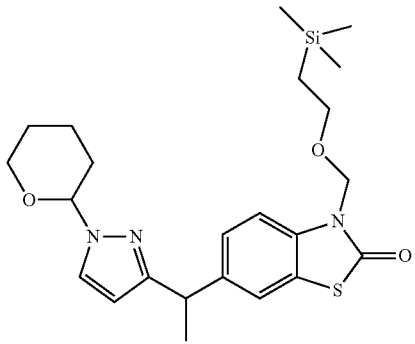 [SMILES: CC(c1ccc2c(c1)sc(=O)n2COCC[Si](C)(C)C)c1ccn(C2CCCCO2)n1]

To a solution of 6-[1-(1-tetrahydropyran-2-ylpyrazol-3-yl)vinyl]-3-(2-trimethylsilylethoxymethyl)-1,3-benzothiazol-2-one (420 mg, 917 umol, 1 equiv.) in ethanol (10 ml) was added 10% Pd/C (150 mg). A hydrogen-filled balloon is connected and the mixture is stirred at ambient temperature for one hour. The mixture is filtered through diatomaceous earth and the filtrate is concentrated to afford 6-[1-(1-tetrahydropyran-2-ylpyrazol-3-yl)ethyl]-3-(2-trimethylsilylethoxymethyl)-1,3-benzothiazol-2-one (401 mg, 0.87 mmol, 95%). LCMS (low pH): r.t.=1.33 min.

Preparation 111: Synthesis of 6-[1-(1H-pyrazol-3-yl)ethyl]-3H-1,3-benzothiazol-2-one

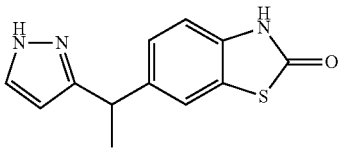 [SMILES: CC(c1ccc2[nH]c(=O)sc2c1)c1cc[nH]n1]

To a solution of 6-[1-(1-tetrahydropyran-2-ylpyrazol-3-yl)ethyl]-3-(2-trimethylsilylethoxymethyl)-1,3-benzothiazol-2-one (8.6 g, 18.71 mmol, 1 equiv.) in dichloromethane (250 ml) is added trifluoroacetic acid (250 ml) and the mixture stirred for 2 hours. The mixture is evaporated and the residue is dissolved in tetrahydrofuran (250 ml) and treated with aqueous concentrated ammonium hydroxide (250 ml) and stirred overnight at room temperature. The mixture is partially concentrated and residue is diluted with brine and extracted with ethyl acetate (3×). The combined extracts are dried with sodium sulfate, filtered, and concentrated. The residue is purified by silica chromatography eluting with 0-6% methanol in dichloromethane to afford 6-[1-(1H-pyrazol-3-yl)ethyl]-3H-1,3-benzothiazol-2-one (2.8 g, 11.41 mmol, 61%) as a white foam. LCMS (low pH): 246, M+H, r.t.=1.54 min.

Preparation 112: Synthesis of 6-[1-[1-[5-(2-hydroxyethyl)-2-pyridyl]pyrazol-3-yl]ethyl]-3H-1,3-benzothiazol-2-one

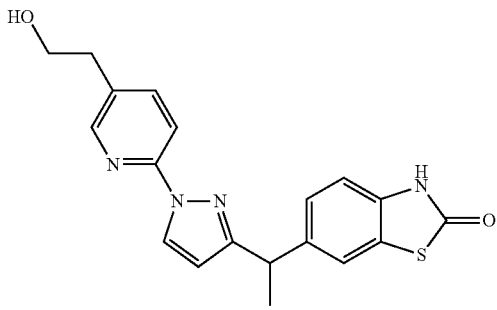 [SMILES: CC(c1ccc2[nH]c(=O)sc2c1)c1ccn(-c2ccc(CCO)cn2)n1]

To a solution of 6-[1-[1-[5-(2-tetrahydropyran-2-yloxyethyl)-2-pyridyl]pyrazol-3-yl]ethyl]-3H-1,3-benzothiazol-2-one (2.25 g, 4.99 mmol, 1 equiv.) in dichloromethane (55 ml) is added trifluoroacetic acid (55 ml) and the mixture is stirred at room temperature for 4 hours. The mixture is concentrated to an oil which is partitioned between dichloromethane and aqueous saturated sodium bicarbonate. The aqueous layer is extracted with dichloromethane and the combined extracts are washed with brine, dried over sodium sulfate, filtered, and concentrated to an oil. The crude product is dissolved in dichloromethane, treated with aqueous 1N NaOH (25 ml), and stirred for 1 hour. The mixture is adjusted to pH 5 with 1N HCl, and the aqueous layer is extracted with dichloromethane. The combined extracts are washed with water, brine, dried over sodium sulfate, filtered, and concentrated to an oil. The product is purified by silica chromatography eluting with 30%-70% ethyl acetate in hexanes to give 6-[1-[1-[5-(2-hydroxyethyl)-2-pyridyl]pyrazol-3-yl]ethyl]-3H-1,3-benzothiazol-2-one (1.49 g, 4.07 mmol, 81%) as a foam. LCMS (low pH): 367, M+H, r.t.=1.85 min.

EXAMPLE 27

Isolation of 6-[(S)-1-[1-[5-(2-hydroxyethyl)-2-pyridyl]pyrazol-3-yl]ethyl]-3H-1,3-benzothiazol-2-one, Isomer 2

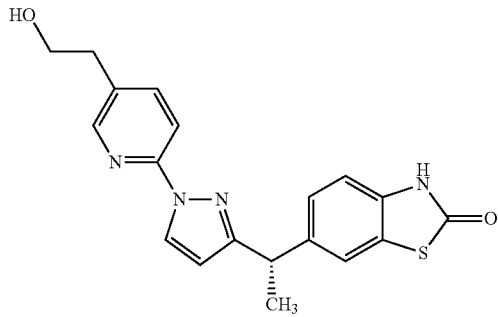 [SMILES: C[C@@H](c1ccc2[nH]c(=O)sc2c1)c1ccn(-c2ccc(CCO)cn2)n1]

Compound 6-[1-[1-[5-(2-hydroxyethyl)-2-pyridyl]pyrazol-3-yl]ethyl]-3H-1,3-benzothiazol-2-one is resolved into its enantiomers by chiral chromatography using Chiralpak® AD-H, 100% 3 A ETOH, 0.60 ml/min, 280 nm, (isomer 2 (S isomer))=18.2 min.

Preparation 113: Synthesis of 6-[1-[1-(5-deuterio-2-pyridyl)pyrazol-3-yl]ethyl]-3-(methoxymethyl)-1,3-benzothiazol-2-one

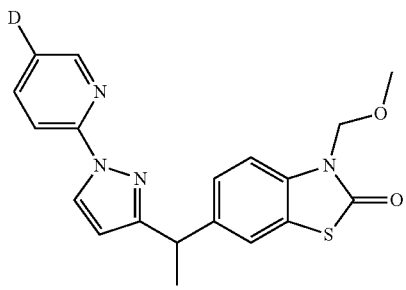

To a 95 mL Parr autoclave with teflon coated stir bar is added 6-[1-[1-(5-bromo-2-pyridyl)pyrazol-3-yl]ethyl]-3-(methoxymethyl)-1,3-benzothiazol-2-one (500 mg, 1.1 mmol), Pd black (300 mg), CDCl$_3$ (7 ml), and triethylamine (210 ul). The vessel is sealed and pressurized with 80 psig of D$_2$ and agitated at 80° C. overnight. The mixture is filtered rinsing with CDCl$_3$ and concentrated to dryness. The mixture is purified by flash chromatography (silica gel, 24 g, eluted hexane to 50% EtOAc/hexane) to yield 6-[1-[1-(5-deuterio-2-pyridyl)pyrazol-3-yl]ethyl]-3-(methoxymethyl)-1,3-benzothiazol-2-one (273 mg; 66%) LCMS (+) 368.2.

EXAMPLE 28

Isolation of 6-[1-[1-(5-deuterio-2-pyridyl)pyrazol-3-yl]ethyl]-3H-1,3-benzothiazol-2-one, Isomer 2

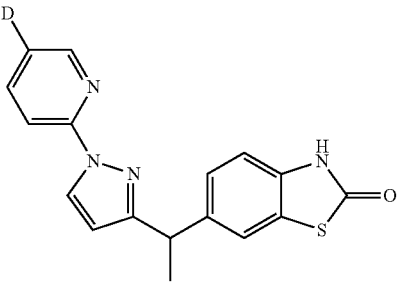

Compound 6-[1-[1-(5-deuterio-2-pyridyl)pyrazol-3-yl]ethyl]-3H-1,3-benzothiazol-2-one is resolved into its enantiomers by chiral chromatography using Chiralpak® AD-H 4.6×150 mm, 9/1 MeOH/ACN 0.2% IPAm, 1 mL/min, 225 nm. Isomer 1 retention time is 3.3 min and isomer 2 is 5.1 min.

Preparation 114: Synthesis of methyl 6-[3-[1-(2-oxo-3H-1,3-benzothiazol-6-yl)ethyl]pyrazol-1-yl]pyridine-3-carboxylate

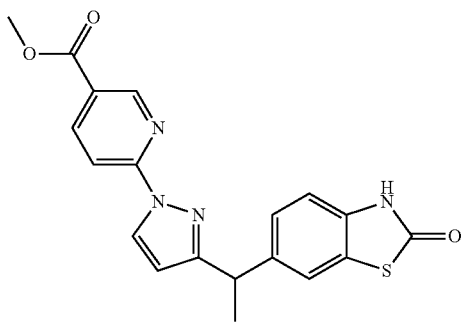 [SMILES: COC(=O)c1ccc(-n2ccc(C(C)c3ccc4[nH]c(=O)sc4c3)n2)nc1]

Methyl 6-[3-[1-[3-(methoxymethyl)-2-oxo-1,3-benzothiazol-6-yl]ethyl]pyrazol-1-yl]pyridine-3-carboxylate (0.62 g, 1.5 mmoles) and trifluoroacetic acid (5 mL; 66 mmoles) is heated at 100° C. for 5.5 h. The mixture is concentrated to dryness. Tetrahydrofuran (5 mL) and 28% ammonium hydroxide (3 mL; 22 mmoles) are added and stirred for 0.5 h. The mixture is partitioned between EtOAc and water. The aqueous phase is extracted with EtOAc (2×). The combined organic phase is washed with brine, dried (Na$_2$SO$_4$) and concentrated to yield methyl 6-[3-[1-(2-oxo-3H-1,3-benzothiazol-6-yl)ethyl]pyrazol-1-yl]pyridine-3-carboxylate (0.44 g, 79%) The material is used in the next step without purification. LCMS (+) 381.0

EXAMPLE 29

Synthesis of 6-[1-[1-[5-(1-hydroxy-1-methyl-ethyl)-2-pyridyl]pyrazol-3-yl]ethyl]-3H-1,3-benzothiazol-2-one, Isomer 1

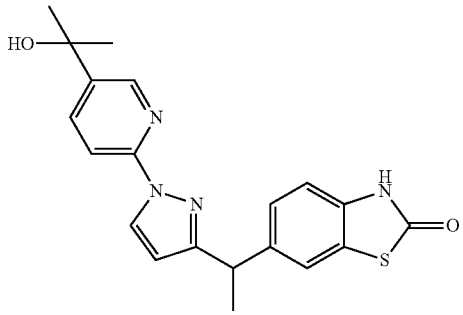 [SMILES: CC(c1ccc2[nH]c(=O)sc2c1)c1ccn(-c2ccc(C(C)(C)O)cn2)n1]

To a mixture of methyl 6-[3-[1-(2-oxo-3H-1,3-benzothiazol-6-yl)ethyl]pyrazol-1-yl]pyridine-3-carboxylate (440 mg, 1.2 mmoles) and tetrahydrofuran (10 mL) is added a 3.0 M solution of methylmagnesium bromide in ether (2.3 mL, 7 mmol). A solid formed, and more tetrahydrofuran (5 mL) is added to aid stirring. After 2 h, LCMS showed approx. 25% starting material remained. Additional methylmagnesium bromide in ether (3 M, 1.2 mL, 3.5 mmol) is added and stirred for 1 h. The reaction is quenched with saturated NH$_4$Cl. The mixture is partitioned between EtOAc and water. The aqueous phase is extracted with EtOAc (2×). The combined organic phase is washed with brine, dried (Na$_2$SO$_4$) and concentrated. The material is purified by flash chromatography (silica gel, 24 g, eluted 30-80% EtOAc/hexane) to obtain 6-[1-[1-[5-(1-hydroxy-1-methyl-ethyl)-2-pyridyl]pyrazol-3-yl]ethyl]-3H-1,3-benzothiazol-2-one (0.33 g, 75%) LCMS (+) 381.2

Racemic 6-[1-[1-[5-(1-hydroxy-1-methyl-ethyl)-2-pyridyl]pyrazol-3-yl]ethyl]-3H-1,3-benzothiazol-2-one is resolved into its enantiomers by chiral chromatography using Chiralcel® OJ-H, 4.6×150 mm, 40% MeOH/CO$_2$, 5 mL/min, 225 nm Isomer 1 retention time is 1.5 min and isomer 2 is 2.0 min.

Preparation 115: Synthesis of 6-[1-[1-[5-(3-hydroxy-3-methyl-butyl)-2-pyridyl]pyrazol-3-yl]ethyl]-3H-1,3-benzothiazol-2-one

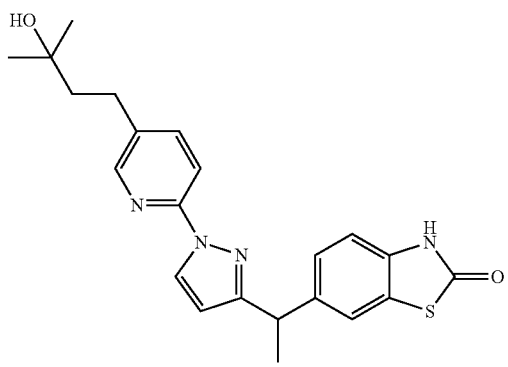 [SMILES: CC(c1ccc2[nH]c(=O)sc2c1)c1ccn(-c2ccc(CCC(C)(C)O)cn2)n1]

Cool a solution of 2-methyl-3-buten-2-ol, (43.07 g, 52.42 mL, 500 mmol) in THF (250 mL) to 5° C. Add 9-borabicyclo[3.3.1]nonane (1.07 kg, 1.20 L, 600 mmol) over 3 h at 5° C. Stir for 16 h while warming to 23° C. Add a 1 M aqueous solution of sodium hydroxide (629.37 mL, 629.37 mmol) at 23° C. and stir for 30 min Add then 6-[1-[1-(5-bromo-2-pyridyl)pyrazol-3-yl]ethyl]-3H-1,3-benzothiazol-2-one (70 g, 143 mmol) at 23° C. and stir for 30 min Finally add (1,1'-bis(diphenylphosphino)ferrocene)palladium(II) chloride (2.98 g, 3.58 mol) and stir the mixture at 75° C. for 3 h. Add dichloromethane (1 L) and separate the aqueous phase and wash this aqueous phase with more dichloromethane (3×500 mL). Add then a 1 M aqueous solution of hydrochloric acid (ca. 230 mL) slowly until pH 8. Wash the solution with EtOAc (2×300 mL), dry the combined organic phase with sodium sulphate and evaporate. Purify the residue by silica gel chromatography (EtOAc/dicloromethane/hexanes 50:25:25 to EtOAc/dicloromethane/hexanes 60:20:20) to afford the title compound as a foam (30.8 g, 52%). M+1=409.

EXAMPLE 30

Isolation of 6-[(1S)-1-[1-[5-(3-hydroxy-3-methyl-butyl)-2-pyridyl]pyrazol-3-yl]ethyl]-3H-1,3-benzothiazol-2-one, Isomer 1

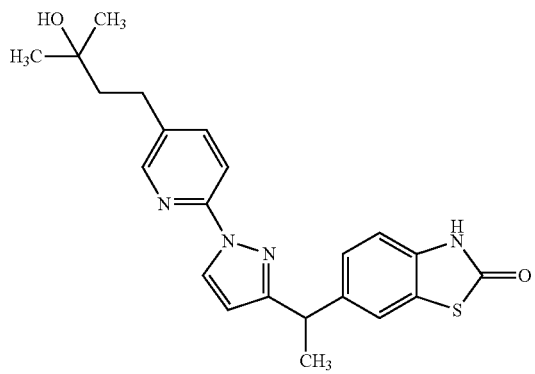 [SMILES: CC(c1ccc2[nH]c(=O)sc2c1)c1ccn(-c2ccc(CCC(C)(C)O)cn2)n1]

Racemic 6-[1-[1-[5-(3-hydroxy-3-methyl-butyl)-2-pyridyl]pyrazol-3-yl]ethyl]-3H-1,3-benzothiazol-2-one, (11.2 g) is resolved into its enantiomer by chiral chromatography using Cellulose Lux 2, 25% EtOH/n-hexane (0.2% DMEA), 300 mL/min, 254 nm and Chiralcel® OJ-H, 35% MeOH (0.2% DMEA)/CO2, 65 mL/min, 260 nm. (isomer 1 retention time is 2.27 min and isomer 2 is 2.77 min) to afford desired compound as a white solid (5.07 g, ee 98%).

Preparation 116: Synthesis of 6-[1-[1-[5-(3-tetrahydropyran-2-yloxypropoxy)-2-pyridyl]pyrazol-3-yl]ethyl]-3-(2-trimethylsilylethoxymethyl)-1,3-benzothiazol-2-one

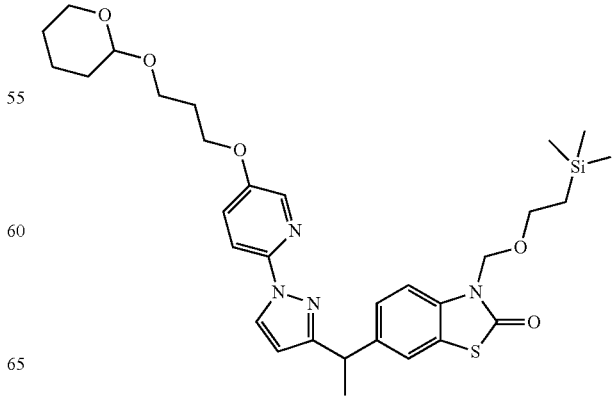

To a mixture of 6-[1-[1-(5-hydroxy-2-pyridyl)pyrazol-3-yl]ethyl]-3-(2-trimethylsilylethoxymethyl)-1,3-benzothiazol-2-one (500 mg, 1.1 mmoles), acetonitrile (4 mL), and potassium carbonate (442 mg, 3.20 mmoles) is added 2-(3-bromopropoxy)tetrahydro-2H-pyran (595 mg, 2.7 mmoles). The mixture is heated at 70° C. for 3 days. The mixture is partitioned between EtOAc and water, and the aqueous phase is extracted with EtOAc (2×). The combined organic phase is washed with brine, dried (Na2SO4) and concentrated.

EXAMPLE 31

Isolation of 6-[1-[1-[5-(3-hydroxy-2,2-dimethyl-propoxy)-2-pyridyl]pyrazol-3-yl]ethyl]-3H-1,3-benzothiazol-2-one, Isomer 1

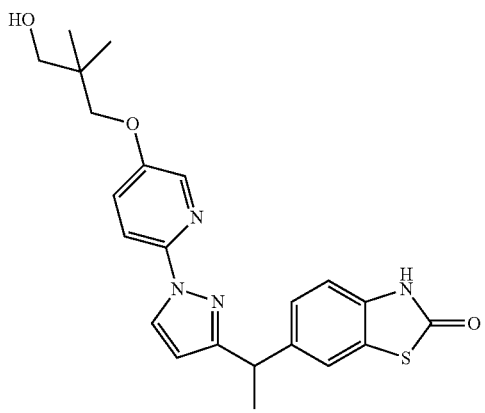 [SMILES: CC(c1ccc2[nH]c(=O)sc2c1)c1ccn(-c2ccc(OCC(C)(C)CO)cn2)n1]

Racemic 6-[1-[1-[5-(3-hydroxy-2,2-dimethyl-propoxy)-2-pyridyl]pyrazol-3-yl]ethyl]-3H-1,3-benzothiazol-2-one one is resolved into its enantiomers by chiral chromatography using Chiralpak® IA, 4.6×150 mm, 3/2 EtOH/ACN 0.2 IPAm, 1 mL/min, 225 nm. Isomer 1 retention time is 3.25 min and isomer 2 is 7.94 min.

Preparation 117: Isolation of methyl 6-[3-[1-[3-(methoxymethyl)-2-oxo-1,3-benzothiazol-6-yl]ethyl]pyrazol-1-yl]pyridazine-3-carboxylate, isomer 2

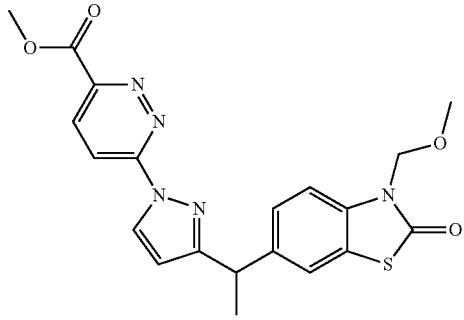 [SMILES: COCn1c(=O)sc2cc(C(C)c3ccn(-c4ccc(C(=O)OC)nn4)n3)ccc21]

Racemic methyl 6-[3-[1-[3-(methoxymethyl)-2-oxo-1,3-benzothiazol-6-yl]ethyl]pyrazol-1-yl]pyridazine-3-carboxylate is resolved into its enantiomers by chiral chromatography using Chiralpak® AD-H, 4.6×150 mm, 40/60 ACN/EtOH, 0.6 mL/min, 280 nm. Isomer 1 retention time is 6.5 min and isomer 2 is 7.7 min Isomer 2 is carried to next step.

EXAMPLE 32

Synthesis of 6-[3-[1-(2-oxo-3H-1,3-benzothiazol-6-yl)ethyl]pyrazol-1-yl]pyridazine-3-carboxamide, Isomer 1

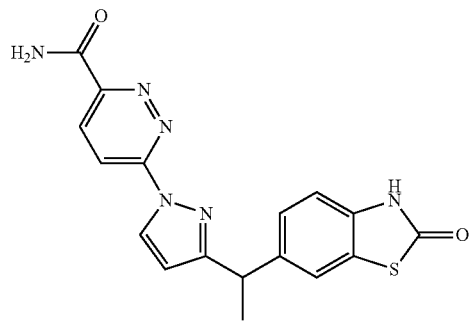 [SMILES: CC(c1ccc2[nH]c(=O)sc2c1)c1ccn(-c2ccc(C(N)=O)nn2)n1]

A mixture of ethyl 6-[3-[1-[3-(methoxymethyl)-2-oxo-1,3-benzothiazol-6-yl]ethyl]pyrazol-1-yl]pyridazine-3-carboxylate (Isomer 2) (0.89 g, 2.0 mmoles) and trifluoroacetic acid (20 mL) is heated at 70° C. overnight. The mixture is concentrated to dryness, and tetrahydrofuran (20 mL) and 28% Ammonium Hydroxide (15 mL) are added and stirred at room temperature for 3 h. The mixture is partitioned between EtOAc and water. The aqueous phase is extracted with EtOAc (3×). The combined organic phase is washed with brine, dried (Na$_2$SO$_4$) and concentrated. The material is purified by reverse phase chromatography (150 g C18 RediSepRf Gold®, 25-75% 0.1% formic acid in acetonitrile/ 0.1% formic acid in water, 60 mL/min). The solid obtained after concentrating fractions is triturated with EtOH and dried. LCMS (+) 367.0, Chiral Analysis using Chiralpak® AD-H, 4.6×150 mm, 9/1 MeOH/ACN 0.2% IPAm, 1.0 mL/min, 225 nm. Isomer 1 retention time is 4.8 min.

Preparation 118: Synthesis of 1-(6-fluoro-3-pyridyl)-2-methyl-propan-2-ol

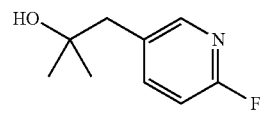

Charge a flame dried 1 L round bottom flask with 5-bromo-2-fluoro pyridine (10 g, 56.8 mmol) and diethyl ether (200 mL). Cool this mixture to −78° C. with dry ice/acetone under an atmosphere of nitrogen. To this milky white suspension add a solution of n-butyl lithium (25 mL of 2.5M, 62.5 mmol) dropwise. Stir for 1 hr at this temperature, then add 2,2-dimethyloxirane (10.1 mL, 113.6 mmol) slowly and remove the ice bath. After 2 hrs quench the reaction with water and wash the organic layer with an aqueous solution of saturated sodium chloride. Dry the organic layer over sodium sulfate, filter and evaporate to dryness. Purify this residue via silica gel (330 g, 50% EtOAc in hexanes) to give 1-(6-fluoro-3-pyridyl)-2-methyl-propan-2-ol as a yellow brown oil (4 g, 41%). MS=170 (M+1).

EXAMPLE 33

Synthesis of 6-[1-[1-[5-(2-hydroxy-2-methyl-propyl)-2-pyridyl]pyrazol-3-yl]ethyl]-3H-1,3-benzothiazol-2-one, Isomer 1

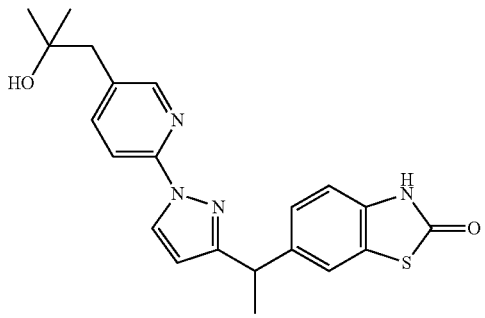 [SMILES: CC(c1ccc2[nH]c(=O)sc2c1)c1ccn(-c2ccc(CC(C)(C)O)cn2)n1]

Dissolve 6-[1-(1H-pyrazol-3-yl)ethyl]-3H-1,3-benzothiazol-2-one (1.2 g, 4.89 mmol) in dimethylformamide (14 mL) and add lithium t-butoxide (17.2 g, 19.57 mmol) to this solution and stir at ambient temperature under a nitrogen atmosphere for 10 min. Add 1-(6-fluoro-3-pyridyl)-2-methyl-propan-2-ol (4 g, 23.7 mmol) to this mixture and heat to reflux for 18 hrs. Cool the reaction to ambient temperature and partition between ethyl acetate and an aqueous saturated solution of ammonium chloride. Extract the aqueous layer with ethyl acetate and dry the combined organics with magnesium sulfate. Filter the organics and evaporate the liquid. Purify the resulting residue with silica gel (40 g, 50% EtOAc in hexanes) to give 6-[1-[1-[5-(2-hydroxy-2-methyl-propyl)-2-pyridyl]pyrazol-3-yl]ethyl]-3H-1,3-benzothiazol-2-one as clear thick oil (1.89 g, 97%). M+1=395.

Racemic 6-[1-[1-[5-(2-hydroxy-2-methyl-propyl)-2-pyridyl]pyrazol-3-yl]ethyl]-3H-1,3-benzothiazol-2-one is resolved into its enantiomers by chiral chromatography using Lux Amylose-2, 30% MeOH/CO2, 5 mL/min, 225 nm Isomer 1 retention time is 2.44 min and isomer 2 is 2.92 min.

EXAMPLE 34

Synthesis of 6-[1-[1-[5-(1-methylimidazol-2-yl)sulfanyl-2-pyridyl]pyrazol-3-yl]ethyl]-3H-1,3-benzothiazol-2-one Hydrochloride, Isomer 1

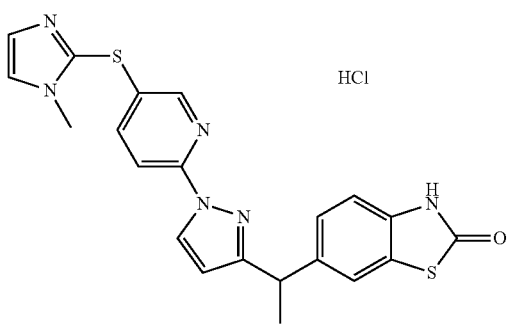 [SMILES: CC(c1ccc2[nH]c(=O)sc2c1)c1ccn(-c2ccc(Sc3nccn3C)cn2)n1 ; Cl]

The two enantiomers of 6-[1-[1-[5-(1-methylimidazol-2-yl)sulfanyl-2-pyridyl]pyrazol-3-yl]ethyl]-3H-1,3-benzothiazol-2-one are separated by chiral chromatography using Chiralcel® OJ-H, 21×250 mm, 80% 70% CO2/30% MeOH (W/0.2% IPAm), 70 mL/min., 225 nm. Isomer 1 retention time is 6.0 min, (74.61 mg, 20%) as a white solid and Isomer 2 is 7.3 min, (80.8 mg, 20%) as a white solid.

HCl salt preparation: Separately, the isolated isomers are transferred to a tared bottle with DCM and concentrated in vacuo to a white solid (assume 100% transfer). Dissolve in MeOH (3 mL) and DCM (2 mL), and the clear and treat with 1.0 M HCl in Et2O (Aldrich). The solution is swirled for a few minutes, then concentrate, add Et2O (5 mL) and re-concentrate, place under high vacuum for an hour to afford the HCl salts of 6-[1-[1-[5-(1-methylimidazol-2-yl)sulfanyl-2-pyridyl]pyrazol-3-yl]ethyl]-3H-1,3-benzothiazol-2-one hydrochloride (Isomer 1), (80.1 mg, 20%) as a white solid and Isomer 2 (80 mg, 20% as a white solid.

EXAMPLE 35

Synthesis of 6-[1-[1-[5-(Triazol-1-ylmethyl)-2-pyridyl]pyrazol-3-yl]ethyl]-3H-1,3-benzothiazol-2-one hydrochloride, Isomer 1

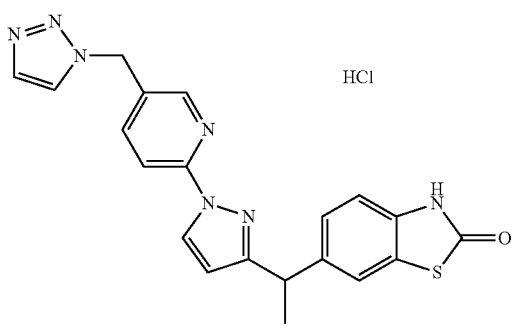 [SMILES: CC(c1ccc2[nH]c(=O)sc2c1)c1ccn(-c2ccc(Cn3ccnn3)cn2)n1 ; Cl]

The two enantiomers of 6-[1-[1-[5-(triazol-1-ylmethyl)-2-pyridyl]pyrazol-3-yl]ethyl]-3H-1,3-benzothiazol-2-one are separated by chiral chromatography using Chiralcel® OJ-H, 21×250 mm, 60% CO2/40% MeOH, 70 mL/min, 225 nm. Isomer 1 retention time is 3.6 min, (80.1 mg) as a white solid and Isomer 2 is 5.8 min, (79.8 mg) as a white solid Separately, the separated isomers were transferred to a tared bottle with DCM and concentrated in vacuo to a white solid (assume 100% transfer). Dissolve in MeOH (3 mL) and DCM (2 mL), and the clear and treat with 1.0 M HCl in Et2O (Aldrich). The solution is swirled for a few minutes, then concentrate, add Et2O (5 mL) and re-concentrate, place under high vacuum for an hour to afford the HCl salts 6-[1-[1-[5-(Triazol-1-ylmethyl)-2-pyridyl]pyrazol-3-yl]ethyl]-3H-1,3-benzothiazol-2-one hydrochloride (83.3 mg, 15%)(Isomer 1). Mass spectrum (m/z): 404 (M+1) and Isomer 2 (83.5 mg, 15%) Mass spectrum (m/z): 404 (M+1) as a white solids.

EXAMPLE 36

Isolation of 2-[[6-[3-[1-(2-Oxo-3H-1,3-benzothiazol-6-yl)ethyl]pyrazol-1-yl]-3-pyridyl]oxy]acetonitrile, Isomer 2

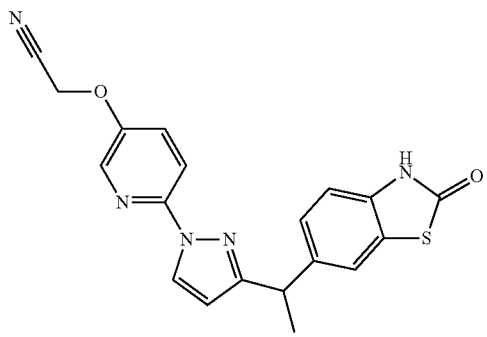 [SMILES: CC(c1ccc2[nH]c(=O)sc2c1)c1ccn(-c2ccc(OCC#N)cn2)n1]

The two enantiomers of 2-[[6-[3-[1-(2-Oxo-3H-1,3-benzothiazol-6-yl)ethyl]pyrazol-1-yl]-3-pyridyl]oxy]acetonitrile are separated by chiral chromatography using Chiralpak®, 3×25 cm, 20% ACN/80% MeOH, 30 mL/min, 225 nm Isomer 1 retention time is 9.1 min, (104 mg, 30%) as a white solid. Mass spectrum (m/z): 378 (M+1), and Isomer 2 is 14.6 min, (101 mg, 30%) as a white solid. Mass spectrum (m/z): 378 (M+1).

Preparation 119: Synthesis of 2-[[6-[3-[(1S)-1-(2-oxo-3H-1,3-benzothiazol-6-yl)ethyl]pyrazol-1-yl]-3-pyridyl]oxy]ethyl 2-(tert-butoxycarbonylamino)acetate

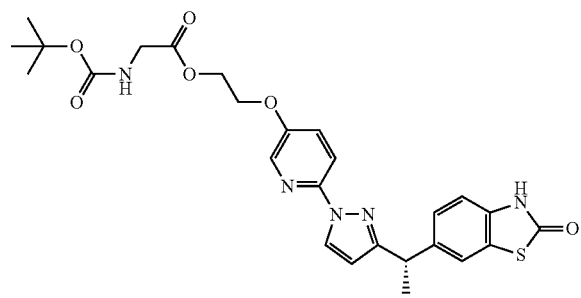 [SMILES: C[C@@H](c1ccc2[nH]c(=O)sc2c1)c1ccn(-c2ccc(OCCOC(=O)CNC(=O)OC(C)(C)C)cn2)n1]

To a solution of 2-(tert-butoxycarbonylamino)acetic acid (2.87 mmol, 504 mg) in dichloromethane (50 mL) is added 6-[(1S)-1-[1-[5-(2-hydroxyethoxy)-2-pyridyl]pyrazol-3-yl]ethyl]-3H-1,3-benzothiazol-2-one (2.6 mmol, 1.0 g), 1-(3-dimethylaminopropyl)-3-ethylcarbodiimide hydrochloride (2.88 mmol, 552 mg), 4-DMAP (0.53 mmol, 65 mg) and TEA (5.5 mmol, 0.77 mL) and stirred at room temperature for 18 h. Pour mixture into a separatory funnel with DCM (100 mL) and water (50 mL). Wash organic layer with water (50 mL) then brine (50 mL). Dry organic layer over Na$_2$SO$_4$, filter, and concentrate. Purify by LC (80 g silica) eluting with a gradient of EtOAc/Hexanes 2:8 to 100% EtOAc to give the title intermediate (1.1 g, 78%) as a white foam. Mass spectrum (m/z): 540 (M+1).

EXAMPLE 37

Synthesis of 2-[[6-[3-[(1S)-1-(2-oxo-3H-1,3-benzothiazol-6-yl)ethyl]pyrazol-1-yl]-3-pyridyl]oxy]ethyl 2-aminoacetate hydrochloride

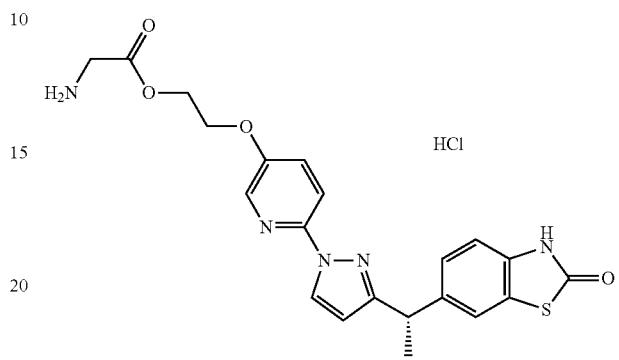

A solution of 2-[[6-[3-[(1S)-1-(2-oxo-3H-1,3-benzothiazol-6-yl)ethyl]pyrazol-1-yl]-3-pyridyl]oxy]ethyl 2-(tert-butoxycarbonylamino)acetate (0.834 mmol, 450 mg) in ethyl acetate (9 mL) is added to hydrochloric acid (4 M in 1,4-dioxane, 2.5 mmol, 0.63 mL) and let stir over night. Filter, wash with EtOAc and dry in vacuum oven to afford the title compound (221 mg, 56%) as a white solid. Mass spectrum (m/z): 440 (M+1).

Preparation 120: Synthesis of 6-[(1S)-1-[1-[5-(2-bromoethoxy)-2-pyridyl]pyrazol-3-yl]ethyl]-3H-1,3-benzothiazol-2-one

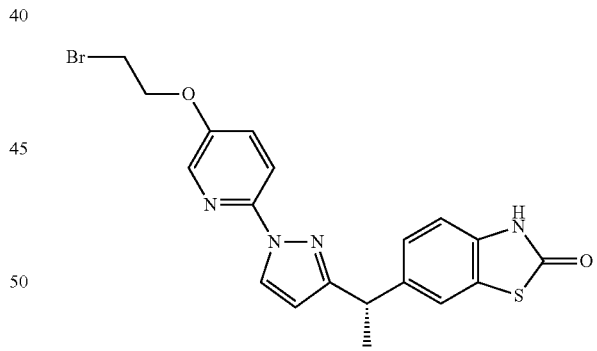

A slurry of 6-[(1S)-1-[1-[5-(2-hydroxyethoxy)-2-pyridyl]pyrazol-3-yl]ethyl]-3H-1,3-benzothiazol-2-one (0.523 mmol, 200 mg) in DCM (15 mL) is added carbon tetrabromide (0.829 mmol, 275 mg) and triphenylphosphine (0.629 mmol, 165 mg). Stir at room temperature for 3 hr then pour mixture into a separatory funnel with DCM (100 mL) and water (50 mL). Wash organic layer with water (2×) then brine (1×), and dry organic layer over Na$_2$SO$_4$, filter, and concentrate. Purify by LC (80 g silica) eluting with EtOAc/Hexane (2:8) gradient to 100% EtOAc to give the titled intermediate (100 mg, 43%) as a clear oil. Mass spectrum (m/z): 447 (M+1).

EXAMPLE 38

Synthesis of 6-[(1S)-1-[1-[5-(2-morpholinoethoxy)-2-pyridyl]pyrazol-3-yl]ethyl]-3H-1,3-benzothiazol-2-one hydrochloride

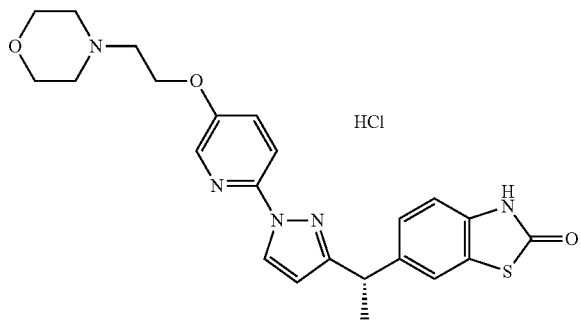 [SMILES: C[C@@H](c1ccc2[nH]c(=O)sc2c1)c1ccn(-c2ccc(OCCN3CCOCC3)cn2)n1 ; Cl]

A slurry of 6-[(1S)-1-[1-[5-(2-bromoethoxy)-2-pyridyl]pyrazol-3-yl]ethyl]-3H-1,3-benzothiazol-2-one (0.853 mmol, 380 mg) in 1,4-dioxane (8 mL) is added potassium carbonate (2.53 mmol, 350 mg) and Morpholine (2.5 mmol, 0.22 mL). Heat to 70° C. with stirring for 4 hours. Pour into a separatory funnel with EtOAc (100 mL) and water (50 mL). Wash organic layer with water (50 mL) then brine (50 mL). Dry organic layer over $Na_2SO_4$, filter, and concentrate. Purify by LC (120 g silica) eluting with a gradient of DCM/7M $NH_3$ in MeOH (98:2) to (90:10) to afford the free base of the title compound (240 mg, 62%) as a white solid. HCl salt prepared by dissolving in DCM (2 mL), adding 1.1 eq 1M HCl in Diethyl ether, and concentrating to afford the title compound (242 mg, 58%). Mass spectrum (m/z): 452 (M+1).

Preparation 121: Synthesis of 6-[1-[1-(5-bromo-2-pyridyl)pyrazol-3-yl]vinyl]-3H-1,3-benzothiazol-2-one

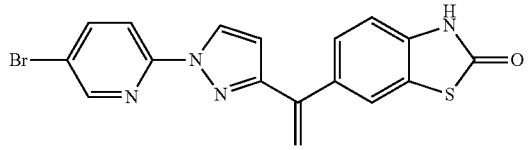

Add methylmagnesium bromide (3.2 M in MeTHF) (1.57 L, 5.02 mol) to a yellow suspension of 6-[1-(5-bromo-2-pyridyl)pyrazole-3-carbonyl]-3H-1,3-benzothiazol-2-one (650 g, 1.62 mol) in THF (6.50 L) at 23° C. dropwise over 30 minutes, turning to a dark green mixture and increasing the internal temperature to 43° C. Stir for 1 h while cooling to 23° C. Cool the mixture to 15° C. and quench the reaction by addition isopropyl alcohol (3.25 L, 42.51 mol) over 30 mins (reaction mixture turning to orange in colour and internal temperature rising to 45° C.). Cool again to 20° C. and add an ammonium chloride saturated aqueous solution (3 L and EtOAc (3 L). Wash organic layer with water (3 L) and evaporate the solvents.

The crude residue is suspended in THF (3.4 L) and isopropanol (1.7 L) and cooled to 10° C. Add Sulfuric Acid 98% (105.58 mL, 1.94 mol) dropwise over 20 minutes (internal temperature rises to 30° C.). Stir the mixture at 50° C. for 30 minutes. Cool again to 10° C. and add water (3 L) and methyl tert-butyl ether (2.5 L). Wash organic layer with water (1 L), saturated aqueous sodium carbonate (1 L) and brine (1 L). Evaporate solvent to afford desired compound as a yellow solid (592 g, 92%). M+1=400.

Preparation 122: Synthesis of 6-[1-[1-(5-bromo-2-pyridyl)pyrazol-3-yl]ethyl]-3H-1,3-benzothiazol-2-one

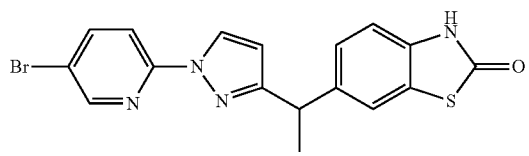 [SMILES: C=C(c1ccc2[nH]c(=O)sc2c1)c1ccn(-c2ccc(Br)cn2)n1]

Add a slurry of platinum on C (5%, sulphided) (31.46 g, 159.67 mmol) in ethyl acetate (157 mL) to a solution of 6-[1-[1-(5-bromo-2-pyridyl)pyrazol-3-yl]vinyl]-3H-1,3-benzothiazol-2-one (314.63 g, 788 mmol) in DMF (470 mL) and ethyl acetate (2.05 L). Stir the mixture under an atmosphere of hydrogen (60 psi) at 60° C. for 60 h. After cooling, filter through a pad of diatomaceous earth and wash the cake with DMF:EtOAc (1:20). Wash the filtrate with water (2×1.0 L) and re-extract the aqueous layer with EtOAc (1.0 L). Combine organic layers and wash with brine (3×1.0 L). Dry with magnesium sulphate and evaporate to afford the desired material (237.1 g, 75%). M+1=402.

Preparation 123: Synthesis of 6-[1-[1-(5-bromo-2-pyridyl)pyrazol-3-yl]ethyl]-3-(2-trimethylsilylethoxymethyl)-1,3-benzothiazol-2-one

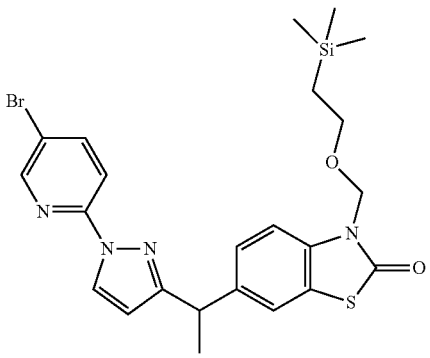 [SMILES: CC(c1ccc2c(c1)sc(=O)n2COCC[Si](C)(C)C)c1ccn(-c2ccc(Br)cn2)n1]

Add potassium carbonate (764.40 g, 5.48 mol) to a solution of 6-[1-[1-(5-bromo-2-pyridyl)pyrazol-3-yl]ethyl]-3H-1,3-benzothiazol-2-one (764.4 g, 895.29 mmol) in DMF (3.8 L) and stir for 10 minutes. Add 2-(trimethylsilyl)ethoxymethyl chloride (235.68 g, 250.62 mL, 1.34 mol) over 20 min and then stir the mixture for 16 h at 23° C. Add additional 2-(trimethylsilyl)ethoxymethyl chloride (39.28 g, 41.77 mL, 223.82 mmol) and stir for 24 h. Add methyl tert-butyl ether (5 L) and water (3 L), stir 5 min and let the mixture settle. Take the upper layer and evaporate the solvent. Purify the crude product by silica gel plug (100% dichloromethane) to give desired compound as an orange oil (450 g, 45%). M+1=532.

Preparation 124: Synthesis of 6-[1-[1-(5-hydroxy-2-pyridyl)pyrazol-3-yl]ethyl]-3-(2-trimethylsilylethoxymethyl)-1,3-benzothiazol-2-one

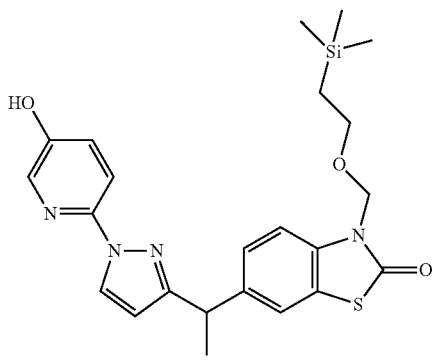 [SMILES: CC(c1ccc2c(c1)sc(=O)n2COCC[Si](C)(C)C)c1ccn(-c2ccc(O)cn2)n1]

Stir a suspension of 6-[1-[1-(5-bromo-2-pyridyl)pyrazol-3-yl]ethyl]-3-(2-trimethylsilylethoxymethyl)-1,3-benzothiazol-2-one (535 g, 1.01 mol) in 2-methyltetrahydrofuran (4 L) at 23° C. Add portionwise bis(pinacolato)diboron (281.15 g, 1.11 mol) and potassium acetate (296.34 g, 3.02 mol). Stir the mixture under nitrogen atmosphere and add (1,1'-bis(diphenylphosphino)ferrocene)palladium(II) chloride (25.16 g, 30.19 mmol). Stir then the reaction at 80° C. for 4 h. Cool down the mixture, add water (2 L) and discard the lower aqueous phase. Add sodium hydroxide (2.62 kg, 2.52 mol) to the organic phase (now ca. 30° C. internal), and stir for 10 min. Then add hydrogen peroxide (205.62 mL, 228.24 g, 2.01 mol) in 20 mL portions over 30 min and stir the whole mixture for 30 min and let it stand. Separate the organic layer and wash with sodium thiosulfate solution (0.5 L) and 10% aq. citric acid (1 L). Evaporate the organic layer to give a solid crude. Purify by silica gel plug (100% hexanes then 30% EtOAc in hexanes) to afford desired compound as a white solid (400 g, 74%). M+1=469.

Preparation 125: Synthesis of 6-[1-[1-[5-(2-Tetrahydropyran-2-yloxyethoxy)-2-pyridyl]pyrazol-3-yl]ethyl]-3-(2-trimethylsilylethoxymethyl)-1,3-benzothiazol-2-one

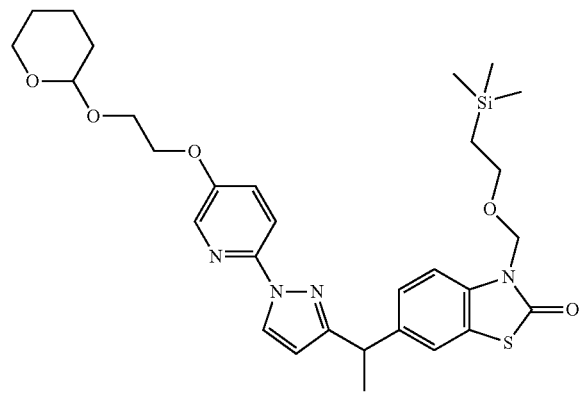 [SMILES: CC(c1ccc2c(c1)sc(=O)n2COCC[Si](C)(C)C)c1ccn(-c2ccc(OCCOC3CCCCO3)cn2)n1]

Add cesium carbonate (725.82 g, 2.23 mol) and 2-(2-chloroethoxyl)tetrahydro-2H-pyran (183.37 g, 167.01 mL, 1.50 equiv) to a solution of 6-[1-[1-(5-hydroxy-2-pyridyl)pyrazol-3-yl]ethyl]-3-(2-trimethylsilylethoxymethyl)-1,3-benzothiazol-2-one (400 g, 742.56 mmol) in acetonitrile (2 L). Stir the mixture at 90° C. for 3 h. Cool down the reaction and add cyclohexane (4 L) and water (4 L) and separate phases. Re-extract the aqueous layer with cyclohexane (2.5 L) and evaporate the combined organic layers to afford the desired compound as a brown oil (420 g, 81%). M+1=597.

Preparation 126: Synthesis of 6-acetyl-3-(2-trimethylsilylethoxymethyl)-1,3-benzothiazol-2-one

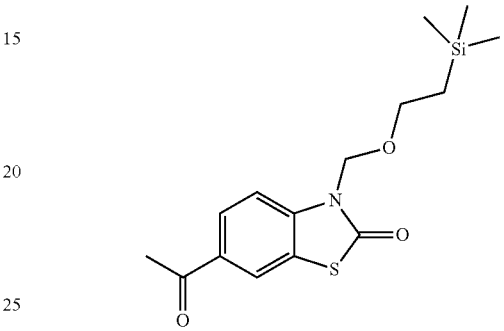

To a solution of 6-acetylbenzo[d]thiazol-2(3H)-one (780 g, 4.04 mol) in DMF (11.7 L) cooled at −10° C. is added sodium hydride (193.76 g, 8.07 mol) in 5 equal portions over 20 min Stir for 20 min at 0° C. and then add 2-(trimethylsilyl)ethoxymethyl chloride (857.3 mL, 4.84 mol) over 15 min Stir the mixture at 0° C. for 20 min and quench carefully with by addition of an aqueous saturated ammonium chloride solution (1 L) and water (1 L). Extract the mixture with EtOAc (5 L) and re-extract the aqueous phase with more EtOAc (3×2 L). Dry combined organic layers with sodium sulphate and evaporate the solvent a give the desired crude compound as a yellow oil (1 kg, 77%). M+1=324.

Preparation 127: Synthesis of 6-[1-(1H-pyrazol-5-yl)vinyl]-3-(2-trimethylsilylethoxymethyl)-1,3-benzothiazol-2-one

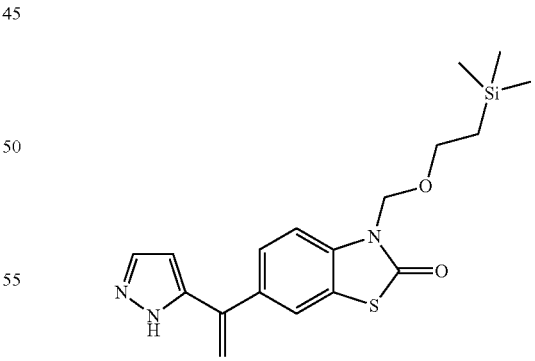

Cool a solution of 1-tetrahydropyran-2-yl-pyrazole (395.2 g, 2.60 mol) in THF (6.4 L) to −78° C. Add n-Butyl Lithium (2.5 M in hexane) (0.89 L, 2.225 mol) dropwise at −78° C., and stir the mixture for 60 min at that temperature. Then add a solution 6-acetyl-3-((2-(trimethylsilyl)ethoxy)methyl)benzo[d]thiazol-2(3H)-one (400 g, 1.24 mol) in THF (1.2 L) dropwise over 45 min and stir the whole reaction mixture at −78° C. for 3 h. Quench the reaction with isopropanol (0.89

L) at −78° C. and stirred for 16 h while warming to 23° C. Add then sulfuric acid (405 mL) at 23° C. and stir the mixture at 80° C. for 18 h. Cool the reaction mixture to 0° C. and add an aqueous solution of 2 M NaOH slowly until pH 11. Extract with EtOAc (2×3 L) and wash the organic phase with brine (2 L) and water (2×2 L). Dry over sodium sulphate and evaporate to give the crude material. Purify using a silica gel chromatography (0-3% MeOH in DCM) to yield the desired compound as a dark brown oil (382.3 g, 65%). M+1=476.

Preparation 128: Synthesis of 6-[1-(1H-pyrazol-5-yl)ethyl]-3-(2-trimethylsilylethoxymethyl)-1,3-benzothiazol-2-one

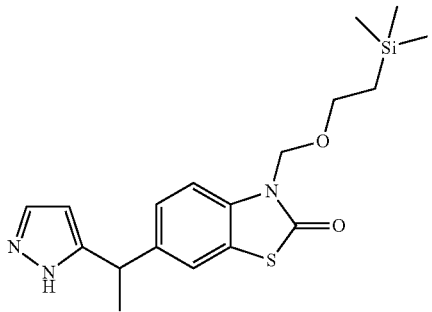 [SMILES: CC(c1ccc2c(c1)sc(=O)n2COCC[Si](C)(C)C)c1ccn[nH]1]

Add 10% palladium on carbon, 50% Wet (200 g, 0.5% W/W) to a solution of 6-(1-(1H-pyrazol-5-yl)vinyl)-3-(methoxymethyl)benzo[d]thiazol-2(3H)-one (400 g, 2.41 mol) in EtOAc (3.2 L). Place the mixture in a Parr reactor under a hydrogen atmosphere (20 psi) and stir at 23° C. for 16 h. Filter the mixture through diatomaceous earth, wash the cake with EtOAc (3×1 L) and evaporate the combined filtrates to give a dark yellow viscous oil. Purify by neutral alumina chromatography (1-10% EtOAc in hexanes) to afford desired compound as a solid (95.7 g, 23%). M+1=376.

Preparation 129: Synthesis of 6-[1-[1-(5-iodo-2-pyridyl)pyrazol-3-yl]ethyl]-3-(2-trimethylsilylethoxymethyl)-1,3-benzothiazol-2-one

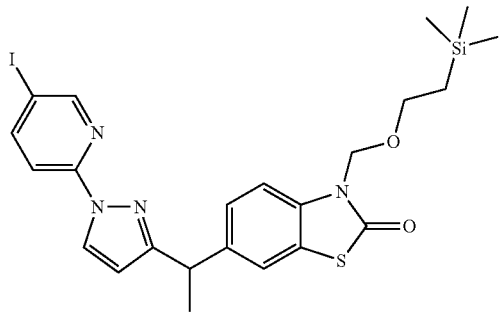 [SMILES: CC(c1ccc2c(c1)sc(=O)n2COCC[Si](C)(C)C)c1ccn(-c2ccc(I)cn2)n1]

Combine 6-(1-(1H-pyrazol-5-yl)ethyl)-3-((2-(trimethylsilyl)ethoxy)methyl)benzo[d]thiazol-2(3H)-one (350 g, 0.87 mol), 2-fluoro-5-iodopyridine (233.3 g, 1.05 mol) and cesium carbonate (642 g, 1.96 mol) in THF (1.2 L). Stir the mixture at 75° C. for 16 h. Evaporate the solvent and add toluene (5 L) to the residue. Filter the slurry and wash the cake with toluene (2×2 L). Evaporate combined organic filtrates and purify the residue using silica gel chromatography (0-15% EtOAc in hexanes) to afford the desired compound as a light yellow oil (337.5 g, 57%). M+1=579.

Preparation 130: Synthesis of 1-(6-fluoro-3-pyridyl)pent-4-en-1-ol

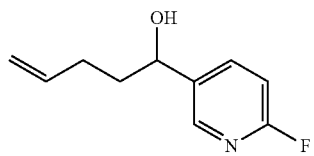

Dissolve 2-fluoro-5-formyl pyridine (5.70 g, 45.6 mmol) in THF (100 mL) and cool to −78° C. Slowly add via cannula, a solution of 3-butenylmagnesium bromide (100 mL, 50 mmol) over 20 min Stir the resulting mixture at −78° C. for 45 min, then warm to 0° C. and stir for 2 h, then allow mixture to warm to room temperature over 1 h. Slowly add saturated aq. solution of NaHCO$_3$ (100 mL) and pour the mixture into water (100 mL). Extract the mixture with diethyl ether (3×100 mL) and combine the organic solutions. Wash the organic solution with water (2×100 mL) and brine (100 mL), then dry over Na$_2$SO$_4$, filter and concentrate in vacuo. Purify the crude oil by flash chromatography, using a linear gradient of 100% hexanes to 80% EtOAc/hexanes as eluant, to give the title compound (5.16 g, 62%) as a clear colorless oil. MS [EI+] 182.0 (M+H)$^+$. $^1$H NMR (400 MHz, CDCl$_3$): δ 8.12 (m, 1H), 7.88 (dt, 1H, J=2.5, 8.3), 7.09 (dd, 1H, J=2.8, 8.5), 5.78 (m, 1H), 5.38 (d, 1H, J=4.6), 4.96 (m, 1H), 4.90 (m, 1H), 4.78 (m, 1H), 2.01 (m, 2H), 1.65 (m, 2H).

Preparation 131: Synthesis of [5-(6-fluoro-3-pyridyl)tetrahydrofuran-2-yl]methanol

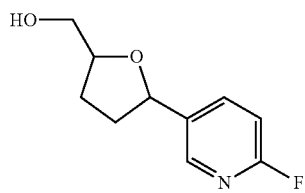 [SMILES: OCC1CCC(c2ccc(F)nc2)O1]

Dissolve 1-(6-fluoro-3-pyridyl)pent-4-en-1-ol (5.14 g, 28.4 mmol) in CH$_2$Cl$_2$ (280 mL) and cool to 0° C., then treat with m-chloroperoxybenzoic acid (5.34 g, 30.9 mmol). Stir the solution for 10 min at 0° C. then warm to room temperature and stir for 60 h. Add additional CH$_2$Cl$_2$ and wash the organic solution with aq. satd NaHCO$_3$ (200 mL), then dry the organic solution over MgSO$_4$, filter and concentrate in vacuo. Purify the crude material by flash chromatography, using a linear gradient of 10% EtOAc/hexanes to 100% EtOAc as eluant, to give the title compound (3.71 g, 66%) as a clear, colorless oil. MS [EI+] 198.0 (M+H)+. $^1$H NMR (400 MHz, DMSO-d$_6$): 8.17 (m, 1H), 7.92 (dt, 1H, J=2.8, 8.7), 7.11 (dd, 1H, J=2.8, 8.6), 4.88 (m, 1H), 4.72 (dt, 1H, J=5.5, 12.9), 4.06 (m, 1H), 3.44 (t, 1H, J=5.6), 3.39 (t, 1H, J=5.5) 2.26 (m, 1H), 1.95 (m, 1H), 1.70 (m, 2H).

Preparation 132: Synthesis of methyl 6-[3-[1-[2-oxo-3-(2-trimethylsilylethoxymethyl)-1,3-benzothiazol-6-yl]ethyl]pyrazol-1-yl]pyridine-3-carboxylate

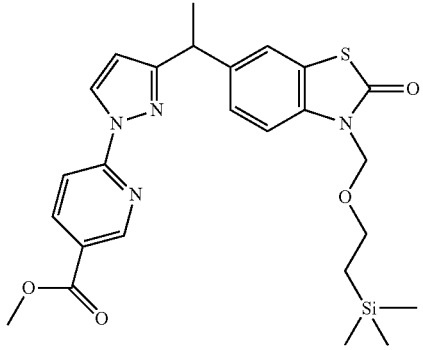

Dissolve 6-[3-[1-(2-oxo-3H-1,3-benzothiazol-6-yl)ethyl]pyrazol-1-yl]pyridine-3-carboxylate (23.8 g, 62.6 mmol) in dimethylformamide (350 mL) and cool to 0° C. Add sodium hydride (3.75 g, 93.8 mmol) in portions then, after 30 minutes add the 2-(trimethylsilyl)ethoxymethyl chloride (14.4 mL, 81.3 mmol) dropwise. Stir the mixture for three hours at room temperature then dilute with saturated sodium chloride, brine and ethyl acetate. Extract the aqueous twice with ethyl acetate then dry the combined organics with sodium sulfate, filter and evaporate. Chromatograph the mixture using a gradient from hexane to 20% ethyl acetate/hexane to give methyl 6-[3-[1-[2-oxo-3-(2-trimethylsilylethoxymethyl)-1,3-benzothiazol-6-yl]ethyl]pyrazol-1-yl]pyridine-3-carboxylate (15.7 g, 30.7 mmol, 49%). LCMS (low) rt=1.67 min, M+1=511.

Preparation 133: Synthesis of 6-[1-[1-[5-(hydroxymethyl)-2-pyridyl]pyrazol-3-yl]ethyl]-3-(2-trimethylsilylethoxymethyl)-1,3-benzothiazol-2-one

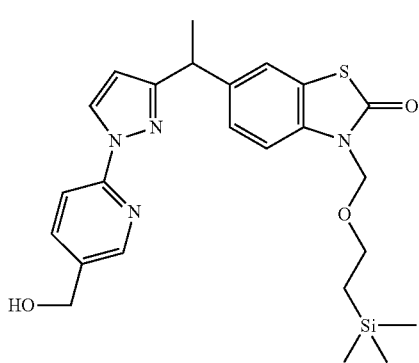 [SMILES: CC(c1ccc2c(c1)sc(=O)n2COCC[Si](C)(C)C)c1ccn(-c2ccc(CO)cn2)n1]

Dissolve methyl 6-[3-[1-[2-oxo-3-(2-trimethylsilylethoxymethyl)-1,3-benzothiazol-6-yl]ethyl]pyrazol-1-yl]pyridine-3-carboxylate (15.8 g, 30.9 mmol) in tetrahydrofuran (235 mL) and add lithium borohydride (2.02 mg, 92.8 mmol) at room temperature. Heat the mixture to 55° C. for four hours. Cool the mixture to 0° C. and carefully add aqueous saturated ammonium chloride solution then extract twice with ethyl acetate. Dry the organics with sodium sulfate then filter and evaporate to give 6-[1-[1-[5-(hydroxymethyl)-2-pyridyl]pyrazol-3-yl]ethyl]-3-(2-trimethylsilylethoxymethyl)-1,3-benzothiazol-2-one as a white solid (14.5 g, 28.5 mmol, 92%). LCMS (low) rt=1.45 min, M+1=483.

Preparation 134: Synthesis of 6-[3-[1-[2-oxo-3-(2-trimethylsilylethoxymethyl)-1,3-benzothiazol-6-yl]ethyl]pyrazol-1-yl]pyridine-3-carbaldehyde

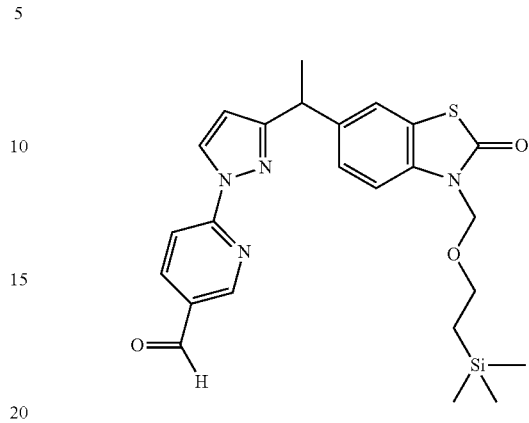

Dissolve 6-[1-[1-[5-(hydroxymethyl)-2-pyridyl]pyrazol-3-yl]ethyl]-3-(2-trimethylsilylethoxymethyl)-1,3-benzothiazol-2-one (14.5 g, 28.5 mmol) in chloroform (300 mL) and add manganese dioxide (24.8 g, 285 mmol). Heat the mixture to reflux for three hours then cool to room temperature and filter through diatomaceous earth. Evaporate the filtrate to give 6-[3-[1-[2-oxo-3-(2-trimethylsilylethoxymethyl)-1,3-benzothiazol-6-yl]ethyl]pyrazol-1-yl]pyridine-3-carbaldehyde as a light yellow oil (14.1 g, 28.5 mmol, 100%). LCMS (low) rt=1.58 min, M+1=481.

Preparation 135: Synthesis of 6-[1-[1-[5-(1-hydroxyethyl)-2-pyridyl]pyrazol-3-yl]ethyl]-3-(2-trimethylsilylethoxymethyl)-1,3-benzothiazol-2-one

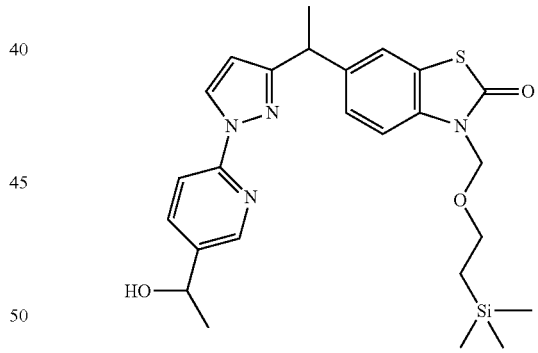

Dissolve 6-[3-[1-[2-oxo-3-(2-trimethylsilylethoxymethyl)-1,3-benzothiazol-6-yl]ethyl]pyrazol-1-yl]pyridine-3-carbaldehyde (14.1 g, 28.5 mmol) in tetrahydrofuran (140 mL) and cool the mixture to 0° C. Slowly add methylmagnesiumbromide (19 mL, 56.9 mmol, 3M in diethyl ether) and warm the mixture to room temperature for one hour. Dilute the mixture with saturated ammonium chloride and extract the mixture twice with ethyl acetate. Dry the organics with sodium sulfate then filter and evaporate the solution. Chromatograph the residue using a gradient from hexane to 70% ethyl acetate/hexane to give 6-[1-[1-[5-(1-hydroxyethyl)-2-pyridyl]pyrazol-3-yl]ethyl]-3-(2-trimethylsilylethoxymethyl)-1,3-benzothiazol-2-one as a yellow solid (9.3 g, 17.4 mmol, 61%). LCMS (low) rt=1.52 min, M+1=497.

Preparation 136: Synthesis of ethyl 2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetate

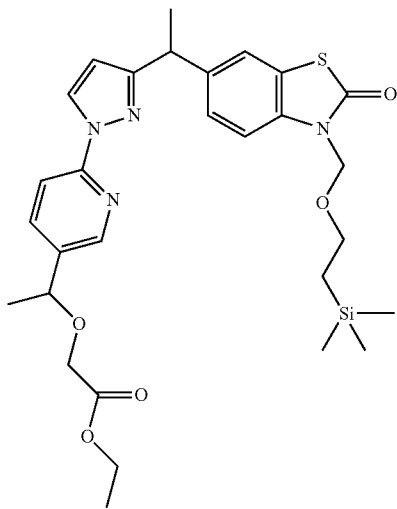 [SMILES: CCOC(=O)COC(C)c1ccc(-n2ccc(C(C)c3ccc4c(c3)sc(=O)n4COCC[Si](C)(C)C)n2)nc1]

Dissolve 6-[1-[1-[5-(1-hydroxyethyl)-2-pyridyl]pyrazol-3-yl]ethyl]-3-(2-trimethylsilylethoxymethyl)-1,3-benzothiazol-2-one (2.98 g, 5.6 mmol) in tetrahydrofuran (56 mL) and cool the mixture to 0° C. Add lithium bis(trimethylsilyl)amide (6.7 mL, 6.7 mmol, 1M solution in tetrahydrofuran) and warm the mixture to room temperature for one hour. Cool the mixture to 0° C. and add ethylbromoacetate (1.55 mL, 14 mmol) then allow the mixture to come to room temperature overnight. Dilute the mixture with saturated ammonium chloride and extract the mixture with ethyl acetate three times. Dry the organics with sodium sulfate then filter and evaporate. Chromatograph the residue using a gradient from hexane to 40% ethyl acetate in hexane to give ethyl ethyl 2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetate as a light yellow oil (1.55 g, 2.6 mmol, 46%). LCMS (low) rt=1.67 min, M+1=583.

Preparation 137: Synthesis of 6-[1-[1-[5-[1-(2-hydroxyethoxyl)ethyl]-2-pyridyl]pyrazol-3-yl]ethyl]-3-(2-trimethylsilylethoxymethyl)-1,3-benzothiazol-2-one

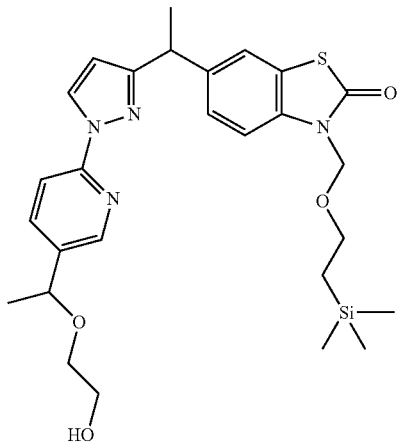 [SMILES: CC(OCCO)c1ccc(-n2ccc(C(C)c3ccc4c(c3)sc(=O)n4COCC[Si](C)(C)C)n2)nc1]

Dissolve ethyl 2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetate (1.54 g, 2.6 mmol) in tetrahydrofuran (33 mL) and add lithium borohydride (173 mg, 7.9 mmol) at room temperature. Heat the mixture to 50° C. for four hours. Cool the mixture to 0° C. and carefully add aqueous saturated ammonium chloride solution then extract twice with ethyl acetate. Dry the organics with sodium sulfate then filter and evaporate to give 6-[1-[1-[5-[1-(2-hydroxyethoxyl)ethyl]-2-pyridyl]pyrazol-3-yl]ethyl]-3-(2-trimethylsilylethoxymethyl)-1,3-benzothiazol-2-one as a clear oil (1.31 g, 2.4 mmol, 92%). LCMS (low) rt=1.52 min, M+1=541.

Preparation 138: Synthesis of 2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetic acid

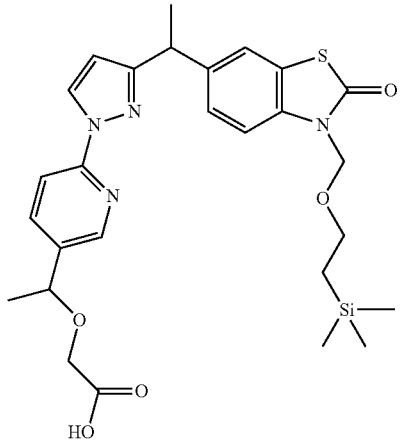 [SMILES: CC(OCC(=O)O)c1ccc(-n2ccc(C(C)c3ccc4c(c3)sc(=O)n4COCC[Si](C)(C)C)n2)nc1]

Dissolve ethyl 2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetate (4.2 g, 7.2 mmol) in tetrahydrofuran (69 mL) and add lithium hydroxide (3 g, 72.1 mmol) and water (16 mL). Stir the mixture overnight at room temperature. Make the solution basic with 1N sodium hydroxide and extract with diethyl ether. Make the aqueous acidic with 1N hydrochloric acid and extract twice with ethyl acetate. Dry the ethyl acetate extracts with sodium sulfate then filter and evaporate to give 2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetic acid as a white solid (4.3 g, 7.8 mmol, 108%). LCMS (low) rt=1.49 min, M+1=455.

Preparation 139: Synthesis of N-methoxy-N-methyl-2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetamide

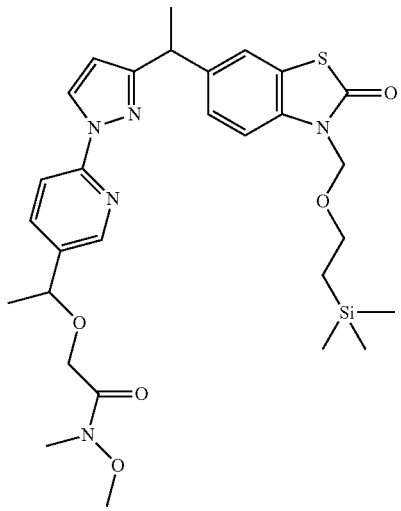 [SMILES: CON(C)C(=O)COC(C)c1ccc(-n2ccc(C(C)c3ccc4c(c3)sc(=O)n4COCC[Si](C)(C)C)n2)nc1]

Dissolve 2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetic acid (1.8 g, 3.3 mmol) in dichloromethane (12 mL) and add 1-(3-dimethylaminopropyl)-3-ethylcarbodiimide hydrochloride (0.91 g, 4.8 mmol), N,O-dimethylhydroxylamine hydrochloride (0.42 g, 4.3 mmol) and pyridine (2.2 mL, 27 mmol). Stir the mixture for three days. Dilute the mixture with saturated sodium bicarbonate and brine and extract twice with dichloromethane. Dry the organic fractions with sodium sulfate, filter and evaporate. Chromatograph the residue using a gradient from 30% ethyl acetate/hexane to 100% ethyl acetate to give N-methoxy-N-methyl-2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetamide as a white solid (3.6 g, 6.0 mmol, 185%). LCMS (low) rt=1.55 min, M+1=598.

Preparation 140: Synthesis of 6-[1-[1-[5-(1-Acetonyloxyethyl)-2-pyridyl]pyrazol-3-yl]ethyl]-3-(2-trimethylsilylethoxymethyl)-1,3-benzothiazol-2-one

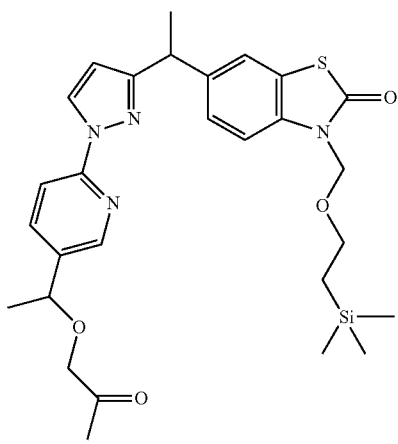 [SMILES: CC(=O)COC(C)c1ccc(-n2ccc(C(C)c3ccc4c(c3)sc(=O)n4COCC[Si](C)(C)C)n2)nc1]

Dissolve N-methoxy-N-methyl-2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetamide (3.6 g, 5.9 mmol) in tetrahydrofuran (60 mL) and cool the mixture to −20° C. Slowly add methylmagnesiumbromide (5.9 mL, 17.7 mmol, 3M solution in diethyl ether) and allow the mixture to warm to room temperature. Stir for an additional 20 minutes then dilute the mixture with saturated ammonium chloride. Extract the mixture 3 times with ethyl acetate. Dry the organics with sodium sulfate then filter and evaporate. Chromatograph the residue using a gradient from hexane to 60% ethyl acetate/hexane to give 6-[1-[1-[5-(1-acetonyloxyethyl)-2-pyridyl]pyrazol-3-yl]ethyl]-3-(2-trimethylsilylethoxymethyl)-1,3-benzothiazol-2-one as a white solid (2.7 g, 4.9 mmol, 83%). LCMS (low) rt=1.59 min, M+1=553.

Preparation 141: Isolation of 6-[1-[1-[5-(1-acetonyloxyethyl)-2-pyridyl]pyrazol-3-yl]ethyl]-3-(2-trimethylsilylethoxymethyl)-1,3-benzothiazol-2-one, isomers 1, 2, 3, and 4

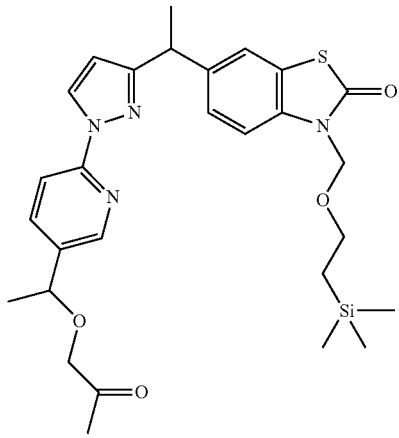 [SMILES: CC(=O)COC(C)c1ccc(-n2ccc(C(C)c3ccc4c(c3)sc(=O)n4COCC[Si](C)(C)C)n2)nc1]

Resolve 6-[1-[1-[5-(1-acetonyloxyethyl)-2-pyridyl]pyrazol-3-yl]ethyl]-3-(2-trimethylsilylethoxymethyl)-1,3-benzothiazol-2-one into its diasteriomers by two chiral chromatographies. In the first separation use Chiralpak® AD-H, 60/40 ACN/MeOH, 0.6 mL/min, 280 nm to obtain Isomer 1 and 2 as a mixture with retention time between 4 and 5.5 min Isomer 3 retention time is 6.5 min and isomer 4 is 13.3 min After separation of the third and forth diasteriomers, separate the first and second diasteriomers using Chiralpak® AD-H, 20/80 ACN/MeOH, 0.6 mL/min, 280 nm. Isomer 1 retention time is 8.1 min and Isomer 2 retention time is 9.9 min.

Preparation 142: Synthesis of 6-[1-[1-[5-[1-(2-hydroxypropoxy)ethyl]-2-pyridyl]pyrazol-3-yl]ethyl]-3-(2-trimethylsilylethoxymethyl)-1,3-benzothiazol-2-one

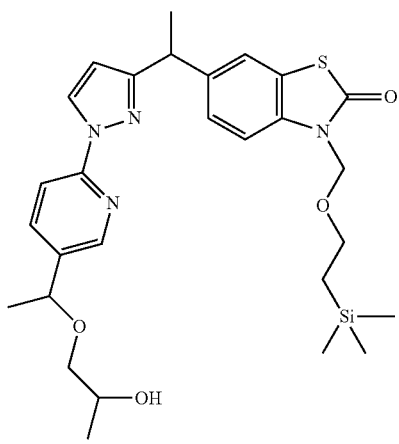 [SMILES: CC(O)COC(C)c1ccc(-n2ccc(C(C)c3ccc4c(c3)sc(=O)n4COCC[Si](C)(C)C)n2)nc1]

Dissolve 6-[1-[1-[5-(1-acetonyloxyethyl)-2-pyridyl]pyrazol-3-yl]ethyl]-3-(2-trimethylsilylethoxymethyl)-1,3-benzothiazol-2-one Isomer 3 (0.468 g, 0.85 mmol) in tetrahydrofuran (10 mL) and add lithium borohydride (55 mg, 2.5 mmol) at room temperature. Stir the mixture at room temperature for 3 hours. Cool the mixture to 0° C. and carefully add aqueous saturated ammonium chloride solution then extract twice with ethyl acetate. Dry the organics with sodium sulfate then filter and evaporate to give 6-[1-[1-[5-[1-(2-hydroxypropoxy)ethyl]-2-pyridyl]pyrazol-3-yl]ethyl]-3-(2-trimethylsilylethoxymethyl)-1,3-benzothiazol-2-one as a clear oil (0.43 g, 0.78 mmol, 92%). LCMS (low) rt=1.57 min, M+1=555.

Preparation 143: Synthesis of 6-[1-[1-[5-[2-(hydroxymethyl)morpholin-4-yl]-2-pyridyl]pyrazol-3-yl]ethyl]-3-(2-trimethylsilylethoxymethyl)-1,3-benzothiazol-2-one

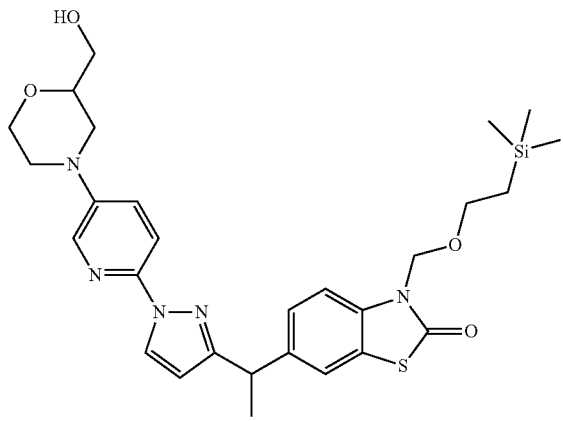 [SMILES: CC(c1ccc2c(c1)sc(=O)n2COCC[Si](C)(C)C)c1ccn(-c2ccc(N3CCOC(CO)C3)cn2)n1]

Potassium phosphate, tribasic (369 mg, 1.7 mmol, 2 equiv.) is added to a mixture of 6-[1-[1-[5-(5-iodo-2-pyridyl)pyrazol-3-yl]ethyl]-3-(2-trimethylsilylethoxymethyl)-1,3-benzothiazol-2-one (504 mg, 871 umol, 1 equiv.), morpholin-2-ylmethanol (153 mg, 1.3 mmol, 1.5 equiv.), 1,1¹-Bi-2-naphthol (50 mg, 174 umol, 0.2 equiv.), and copper(I) bromide (25 mg, 174 umol, 0.2 equiv.) in N,N-dimethylformamide (0.9 ml). The mixture is sparged with nitrogen for 3-4 minutes, and heated at 85° C. overnight. The mixture is diluted with tetrahydrofuran and then filtered through diatomaceous earth. The filtrate is concentrated to an oil which was purified by silica chromatography eluting with 20%-60% ethyl acetate in hexanes to give 6-[1-[1-[5-[2-(hydroxymethyl)morpholin-4-yl]-2-pyridyl]pyrazol-3-yl]ethyl]-3-(2-trimethylsilylethoxymethyl)-1,3-benzothiazol-2-one (102 mg, 0.21 mmol, 20%) as an oil. LCMS (low pH): 568, M+H, r.t.=1.46 min.

Preparation 144: Synthesis of 6-[1-[1-[5-(1-methylimidazol-2-yl)sulfanyl-2-pyridyl]pyrazol-3-yl]ethyl]-3-(2-trimethylsilylethoxymethyl)-1,3-benzothiazol-2-one

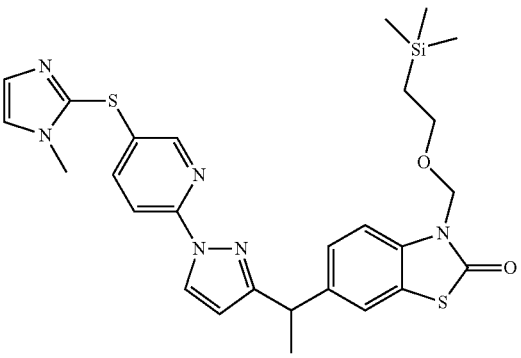 [SMILES: CC(c1ccc2c(c1)sc(=O)n2COCC[Si](C)(C)C)c1ccn(-c2ccc(Sc3nccn3C)cn2)n1]

Under an atmosphere of nitrogen add 6-[1-[1-(5-iodo-2-pyridyl)pyrazol-3-yl]ethyl]-3-(2-trimethylsilylethoxymethyl)-1,3-benzothiazol-2-one (1.2 g, 2.1 mmol), 3-methyl-1H-imidazole-2-thione (1.7 mmol, 200 mg), KOH (3.5 mmol, 200 mg) copper(I) oxide (12 mg, 0.083 mmol) and dioxane (7.0 mL) to a sealed vial. Heat to 110° C. for 16 hours, filter through diatomaceous earth and wash with EtOAc. Pour filtrate into a separatory funnel with EtOAc (100 mL) and water (50 mL). Wash organic layer with water (50 mL) then brine (50 mL). Dry organic layer over $Na_2SO_4$, filter, and concentrate. Purify via LC (120 g silica): dissolve crude mixture in minimum volume of DCM, add to column and elute with EtOAc/Hexane. 5:95 to EtOAc over 45 minutes to afford the title intermediate (1.1 g, 93%) as a clear foam. Mass spectrum (m/z): 565 (M+1).

Preparation 145: Synthesis of methyl 2,2-dimethyl-3-[[6-[3-[1-[2-oxo-3-(2-trimethylsilylethoxymethyl)-1,3-benzothiazol-6-yl]ethyl]pyrazol-1-yl]-3-pyridyl]oxy]propanoate

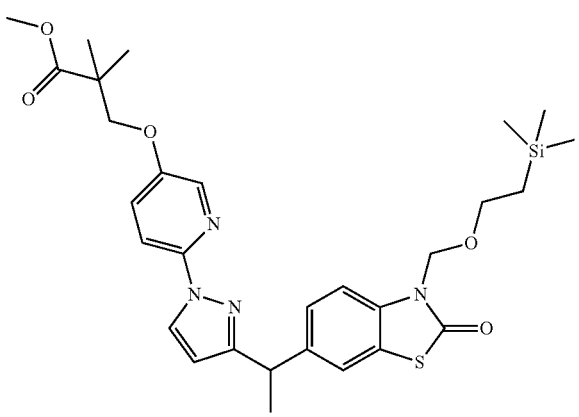

To a Screw-cap Vial is added 6-[1-[1-(5-hydroxy-2-pyridyl)pyrazol-3-yl]ethyl]-3-(2-trimethylsilylethoxymethyl)-1,3-benzothiazol-2-one (500 mg, 1.1 mmoles), 1,4-dioxane (6 mL), methyl 2,2-dimethyl-3-hydroxypropionate (155 mg, 1.2 mmoles), and triphenylphosphine (336 mg, 1.3 mmoles). The mixture is cooled in an ice bath and diisopropyl azodicarboxylate (254 μL, 1.3 mmoles) is added. The cooling bath is removed, and the mixture is stirred at room temperature for 4 h and then heated at 95° C. overnight. The mixture is partitioned between EtOAc and water. The aqueous phase is extracted with EtOAc (2×). The combined organic phase is washed with brine, dried (Na$_2$SO$_4$) and concentrated. The material is purified by flash chromatography (silica gel, 40 g, eluted hexane to 30% EtOAc/hexane) to yield methyl 2,2-dimethyl-3-[[6-[3-[1-[2-oxo-3-(2-trimethylsilylethoxymethyl)-1,3-benzothiazol-6-yl]ethyl]pyrazol-1-yl]-3-pyridyl]oxy]propanoate (422 mg, 68%). LCMS 93% (+) 583.3

Preparation 146: Synthesis of 6-[1-[1-[5-(3-hydroxy-2,2-dimethyl-propoxy)-2-pyridyl]pyrazol-3-yl]ethyl]-3-(2-trimethylsilylethoxymethyl)-1,3-benzothiazol-2-one

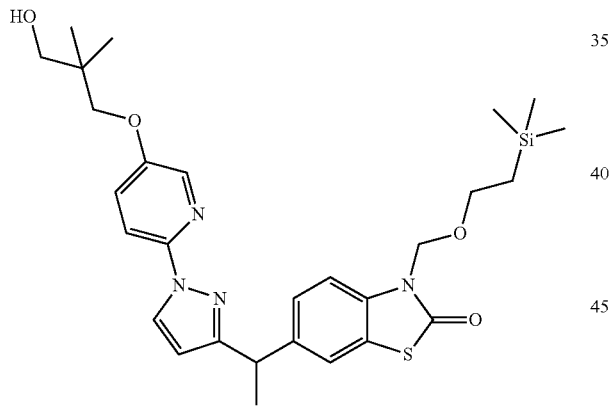

To a mixture of 6-[1-[1-[5-(3-tetrahydropyran-2-yloxypropoxy)-2-pyridyl]pyrazol-3-yl]ethyl]-3-(2-trimethylsilylethoxymethyl)-1,3-benzothiazol-2-one (420 mg, 0.72 mmoles) in tetrahydrofuran (7 mL) is added lithium borohydride (47 mg, 2.2 mmoles). The mixture is heated at 50° C. overnight. The mixture is partitioned between EtOAc and water. The aqueous phase is extracted with EtOAc (2×). The combined organic phase is washed with brine, dried (Na$_2$SO$_4$) and concentrated. The material is purified by flash chromatography (silica gel, 40 g, eluted hexane to 60% EtOAc/hexane) to yield 6-[1-[1-[5-(3-hydroxy-2,2-dimethyl-propoxy)-2-pyridyl]pyrazol-3-yl]ethyl]-3-(2-trimethylsilylethoxymethyl)-1,3-benzothiazol-2-one (230 mg, 58%). LCMS (+) 555.4.

Preparation 147: Synthesis of 6-[1-[1-(5-bromo-2-pyridyl)pyrazol-3-yl]ethyl]-3H-1,3-benzothiazol-2-one

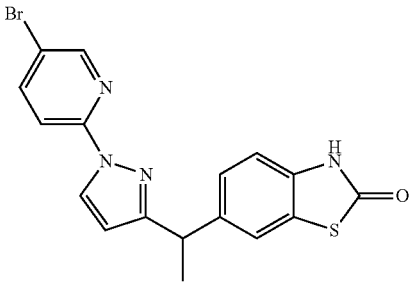 [SMILES: CC(c1ccc2[nH]c(=O)sc2c1)c1ccn(-c2ccc(Br)cn2)n1]

Dissolve 6-[1-[1-(5-bromo-2-pyridyl)pyrazol-3-yl]ethyl]-3-(methoxymethyl)-1,3-benzothiazol-2-one (38 mmol, 17 g) in TFA (115 mL) and heat to 70° C. for 18 h. Cool to room temperature and concentrate to an oil. Dissolve in THF (115 mL) add 28% aq.

NH$_4$OH (15 mL) and stir at room temperature for 30 minutes. Dilute with EtOAc (300 mL) and wash with water (100 mL) then Brine (100 mL). Dry over Sodium sulfate, filter, and concentrate to give a pale yellow solid. Slurry in EtOAc, filter and wash with 1:1 EtOAc/Hexanes to give the title intermediate (13 g, 85%) as a tan solid. Mass spectrum (m/z): 403 (M+1).

Preparation 148: Synthesis of 6-[1-[1-(5-Bromo-2-pyridyl)pyrazol-3-yl]ethyl]-3-(2-trimethylsilylethoxymethyl)-1,3-benzothiazol-2-one

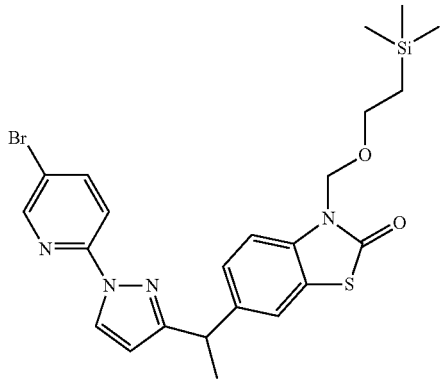 [SMILES: CC(c1ccc2c(c1)sc(=O)n2COCC[Si](C)(C)C)c1ccn(-c2ccc(Br)cn2)n1]

To a slurry of 6-[1-[1-(5-bromo-2-pyridyl)pyrazol-3-yl]ethyl]-3H-1,3-benzothiazol-2-one (32 mmol, 13 g), K$_2$CO$_3$ (101 mmol, 14 g) in DMF (97 mL) is added 2-(trimethylsilyl)ethoxymethyl chloride (46 mmol, 7.7 g). Stir at room temperature for 18 h. Dilute with EtOAc (300 mL) and wash with water (200 mL). Dry organic layer over sodium sulfate, filter, and concentrate. Purify by flash chromatography (silica) eluting with EtOAc/Hexanes 20:80 to give the title intermediate (10 g, 58%) as a clear oil.

Preparation 149: Synthesis of 6-[1-[1-(5-hydroxy-2-pyridyl)pyrazol-3-yl]ethyl]-3-(2-trimethylsilylethoxymethyl)-1,3-benzothiazol-2-one

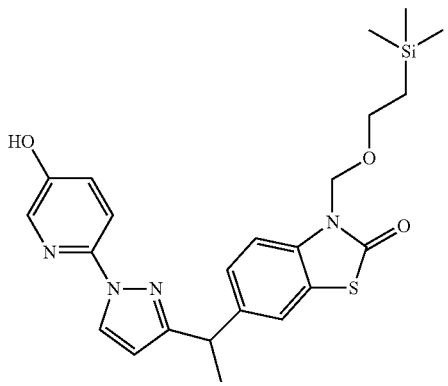 [SMILES: CC(c1ccc2c(c1)sc(=O)n2COCC[Si](C)(C)C)c1ccn(-c2ccc(O)cn2)n1]

To a mixture of 6-[1-[1-(5-bromo-2-pyridyl)pyrazol-3-yl]ethyl]-3-(2-trimethylsilylethoxymethyl)-1,3-benzothiazol-2-one (19 mmol, 10 g) in THF (190 mL) Add Bis(pinacolato)diboron (21 mmol, 5.3 g) and potassium acetate (56 mmol, 5.5 g). The reaction mixture is purged with $N_2$ for 30 min Add 1,1'-Bis(diphenylphosphino)ferrocene (0.56 mmol, 0.32 g). Heat to 80° C., purge for 5 minutes with nitrogen. Remove purge tube and heat for 3 h (internal temp 67° C.). Remove from heat and add water (40 mL) and transfer to a separatory funnel, when the internal temperature reaches 40° C. discard the water layer and return organic layer back to the flask. Add aqueous sodium hydroxide (1 M, 47 mL) and let stir for 10 minutes. Add aqueous hydrogen peroxide (10.6 M, 3.5 mL) in 3 portions over 10 min (an exotherm of 10° C. is observed). After 1.5 hours, add saturated aqueous sodium thiosulfate (~33 mmol, 10 mL). Transfer to a separatory funnel and vigorously shake and separate layers. Add aqueous citric acid (10%, 100 mL) and EtOAc (100 mL) and partition the phases. Dry organic layer over sodium sulfate, filter, and concentrate. Purify by LC (silica, 330 g) eluting with EtOAc/hexanes gradient from (30:70) to 100% EtOAc to afford the title intermediate (8.11 g, 92%). Mass spectrum (m/z): 469 (M+1).

Preparation 150: Synthesis of 2-[[6-[3-[1-[2-Oxo-3-(2-trimethylsilylethoxymethyl)-1,3-benzothiazol-6-yl]ethyl]pyrazol-1-yl]-3-pyridyl]oxy]acetonitrile

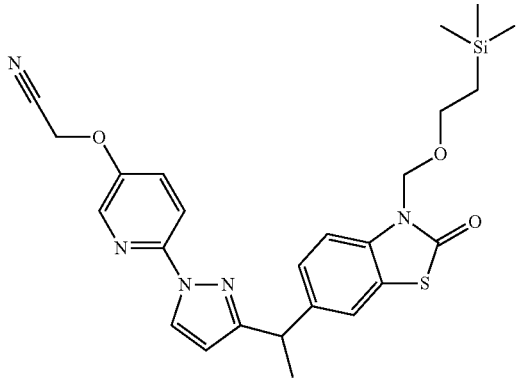 [SMILES: CC(c1ccc2c(c1)sc(=O)n2COCC[Si](C)(C)C)c1ccn(-c2ccc(OCC#N)cn2)n1]

Add cesium carbonate (4.27 mmol, 1.39 g) and bromoacetonitrile (32 mmol, 2.2 mL) to a solution of 6-[1-[1-(5-hydroxy-2-pyridyl)pyrazol-3-yl]ethyl]-3-(2-trimethylsilylethoxymethyl)-1,3-benzothiazol-2-one (2.1 mmol, 1.0 g) in DMF (8.5 mL), and stir overnight at room temperature. Pour the reaction mixture into a separatory funnel and dilute with EtOAc (200 ml) and water (100 mL). Partition the layers and wash organic layer with water (100 mL) then brine (100 mL). Dry the organic layer over $Na_2SO_4$, filter, and concentrate. Purify by LC (120 g silica) eluting with a gradient of EtOAc/hexanes (2:8) to (1:1) to afford the title intermediate (1.0 g, 92%) as a clear oil. Mass spectrum (m/z): 508 (M+1).

Preparation 151: Synthesis of 2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetic acid

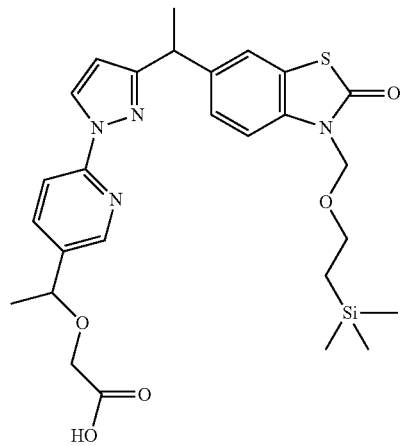 [SMILES: CC(OCC(=O)O)c1ccc(-n2ccc(C(C)c3ccc4c(c3)sc(=O)n4COCC[Si](C)(C)C)n2)nc1]

Dissolve ethyl 2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetate (4.2 g, 7.2 mmol) in tetrahydrofuran (69 mL) and add lithium hydroxide (3 g, 72.1 mmol) and water (16 mL). Stir the mixture overnight at room temperature. Make the solution basic with 1N sodium hydroxide and extract with diethyl ether. Make the aqueous acidic with 1N hydrochloric acid and extract twice with ethyl acetate. Dry the ethyl acetate extracts with sodium sulfate then filter and evaporate to give 2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetic acid as a white solid (4.3 g, 7.8 mmol, 108%). LCMS (low) rt=1.49 min, M+1=455.

Preparation 152: Synthesis of N-Methoxy-N-methyl-2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetamide

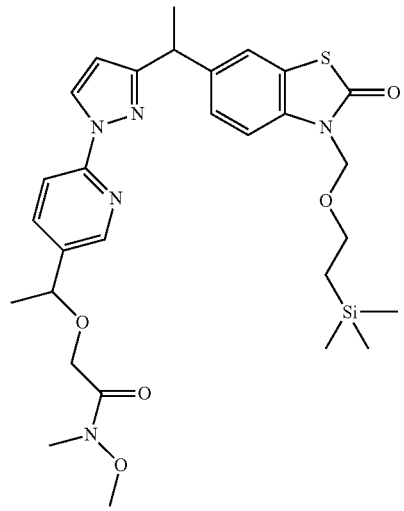 [SMILES: CON(C)C(=O)COC(C)c1ccc(-n2ccc(C(C)c3ccc4c(c3)sc(=O)n4COCC[Si](C)(C)C)n2)nc1]

Dissolve 2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetic acid (1.8 g, 3.3 mmol) in dichloromethane (12 mL) and add 1-(3-dimethylaminopropyl)-3-ethylcarbodiimide hydrochloride (0.91 g, 4.8 mmol), N,O-dimethylhydroxylamine hydrochloride (0.42 g, 4.3 mmol) and pyridine (2.2 mL, 27 mmol). Stir the mixture for three days. Dilute the mixture with saturated sodium bicarbonate and brine and extract twice with dichloromethane. Dry the organic fractions with sodium sulfate, filter and evaporate. Chromatograph the residue using a gradient from 30% ethyl acetate/hexane to 100% ethyl acetate to give N-methoxy-N-methyl-2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetamide as a white solid (3.6 g, 6.0 mmol, 185%). LCMS (low) rt=1.55 min, M+1=598.

Preparation 153: Synthesis of 6-[1-[1-[5-(1-acetonyloxyethyl)-2-pyridyl]pyrazol-3-yl]ethyl]-3-(2-trimethylsilylethoxymethyl)-1,3-benzothiazol-2-one

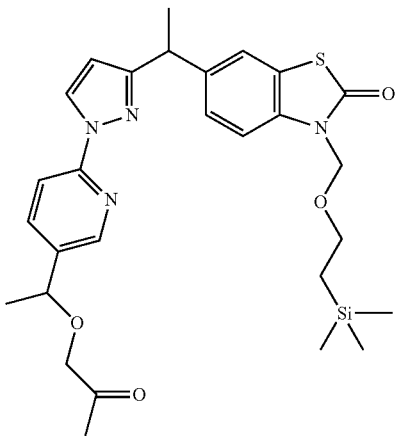 [SMILES: CC(=O)COC(C)c1ccc(-n2ccc(C(C)c3ccc4c(c3)sc(=O)n4COCC[Si](C)(C)C)n2)nc1]

Dissolve N-methoxy-N-methyl-2-[1-[6-[3-[1-[2-oxo-3-(2-trimethylsilylethoxymethyl)-1,3-benzothiazol-6-yl]ethyl]pyrazol-1-yl]-3-pyridyl]ethoxy]acetamide (3.6 g, 5.9 mmol) in tetrahydrofuran (60 mL) and cool the mixture to −20° C. Slowly add methylmagnesiumbromide (5.9 mL, 17.7 mmol, 3M solution in diethyl ether) and allow the mixture to warm to room temperature. Stir for an additional 20 minutes then dilute the mixture with saturated ammonium chloride. Extract the mixture 3 times with ethyl acetate. Dry the organics with sodium sulfate then filter and evaporate. Chromatograph the residue using a gradient from hexane to 60% ethyl acetate/hexane to give 6-[1-[1-[5-(1-acetonyloxyethyl)-2-pyridyl]pyrazol-3-yl]ethyl]-3-(2-trimethylsilylethoxymethyl)-1,3-benzothiazol-2-one as a white solid (2.7 g, 4.9 mmol, 83%). LCMS (low) rt=1.59 min, M+1=553.

Preparation 154: Synthesis of 6-[1-[1-[5-(1-acetonyloxyethyl)-2-pyridyl]pyrazol-3-yl]ethyl]-3-(2-trimethylsilylethoxymethyl)-1,3-benzothiazol-2-one, isomers 1, 2, 3 and 4

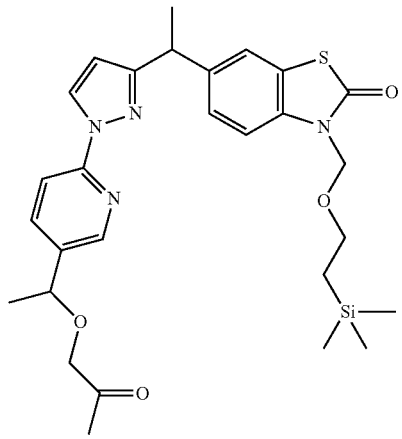 [SMILES: CC(=O)COC(C)c1ccc(-n2ccc(C(C)c3ccc4c(c3)sc(=O)n4COCC[Si](C)(C)C)n2)nc1]

Resolve 6-[1-[1-[5-(1-acetonyloxyethyl)-2-pyridyl]pyrazol-3-yl]ethyl]-3-(2-trimethylsilylethoxymethyl)-1,3-benzothiazol-2-one into its diasteriomers by two chiral chromatographies. In the first separation use Chiralpak® AD-H, 60/40 ACN/MeOH, 0.6 mL/min, 280 nm to obtain Isomer 1 and 2 as a mixture with retention time between 4 and 5.5 min Isomer 3 retention time is 6.5 min and isomer 4 is 13.3 min After separation of the third and forth diasteriomers, separate the first and second diasteriomers using Chiralpak® AD-H, 20/80 ACN/MeOH, 0.6 mL/min, 280 nm. Isomer 1 retention time is 8.1 min and Isomer 2 retention time is 9.9 min.

Preparation 155: Synthesis of 6-[1-[1-[5-[1-(2-hydroxypropoxy)ethyl]-2-pyridyl]pyrazol-3-yl]ethyl]-3-(2-trimethylsilylethoxymethyl)-1,3-benzothiazol-2-one

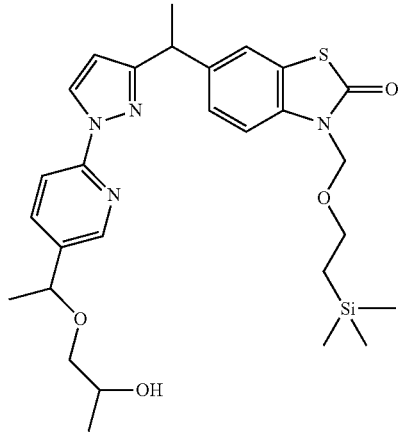 [SMILES: CC(O)COC(C)c1ccc(-n2ccc(C(C)c3ccc4c(c3)sc(=O)n4COCC[Si](C)(C)C)n2)nc1]

Dissolve 6-[1-[1-[5-(1-acetonyloxyethyl)-2-pyridyl]pyrazol-3-yl]ethyl]-3-(2-trimethylsilylethoxymethyl)-1,3-benzothiazol-2-one Isomer 3 (0.468 g, 0.85 mmol) in tetrahydrofuran (10 mL) and add lithium borohydride (55 mg, 2.5 mmol) at room temperature. Stir the mixture at room temperature for 3 hours. Cool the mixture to 0° C. and carefully add aqueous saturated ammonium chloride solution then extract twice with ethyl acetate. Dry the organics with sodium sulfate then filter and evaporate to give 6-[1-[1-[5-[1-(2-hydroxypropoxy)ethyl]-2-pyridyl]pyrazol-3-yl]ethyl]-

3-(2-trimethylsilylethoxymethyl)-1,3-benzothiazol-2-one as a clear oil (0.43 g, 0.78 mmol, 92%). LCMS (low) rt=1.57 min, M+1=555.

Preparation 156: Synthesis of 6-[1-[1-[5-(2-hydroxyethoxy)-2-pyridyl]pyrazol-3-yl]ethyl]-3H-1,3-benzothiazol-2-one

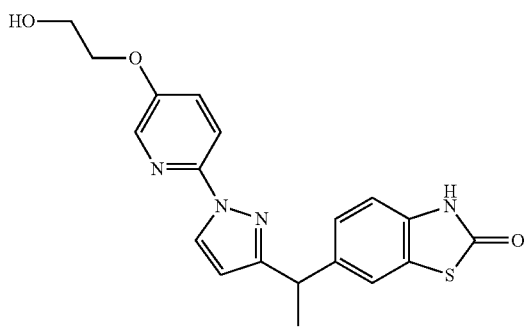 [SMILES: CC(c1ccc2[nH]c(=O)sc2c1)c1ccn(-c2ccc(OCCO)cn2)n1]

Add 6-[1-[1-[5-(2-tetrahydropyran-2-yloxyethoxy)-2-pyridyl]pyrazol-3-yl]ethyl]-3-(2-trimethylsilylethoxymethyl)-1,3-benzothiazol-2-one (269 g, 451 mmol) over 15 min. to trifluoroacetic acid (270 mL) and stir the mixture for 24 h at 23° C. Then add this mixture portionwise to an aqueous 2 M solution of sodium hydroxide (2.15 L) and stir 30 min Add CH$_2$Cl$_2$ (1 L), stir the mixture 15 min and let it settle. Discard the bottom organic layer and wash the upper layer with more CH$_2$Cl$_2$ (1 L). Discard bottom layer. Add an aqueous 5 M solution of ammonium chloride (1.07 kg, 1.08 L, 5.38 mol) and 2-methyltetrahydrofuran (1.6 L) to the upper layer and stir vigorously for 10 min Separate layers and re-extract aqueous phase with 2-methyltetrahydrofuran (0.8 L). Combined both organic layers and evaporate. Purifiy the residue using a silica gel plug (100% EtOAc) to afford desired compound as a white solid (103.4 g, 60%). M+1=383.

The following compounds are prepared essentially by the method of Preparation 156.

| Preparation | Name | Structure | mass |
|---|---|---|---|
| 157 | 6-[1-[1-[5-[1-(2-Hydroxyethoxy)ethyl]-2-pyridyl]pyrazol-3-yl]ethyl]-3H-1,3-benzothiazol-2-one | 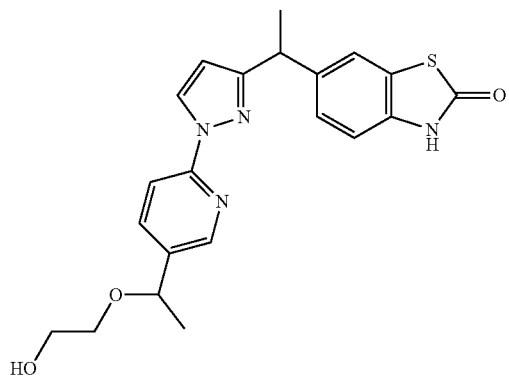 [SMILES: CC(OCCO)c1ccc(-n2ccc(C(C)c3ccc4[nH]c(=O)sc4c3)n2)nc1] | 411 |
| 158 | 6-[1-[1-[5-[1-(2-Hydroxypropoxy)ethyl]-2-pyridyl]pyrazol-3-yl]ethyl]-3H-1,3-benzothiazol-2-one | 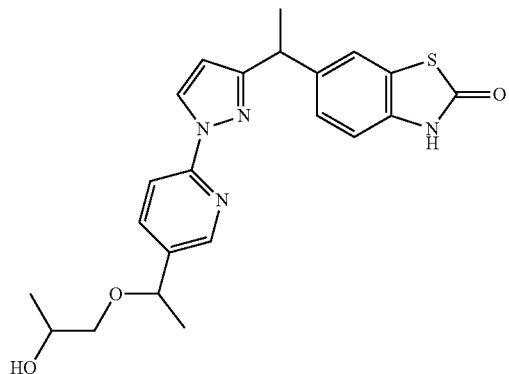 [SMILES: CC(O)COC(C)c1ccc(-n2ccc(C(C)c3ccc4[nH]c(=O)sc4c3)n2)nc1] | 425 |

-continued
| Preparation | Name | Structure | mass |
|---|---|---|---|
| 159 | 6-(1-(1-(5-(4-hydroxy-4-methylpiperidin-1-yl)pyridin-2-yl)-1H-pyrazol-3-yl)ethyl)benzo[d]thiazol-2(3H)-one | 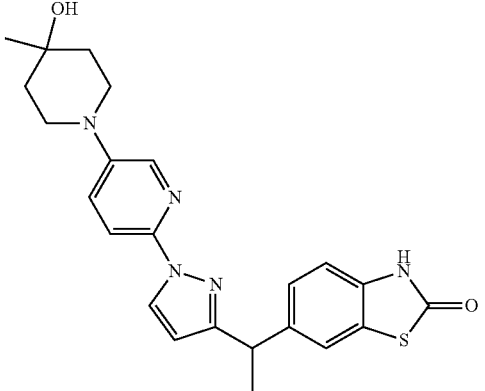 [SMILES: CC(c1ccc2[nH]c(=O)sc2c1)c1ccn(-c2ccc(N3CCC(C)(O)CC3)cn2)n1] | 436 |
| 160 | 6-(1-(1-(5-(4-(2-hydroxyethyl)piperidin-1-yl)pyridin-2-yl)-1H-pyrazol-3-yl)ethyl)benzo[d]thiazol-2(3H)-one | 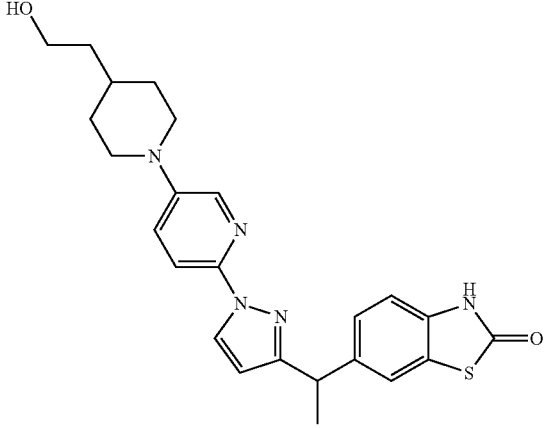 [SMILES: CC(c1ccc2[nH]c(=O)sc2c1)c1ccn(-c2ccc(N3CCC(CCO)CC3)cn2)n1] | 450 |
| 161 | 6-(1-(1-(5-((2-hydroxypropyl)thio)pyridin-2-yl)-1H-pyrazol-3-yl)ethyl)benzo[d]thiazol-2(3H)-one | 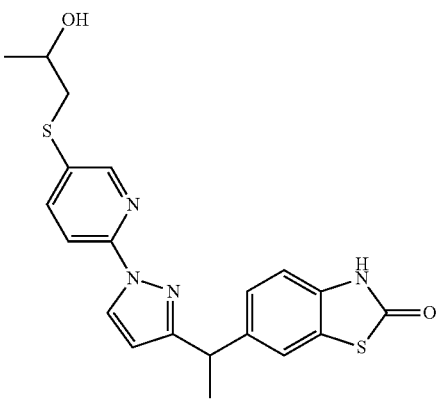 [SMILES: CC(O)CSc1ccc(-n2ccc(C(C)c3ccc4[nH]c(=O)sc4c3)n2)nc1] | 413 |

-continued
| Preparation | Name | Structure | mass |
|---|---|---|---|
| 162 | 6-(1-(1-(5-((1-hydroxypropan-2-yl)thio)pyridin-2-yl)-1H-pyrazol-3-yl)ethyl)benzo[d]thiazol-2(3H)-one | 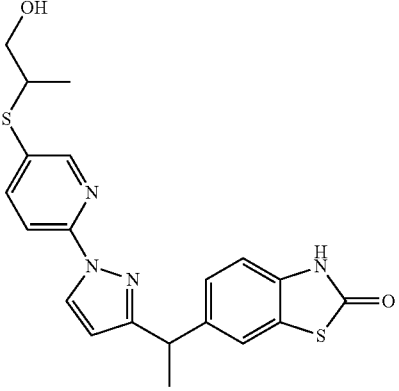 [SMILES: CC(CO)Sc1ccc(-n2ccc(C(C)c3ccc4[nH]c(=O)sc4c3)n2)nc1] | 413 |
| 163 | 6-(1-(1-(5-(3-hydroxy-3-methylazetidin-1-yl)pyridin-2-yl)-1H-pyrazol-3-yl)ethyl)benzo[d]thiazol-2(3H)-one | 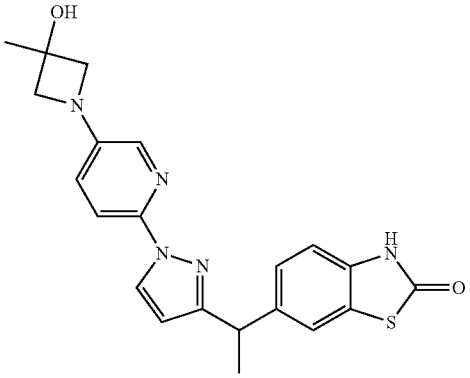 [SMILES: CC(c1ccc2[nH]c(=O)sc2c1)c1ccn(-c2ccc(N3CC(C)(O)C3)cn2)n1] | 408 |
| 164 | 6-(1-(1-(5-(3-methoxyazetidin-1-yl)pyridin-2-yl)-1H-pyrazol-3-yl)ethyl)benzo[d]thiazol-2(3H)-one | 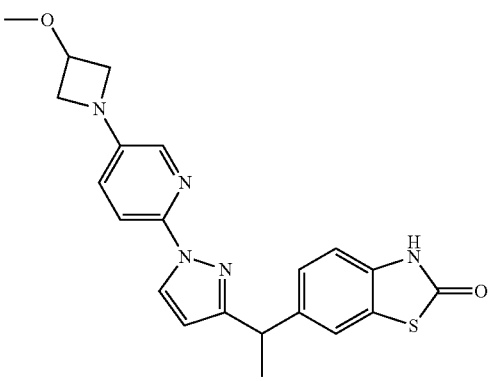 [SMILES: COC1CN(c2ccc(-n3ccc(C(C)c4ccc5[nH]c(=O)sc5c4)n3)nc2)C1] | 408 |
| 165 | 6-(1-(1-(5-(3-methoxy-3-methylazetidin-1-yl)pyridin-2-yl)-1H-pyrazol-3-yl)ethyl)benzo[d]thiazol-2(3H)-one | 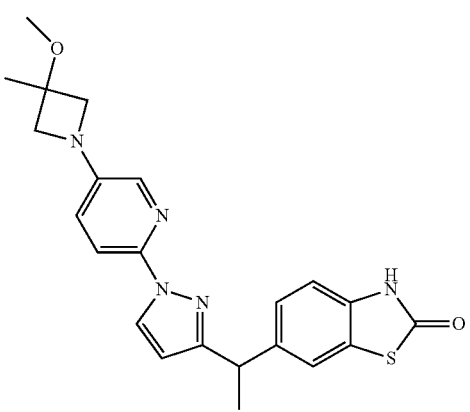 [SMILES: COC1(C)CN(c2ccc(-n3ccc(C(C)c4ccc5[nH]c(=O)sc5c4)n3)nc2)C1] | 422 |

-continued
| Preparation | Name | Structure | mass |
|---|---|---|---|
| 166 | 6-[1-[1-[5-[2-(hydroxymethyl)morpholin-4-yl]-2-pyridyl]pyrazol-3-yl]ethyl]-3H-1,3-benzothiazol-2-one | 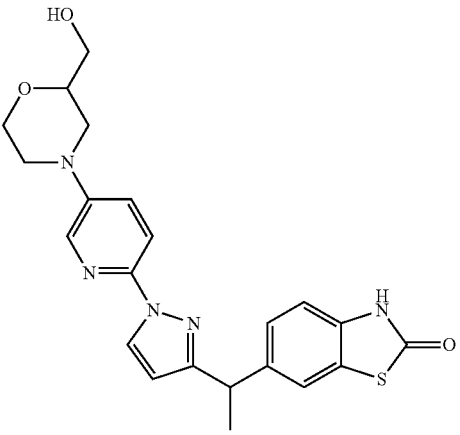 [SMILES: CC(c1ccc2[nH]c(=O)sc2c1)c1ccn(-c2ccc(N3CCOC(CO)C3)cn2)n1] | 438 |
| 167 | 6-[1-[1-[5-(3-hydroxy-2,2-dimethyl-propoxy)-2-pyridyl]pyrazol-3-yl]ethyl]-3H-1,3-benzothiazol-2-one | 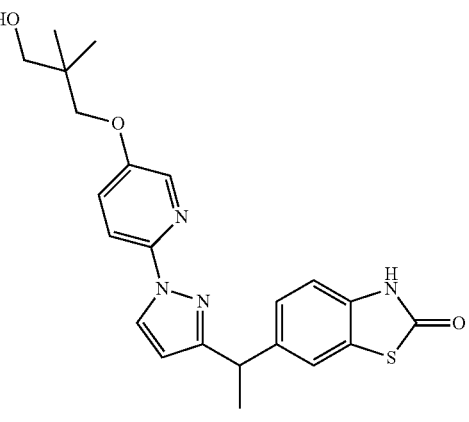 | 425 |
| 168 | 6-[1-[1-[5-(1-methylimidazol-2-yl)sulfanyl-2-pyridyl]pyrazol-3-yl]ethyl]-3H-1,3-benzothiazol-2-one hydrochloride | 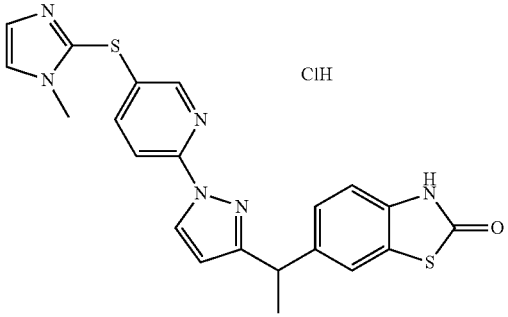 [SMILES: CC(c1ccc2[nH]c(=O)sc2c1)c1ccn(-c2ccc(Sc3nccn3C)cn2)n1 ; Cl] | 435 |
| 169 | 2-[[6-[3-[1-(2-Oxo-3H-1,3-benzothiazol-6-yl)ethyl]pyrazol-1-yl]-3-pyridyl]oxy]acetonitrile | 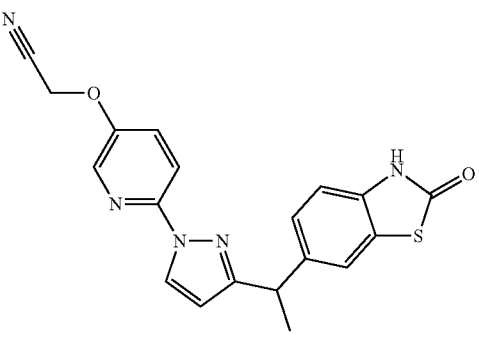 [SMILES: CC(c1ccc2[nH]c(=O)sc2c1)c1ccn(-c2ccc(OCC#N)cn2)n1] | 378 |

EXAMPLE 39 & 40

Isolation of 6-[1-[1-[5-[1-(2-hydroxyethoxyl)ethyl]-2-pyridyl]pyrazol-3-yl]ethyl]-3H-1,3-benzothiazol-2-one, iisomer 1

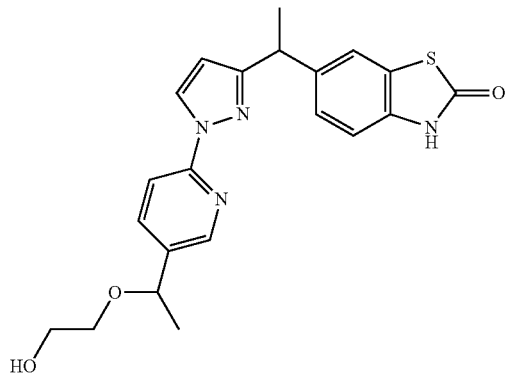 [SMILES: CC(OCCO)c1ccc(-n2ccc(C(C)c3ccc4[nH]c(=O)sc4c3)n2)nc1]

6-[1-[1-[5-(2-hydroxypropoxymethyl)-2-pyridyl]pyrazol-3-yl]ethyl]-3H-1,3-benzothiazol-2-one is resolved into its diasteriomers by two chiral chromatographies. In the first separation use Chiralpak® AD-H, 80/20 EtOH/ACN, 0.6 mL/min, 260 nm to obtain Isomer 1 and 2 as a mixture with retention time between 5 and 6.5 min Isomer 3 retention time is 7.6 min and isomer 4 is 14.3 min After separation of the third and forth diasteriomers, separate the first and second diasteriomers using Lux 10 u Cellulose-2, 60%/40% EtOH/heptane, 0.6 mL/min, 260 nm. Isomer 1 retention time is 5.9 min and Isomer 2 retention time is 8.1 min.

EXAMPLE 41

Isolation of 6-[1-[1-[5-[1-(2-hydroxypropoxyl)ethyl]-2-pyridyl]pyrazol-3-yl]ethyl]-3H-1,3-benzothiazol-2-one, Isomer 1

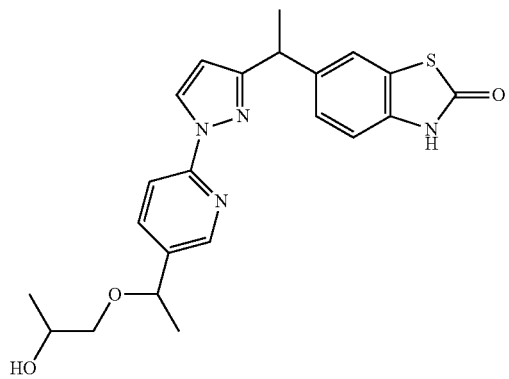 [SMILES: CC(O)COC(C)c1ccc(-n2ccc(C(C)c3ccc4[nH]c(=O)sc4c3)n2)nc1]

Resolve 6-[1-[1-[5-[1-(2-hydroxypropoxyl)ethyl]-2-pyridyl]pyrazol-3-yl]ethyl]-3H-1,3-benzothiazol-2-one into its stereoisomers by chiral chromatography using Chiralpak® AD-H, 90/10 MeOH/ACN (0.2% IPA), 1 mL/min., 225 nm. Isomer 1 retention time is 3.34 min and isomer 2 is 4.52 min.

EXAMPLE 42

Isolation of 6-(1-(1-(5-(4-hydroxy-4-methylpiperidin-1-yl)pyridin-2-yl)-1H-pyrazol-3-yl)ethyl)benzo[d]thiazol-2(3H)-one, Isomer 1

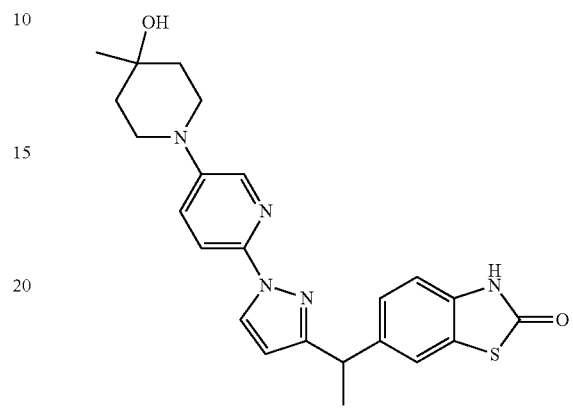

Compound 6-(1-(1-(5-(4-hydroxy-4-methylpiperidin-1-yl)pyridin-2-yl)-1H-pyrazol-3-yl)ethyl)benzo[d]thiazol-2(3H)-one (71 mg, 163.01 μmoles) is resolved into its enantiomers by SFC chiral chromatography using Lux Amylose-2, 40% MeOH/$CO_2$, 5 ml/min, 225 nm. Isomer 1 retention time is 2.6 min and isomer 2 is 3.1 min.

EXAMPLE 43

Isolation of 6-(1-(1-(5-(4-(2-hydroxyethyl)piperidin-1-yl)pyridin-2-yl)-1H-pyrazol-3-yl)ethyl)benzo[d]thiazol-2(3H)-one, Isomer 1

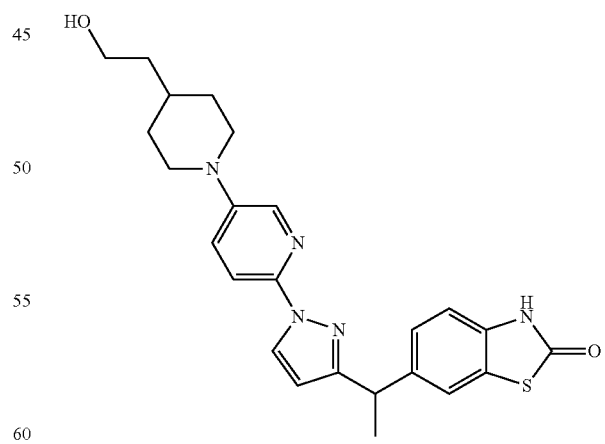

Compound 6-(1-(1-(5-(4-(2-hydroxyethyl)piperidin-1-yl)pyridin-2-yl)-1H-pyrazol-3-yl)ethyl)benzo[d]thiazol-2(3H)-one is resolved into its enantiomers using 3/2 MeOH/ACN 0.2% IPAm on Chiralpak® IA, 1.0 mL/min, 225 nm Isomer 1 retention time is 5.4 min and isomer 2 is 9.1 min.

EXAMPLE 46 & 47

Isolation of 6-(1-(1-(5-((2-hydroxypropyl)thio)pyridin-2-yl)-1H-pyrazol-3-yl)ethyl)benzo[d]thiazol-2(3H)-one, Isomer 3 and Isomer 4

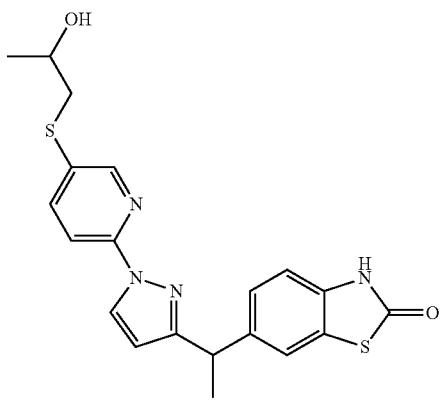 [SMILES: CC(O)CSc1ccc(-n2ccc(C(C)c3ccc4[nH]c(=O)sc4c3)n2)nc1]

Compound 6-(1-(1-(5-((2-hydroxypropyl)thio)pyridin-2-yl)-1H-pyrazol-3-yl)ethyl)benzo[d]thiazol-2(3H)-one is resolved into its enantiomers using Chiralpak® AD-H, 100% MeOH 0.2% IPAm, 1.0 mL/min, 225 nm Isomer 3 retention time is 6.8 min and isomer 4 is 8.0 min.

Preparation 170: Synthesis of 6-[(4-bromothiazol-2-yl)-hydroxy-methyl]-3H-1,3-benzothiazol-2-one

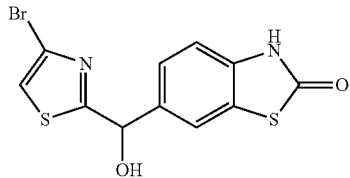

Add a solution of isopropylmagnesium chloride (4.2 L, 8.39 mol, 2 M in THF) dropwise over 30 min to a solution of 2,4-dibromo-1,3-thiazole (1529 g, 6.29 mol) in THF (1.5 L) cooled at −20° C. Stir the reaction at −20° C. for additional 30 min Add this cooled solution to a suspension of 2-oxo-2,3-dihydrobenzo[d]thiazole-6-carbaldehyde (376 g, 2.09 mol) in THF (2.6 L) at −20° C. dropwise over 30 min to maintain the internal temperature around −20° C. Remove the cooling bath and stir the mixture for 30 min. while warming up to 23° C. Quench the reaction by slow addition of a solution of saturated ammonium chloride (3 L) and extract with EtOAc (2×7.5 L). Wash the organic layer with brine (2×5 L), dry over sodium sulphate and evaporate the solvents to give a crude thick oil. Slurry the crude material with diethyl ether (1.5 L) for 30 min Filter, wash with diethyl ether (1 L) and dry under vacuum to afford the desired compound as a brown solid (558 g, 77%). M+1=344.

Preparation 171: Synthesis of 6-(4-bromothiazole-2-carbonyl)-3H-1,3-benzothiazol-2-one

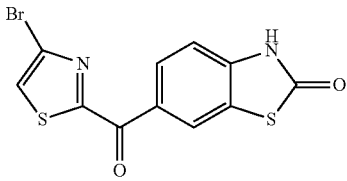

To a mechanical stirred solution of 6-[(4-bromothiazol-2-yl)-hydroxy-methyl]-3H-1,3-benzothiazol-2-one (1024 g, 3.03 mol) in 1,4-dioxane (6.24 L) at 60° C. is added MnO$_2$ (1711 g, 19.69 mol). Stir the mixture at 70° C. for 5 h. Filter the hot mixture through diatomaceous earth and wash the cake with hot 1,4-dioxane (10 L). Evaporate the combined filtrates to give the desired compound as a pale yellow solid (917 g, 88%). M+1=342.

Preparation 172: Synthesis of 6-[1-(4-bromothiazol-2-yl)-1-hydroxy-ethyl]-3H-1,3-benzothiazol-2-one

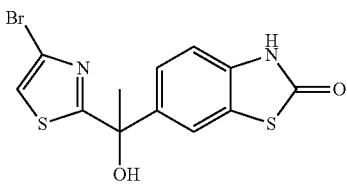 [SMILES: CC(O)(c1ccc2[nH]c(=O)sc2c1)c1nc(Br)cs1]

Cool to 0° C. a suspension of 6-[(4-bromothiazol-2-carbonyl)-benzo[d]thiazol-2-(3H)-one (220 g, 0.64 mol) in THF (4.4 L). Add a solution of methylmagnesium bromide (1.29 L, 1.93 mol, 1.5 M in THF) dropwise over 30 min at 0° C. Stir the mixture for 30 min while warming to 23° C. Quench the reaction by addition of a solution of saturate ammonium chloride (1.2 L) at 0° C. and extract with EtOAc (2×5 L). Wash the combined organic layers with brine (2×2.5 L), dry over sodium sulphate, and evaporate the solvent to yield the desired compound as a yellow foamy solid (215 g, 93%). M+1=357.

Preparation 173: Synthesis of 6-[1-(4-bromothiazol-2-yl)ethyl]-3H-1,3-benzothiazol-2-one

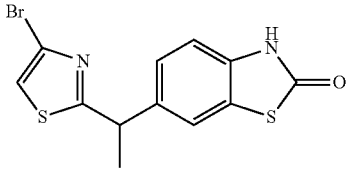

To a suspension of 6-(1-(4-bromothiazol-2-yl)-1-hydroxyethyl)benzo[d]thiazol-2(3H)-one (160 g, 0.45 mol) in dichloromethane (1.63 L) and trifluoroacetic acid (1.59 L) add triethylsilane (1073 mL, 6.74 mol) at 23° C. Stir the mixture at 23° C. for 24 h. Evaporate all volatiles and add THF (1.6 L) and a 0.2 M aqueous solution of ammonium hydroxide (1.6 L) to the residue and stir at 23° C. for 1 h.

Add then EtOAc (3 L) and a saturated aqueous solution of ammonium chloride (2.5 L). Separate the organic layer, washed with brine (1 L), dry over sodium sulphate and evaporate the volatiles. Dissolve the crude in EtOAc (470 mL) and add n-hexane (5 L) over 15 min at 23° C. and stir for 30 additional min Filter the solid, wash with n-hexane (500 mL) and dry under vacuum to obtain the desired compound as a yellow solid (112 g, 73%). M+1=342.

Preparation 174: Synthesis of 6-[1-(4-bromothiazol-2-yl)ethyl]-3-(methoxymethyl)-1,3-benzothiazol-2-one

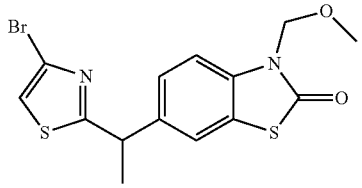 [SMILES: COCn1c(=O)sc2cc(C(C)c3nc(Br)cs3)ccc21]

Mix Cs₂CO₃ (238.6 g, 0.73 mol) with a solution of 6-(1-(4-bromothiazol-2-yl)ethyl)benzo[d]thiazol-2(3H)-one (100 g, 0.29 mol) in THF (1.5 L) and stir for 30 min. at 23° C. Add then chloromethyl methyl ether (33.0 g, 31.1 mL, 0.41 mol) dropwise over 15 min at 23° C. and stir for 2 h at that same temperature. Evaporate the reaction mixture, dissolve the crude oil with EtOAc (3 L) and wash with water (2 L). Separate the organic layer and wash with brine (2×500 mL), dry over sodium sulphate, and evaporate. Purify the residue by silica gel chromatography (30% EtOAc in hexanes) to afford the desired compound as a thick yellow oil (71.8 g, 63%). M+1=386.

Preparation 175: Synthesis of 2-bromo-5-(2-tetrahydropyran-2-yloxyethoxy)pyridine

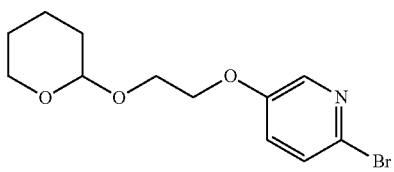 [SMILES: Brc1ccc(OCCOC2CCCCO2)cn1]

To a mixture of 2-bromo-5-hydroxypyridine (80 g, 450 mmol) in N,N-dimethylformamide (1 L) is added Cesium carbonate (293 g, 899 mmol) and 2-(2-bromoethoxyl)tetrahydropyran (71 mL, 451 mmol). The mixture is stirred at room temperature overnight. The mixture is filtered, and the filtrate is partitioned between EtOAc and water. The organic phase is washed with water and brine, dried (Na₂SO₄), and concentrated. The material is purified by flash chromatography (silica gel, 1000 g, eluting with 20% EtOAc/hexane) to give 2-bromo-5-(2-tetrahydropyran-2-yloxyethoxy)pyridine (123.7 g, 91%). LCMS (+) 302.0

Preparation 176: Synthesis of 3-(methoxymethyl)-6-[1-[4-[5-(2-tetrahydropyran-2-yloxyethoxy)-2-pyridyl]thiazol-2-yl]ethyl]-1,3-benzothiazol-2-one

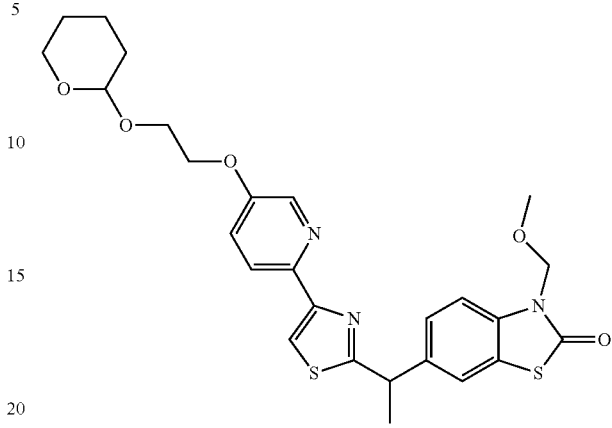

Compound 6-[1-(4-bromothiazol-2-yl)ethyl]-3-(methoxymethyl)-1,3-benzothiazol-2-one (10.7 g, 28 mmols) is dissolved in 1,4-Dioxane (230 mL) and to this added Bis(pinacolato)diboron (9 g, 35 mmoles), tris(dibenzylideneacetone)dipalladium (0) (1.3 g, 1.4 mmoles), potassium acetate (11 g, 112 mmols), and 2-(dicyclohexylphosphino)-2',4',6'-triisopropylbiphenyl (2.2 g, 4.5 mmoles). After the mixture is sparged with nitrogen for several minutes, the mixture is heated at 110° C. under nitrogen for 4 h. The mixture is cooled to room temperature, and a solution of 2-bromo-5-(2-tetrahydropyran-2-yloxyethoxy)pyridine (10.5 g, 35 mmoles) in 1,4-dioxane (6 mL) and a solution of potassium phosphate, tribasic, N-hydrate (26 g, 119 mmoles) in water (56 mL) are added. The mixture is heated at 110° C. overnight. The mixture is cooled to ambient temperature and diluted with EtOAc. The mixture is filtered through diatomaceous earth. The filtrate is washed with brine (2×), dried (Na2SO4), and concentrated. The material is purified by flash chromatography (silica gel, 330 g, 10% EtOAc/hexane to 30% EtOAc/hexane) to obtain 3-(methoxymethyl)-6-[1-[4-[5-(2-tetrahydropyran-2-yloxyethoxy)-2-pyridyl]thiazol-2-yl]ethyl]-1,3-benzothiazol-2-one (14 g, 95%). LCMS (+) 528.2.

EXAMPLE 48

Synthesis of 6-[1-[4-[5-(2-hydroxyethoxy)-2-pyridyl]thiazol-2-yl]ethyl]-3H-1,3-benzothiazol-2-one, Isomer 2

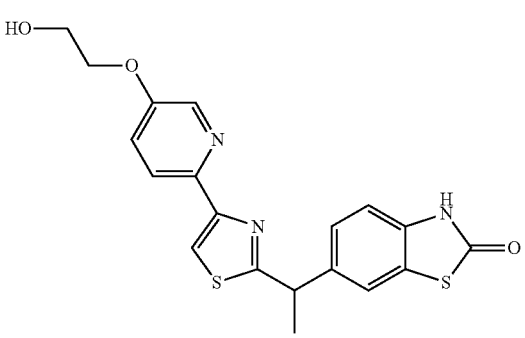 [SMILES: CC(c1ccc2[nH]c(=O)sc2c1)c1nc(-c2ccc(OCCO)cn2)cs1]

A mixture of 3-(methoxymethyl)-6-[1-[4-[5-(2-tetrahydropyran-2-yloxyethoxy)-2-pyridyl]thiazol-2-yl]ethyl]-1,3-benzothiazol-2-one (664 mg, 1.3 mmoles) and trifluoroacetic acid (15 mL) is heated at 70° C. overnight. The mixture is concentrated to dryness and, tetrahydrofuran (15 mL) and 28% ammonium hydroxide are added, and the mixture is stirred at room temperature for 1 h. The solvent is removed in vacuo, and the residue is purified by flash chromatography (silica gel, 80 g, eluted EtOAc to 50% THF/EtOAc to obtain racemic 6-[1-[4-[5-(2-hydroxyethoxy)-2-pyridyl]thiazol-2-yl]ethyl]-3H-1,3-benzothiazol-2-one (390 mg; 77% yield). LCMS (+) 400.0.

Racemic 6-[1-[4-[5-(2-hydroxyethoxy)-2-pyridyl]thiazol-2-yl]ethyl]-3H-1,3-benzothiazol-2-one is resolved into its enantiomers by chiral chromatography using Chiralpak® IA, 4.6×150 mm, 3/2 EtOH/ACN 0.2 IPAm, 1 mL/min, 225 nm. Isomer 1 retention time is 2.85 min and isomer 2 is 5.10 min.

Preparation 177: Synthesis of 2-chloro-5-(2-tetrahydropyran-2-yloxyethyl)pyridine

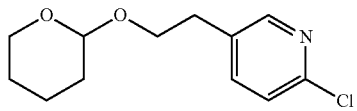 [SMILES: Clc1ccc(CCOC2CCCCO2)cn1]

A mixture of 2-(6-chloro-3-pyridyl)ethanol (4.6 g, 29.2 mmoles), dihydropyran (2.9 mL, 32 mmoles), dichloromethane (37 mL), and p-toluenesulfonic acid (251 mg, 1.46 mmoles) is stirred at room temperature for 2 hours. The solvent is evaporated to dryness, and the mixture purified by flash chromatography (120 g silica gel, using hexane MTBE from 20 to 60%) to give 2-chloro-5-(2-tetrahydropyran-2-yloxyethyl)pyridine (5.8 g, 82%) as a colorless oil. LCMS (+) 242.1

Preparation 178: Synthesis of 6-(4-bromothiazole-2-carbonyl)-3-(2-trimethylsilylethoxymethyl)-1,3-benzothiazol-2-one

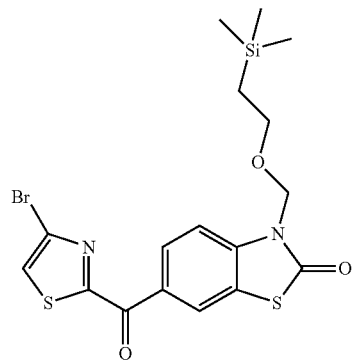 [SMILES: C[Si](C)(C)CCOCn1c(=O)sc2cc(C(=O)c3nc(Br)cs3)ccc21]

To a suspension cooled with an ice-water bath of 6-(4-bromothiazole-2-carbonyl)-3H-1,3-benzothiazol-2-one (6 g, 17.6 mmoles) in tetrahydrofuran (36 mL) is added portionwise sodium hydride (1.4 g, 35.2 mmoles, 60% dispersion). The suspension is stirred for 15 min and then 2-(trimethylsilyl)ethoxymethyl chloride (4.36 mL, 24.6 mmoles) is added dropwise over 10 min After 1 h, the reaction is quenched by addition of aqueous sat NH$_4$Cl dropwise. The phases are decanted, and the aqueous phase is washed with ethyl acetate (2×25 ml). The combined organic phase is washed with water and brine, dried (Na$_2$SO$_4$), and concentrated. The crude material (6 g) is purified by flash chromatography (hexanes-EtOAc 5%→25%) to obtain 6-(4-bromothiazole-2-carbonyl)-3-(2-trimethylsilylethoxymethyl)-1,3-benzothiazol-2-one (4.25 g, 51%) as a yellow solid. LCMS (+) 472.

Preparation 179: Synthesis of 6-[4-[5-(2-tetrahydropyran-2-yloxyethyl)-2-pyridyl]thiazole-2-carbonyl]-3-(2-trimethylsilylethoxymethyl)-1,3-benzothiazol-2-one

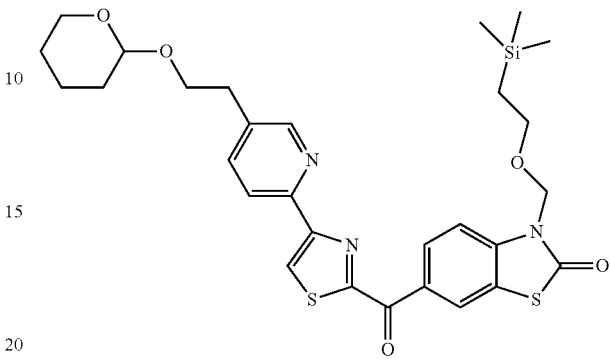

6-(4-Bromothiazole-2-carbonyl)-3-(2-trimethylsilylethoxymethyl)-1,3-benzothiazol-2-one (2 g, 4.2 mmoles) is dissolved in 1,4-dioxane (14 mL) and to this added bis (pinacolato)diboron (1.1 g, 4.24 mmoles), tris(dibenzylideneacetone)dipalladium (0) (78 mg, 85 μmoles), potassium acetate (833 mg, 8.5 mmoles) and 2-(dicyclohexylphosphino)-2',4',6'-triisopropylbiphenyl (324 mg, 0.67 mmoles). The mixture is heated 110° C. under nitrogen. After 2 h, a solution of 2-chloro-5-(2-tetrahydropyran-2-yloxyethyl) pyridine (1.0 g, 4.2 mmoles) and potassium phosphate, tribasic, N-hydrate (4.5 g, 17 mmoles) in 1,4-dioxane (1 mL) is added. The mixture is heated at 110° C. overnight. The mixture is cooled to ambient temperature and diluted with MeOH. The mixture is filtered through diatomaceous earth and the solvent removed. The residue is purified by flash chromatography (silica gel, 330 g, 30% EtOAc/hexane) to give 6-[4-[5-(2-tetrahydropyran-2-yloxyethyl)-2-pyridyl]thiazole-2-carbonyl]-3-(2-trimethylsilylethoxymethyl)-1,3-benzothiazol-2-one (0.85 g, 34%). LCMS (+) 854.

Preparation 180: Synthesis of 6-[1-hydroxy-1-[4-[5-(2-tetrahydropyran-2-yloxyethyl)-2-pyridyl]thiazol-2-yl]ethyl]-3-(2-trimethylsilylethoxymethyl)-1,3-benzothiazol-2-one

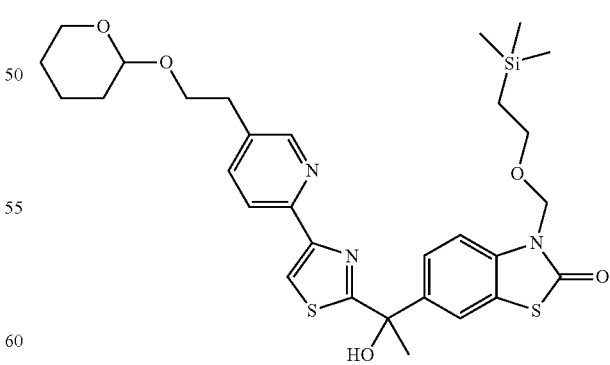

To a mixture of 6-[4-[5-(2-tetrahydropyran-2-yloxyethyl)-2-pyridyl]thiazole-2-carbonyl]-3-(2-trimethylsilylethoxymethyl)-1,3-benzothiazol-2-one (0.99 g 1.7 mmoles) in tetrahydrofuran (7 mL) at 0° C. is added a 3 M solution of methylmagnesium bromide in diethyl ether (1.7 mL, 5 mmoles). After a few minutes the cooling bath is removed, and the reaction mixture is warmed to room temperature. After 2.5 h, the mixture is partitioned between EtOAc and water. The aqueous phase is extracted with EtOAc (2×). The combined organic phase is washed with brine, dried (Na₂SO₄), and concentrated. The material is purified by flash chromatography (80 g silica gel, eluted 20-60% EtOAc/hexane) to yield 6-[1-hydroxy-1-[4-[5-(2-tetrahydropyran-2-yloxyethyl)-2-pyridyl]thiazol-2-yl]ethyl]-3-(2-trimethylsilylethoxymethyl)-1,3-benzothiazol-2-one (0.6 g, 59%). LCMS (+) 614.2.

Preparation 181: Synthesis of 6-[1-[4-[5-(2-hydroxyethyl)-2-pyridyl]thiazol-2-yl]vinyl]-3H-1,3-benzothiazol-2-one

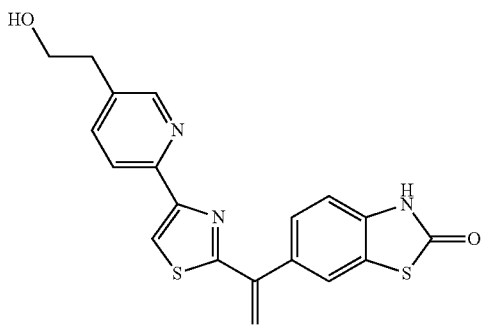 [SMILES: C=C(c1ccc2[nH]c(=O)sc2c1)c1nc(-c2ccc(CCO)cn2)cs1]

To a mixture of 6-[1-hydroxy-1-[4-[5-(2-tetrahydropyran-2-yloxyethyl)-2-pyridyl]thiazol-2-yl]ethyl]-3-(2-trimethylsilylethoxymethyl)-1,3-benzothiazol-2-one (600 mg, 0.98 mmoles) in Dichloromethane (5 mL) is added Trifluoroacetic Acid (5 mL). The mixture is stirred at room temperature for 5 h and then concentrated to dryness. Tetrahydrofuran (5 mL) and 28% Ammonium Hydroxide (5 mL) are added, and the mixture is stirred for 1 h. The mixture is partitioned between EtOAc and water. The aqueous phase is extracted with EtOAc (2×). The combined organic phase is washed with brine, dried (Na₂SO₄), and concentrated. The material is purified by flash chromatography (silica gel, hexane to 100% EtOac/hexane) to obtain 6-[1-[4-[5-(2-hydroxyethyl)-2-pyridyl]thiazol-2-yl]vinyl]-3H-1,3-benzothiazol-2-one (0.21 g; 56%). LCMS (+) 382.2

EXAMPLE 49

Synthesis of 6-[1-[4-[5-(2-hydroxyethyl)-2-pyridyl]thiazol-2-yl]ethyl]-3H-1,3-benzothiazol-2-one, Isomer 2

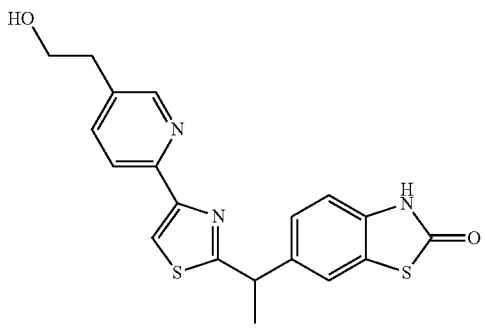 [SMILES: CC(c1ccc2[nH]c(=O)sc2c1)c1nc(-c2ccc(CCO)cn2)cs1]

A mixture of 6-[1-[4-[5-(2-hydroxyethyl)-2-pyridyl]thiazol-2-yl]vinyl]-3H-1,3-benzothiazol-2-one (0.21 g, 0.55 mmoles), Methanol (30 mL), and 10% palladium on carbon (50 mg is placed under a hydrogen blanket and stirred overnight. The mixture is filtered through a pad of diatomaceous earth and concentrated. The material is purified by flash chromatography (silica gel, eluted 4% MeOH/DCM) to obtain racemic 6-[1-[4-[5-(2-hydroxyethyl)-2-pyridyl]thiazol-2-yl]ethyl]-3H-1,3-benzothiazol-2-one (55 mg, 26%). LCMS (+) 383.8

Racemic 6-[1-[4-[5-(2-hydroxyethyl)-2-pyridyl]thiazol-2-yl]ethyl]-3H-1,3-benzothiazol-2-one is resolved into its enantiomers by chiral chromatography using Chiralpak® AD-H, 4.6×150 mm, 3/2 EtOH/ACN 0.2% IPAm, 1 mL/min, 225 nm. Isomer 1 retention time is 2.67 min and isomer 2 is 3.67 min.

Preparation 182: Synthesis of 4-(6-bromo-3-pyridyl)-2-methyl-but-3-yn-2-ol

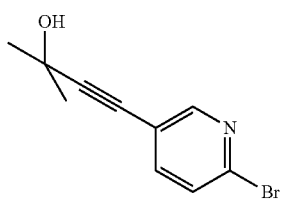

To a flask is added copper(I) iodide (326 mg, 1.7 mmoles) and bis(triphenylphosphine)palladium(II) chloride (1.2 g, 1.7 mmoles). The flask is evacuated and flushed with nitrogen. 2-Bromo-5-iodopyridine (4.76 g, 17 mmoles), triethylamine (0.2 M; 84 mL), and 3-methyl butynol (2.1 g, 25 mmoles) are added, and nitrogen is bubbled into mixture for several minutes. The mixture is stirred at room temperature for 0.5 h. Saturated NH₄Cl is added, and the mixture is partitioned between EtOAc and water. The aqueous phase is extracted with EtOAc (2×). The combined organic phase is washed with brine, dried (Na₂SO₄) and concentrated. The material is purified by flash chromatography (silica gel, 330 g, eluted hexane to 70% EtOAc/hexane) to obtain 4-(6-bromo-3-pyridyl)-2-methyl-but-3-yn-2-ol (3.38 g; 84%).

Preparation 183: Synthesis of 2-bromo-5-(3-methyl-3-tetrahydropyran-2-yloxy-but-1-ynyl)pyridine

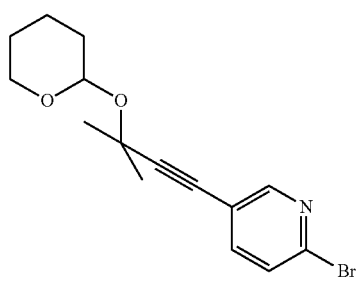 [SMILES: CC(C)(C#Cc1ccc(Br)nc1)OC1CCCCO1]

A mixture of 4-(6-bromo-3-pyridyl)-2-methyl-but-3-yn-2-ol (3.38 g, 14.1 mmoles), dichloromethane (35 mL), dihydropyran (1.5 mL, 17 mmoles; 1.54 mL), and p-toluenesulfonic acid (134 mg, 0.7 mmoles) is stirred at room temperature overnight. Saturated NH₄Cl is added, and the mixture is partitioned between DCM and water. The organic phase is washed with brine, dried (Na₂SO₄) and concentrated. The material is purified by flash chromatography (silica gel, 330 g, eluted hexane to 60% EtOAc/hexane) to obtain 2-bromo-5-(3-methyl-3-tetrahydropyran-2-yloxy-but-1-ynyl)pyridine (2.68 g; 59%).

Preparation 184: Synthesis of 3-(methoxymethyl)-6-[1-[4-[5-(3-methyl-3-tetrahydropyran-2-yloxy-but-1-ynyl)-2-pyridyl]thiazol-2-yl]ethyl]-1,3-benzothiazol-2-one

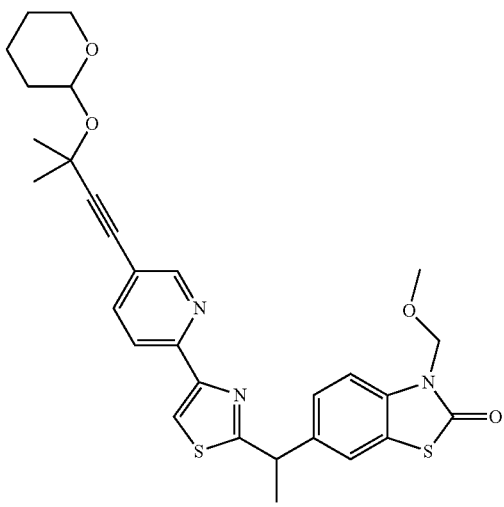 [SMILES: COCn1c(=O)sc2cc(C(C)c3nc(-c4ccc(C#CC(C)(C)OC5CCCCO5)cn4)cs3)ccc21]

A flame dried flask is charged with 2-bromo-5-(3-methyl-3-tetrahydropyran-2-yloxy-but-1-ynyl)pyridine (1.2 g, 3.7 mmoles) and tetrahydrofuran (9 mL). The mixture is cooled in a dry ice acetone bath, and a 2.5 M solution of butyl lithium in hexane (1.5 mL, 3.7 mmoles) is added dropwise. The mixture is stirred for 20 minutes, and a solution of zinc dichloride (555 mg, 4.1 mmoles) in tetrahydrofuran (15 mL) is added. The cooling bath is removed, and the mixture is allowed to warm to room temperature. PEPPSI™ (76 mg, 0.11 mmoles) is added followed by a solution of 6-[1-(4-bromothiazol-2-yl)ethyl]-3-(methoxymethyl)-1,3-benzothiazol-2-one (713 mg, 1.9 mmoles) in Tetrahydrofuran (9 mL). Nitrogen is bubbled into the mixture for 5 minutes, and then the mixture is heated at 65° C. for 1.5 h. The mixture is diluted with ethyl acetate and washed with 50% ammonium hydroxide and then saturated aqueous sodium chloride. The organic phase is dried over sodium sulfate, filtered and concentrated. The material is purified by flash chromatography (silica gel, 80 g, eluted hexane to 40% EtOAc/hexane) to obtain 3-(methoxymethyl)-6-[1-[4-[5-(3-methyl-3-tetrahydropyran-2-yloxy-but-1-ynyl)-2-pyridyl]thiazol-2-yl]ethyl]-1,3-benzothiazol-2-one (0.89 g, 88%). LCMS (+) 550.0.

Preparation 185: Synthesis of 3-(methoxymethyl)-6-[1-[4-[5-(3-methyl-3-tetrahydropyran-2-yloxy-butyl)-2-pyridyl]thiazol-2-yl]ethyl]-1,3-benzothiazol-2-one

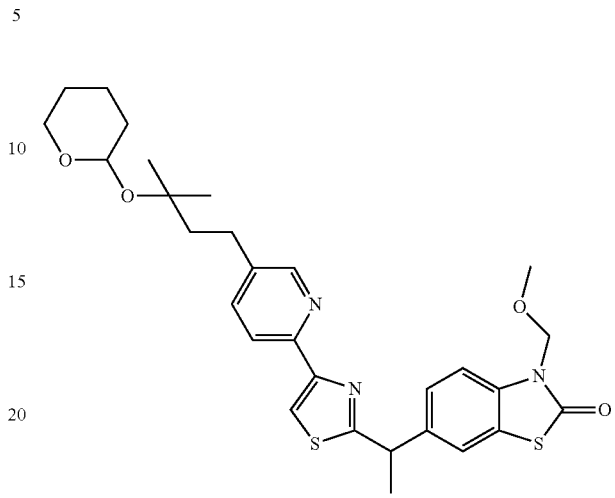

A 250 ml Parr bottle is charged with 10% Pd/C (0.125 g; 1.2 mmoles) and purged with N₂. The catalyst is wetted with 20 mL of methanol. 3-(Methoxymethyl)-6-[1-[4-[5-(3-methyl-3-tetrahydropyran-2-yloxy-but-1-ynyl)-2-pyridyl]thiazol-2-yl]ethyl]-1,3-benzothiazol-2-one (0.89 g, 1.6 mmoles) is added to the slurry together with another 30 mL methanol. The bottle is sealed, purged with N₂, purged with H₂ and pressurized with H₂ (60 psig). The mixture is agitated at room temperature for 18 h, filtered, and concentrated to yield 3-(methoxymethyl)-6-[1-[4-[5-(3-methyl-3-tetrahydropyran-2-yloxy-butyl)-2-pyridyl]thiazol-2-yl]ethyl]-1,3-benzothiazol-2-one (0.84 g, 93%). LCMS (+) 554.2.

EXAMPLE 50

Synthesis of 6-[1-[4-[5-(3-hydroxy-3-methyl-butyl)-2-pyridyl]thiazol-2-yl]ethyl]-3H-1,3-benzothiazol-2-one, Isomer 1

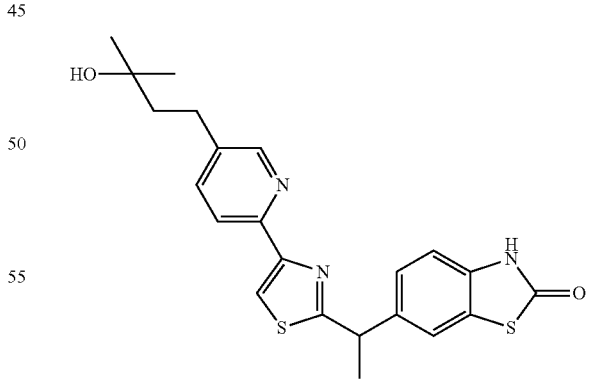

A mixture of 3-(methoxymethyl)-6-[1-[4-[5-(3-methyl-3-tetrahydropyran-2-yloxy-butyl)-2-pyridyl]thiazol-2-yl]ethyl]-1,3-benzothiazol-2-one (0.83 g, 1.50 mmoles) and trifluoroacetic acid (15 mL) is heated at 80° C. overnight. The mixture is concentrated to dryness and tetrahydrofuran (20 mL) and 28% ammonium hydroxide (15 mL) are added. The mixture is stirred at room temperature for 1 h then concentrated to dryness. The crude material is purified by flash chromatography (silica gel, 24 g, eluted DCM to 5% MeOH/DCM) to obtain 6-[1-[4-[5-(3-hydroxy-3-methyl-butyl)-2-pyridyl]thiazol-2-yl]ethyl]-3H-1,3-benzothiazol-2-one (0.23 g, 36%). LCMS (+) 426.2

Racemic 6-[1-[4-[5-(3-hydroxy-3-methyl-butyl)-2-pyridyl]thiazol-2-yl]ethyl]-3H-1,3-benzothiazol-2-one is resolved into its enantiomers by chiral chromatography using Lux Cell-4, 40% EtOH/CO2, 5 mL/min, 225 nm Isomer 1 retention time is 3.02 min. and isomer 2 is 3.83 min.

Preparation 186: Synthesis of tert-butyl 2-[3-(methoxymethyl)-2-oxo-1,3-benzothiazol-6-yl]acetate

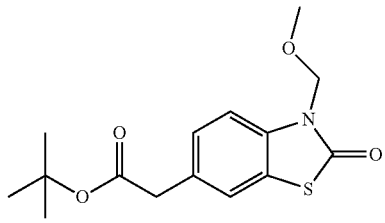 [SMILES: COCn1c(=O)sc2cc(CC(=O)OC(C)(C)C)ccc21]

To a flask is added 6-bromo-3-(methoxymethyl)-1,3-benzothiazol-2-one (3.5 g, 12.8 mmoles), PEPPSI-ipr (260 mg, 0.38 mmoles), and tetrahydrofuran (64 mL). The mixture is purged with nitrogen for several minutes. A 0.5 M solution of (2-tert-butoxy-2-oxoethyl)zinc(II) chloride (77 mL, 38 mmoles) in diethyl ether is added, and the mixture is purged with nitrogen. The mixture is heated to 80° C. (venting the vessel until the ether from the zincate reagent is blown off) for 3 days. The mixture is partitioned between EtOAc and water. The aqueous phase is extracted with EtOAc (2×). The combined organic phase is washed with brine, dried (Na$_2$SO$_4$) and concentrated. The material is purified by flash chromatograph (silica gel, 330 g, eluted hexane to 30% EtOAc/hexane) to obtain tert-butyl 2-[3-(methoxymethyl)-2-oxo-1,3-benzothiazol-6-yl]acetate (2.64 g; 67%).

Preparation 187: Synthesis of tert-butyl 2-[3-(methoxymethyl)-2-oxo-1,3-benzothiazol-6-yl]propanoate

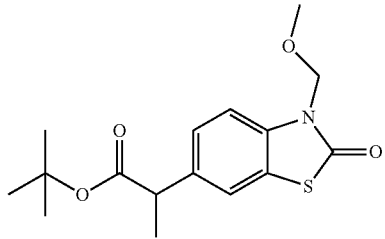 [SMILES: COCn1c(=O)sc2cc(C(C)C(=O)OC(C)(C)C)ccc21]

A mixture of tert-butyl 2-[3-(methoxymethyl)-2-oxo-1,3-benzothiazol-6-yl]acetate (2.6 g, 8.4 mmoles) and tetrahydrofuran (42 mL) is cooled to −78° C., and a 1.0 M solution of lithium bis(trimethylsilyl)amide (9.2 mL, 9.2 mmoles) in tetrahydrofuran is added. After the mixture is stirred for 20 min, methyl iodide (550 µL, 8.8 mmoles) is added, and stirred for 1 h. The reaction is quenched with sat. NH$_4$Cl. The mixture is partitioned between EtOAc and water. The aqueous phase is extracted with EtOAc (2×). The combined organic phase is washed with brine, dried (Na$_2$SO$_4$) and concentrated. The material is purified by flash chromatography (silica gel, 20 g, eluted hexane to 30% EtOAc/hexane) to obtain tert-butyl 2-[3-(methoxymethyl)-2-oxo-1,3-benzothiazol-6-yl]propanoate (1.94 g; 71%). LCMS (+) 292.0

Preparation 188: Synthesis of 2-[3-(methoxymethyl)-2-oxo-1,3-benzothiazol-6-yl]propanoic acid

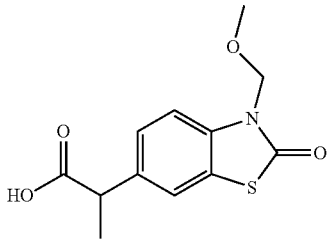 [SMILES: COCn1c(=O)sc2cc(C(C)C(=O)O)ccc21]

To a mixture of tert-butyl 2-[3-(methoxymethyl)-2-oxo-1,3-benzothiazol-6-yl]propanoate (1.9 g, 5.9 mmoles) and dichloromethane (20 mL) is added trifluoroacetic acid (10 mL; 132 mmoles), and the mixture is stirred at room temperature for 6.5 h. The mixture is concentrated in vacuo to yield impure 2-[3-(methoxymethyl)-2-oxo-1,3-benzothiazol-6-yl]propanoic acid which is used without purification in the next step. LCMS (+) 267.0

Preparation 189: Synthesis of 2-[3-(methoxymethyl)-2-oxo-1,3-benzothiazol-6-yl]propanamide

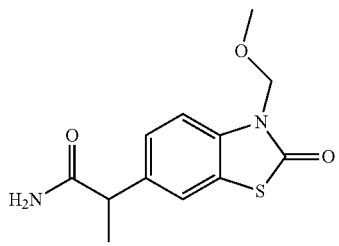 [SMILES: COCn1c(=O)sc2cc(C(C)C(N)=O)ccc21]

To a solution of 2-[3-(methoxymethyl)-2-oxo-1,3-benzothiazol-6-yl]propanoic acid (1.57 g, 5.9 mmoles) in tetrahydrofuran (59 mL) cooled to −20° C. is added triethylamine (1.6 mL, 11.7 mmoles) and then ethyl chloroformate (0.67 mL 7.0 mmoles). The mixture is stirred for 30 min during which a thick white precipitate is observed. To the thick white slurry mixture is added 28% ammonium hydroxide (3.8 mL, 29 mmoles), and the mixture is allowed to warm to 0° C. and stirred for 1.5 h. The mixture is partitioned between EtOAc and water. The aqueous is extracted with EtOAc (2×). The combined organic phase is washed with brine, dried (Na$_2$SO$_4$) and concentrated to give impure (approx. 85%) 2-[3-(methoxymethyl)-2-oxo-1,3-benzothiazol-6-yl]propanamide (1.5 g, 96%). LCMS (+) 267.0.

Preparation 190: Synthesis of 2-[3-(methoxymethyl)-2-oxo-1,3-benzothiazol-6-yl]propanethioamide

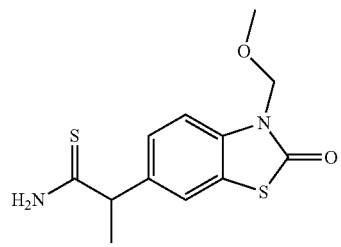 [SMILES: COCn1c(=O)sc2cc(C(C)C(N)=S)ccc21]

To a solution of 2-[3-(methoxymethyl)-2-oxo-1,3-benzothiazol-6-yl]propanamide (1.51 g, 5.7 mmoles) in tetrahydrofuran (57 mL) is added Lawesson's Reagent (2.3 g, 5.7 mmoles), and the mixture is stirred at room temperature for 2 h. The mixture is partitioned between EtOAc and water. The organic phase is extracted with EtOAc (2×). The combined organic phase is washed with brine, dried (Na2SO4) and concentrated. The material is purified by flash chromatography) silica gel, 80 g, eluted 2% MeOH/DCM) to give 1.72 g of impure material which is further purified by flash chromatography (silica gel, 80 g, eluted hexane to 70% EtOAc/hexane) to obtain 2-[3-(methoxymethyl)-2-oxo-1,3-benzothiazol-6-yl]propanethioamide (0.89 g; 56% yield). LCMS 100% (+) 283.0.

Preparation 191: Synthesis of 3-(methoxymethyl)-6-[1-(4-pyridazin-3-ylthiazol-2-yl)ethyl]-1,3-benzothiazol-2-one

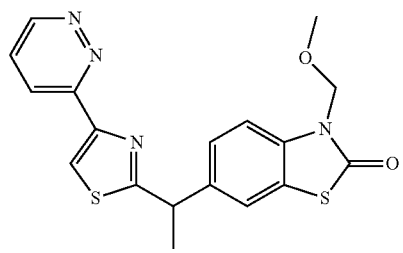 [SMILES: COCn1c(=O)sc2cc(C(C)c3nc(-c4cccnn4)cs3)ccc21]

A mixture of 2-[3-(methoxymethyl)-2-oxo-1,3-benzothiazol-6-yl]propanethioamide (0.89 g, 3.2 mmoles), 2-bromo-1-(pyridazin-3-yl)ethanone (697 mg, 3.5 mmoles), and ethanol (20 mL) is heated at 70° C. for 3 h. The mixture is concentrated to dryness and purified by flash chromatography (silica gel, 120 g, eluted 40% EtOAc/hexane to 100% EtOAc) to give 3-(methoxymethyl)-6-[1-(4-pyridazin-3-ylthiazol-2-yl)ethyl]-1,3-benzothiazol-2-one (0.47 g, 38%). LCMS (+) 385.0.

EXAMPLE 51

Synthesis of 6-[1-(4-pyridazin-3-ylthiazol-2-yl)ethyl]-3H-1,3-benzothiazol-2-one, isomer 2

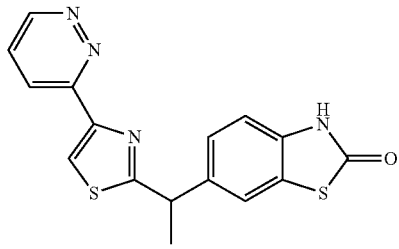 [SMILES: CC(c1ccc2[nH]c(=O)sc2c1)c1nc(-c2cccnn2)cs1]

A mixture of 3-(methoxymethyl)-6-[1-(4-pyridazin-3-ylthiazol-2-yl)ethyl]-1,3-benzothiazol-2-one (0.46 g, 1.2 mmoles) and trifluoroacetic acid (5 mL) is heated at 70° C. for 18 h. The temperature is increased to 90° C., and the mixture is heated another 24 h. The mixture is concentrated to dryness, and tetrahydrofuran (15 mL) and 28% ammonium hydroxide (10 mL) are added. The mixture is stirred at room temperature for 1 h and partitioned between DCM and water. The aqueous phase is extracted with DCM (2×). The combined organic phase is washed with brine, dried (Na2SO4) and concentrated. The material is purified by flash chromatography (silica gel, 40 g, eluted 40% EtOAc/hexane to 100% EtOAc) to yield 6-[1-(4-pyridazin-3-ylthiazol-2-yl)ethyl]-3H-1,3-benzothiazol-2-one (240 mg, 59%). LCMS (+) 341.0.

Racemic 6-[1-(4-pyridazin-3-ylthiazol-2-yl)ethyl]-3H-1,3-benzothiazol-2-one is resolved into its enantiomers by chiral chromatography using Chiralpak® AD-H, 4.6×150 mm, 4/1 EtOH/ACN 0.2% IPAm, 1 mL/min, 225 nm. Isomer 1 retention time is 2.93 min and isomer 2 is 4.00 min.

Preparation 192: Synthesis of 5-[2-(tert-butyl-diphenyl-silanyloxy)-ethyl]-2-chloro-pyridine

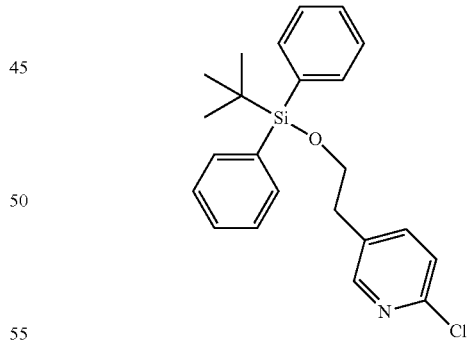

To a mixture of 2-(6-chloro-pyridin-3-yl)-ethanol (9 g, 57 mmoles) and imidazole (15.5 g, 228 mmoles) in dichloromethane (100 mL) at 0° C. is added tert-Butyl-chlorodiphenyl-silane (23.47 g, 85 mmoles). The cold bath is removed and the mixture stirred at room temperature for 12 hours. The mixture is diluted with dichloromethane, washed with water and concentrated. Purification on silica gel eluting with 5-8% ethyl acetate in hexanes gives 20.05 g of 5-[2-(tert-butyl-diphenyl-silanyloxy)-ethyl]-2-chloro-pyridine as an oil. LCMS (5 mM AA-3 min) rt=2.38 min M+1=396.26/398.24

Preparation 193: Synthesis of 5-[2-(tert-butyl-diphenyl-silanyloxy)-ethyl]-pyridine-2-carbonitrile

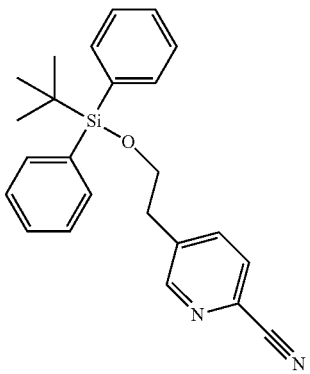 [SMILES: CC(C)(C)[Si](OCCc1ccc(C#N)nc1)(c1ccccc1)c1ccccc1]

A mixture of 5-[2-(tert-butyl-diphenyl-silanyloxy)-ethyl]-2-chloro-pyridine (20 g, 50.6 mmoles), zinc cyanide (3.86 g, 32 mmoles), and zinc dust (0.65 g, 10 mmoles) in dimethylacetamide (70 mL) in a pressure vessel is sparged with nitrogen for 10 minutes. Tris(dibenzylideneacetone)dipalladium(0) (0.915 g, 1 mmole) and 1,1'-Bis(diphenylphosphino)ferrocene-palladium(II)dichloride dichloromethane complex (1.62 g, 2 mmoles) are added and the vessel is sealed and heated at 90° C. for 3-4 hours. The mixture is cooled to room temperature and filtered. The filtrate is partitioned between ethyl acetate and saturated sodium bicarbonate. The organic layer is concentrated and purified on silica gel eluting with 10-12% ethyl acetate in hexanes to give 16.15 g of 5-[2-(tert-Butyl-diphenyl-silanyloxy)-ethyl]-pyridine-2-carbonitrile as an oil.

Preparation 194: Synthesis of 5-[2-(tert-butyl-diphenyl-silanyloxy)-ethyl]-pyridine-2-carbothioic acid amide

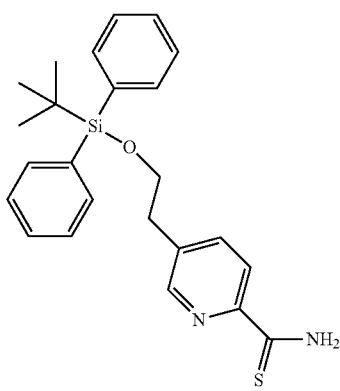 [SMILES: CC(C)(C)[Si](OCCc1ccc(C(N)=S)nc1)(c1ccccc1)c1ccccc1]

A mixture of 5-[2-(tert-butyl-diphenyl-silanyloxy)-ethyl]-pyridine-2-carbonitrile (15.5 g, 40 mmoles), ammonium sulfide (45% in water, 6 g, 40 mmoles), triethylamine (4.84 g, 48 mmoles) and pyridine (100 mL) is heated to 50° C. for 6 hours. The mixture is diluted with ethyl acetate, washed with water and concentrated to give 16.1 g of 5-[2-(tert-butyl-diphenyl-silanyloxy)-ethyl]-pyridine-2-carbothioic acid amide as a yellow solid which is used without further purification. LCMS (5 mM AA-3 min) rt=2.23 min, M+1=421.16.

Preparation 195: Synthesis of 2-{5-[2-(tert-Butyl-diphenyl-silanyloxy)-ethyl]-pyridin-2-yl}-thiazole-4-carboxylic acid ethyl ester

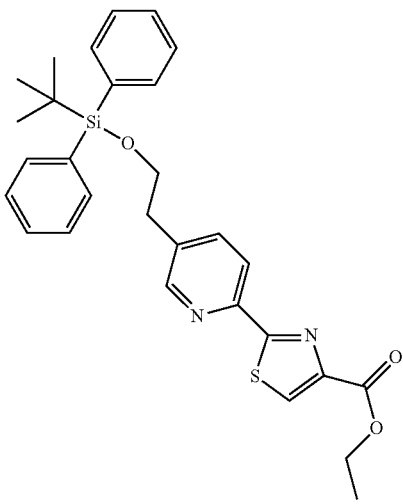 [SMILES: CCOC(=O)c1csc(-c2ccc(CCO[Si](c3ccccc3)(c3ccccc3)C(C)(C)C)cn2)n1]

A mixture of 5-[2-(tert-Butyl-diphenyl-silanyloxy)-ethyl]-pyridine-2-carbothioic acid amide (16 g, 38 mmoles) and ethyl 2-bromopyruvate (8.15 g, 41 mmoles) in ethanol (150 mL) is heated to 60° C. for 3 hours, cooled to room temperature and concentrated on the rotovap. The residue is partitioned between ethyl acetate and water. The combined organics are concentrated and purified on silica gel eluting with 10-12% ethyl acetate in hexanes to give 12.05 g of 2-{5-[2-(tert-Butyl-diphenyl-silanyloxy)-ethyl]-pyridin-2-yl}-thiazole-4-carboxylic acid ethyl ester as an oil. LCMS (5 mM AA-3 min) rt=2.41 min, M+1=517.23.

Preparation 196: Synthesis of 2-{5-[2-(tert-butyl-diphenyl-silanyloxy)-ethyl]-pyridin-2-yl}-thiazole-4-carboxylic acid

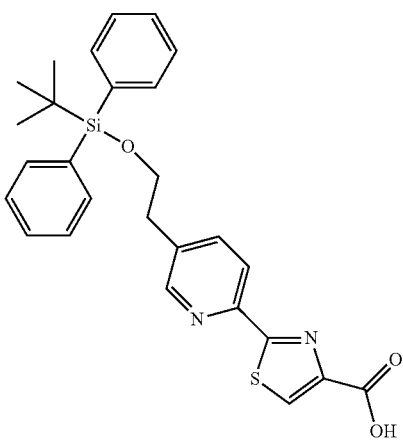 [SMILES: CC(C)(C)[Si](OCCc1ccc(-c2nc(C(=O)O)cs2)nc1)(c1ccccc1)c1ccccc1]

To 2-{5-[2-(tert-Butyl-diphenyl-silanyloxy)-ethyl]-pyridin-2-yl}-thiazole-4-carboxylic acid ethyl ester (12 g, 23.2 mmoles) in tetrahydrofuran (100 mL) is added a solution of lithium hydroxide (4.86 g, 116 mmoles) in water (50 mL). After stirring ~12 hours at room temperature, the mixture is concentrated on rotovap to remove most of the tetrahydrofuran. The pH is adjusted to 5 by addition of 2N hydrochloric acid. The mixture is extracted with ethyl acetate and the combined organics concentrated to give 8.4 g of 2-{5-[2-(tert-Butyl-diphenyl-silanyloxy)-ethyl]-pyridin-2-yl}-thiazole-4-carboxylic acid as an off-white solid. LCMS (5 mM AA-3 min) retention time=1.63 min, M+1=489.18.

Preparation 197: Synthesis of 2-{5-[2-(tert-butyl-diphenyl-silanyloxy)-ethyl]-pyridin-2-yl}-thiazole-4-carboxylic acid methoxy-methyl-amide

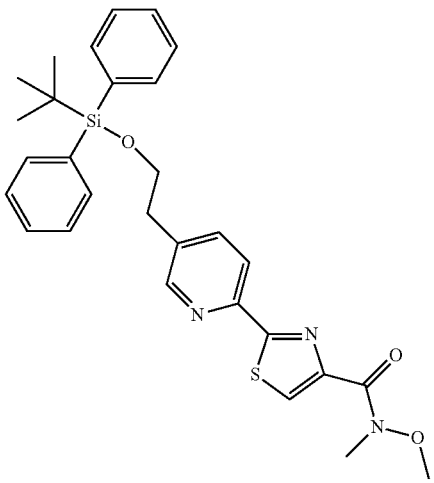 [SMILES: CON(C)C(=O)c1csc(-c2ccc(CCO[Si](c3ccccc3)(c3ccccc3)C(C)(C)C)cn2)n1]

To 2-{5-[2-(tert-butyl-diphenyl-silanyloxy)-ethyl]-pyridin-2-yl}-thiazole-4-carboxylic acid (6 g, 12.2 mmoles) in Dimethylformamide (50 mL) is added N,N-diisopropyl ethylamine (6.2 g, 48 mmoles) followed by N,O-Dimethylhydroxyamine Hydrochloride (2.39 g, 24.5 mmoles), then O-(Benzotriazol-1-yl)-N,N,N',N'-tetramethyluronium tetrafluoroborate (5.77 g, 18 mmoles). After stirring ~4 hours, the mixture is partitioned between ethyl acetate and water. The organic layer is concentrated to give 6.05 g of 2-{5-[2-(tert-Butyl-diphenyl-silanyloxy)-ethyl]-pyridin-2-yl}-thiazole-4-carboxylic acid methoxy-methyl-amide as a brown solid, which is carried on crude.

Preparation 198: Synthesis of 1-(2-{5-[2-(tert-butyl-diphenyl-silanyloxy)-ethyl]-pyridin-2-yl}-thiazol-4-yl)-ethanone

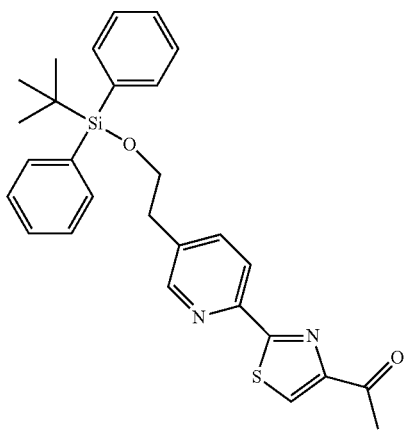 [SMILES: CC(=O)c1csc(-c2ccc(CCO[Si](c3ccccc3)(c3ccccc3)C(C)(C)C)cn2)n1]

Methyl magnesium bromide (3M in diethyl ether, 11.28 mL, 33.8 mmoles) is added to a solution of 2-{5-[2-(tert-Butyl-diphenyl-silanyloxy)-ethyl]-pyridin-2-yl}-thiazole-4-carboxylic acid methoxy-methyl-amide (6 g, 11.3 mmoles) in tetrahydrofuran (50 mL) at 0° C. Upon complete consumption of the ketone, the reaction is quenched with saturated ammonium hydroxide. The layers are separated and the aqueous layer extracted with ethyl acetate. The combined organics are concentrated and purified on silica gel eluting with 15-18% ethyl acetate in hexanes to give 2.55 g of 1-(2-{5-[2-(tert-Butyl-diphenyl-silanyloxy)-ethyl]-pyridin-2-yl}-thiazol-4-yl)-ethanone as a pale yellow solid. LCMS (METHOD-6) rt=4.26 min, M+1=487.21.

Preparation 199: Synthesis of N—[(Z)-1-[2-[5-[2-[tert-butyl(diphenyl)silyl]oxyethyl]-2-pyridyl]thiazol-4-yl]ethylideneamino]-4-methyl-benzenesulfonamide

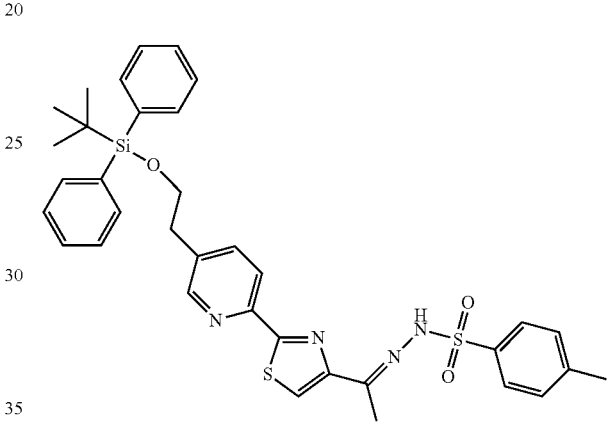

A mixture of 1-(2-{5-[2-(tert-Butyl-diphenyl-silanyloxy)-ethyl]-pyridin-2-yl}-thiazol-4-yl)-ethanone (2.5 g, 5.1 mmoles) and 4-methylbenzenesulfonohydrazide (1.43 g, 7.7 mmoles) in methanol (35 mL) is heated to 50° C. After consumption of the ketone, the solvent is removed and the material is taken on without purification. LCMS (5 mM AA-3 min) retention time=2.40 and 2.46 min, M+1=655.23.

Preparation 200: Synthesis of 6-bromo-3-methoxymethyl-3H-benzothiazol-2-one

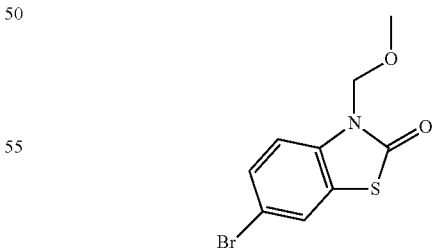

Cesium Carbonate (73.6 g, 226 mmoles) is added to a solution of 6-bromo-2-benzothiazolinone (26.0 g, 113 mmoles) in dimethylformamide (565 mL) followed by chloro-methoxy-methane (13.65 g, 169.5 mmoles). After stirring ~24 hours, the mixture is partitioned between ethyl acetate and water. The organic layer is washed with saturated aqueous sodium chloride, dried over sodium sulfate, filtered and concentrated to give 30 g 6-bromo-3-methoxymethyl-3H-benzothiazol-2-one as a white solid. LCMS (low) retention time=2.1 min, does not ionize to give M+1 signal.

Preparation 201: Synthesis of 3-(methoxymethyl)-6-(4,4,5,5-tetramethyl-1,3,2-dioxaborolan-2-yl)-1,3-benzothiazol-2-one

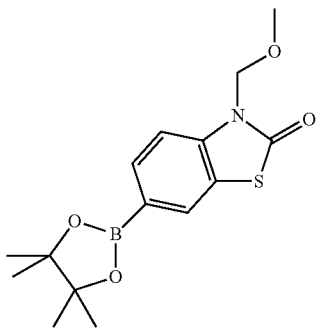 [SMILES: COCn1c(=O)sc2cc(B3OC(C)(C)C(C)(C)O3)ccc21]

A mixture of 6-bromo-3-(methoxymethyl)-1,3-benzothiazol-2-one (5 g, 18.2 mmoles), 4,4,4',4',5,5,5',5'-octamethyl-2,2'-bi(1,3,2-dioxaborolane) (6.02 g, 23.7 mmoles), potassium acetate (4.475 g, 45.6 mmoles) and 1,4-dioxane (75 mL) in a pressure flask is degassed with argon gas for 15 min. (1,1'-bis(diphenylphosphino)ferrocene)palladium(II) chloride (0.744 g, 0.91 mmoles) is added and the mixture is again degassed for 5 min, then heated at 110° C. for 2.5 h. The mixture is cooled to room temperature, concentrated and partitioned between ethyl acetate and water. The organic layer is dried over sodium sulfate, filtered, concentrated and purified on silica gel eluting with 6% ethyl acetate in hexanes to give 5.5 g of 3-(methoxymethyl)-6-(4,4,5,5-tetramethyl-1,3,2-dioxaborolan-2-yl)-1,3-benzothiazol-2-one as a white solid. LCMS (5 mM AA-3-5 min) retention time=2.367 min, M+1=322.0.

Preparation 202: Synthesis of [3-(methoxymethyl)-2-oxo-1,3-benzothiazol-6-yl]Boronic Acid

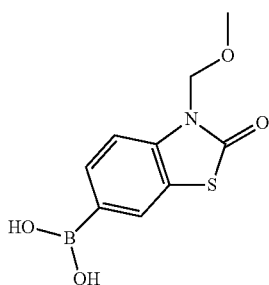

Sodium periodate (10.99 g, 51.37 mmoles) and ammonium acetate (3.96 g, 51.37 mmoles) are added to 3-(methoxymethyl)-6-(4,4,5,5-tetramethyl-1,3,2-dioxaborolan-2-yl)-1,3-benzothiazol-2-one (5.50 g, 17.1 mmoles) in a mixture of acetone (84 mL) and water (42 mL) and the mixture is stirred at room temperature for 20 hours. The mixture is concentrated on rotovap and partitioned between ethyl acetate and water. The organics are washed with saturated aqueous sodium chloride, dried over sodium sulfate, filtered and concentrated. LCMS (5 mM AA-3-5 min) retention time=1.34 min, M−1=238.0.

Preparation 23: Synthesis of 6-[1-(2-{5-[2-(tert-butyl-diphenyl-silanyloxy)-ethyl]-pyridin-2-yl}-thiazol-4-yl)-ethyl]-3-methoxymethyl-3H-benzothiazol-2-one

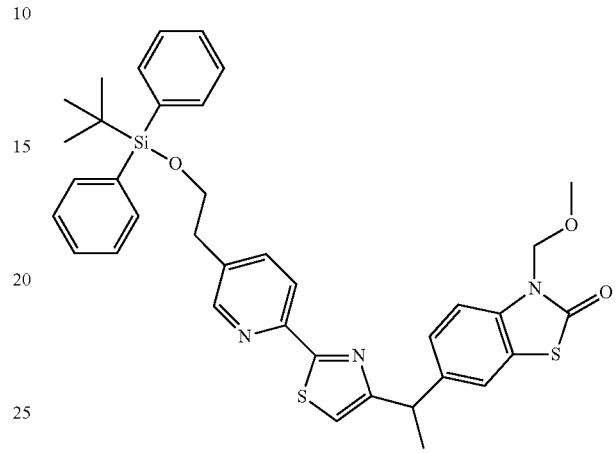

A mixture of N—[(Z)-1-[2-[5-[2-[tert-butyl(diphenyl)silyl]oxyethyl]-2-pyridyl]thiazol-4-yl]ethylideneamino]-4-methyl-benzenesulfonamide (1.5 g, 2.2 mmoles), [3-(methoxymethyl)-2-oxo-1,3-benzothiazol-6-yl]boronic acid (0.685 g, 2.8 mmoles) and potassium carbonate (0.474 g, 3.4 mmoles) in dioxane (10 mL) is boiled under nitrogen for ~18 hours. The mixture is cooled to room temperature and partitioned between ethyl acetate and cold water. The organic layer is concentrated and purified on silica gel eluting with 0 to 10% ethyl acetate in hexanes to give 0.75 g of 6-[1-(2-{5-[2-(tert-butyl-diphenyl-silanyloxy)-ethyl]-pyridin-2-yl}-thiazol-4-yl)-ethyl]-3-methoxymethyl-3H-benzothiazol-2-one. LCMS (5 mM-NP) retention time=2.48 min, M+1 666.26.

EXAMPLE 52

Synthesis of 6-(1-{2-[5-(2-hydroxy-ethyl)-pyridin-2-yl]-thiazol-4-yl}-ethyl)-3H-benzothiazol-2-one, Isomer 2

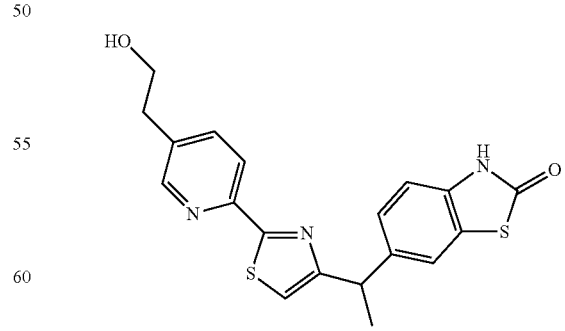

A solution of 6-[1-(2-{5-[2-(tert-butyl-diphenyl-silanyloxy)-ethyl]-pyridin-2-yl}-thiazol-4-yl)-ethyl]-3-methoxymethyl-3H-benzothiazol-2-one (0.700 g, 1.05 mmoles) in trifluoroacetic acid (10 mL) is heated to 70° C.

for about 18 hours. The mixture is concentrated and redissolved in tetrahydrofuran (~10 mL). 28% ammonia solution (~3 mL) is added and the mixture stirred at room temperature 2 hours. The mixture is partitioned between ethyl acetate and cold water. The organic layer is concentrated and purified on silica gel eluting with 60% ethyl acetate in hexanes to give 45 mg of 6-(1-{2-[5-(2-hydroxy-ethyl)-pyridin-2-yl]-thiazol-4-yl}-ethyl)-3H-benzothiazol-2-one as a white solid. This is separated into its enantiomers by chiral chromatography. Chiralpak® AD-H (3×25 cm, 5 um, methanol with 0.2% isopropylamine, 30 mL/min) LCMS (QC_T0) retention time=1.87 min, M+1=384.2.

Preparation 204: Synthesis of 6-[hydroxy-(2-pyridin-2-yl-thiazol-4-yl)-methyl]-3H-benzothiazol-2-one

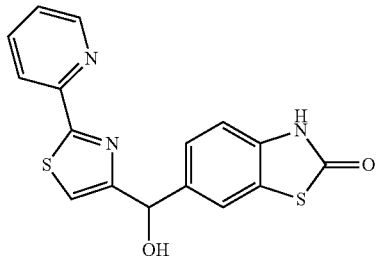 [SMILES: O=c1[nH]c2ccc(C(O)c3csc(-c4ccccn4)n3)cc2s1]

To 6-bromo-3H-benzothiazol-2-one (2.0 g, 8.69 mmoles) in tetrahydrofuran 40 mL cooled to about −78° C. Methyl magnesiumbromide (3M in diethyl ether, 3.25 mL) is added. After stirring ~15 minute, the mixture is diluted with tetrahydrofuran (40 mL). After an additional 15 minutes, t-butyl lithium (1.7M in pentane, 11.2 mL, 19.0 mmoles) is added. After 15 minutes, a solution of 2-pyridin-2-yl-thiazole-4-carbaldehyde (1.9 g, 9.98 mmoles) in tetrahydrofuran (20 mL) is added. After 15 minutes, the cold bath is removed. After consumption of the starting material, the mixture is quenched with saturated ammonium chloride. The mixture is extracted with ethyl acetate (3×100 mL). The organic layer is dried over sodium sulfate, filtered and concentrated. Purification on silica gel eluting with 50% ethyl acetate in hexanes gives 1.6 g of 6-[hydroxy-(2-pyridin-2-yl-thiazol-4-yl)-methyl]-3H-benzothiazol-2-one. LCMS (5 mM AA-3-5 min) retention time=1.16 min, M+1=342.15.

Preparation 205: Synthesis of 6-(2-pyridin-2-yl-thiazole-4-carbonyl)-3H-benzothiazol-2-one

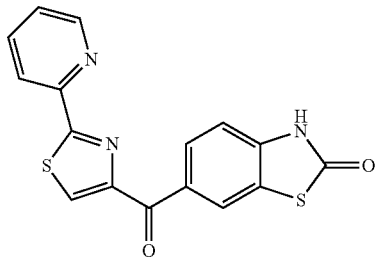 [SMILES: O=C(c1ccc2[nH]c(=O)sc2c1)c1csc(-c2ccccn2)n1]

A mixture of 6-[hydroxy-(2-pyridin-2-yl-thiazol-4-yl)-methyl]-3H-benzothiazol-2-one (1.6 g, 4.6 mmoles) and manganese dioxide (1.63 g, 18.7 mmoles) in tetrahydrofuran (50 mL) is boiled for 3 hour. The solids are filtered off and washed with ethyl acetate, 5% methanol in chloroform and chloroform. The combined filtrates are concentrated to give 6-(2-pyridin-2-yl-thiazole-4-carbonyl)-3H-benzothiazol-2-one, which is carried on without further purification. LCMS (5 mM AA-3-5 min) retention time=1.47 min, M+1=339.91

Preparation 206: Synthesis of 3-methoxymethyl-6-(2-pyridin-2-yl-thiazole-4-carbonyl)-3H-benzothiazol-2-one

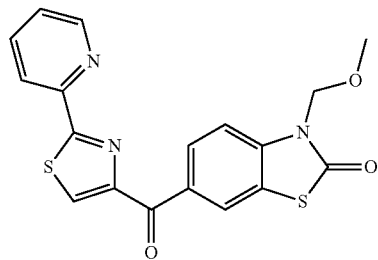 [SMILES: COCn1c(=O)sc2cc(C(=O)c3csc(-c4ccccn4)n3)ccc21]

A solution of 6-(2-pyridin-2-yl-thiazole-4-carbonyl)-3H-benzothiazol-2-one (1.5 g, 4.44 mmoles) in N,N-dimethylformamide (10 mL) is added to a suspension of sodium hydride (60%, 0.15 g, 6.62 mmoles) in N,N-Dimethylformamide (40 mL) cooled in an ice water bath. Methyl chloromethyl ether (0.71 g, 8.82 mmoles) is then added. After 10 minutes, the cold bath is removed. After complete consumption of the starting material, ice is added to quench to reaction, resulting in the formation of a solid. The solid is collected, washed with water and diethylether and dried to give 1.60 g of 3-methoxymethyl-6-(2-pyridin-2-yl-thiazole-4-carbonyl)-3H-benzothiazol-2-one which is carried on without further purification.

Preparation 207: Synthesis of 6-[1-hydroxy-1-(2-pyridin-2-yl-thiazol-4-yl)-ethyl]-3-methoxymethyl-3H-benzothiazol-2-one

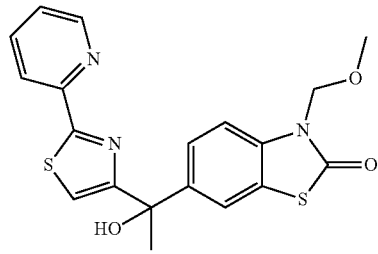 [SMILES: COCn1c(=O)sc2cc(C(C)(O)c3csc(-c4ccccn4)n3)ccc21]

To a solution of 3-methoxymethyl-6-(2-pyridin-2-yl-thiazole-4-carbonyl)-3H-benzothiazol-2-one (1.6 g, 4.17 mmoles) in tetrahydrofuran (50 mL) at 0° C. is added methyl magnesiumbromide (3M in diethyl ether, 2.09 mL, 6.27 mmoles) dropwise. After 15 minutes, the cold bath is removed. Upon complete consumption of the starting material, the mixture is cooled back to 0° C., quenched with saturated ammonium chloride and the layers are separated. The water layer is extracted with ethyl acetate. The combined organic layers are dried over sodium sulfate, filtered and concentrated. The material is carried on without further purification. LCMS (5 mM AA-3-5 min) retention time=1.52 min, M+1=400.36.

Preparation 208: Synthesis of 3-methoxymethyl-6-[1-(2-pyridin-2-yl-thiazol-4-yl)-ethyl]-3H-benzothiazol-2-one

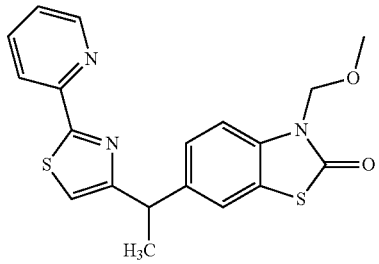 [SMILES: COCn1c(=O)sc2cc(C(C)c3csc(-c4ccccn4)n3)ccc21]

To an ice cold solution of 6-[1-hydroxy-1-(2-pyridin-2-yl-thiazol-4-yl)-ethyl]-3-methoxymethyl-3H-benzothiazol-2-one (1.5 g, 3.75 mmoles) and triethylsilane (8.72 g, 75 mmoles) in dichloromethane (50 mL) is added trifluoroacetic acid (8.56 g, 75 mmoles) over 20 minutes and the mixture is allowed to warm to room temperature. After all starting material is consumed, the mixture is quenched with saturated sodium carbonate. The layers are separated and the water layer extracted with more dichloromethane. The combined organics are dried over sodium sulfate, filtered and dried. Purification on silica gel (50% ethyl acetate in hexanes gives a mixture of the desired product and the alkene resulting. The residue is dissolved in ethanol (30 mL), 10% palladium on carbon (100 mg) is added and the mixture is stirred at room temperature under an atmosphere of hydrogen for 2 hours. The catalyst is filtered off to give 3-methoxymethyl-6-[1-(2-pyridin-2-yl-thiazol-4-yl)-ethyl]-3H-benzothiazol-2-one. LCMS (5 mM AA-3-5 min) retention time=1.85 min, M+1=384.19.

Preparation 209: Synthesis of 6-[1-(2-pyridin-2-yl-thiazol-4-yl)-ethyl]-3H-benzothiazol-2-one

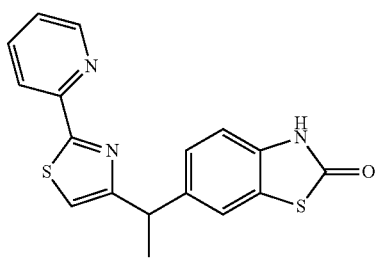 [SMILES: CC(c1ccc2[nH]c(=O)sc2c1)c1csc(-c2ccccn2)n1]

3-Methoxymethyl-6-[1-(2-pyridin-2-yl-thiazol-4-yl)-ethyl]-3H-benzothiazol-2-one (1.0 g, 2.6 mmoles) is boiled in trifluoroacetic acid (50 mL) for 3 hours and cooled to room temperature. The solvent is removed and the residue is partitioned between ethyl acetate and saturated aqueous sodium bicarbonate. The organic layer is dried over sodium sulfate, filtered and concentrated to give 700 mg of intermediate. 450 mg of this material is dissolved in methanol (10 mL), diisopropylethylamine (1.59 g, 12.1 mmoles) is added and the mixture is heated to 80° C. in a microwave for 18 hours. The mixture is concentrated and dissolved in 10% methanol in chloroform. The solution is washed with water and saturated aqueous sodium chloride, dried over sodium sulfate, concentrated and dried to give a white solid. The solid is washed with a mixture of pentane and diethyl ether, then dried under vacuum to give 6-[1-(2-pyridin-2-yl-thiazol-4-yl)-ethyl]-3H-benzothiazol-2-one as an off white solid (335 mg). LCMS (QC_T0) retention time=2.11 min, M+1=340.0.

EXAMPLE 53

Isolation of 6-[1-(2-pyridin-2-yl-thiazol-4-yl)-ethyl]-3H-benzothiazol-2-one, Isomer 2

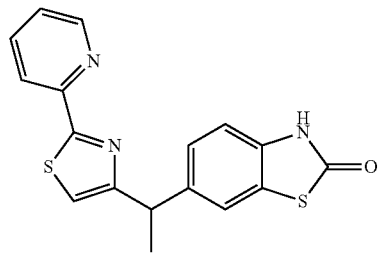 [SMILES: CC(c1ccc2[nH]c(=O)sc2c1)c1csc(-c2ccccn2)n1]

Compound 6-[1-(2-pyridin-2-yl-thiazol-4-yl)-ethyl]-3H-benzothiazol-2-one is resolved into its enantiomers by chiral chromatography (Chiralpak® AD-H, 10% acetonitrile in methanol, 30 mL/min) Isomer 2 has a retention time of 5.43 minutes on a Chiralpak® Ad-H 4.6×150 mm column eluting with 9/1 methanol/acetonitrile with 0.2% isopropyl amine. The oil thus obtained is dissolved in dichloromethane (3 mL). Hexane (6 mL) is added and the mixture is concentrated, then dried under vacuum to give 6-[1-(2-Pyridin-2-yl-thiazol-4-yl)-ethyl]-3H-benzothiazol-2-one, isomer 2 as a white solid. LCMS (Low) retention time 2.30 min, M+1 339.8.

Preparation 210: Synthesis of 2-bromo-5-(2-methyl-[1,3]dioxolan-2-yl)-pyridine

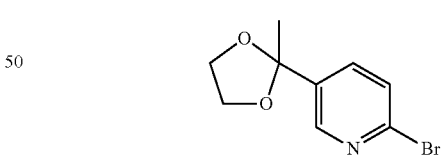

A mixture of 1-(6-bromo-3-pyridyl)ethanone (5.5 g, 27.5 mmoles), p-toluenesulfonic acid monohydrate (1.57 g, 8.25 mmoles) and ethylene glycol (4.6 mL, 82.4 mmoles) in toluene (75 mL) is boiled under nitrogen overnight with azeotropic removal of water via a Dean-Stark trap. The mixture is cooled to room temperature, washed with 2M sodium carbonate and saturated aqueous sodium chloride and concentrated. Purification on 220 g silica gel (5 to 25% ethyl acetate in hexanes, 65 mL/min) gives 2-bromo-5-(2-methyl-1,3-dioxolan-2-yl)pyridine as a waxy white solid (4.92 g). LCMS (Low) retention time 1.89 min, M+1 244.0, 246.0.

Preparation 211: Synthesis of 3-methoxymethyl-6-(1-{4-[5-(2-methyl-[1,3]dioxolan-2-yl)-pyridin-2-yl]-thiazol-2-yl}-ethyl)-3H-benzothiazol-2-one

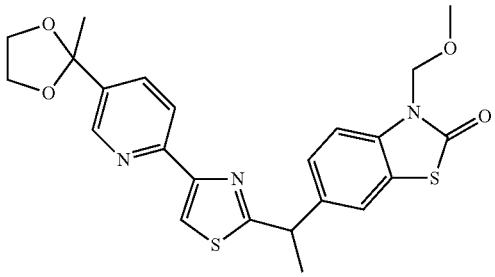 [SMILES: COCn1c(=O)sc2cc(C(C)c3nc(-c4ccc(C5(C)OCCO5)cn4)cs3)ccc21]

A flame dried flask is charged with 2-bromo-5-(2-methyl-1,3-dioxolan-2-yl)pyridine (975 mg, 4 mmoles) and tetrahydrofuran (10 mL). The solution is cooled in a dry ice acetone bath and butyl lithium (2.5M in hexanes, 1.54 mL) is added dropwise. After stirring ~20 minutes, a solution of zinc dichloride (856 mg, 6.28 mmoles) in tetrahydrofuran (6 mL) is added and the cold bath removed. After the mixture reaches room temperature, this solution is added to a mixture of 6-[1-(4-bromo-thiazol-2-yl)-ethyl]-3-methoxymethyl-3H-benzothiazol-2-one (1.1 g, 2.85 mmoles) and PEPPSI (116 mg, 0.17 mmoles) in tetrahydrofuran (6 mL). The vial is flushed with argon and heated to 70° C. Upon completion of the reaction, the mixture is diluted with ethyl acetate, then washed with 10% ammonium hydroxide and saturated aqueous sodium chloride. The organic layer is dried over sodium sulfate, filtered and concentrated. Purification on 80 g silica gel (10 to 40% ethyl acetate in hexanes, 65 mL/min) gives 3-(methoxymethyl)-6-[1-[4-[5-(2-methyl-1,3-dioxolan-2-yl)-2-pyridyl]thiazol-2-yl]ethyl]-1,3-benzothiazol-2-one as a sticky foam (840 mg). LCMS (low) retention time=2.52 min, M+1=470.2.

Preparation 212: Synthesis of 6-{1-[4-(5-acetyl-pyridin-2-yl)-thiazol-2-yl]-ethyl}-3-methoxymethyl-3H-benzothiazol-2-one

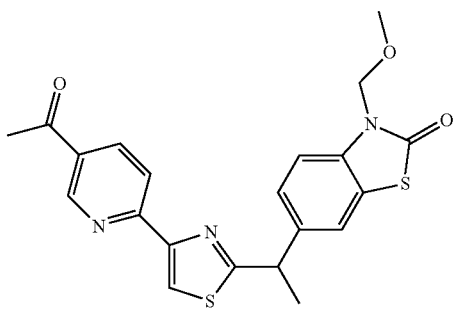 [SMILES: COCn1c(=O)sc2cc(C(C)c3nc(-c4ccc(C(C)=O)cn4)cs3)ccc21]

A mixture of 3-methoxymethyl-6-(1-{4-[5-(2-methyl-[1,3]dioxolan-2-yl)-pyridin-2-yl]-thiazol-2-yl}-ethyl)-3H-benzothiazol-2-one (825 mg), 5N hydrochloric acid (7 mL) and methanol (7 mL) in a sealed vial is placed in a 70° C. heating block. When no starting material is remaining, the mixture is cooled to room temperature and the pH adjusted to ~8 by addition of 5N sodium hydroxide. The mixture is extracted with tetrahydrofuran. The organic layer is dried over sodium sulfate, filtered and concentrated to give 6-{1-[4-(5-acetyl-pyridin-2-yl)-thiazol-2-yl]-ethyl}-3-methoxymethyl-3H-benzothiazol-2-one as an oil (757 mg) that is carried on without purification. LCMS (Low) retention time 2.25 min, M+1 426.0.

Preparation 213: Synthesis of 6-[1-[4-(5-acetyl-2-pyridyl)thiazol-2-yl]ethyl]-3H-1,3-benzothiazol-2-one

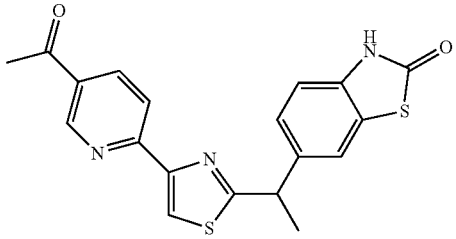 [SMILES: CC(=O)c1ccc(-c2csc(C(C)c3ccc4[nH]c(=O)sc4c3)n2)nc1]

6-[1-[4-(5-acetyl-2-pyridyl)thiazol-2-yl]ethyl]-3-(methoxymethyl)-1,3-benzothiazol-2-one (740 mg) is dissolved in Trifluoroacetic Acid (10 mL) and boiled under nitrogen overnight. The mixture is concentrated, dissolved in tetrahydrofuran (6 mL) and 28% ammonium hydroxide (1 mL) and stirred at room temperature. Upon completion of the reaction, the mixture is concentrated. The material is purified on 80 g silica gel eluting with 0 to 6% methanol in dichloromethane to give 6-[1-[4-(5-acetyl-2-pyridyl)thiazol-2-yl]ethyl]-3H-1,3-benzothiazol-2-one as a white solid (610 mg). LCMS (Low) retention time 2.00 min, M+1 382.0.

EXAMPLE 54

Isolation of 6-[1-[4-(5-acetyl-2-pyridyl)thiazol-2-yl]ethyl]-3H-1,3-benzothiazol-2-one, Isomer 2

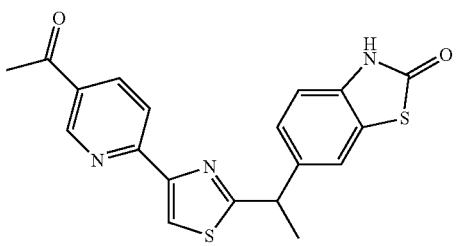 [SMILES: CC(=O)c1ccc(-c2csc(C(C)c3ccc4[nH]c(=O)sc4c3)n2)nc1]

Compound 6-[1-[4-(5-acetyl-2-pyridyl)thiazol-2-yl]ethyl]-3H-1,3-benzothiazol-2-one is resolved by chiral chromatography (Chiralpak® AD (20 uM), 8×40.5 cm, 1/1 methanol/acetonitrile with 0.2% isopropylamine, 425 mL/min). Isomer 2 is obtained as a light yellow solid. Retention time of 6.3 minutes on a Chiralpak® AD-H 4.6×150 mm column eluting with 1/1 methanol/acetonitrile with 0.2% isopropyl amine, 0.6 mL/min LCMS (Low) retention time 2.05 min, M+1 382.0.

Preparation 214: 2-[[6-[3-[1-[3-(Methoxymethyl)-2-oxo-1,3-benzothiazol-6-yl]ethyl]pyrazol-1-yl]-3-pyridyl]methoxy]acetic acid

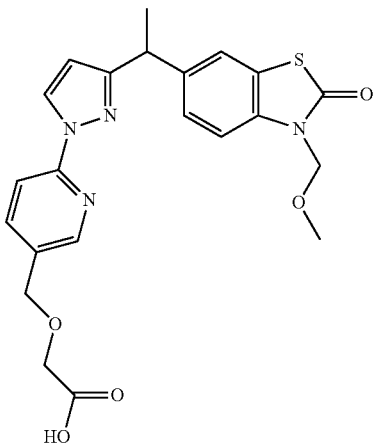 [SMILES: COCn1c(=O)sc2cc(C(C)c3ccn(-c4ccc(COCC(=O)O)cn4)n3)ccc21]

Dissolve ethyl 2-[[6-[3-[1-[3-(methoxymethyl)-2-oxo-1,3-benzothiazol-6-yl]ethyl]pyrazol-1-yl]-3-pyridyl]methoxy]acetate (2.3 g, 4.77 mmol) in tetrahydrofuran (38 mL) and add lithium hydroxide (2 g, 47.66 mmol) and water (9 mL). Stir the mixture overnight at room temperature. Make the solution basic with 1N sodium hydroxide and extract with diethyl ether. Make the aqueous acidic with 1N hydrochloric acid and extract twice with ethyl acetate. Dry the ethyl acetate extracts with sodium sulfate then filter and evaporate to give 2-[[6-[3-[1-[3-(methoxymethyl)-2-oxo-1,3-benzothiazol-6-yl]ethyl]pyrazol-1-yl]-3-pyridyl]methoxy]acetic acid as a white solid (2.25 g, 4.95 mmol, 104%). LCMS (low) rt=1.14 min, M+1=455.

Preparation 215: N-Methoxy-2-[[6-[3-[1-[3-(methoxymethyl)-2-oxo-1,3-benzothiazol-6-yl]ethyl]pyrazol-1-yl]-3-pyridyl]methoxy]-N-methyl-acetamide

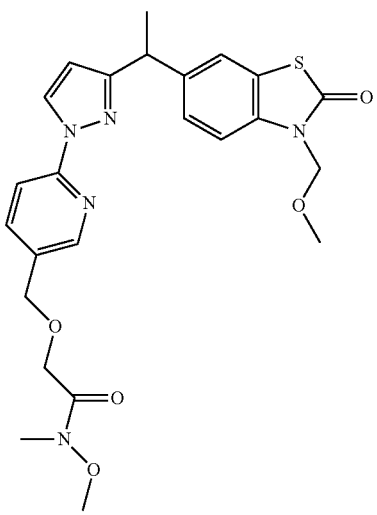 [SMILES: COCn1c(=O)sc2cc(C(C)c3ccn(-c4ccc(COCC(=O)N(C)OC)cn4)n3)ccc21]

Dissolve 2-[[6-[3-[1-[3-(methoxymethyl)-2-oxo-1,3-benzothiazol-6-yl]ethyl]pyrazol-1-yl]-3-pyridyl]methoxy]acetic acid (2.25 g, 4.95 mmol) in dichloromethane (15 mL) and add 1-(3-dimethylaminopropyl)-3-ethylcarbodiimide hydrochloride (1.13 g, 5.89 mmol), N,O-dimethylhydroxylamine hydrochloride (0.52 g, 5.33 mmol) and pyridine (2.7 mL, 33.4 mmol). Stir the mixture for three days. Dilute the mixture with saturated sodium bicarbonate and brine and extract twice with ethyl acetate. Dry the organic fractions with sodium sulfate, filter and evaporate. Chromatograph the residue using a gradient from 30% ethyl acetate/hexane to 100% ethyl acetate to give N-methoxy-2-[[6-[3-[1-[3-(methoxymethyl)-2-oxo-1,3-benzothiazol-6-yl]ethyl]pyrazol-1-yl]-3-pyridyl]methoxy]-N-methyl-acetamide as a white solid (1.27 g, 2.50 mmol). LCMS (low) rt=1.20 min, M+1=498.

Preparation 216: 6-[1-[1-[5-(Acetonyloxymethyl)-2-pyridyl]pyrazol-3-yl]ethyl]-3-(methoxymethyl)-1,3-benzothiazol-2-one

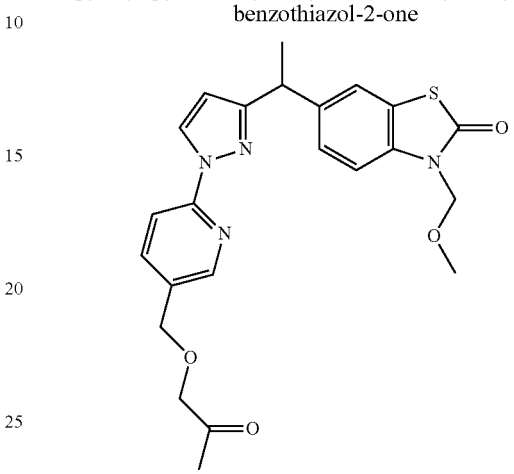

Dissolve N-methoxy-2-[[6-[3-[1-[3-(methoxymethyl)-2-oxo-1,3-benzothiazol-6-yl]ethyl]pyrazol-1-yl]-3-pyridyl]methoxy]-N-methyl-acetamide (1.27 g, 2.55 mmol) in tetrahydrofuran (20 mL) and cool the mixture to −20° C. Slowly add methylmagnesiumbromide (2.5 mL, 7.5 mmol, 3M solution in diethyl ether) and allow the mixture to warm to room temperature. Stir for an additional 20 minutes then dilute the mixture with saturated ammonium chloride. Extract the mixture 3 times with ethyl acetate. Dry the organics with sodium sulfate then filter and evaporate. Chromatograph the residue using a gradient from hexane to 80% ethyl acetate/hexane to give 6-[1-[1-[5-(acetonyloxymethyl)-2-pyridyl]pyrazol-3-yl]ethyl]-3-(methoxymethyl)-1,3-benzothiazol-2-one as a white solid (0.8 g, 69%). LCMS (low) rt=1.22 min, M+1=453.

Preparation 217: 6-[1-[1-[5-(acetonyloxymethyl)-2-pyridyl]pyrazol-3-yl]ethyl]-3H-1,3-benzothiazol-2-one

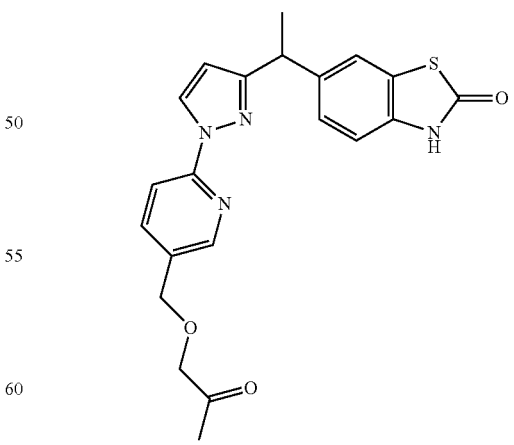

Dissolve 6-[1-[1-[5-(acetonyloxymethyl)-2-pyridyl]pyrazol-3-yl]ethyl]-3-(methoxymethyl)-1,3-benzothiazol-2-one (0.9 g, 1.95 mmol) in trifluoroacetic acid (15 mL) and heat the mixture at 55° C. overnight. Evaporate the mixture and then reconstitute in tetrahydrofuran (15 mL) and add ammonium hydroxide (15 mL). Stir the mixture at room temperature for three hours then evaporate the tetrahydrofuran and dilute the mixture with saturate sodium bicarbonate. Extract the solution three times with ethyl acetate and then dry the organics using sodium sulfate. Filter the mixture then chromatograph using a gradient from hexane to 80% ethyl acetate/hexane to obtain 6-[1-[1-[5-(acetonyloxymethyl)-2-pyridyl]pyrazol-3-yl]ethyl]-3H-1,3-benzothiazol-2-one as a white solid (0.61 g, 1.47 mmol, 75%). LCMS (low) rt=1.07 min, M+1=409.

Preparation 218: 6-[1-[1-[5-(2-hydroxypropoxymethyl)-2-pyridyl]pyrazol-3-yl]ethyl]-3H-1,3-benzothiazol-2-one

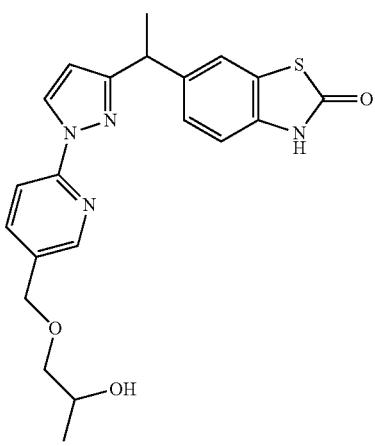 [SMILES: CC(O)COCc1ccc(-n2ccc(C(C)c3ccc4[nH]c(=O)sc4c3)n2)nc1]

Dissolve 6-[1-[1-[5-(acetonyloxymethyl)-2-pyridyl]pyrazol-3-yl]ethyl]-3H-1,3-benzothiazol-2-one (0.60 g, 1.47 mmol) in tetrahydrofuran (20 mL) and add lithium borohydride (96 mg, 4.41 mmol) at room temperature. Stir the mixture at room temperature for ten minutes. Cool the mixture to 0° C. and carefully add aqueous saturated ammonium chloride solution then extract twice with ethyl acetate. Dry the organics with sodium sulfate then filter and evaporate to give 6-[1-[1-[5-(2-hydroxypropoxymethyl)-2-pyridyl]pyrazol-3-yl]ethyl]-3H-1,3-benzothiazol-2-one as a clear oil (0.53 g, 1.3 mmol, 87%). LCMS (low) rt=1.04 min, M+1=411.

EXAMPLE 55 & 56

6-[1-[1-[5-(2-hydroxypropoxymethyl)-2-pyridyl]pyrazol-3-yl]ethyl]-3H-1,3-benzothiazol-2-one Isomer 3 and Isomer 4

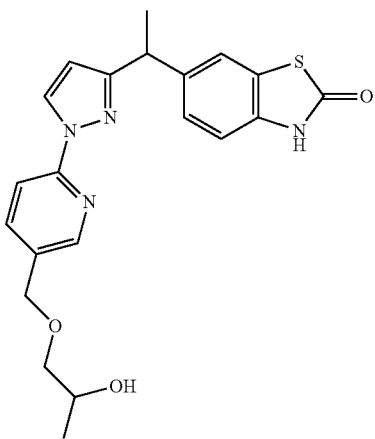 [SMILES: CC(O)COCc1ccc(-n2ccc(C(C)c3ccc4[nH]c(=O)sc4c3)n2)nc1]

6-[1-[1-[5-(2-hydroxypropoxymethyl)-2-pyridyl]pyrazol-3-yl]ethyl]-3H-1,3-benzothiazol-2-one was resolved into its stereoisomers by chiral chromatography using Chiralpak® IA, 80/20 EtOH/ACN (0.2% IPA), 1 mL/min., 225 nm. Isomer 3 retention time is 3.69 min and isomer 4 is 4.63 min.

EXAMPLE 57

Synthesis of 6-[1-[1-[5-(2-fluoroethyl)-2-pyridyl]pyrazol-3-yl]ethyl]-3H-1,3-benzothiazol-2-one, Isomer 2

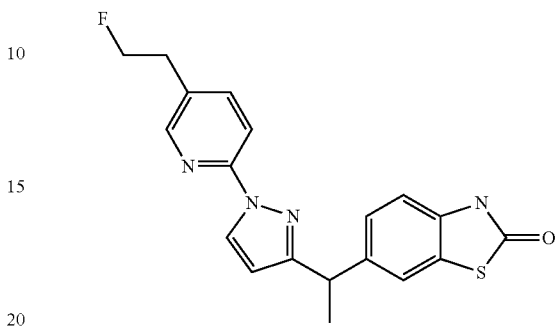

Compound 6-[1-[1-[5-(2-hydroxyethyl)-2-pyridyl]pyrazol-3-yl]ethyl]-3H-1,3-benzothiazol-2-one, isomer 2 (117 mg, 0.32 mmol), is dissolved in anhydrous dichloromethane (3 ml) and cooled in a ice-bath. Add diethylaminosulfur trifluoride (60 mg, 0.35 mmol, 1.1 equiv.) and allow the mixture to warm to ambient temperature. After 1 hr partition between ethyl acetate and aqueous sodium carbonate solution. Wash the organics with brine and dry over sodium sulfate and filter and concentrate the residue onto silica. Purify on silica using a gradient elution of 5 to 50% ethyl acetate in hexanes to afford the title compound (42 mg, 36%) as a gum which solidifies upon standing. LCMS (low) rt=2.22 min, M+1=369.

EXAMPLE 58

Synthesis of 6-[1-[1-[5-[5-(Hydroxymethyl)tetrahydrofuran-2-yl]-2-pyridyl]pyrazol-3-yl]ethyl]-3H-1,3-benzothiazol-2-one Isomer 1 Cis

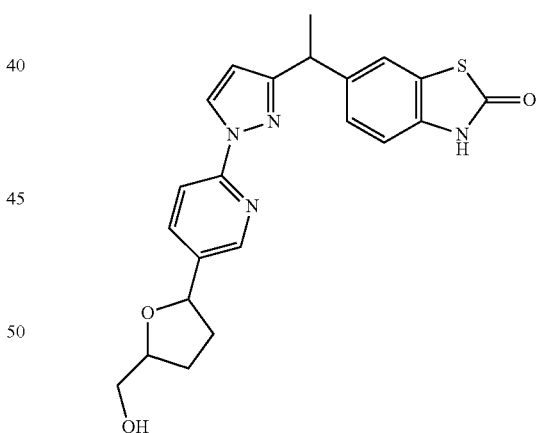

3-(Methoxymethyl)-6-[1-(1H-pyrazol-3-yl)ethyl]-1,3-benzothiazol-2-one, Isomer 1,2

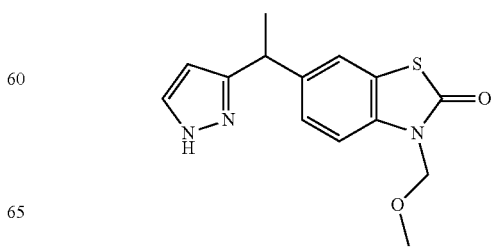

Resolve 3-(methoxymethyl)-6-[1-(1H-pyrazol-3-yl)ethyl]-1,3-benzothiazol-2-one into its enantiomers by chiral chromatography using (R,R) Whelk-O 1, 20% EtOH/CO2, 5 mL/min, 225 nm Isomer 1 has retention time of 2.0 min and Isomer 2 has retention time of 2.7 min. [5-(6-Fluoro-3-pyridyl)tetrahydrofuran-2-yl]methanol, Isomer 1,2,3,4

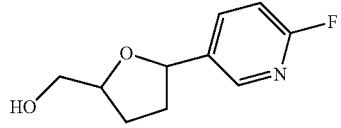 [SMILES: OCC1CCC(c2ccc(F)nc2)O1]

Resolve [5-(6-Fluoro-3-pyridyl)tetrahydrofuran-2-yl]methanol into its diasteriomers by chiral chromatography using two separations. In the first separation use Chiralpak® AD-H, 20% IPA/CO2, 5 mL/min, 270 nm. Isomer 1 and Isomer 2 are a mixture with a retention time of 1 min, Isomer 3 has a retention time of 1.16 min and Isomer 4 is 1.52 min Isomer 1 and 2 are separated using Chiralcel® OJ-H, 40/60 IPA/hexane, 1 mL/min, 270 nm Isomer 1 has a retention time of 5.12 min and Isomer 2 is 5.48 min NOE experimentation indicates that Isomer 1 and 2 are cis diasteriomers and Isomer 3 and 4 are trans diasteriomers. LCMS (low) Isomer 1 rt=0.614 min, M+1=198, Isomer 2 rt=0.615 min, M+1=198, Isomer 3 rt=0.611 min., M+1=198, Isomer 4 rt=0.611 min, M+1=198.

2-Fluoro-5-[5-(tetrahydropyran-2-yloxymethyl)tetrahydrofuran-2-yl]pyridine, Isomer 1

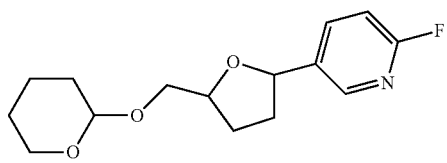

Dissolve the [5-(6-Fluoro-3-pyridyl)tetrahydrofuran-2-yl]methanol (0.9 g, 4.6 mmol) in dichloromethane (5 mL) then add the dihydropyran (500 uL, 5.5 mmoL) and the p-toluenesulphonic acid (39 mg, 0.23 mmol). Stir the mixture at room temperature for 3 days then dilute the mixture with saturated sodium bicarbonate and extract twice using dichloromethane. Dry the organics using sodium sulfate then filter and evaporate. Chromatograph the residue using a gradient from hexane to 60% ethyl acetate in hexane to give 2-fluoro-5-[5-(tetrahydropyran-2-yloxymethyl)tetrahydrofuran-2-yl]pyridine as a clear oil (816 mg, 2.8 mmol, 60%). LCMS (low) Isomer 1 rt=1.073 min.

3-(Methoxymethyl)-6-[1-[1-[5-[5-(tetrahydropyran-2-yloxymethyl)tetrahydrofuran-2-yl]-2-pyridyl]pyrazol-3-yl]ethyl]-1,3-benzothiazol-2-one

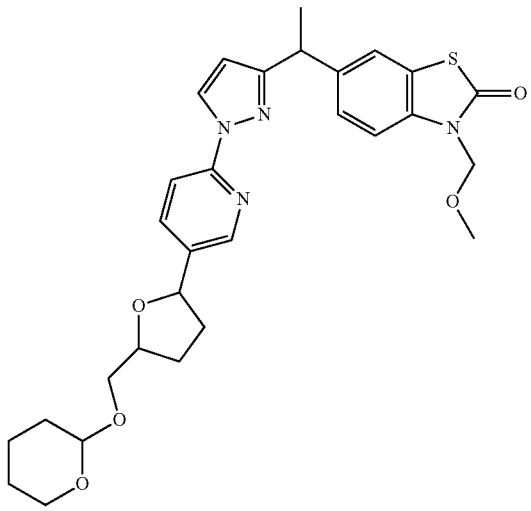 [SMILES: COCn1c(=O)sc2cc(C(C)c3ccn(-c4ccc(C5CCC(COC6CCCCO6)O5)cn4)n3)ccc21]

Dissolve 3-(methoxymethyl)-6-[1-(1H-pyrazol-3-yl)ethyl]-1,3-benzothiazol-2-one Isomer 1 (0.35 g, 1.21 mmol) in dimethylformamide (5 mL) and add lithium t-butoxide (147 mg, 1.81 mmol). After 20 minutes add 2-fluoro-5-[5-(tetrahydropyran-2-yloxymethyl)tetrahydrofuran-2-yl]pyridine Isomer 1 (681 mg, 2.42 mmol) and heat the mixture in a microwave at 120° C. for 2 hours. Cool the mixture to room temperature then dilute with saturated ammonium chloride and ethyl acetate then wash the mixture five times with brine. Dry the organic phase with sodium sulfate then filter and evaporate. Chromatograph the residue using a gradient from hexane to 60% ethyl acetate/hexane to give 3-(methoxymethyl)-6-[1-[1-[5-[5-(tetrahydropyran-2-yloxymethyl)tetrahydrofuran-2-yl]-2-pyridyl]pyrazol-3-yl]ethyl]-1,3-benzothiazol-2-one as a clear oil (148 mg, 0.24 mmol, 20%). LCMS (low) Isomer 1 rt=1.487 min, M+1=551.

6-[1-[1-[5-[5-(hydroxymethyl)tetrahydrofuran-2-yl]-2-pyridyl]pyrazol-3-yl]ethyl]-3H-1,3-benzothiazol-2-one Isomer 1

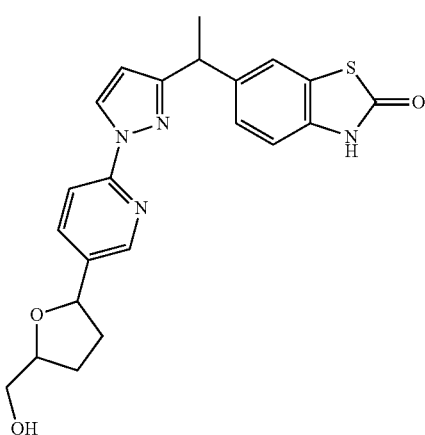 [SMILES: CC(c1ccc2[nH]c(=O)sc2c1)c1ccn(-c2ccc(C3CCC(CO)O3)cn2)n1]

Dissolve 3-(methoxymethyl)-6-[1-[1-[5-[5-(tetrahydropyran-2-yloxymethyl)tetrahydrofuran-2-yl]-2-pyridyl]pyrazol-3-yl]ethyl]-1,3-benzothiazol-2-one (136 mg, 0.24 mmol) in trifluoroacetic acid (7 mL) and heat to 50° C. overnight. Heat the mixture to 70° C. for three hours then cool to room temperature. Evaporate the mixture and then reconstitute in tetrahydrofuran (7 mL) and add ammonium hydroxide (7 mL). Stir the mixture at room temperature for 30 minutes then evaporate the tetrahydrofuran and dilute the mixture with saturate sodium bicarbonate. Extract the solution three times with ethyl acetate and then dry the organics using sodium sulfate. Filter the mixture then chromatograph using a gradient from 50% ethyl acetate/hexane to 100% ethyl acetate to obtain 6-[1-[1-[5-[5-(hydroxymethyl)tetrahydrofuran-2-yl]-2-pyridyl]pyrazol-3-yl]ethyl]-3H-1,3-benzothiazol-2-one as a white solid (83 mg, 0.19 mmol, 77%). LCMS (low) rt=Isomer 1 1.038 min, M+1=423.

EXAMPLE 59

6-[1-[1-[5-[5-(Hydroxymethyl)tetrahydrofuran-2-yl]-2-pyridyl]pyrazol-3-yl]ethyl]-3H-1,3-benzothiazol-2-one, Isomer 2 Cis

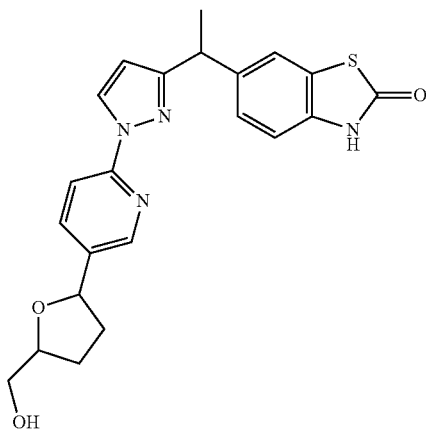 [SMILES: CC(c1ccc2[nH]c(=O)sc2c1)c1ccn(-c2ccc(C3CCC(CO)O3)cn2)n1]

2-Fluoro-5-[5-(tetrahydropyran-2-yloxymethyl)tetrahydrofuran-2-yl]pyridine, Isomer 2

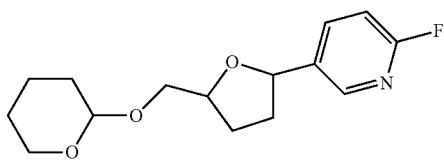 [SMILES: Fc1ccc(C2CCC(COC3CCCCO3)O2)cn1]

Dissolve the [5-(6-Fluoro-3-pyridyl)tetrahydrofuran-2-yl]methanol (1.12 g, 5.7 mmol) in dichloromethane (6 mL) then add the dihydropyran (623 uL, 6.8 mmoL) and the p-toluenesulphonic acid (49 mg, 0.28 mmol). Stir the mixture at room temperature for 3 days then dilute the mixture with saturated sodium bicarbonate and extract twice using dichloromethane. Dry the organics using sodium sulfate then filter and evaporate. Chromatograph the residue using a gradient from hexane to 60% ethyl acetate in hexane to give 2-fluoro-5-[5-(tetrahydropyran-2-yloxymethyl)tetrahydrofuran-2-yl]pyridine as a clear oil (1.1 g, 3.9 mmol, 69%). LCMS (low) Isomer 2 rt=1.079 min.

3-(Methoxymethyl)-6-[1-[1-[5-[5-(tetrahydropyran-2-yloxymethyl)tetrahydrofuran-2-yl]-2-pyridyl]pyrazol-3-yl]ethyl]-1,3-benzothiazol-2-one Isomer 2

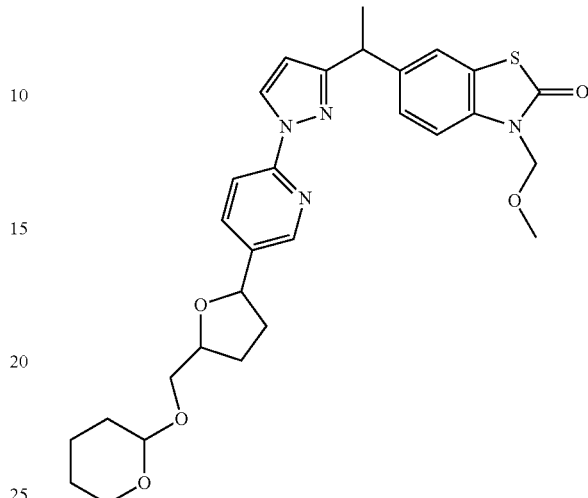

Dissolve 3-(methoxymethyl)-6-[1-(1H-pyrazol-3-yl)ethyl]-1,3-benzothiazol-2-one Isomer 1 (0.57 g, 2.0 mmol) in dimethylformamide (5 mL) and add lithium t-butoxide (241 mg, 3.0 mmol). After 20 minutes add 2-fluoro-5-[5-(tetrahydropyran-2-yloxymethyl)tetrahydrofuran-2-yl]pyridine Isomer 2 (1.1 g, 4.0 mmol) and heat the mixture in a microwave at 120° C. for 3 hours. Cool the mixture to room temperature then dilute with saturated ammonium chloride and ethyl acetate then wash the mixture five times with brine. Dry the organic phase with sodium sulfate then filter and evaporate. Chromatograph the residue using a gradient from hexane to 60% ethyl acetate/hexane to give 3-(methoxymethyl)-6-[1-[1-[5-[5-(tetrahydropyran-2-yloxymethyl)tetrahydrofuran-2-yl]-2-pyridyl]pyrazol-3-yl]ethyl]-1,3-benzothiazol-2-one as a clear oil (516 mg, 0.89 mmol, 45%). LCMS (low) Isomer 2 rt=1.487 min, M+1=551.

6-[1-[1-[5-[5-(hydroxymethyl)tetrahydrofuran-2-yl]-2-pyridyl]pyrazol-3-yl]ethyl]-3H-1,3-benzothiazol-2-one Isomer 2

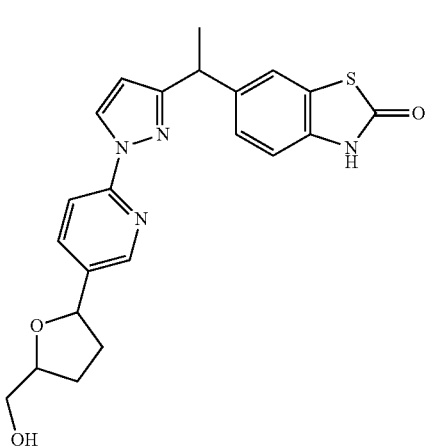 [SMILES: CC(c1ccc2[nH]c(=O)sc2c1)c1ccn(-c2ccc(C3CCC(CO)O3)cn2)n1]

Dissolve 3-(methoxymethyl)-6-[1-[1-[5-[5-(tetrahydropyran-2-yloxymethyl)tetrahydrofuran-2-yl]-2-pyridyl]pyrazol-3-yl]ethyl]-1,3-benzothiazol-2-one (526 mg, 0.96 mmol) in trifluoroacetic acid (10 mL) and heat to 50° C. overnight. Heat the mixture to 80° C. for three hours then cool to room temperature. Evaporate the mixture and then reconstitute in tetrahydrofuran (10 mL) and add ammonium hydroxide (10 mL). Stir the mixture at room temperature for 30 minutes then evaporate the tetrahydrofuran and dilute the mixture with saturate sodium bicarbonate. Extract the solution three times with ethyl acetate and then dry the organics using sodium sulfate. Filter the mixture then chromatograph using a gradient from 50% ethyl acetate/hexane to 100% ethyl acetate to obtain 6-[1-[1-[5-[5-(hydroxymethyl)tetrahydrofuran-2-yl]-2-pyridyl]pyrazol-3-yl]ethyl]-3H-1,3-benzothiazol-2-one as a white solid (141 mg, 0.33 mmol, 35%). LCMS (low) rt=Isomer 2 1.027 min, M+1=423.

EXAMPLE 60

6-[1-[1-[5-[5-(hydroxymethyl)tetrahydrofuran-2-yl]-2-pyridyl]pyrazol-3-yl]ethyl]-3H-1,3-benzothiazol-2-one, Isomer 3 Trans

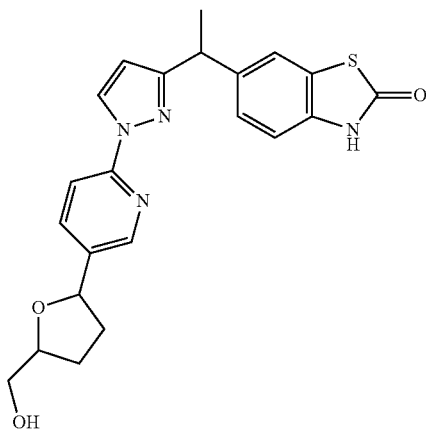 [SMILES: CC(c1ccc2[nH]c(=O)sc2c1)c1ccn(-c2ccc(C3CCC(CO)O3)cn2)n1]

2-Fluoro-5-[5-(tetrahydropyran-2-yloxymethyl)tetrahydrofuran-2-yl]pyridine, Isomer 3

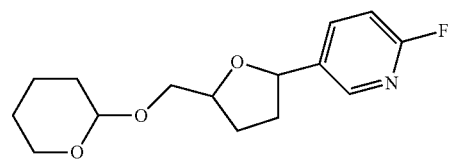 [SMILES: Fc1ccc(C2CCC(COC3CCCCO3)O2)cn1]

Dissolve the [5-(6-Fluoro-3-pyridyl)tetrahydrofuran-2-yl]methanol (0.88 g, 4.5 mmol) in dichloromethane (5 mL) then add the dihydropyran (489 uL, 5.4 mmoL) and the p-toluenesulphonic acid (38 mg, 0.22 mmol). Stir the mixture at room temperature for 3 days then dilute the mixture with saturated sodium bicarbonate and extract twice using dichloromethane. Dry the organics using sodium sulfate then filter and evaporate. Chromatograph the residue using a gradient from hexane to 60% ethyl acetate in hexane to give 2-fluoro-5-[5-(tetrahydropyran-2-yloxymethyl)tetrahydrofuran-2-yl]pyridine as a clear oil (880 mg, 3.0 mmol, 67%). LCMS (low) Isomer 3 rt=1.057 min.

3-(Methoxymethyl)-6-[1-[1-[5-[5-(tetrahydropyran-2-yloxymethyl)tetrahydrofuran-2-yl]-2-pyridyl]pyrazol-3-yl]ethyl]-1,3-benzothiazol-2-one, Isomer 3

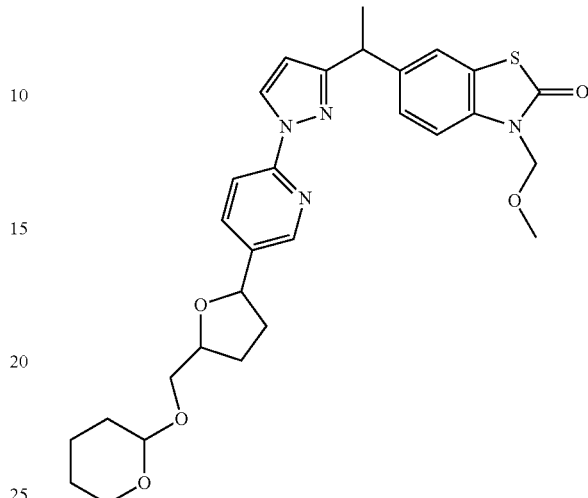

Dissolve 3-(methoxymethyl)-6-[1-(1H-pyrazol-3-yl)ethyl]-1,3-benzothiazol-2-one Isomer 3 (0.36 g, 1.23 mmol) in dimethylformamide (5 mL) and add lithium t-butoxide (150 mg, 1.84 mmol). After 20 minutes add 2-fluoro-5-[5-(tetrahydropyran-2-yloxymethyl)tetrahydrofuran-2-yl]pyridine Isomer 1 (690 mg, 2.45 mmol) and heat the mixture in a microwave at 120° C. for 2 hours. Cool the mixture to room temperature then dilute with saturated ammonium chloride and ethyl acetate then wash the mixture five times with brine. Dry the organic phase with sodium sulfate then filter and evaporate. Chromatograph the residue using a gradient from hexane to 60% ethyl acetate/hexane to give 3-(methoxymethyl)-6-[1-[1-[5-[5-(tetrahydropyran-2-yloxymethyl)tetrahydrofuran-2-yl]-2-pyridyl]pyrazol-3-yl]ethyl]-1,3-benzothiazol-2-one as a clear oil (188 mg, 0.32 mmol, 26%). LCMS (low) Isomer 3 rt=1.477 min, M+1=551.

6-[1-[1-[5-[5-(hydroxymethyl)tetrahydrofuran-2-yl]-2-pyridyl]pyrazol-3-yl]ethyl]-3H-1,3-benzothiazol-2-one, Isomer 3

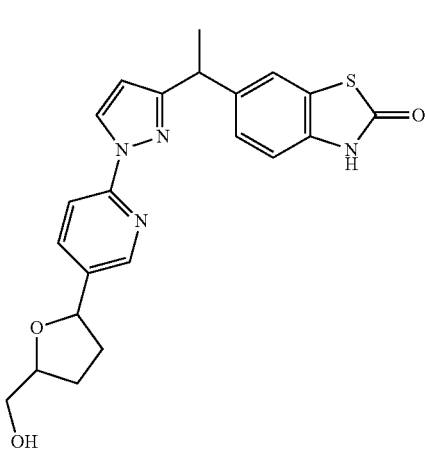 [SMILES: CC(c1ccc2[nH]c(=O)sc2c1)c1ccn(-c2ccc(C3CCC(CO)O3)cn2)n1]

Dissolve 3-(methoxymethyl)-6-[1-[1-[5-[5-(tetrahydropyran-2-yloxymethyl)tetrahydrofuran-2-yl]-2-pyridyl]pyrazol-3-yl]ethyl]-1,3-benzothiazol-2-one (136 mg, 0.23 mmol) in trifluoroacetic acid (7 mL) and heat to 50° C. overnight. Heat the mixture to 70° C. for three hours then cool to room temperature. Evaporate the mixture and then reconstitute in tetrahydrofuran (7 mL) and add ammonium hydroxide (7 mL). Stir the mixture at room temperature for 30 minutes then evaporate the tetrahydrofuran and dilute the mixture with saturate sodium bicarbonate. Extract the solution three times with ethyl acetate and then dry the organics using sodium sulfate. Filter the mixture then chromatograph using a gradient from 40% ethyl acetate/hexane to 100% ethyl acetate to obtain 6-[1-[1-[5-[5-(hydroxymethyl)tetrahydrofuran-2-yl]-2-pyridyl]pyrazol-3-yl]ethyl]-3H-1,3-benzothiazol-2-one as a white solid (99 mg, 0.22 mmol, 96%). LCMS (low) rt=Isomer 3 1.038 min, M+1=423.

EXAMPLE 61

6-[1-[1-[5-[5-(hydroxymethyl)tetrahydrofuran-2-yl]-2-pyridyl]pyrazol-3-yl]ethyl]-3H-1,3-benzothiazol-2-one, Isomer 4 Trans

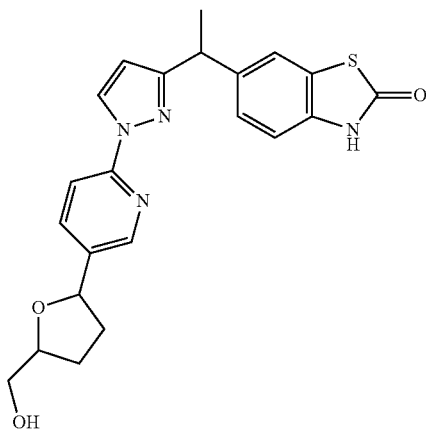 [SMILES: CC(c1ccc2[nH]c(=O)sc2c1)c1ccn(-c2ccc(C3CCC(CO)O3)cn2)n1]

2-Fluoro-5-[5-(tetrahydropyran-2-yloxymethyl)tetrahydrofuran-2-yl]pyridine, Isomer 4

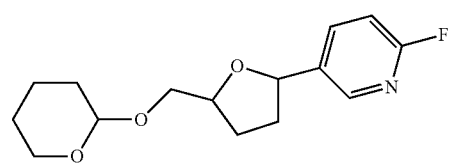 [SMILES: Fc1ccc(C2CCC(COC3CCCCO3)O2)cn1]

Dissolve the [5-(6-Fluoro-3-pyridyl)tetrahydrofuran-2-yl]methanol (0.82 g, 4.2 mmol) in dichloromethane (4 mL) then add the dihydropyran (456 uL, 5.0 mmoL) and the p-toluenesulphonic acid (36 mg, 0.21 mmol). Stir the mixture at room temperature for 3 days then dilute the mixture with saturated sodium bicarbonate and extract twice using dichloromethane. Dry the organics using sodium sulfate then filter and evaporate. Chromatograph the residue using a gradient from hexane to 60% ethyl acetate in hexane to give 2-fluoro-5-[5-(tetrahydropyran-2-yloxymethyl)tetrahydrofuran-2-yl]pyridine as a clear oil (0.87 g, 3.1 mmol, 74%). LCMS (low) Isomer 4 rt=1.061 min.

3-(Methoxymethyl)-6-[1-[1-[5-[5-(tetrahydropyran-2-yloxymethyl)tetrahydrofuran-2-yl]-2-pyridyl]pyrazol-3-yl]ethyl]-1,3-benzothiazol-2-one, Isomer 4

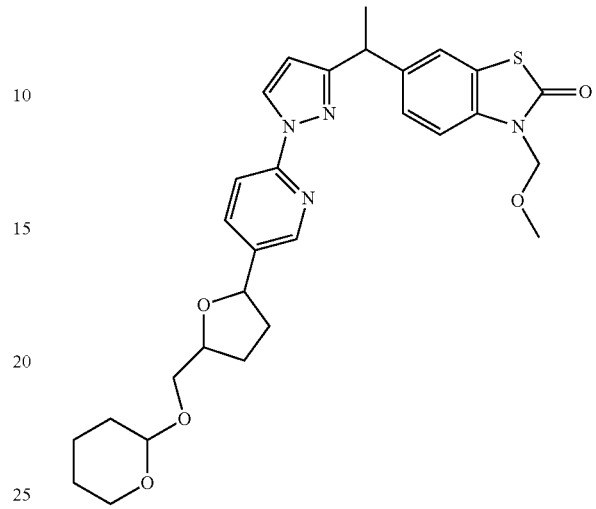

Dissolve 3-(methoxymethyl)-6-[1-(1H-pyrazol-3-yl)ethyl]-1,3-benzothiazol-2-one Isomer 4 (0.35 g, 1.21 mmol) in dimethylformamide (5 mL) and add lithium t-butoxide (147 mg, 1.81 mmol). After 20 minutes add 2-fluoro-5-[5-(tetrahydropyran-2-yloxymethyl)tetrahydrofuran-2-yl]pyridine Isomer 1 (678 mg, 2.41 mmol) and heat the mixture in a microwave at 120° C. for 2 hours. Cool the mixture to room temperature then dilute with saturated ammonium chloride and ethyl acetate then wash the mixture five times with brine. Dry the organic phase with sodium sulfate then filter and evaporate. Chromatograph the residue using a gradient from hexane to 60% ethyl acetate/hexane to give 3-(methoxymethyl)-6-[1-[1-[5-[5-(tetrahydropyran-2-yloxymethyl)tetrahydrofuran-2-yl]-2-pyridyl]pyrazol-3-yl]ethyl]-1,3-benzothiazol-2-one as a clear oil (110 mg, 0.19 mmol, 16%). LCMS (low) Isomer 4 rt=1.477 min, M+1=551.

6-[1-[1-[5-[5-(Hydroxymethyl)tetrahydrofuran-2-yl]-2-pyridyl]pyrazol-3-yl]ethyl]-3H-1,3-benzothiazol-2-one, Isomer 4

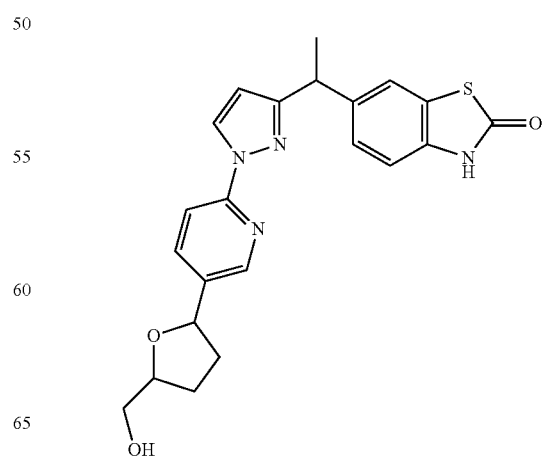

Dissolve 3-(methoxymethyl)-6-[1-[1-[5-[5-(tetrahydropyran-2-yloxymethyl)tetrahydrofuran-2-yl]-2-pyridyl]pyrazol-3-yl]ethyl]-1,3-benzothiazol-2-one (104 mg, 0.18 mmol) in trifluoroacetic acid (7 mL) and heat to 50° C. overnight. Heat the mixture to 70° C. for three hours then cool to room temperature. Evaporate the mixture and then reconstitute in tetrahydrofuran (7 mL) and add ammonium hydroxide (7 mL). Stir the mixture at room temperature for 30 minutes then evaporate the tetrahydrofuran and dilute the mixture with saturate sodium bicarbonate. Extract the solution three times with ethyl acetate and then dry the organics using sodium sulfate. Filter the mixture then chromatograph using a gradient from 50% ethyl acetate/hexane to 100% ethyl acetate to obtain 6-[1-[1-[5-[5-(hydroxymethyl)tetrahydrofuran-2-yl]-2-pyridyl]pyrazol-3-yl]ethyl]-3H-1,3-benzothiazol-2-one as a white solid (60 mg, 0.14 mmol, 79%). LCMS (low) rt=Isomer 4 1.039 min, M+1=423.

Data generated in vitro and in animal studies support a role for TARP γ8 dependent AMPA receptor antagonists, and the compounds of the present invention in particular, in the treatment of seizures. Specifically it is found that the compounds of the present invention selectively antagonize TARP γ8 dependent AMPA receptors. The compounds of the Examples are found to protect against seizures in the rat pentylenetetrazole (PTZ)-induced seizure model. Certain of the compounds of the present invention also are shown to demonstrate analgesic activity in the formalin induced pain model in mice.

To further demonstrate the characteristics of the compounds of the present invention, compounds may be run in the following in vitro and in vivo assays:

FLIPR Antagonist Functional Assay

The TARP subtype-selectivity of AMPA receptor antagonist compounds is demonstrated by comparing activities of compounds at AMPA GluA1 flop isoform receptor subunits co-expressed in CHO-S cells with either a hippocampal enriched TARP (TARP γ-8), or a cerebellar enriched TARP (TARP γ-2). TARP dependency of the AMPA receptor antagonist compounds is demonstrated by comparing the above activities with activity at AMPA GluA1 flip isoform receptor subunits expressed in CHO-S cells in the absence of a co-expressed TARP.

Briefly, CHO-S (Invitrogen) cells are grown in suspension in 50/50 custom media to a density of $1 \times 10^7$ cells/ml. (50/50 custom media is a low calcium media made as a 1:1 (v/v) mixture of CD CHO media (Gibco #10743) and a custom complete media. The custom complete media is made by adding 0.40 mg/L tropolone, 5.00 mg/L insulin, 20 mM HEPES, and 0.075% Pluronic® F68 to a custom basal media having the following formula: (values as mg/L unless otherwise specified) 11.01 anhydrous calcium chloride, 0.050 ferric nitrate-9$H_2O$, 0.420 ferrous sulfate-7$H_2O$, 28.64 anhydrous magnesium chloride, 48.84 anhydrous magnesium sulfate, 312.14 KCl, 5505.96 NaCl, 62.57 monobasic sodium phosphate, 71.28 anhydrous dibasic sodium phosphate, 0.432 zinc sulfate-7$H_2O$, 10.0 ethanolamine HCl, 6000 D-glucose (dextrose), 0.210 DL lipoic acid thioctic, 0.081 putrescine 2 HCl, 4.78 sodium hypoxanthine, 220.24 sodium pyruvate, 0.730 thymidine, 8.90 L-alanine, 211.23 L-arginine HCl, 15.02 L-asparagine $H_2O$, 13.31 L-aspartic acid, 62.67 cystine 2 HCl, 7.360 L-glutamic acid, 146.16 L-Glutamine, 30.0 gylicine, 42.04 L-histidine HCl 2 $H_2O$, 105.11 L-isoluecine, 105.11 L-luecine, 146.16 L-lysine HCl, 30.03 L-methionine, 66.07 L-phenylalanine, 17.27 L-proline, 42.04 L-serine, 95.1 L-threonine, 16.02 L-typtophan, 104.11 L-tyrosine disodium salt, 94.1 L-valine, 8.99 choline chloride, 4.00 folic acid, 12.61 I inositol, 4.00 niacinamide, 4.00 pyridoxal HCl, 0.031 pyridoxine HCl, 0.400 riboflavin, 4.00 sodium pantothenate, 4.00 thiamine HCl, 0.680 vitamin B 12, and 2200 sodium bicarbonate.) Cells are centrifuged at 1000×g for 15 mM and resuspended in fresh 50/50 custom media at $2 \times 10^6$ cells/ml. For batch transfection, 2 mg of total DNA(s) is used for each liter of cells. For GluA1-γ8 transfection of CHO-S cells, human GluA1 Qflop-Cacng8-pBudCE4.1 DNA (Qiagen) and human EAAT3 pAN104 DNA (Qiagen, a glutamine transporter) are mixed in a ratio of 2:3. For GluA1-γ2 transfection of CHO-S cells, human GluA1 Qflop-Cacng2-pBudCE4.1 (Qiagen) is used. For GluA1 flip transfection of CHO-S cells, human GluA1 flip pcDNA3.1 DNA (Qiagen) is used. DNA(s) and FreeStyle™ MAX Reagent (Invitrogen cat#16447-500) are added to basal custom media (see above) in the proportions of 10 μg total DNA: 10 plFreeStyleTm MAX Reagent: 1 ml media, to form a DNA complex. After 15 min., an appropriate volume (20% v/v) of DNA complex is added to the prepared cell culture. Transiently transfected CHO-S cells are harvested after 48 hours and frozen in aliquots for later use. The function and pharmacology of AMPA receptors in transfected cells is verified in both freshly prepared and thawed aliquots of cells.

Frozen transfected CHO-S cells expressing AMPA receptors are thawed and plated in Dulbecco's Modified Eagle Media (DMEM media) (Gibco, cat#11960) containing 5% dialyzed Fetal Bovine Serum (Gibco, cat#26400-036) and 20 mM HEPES at 50,000 cells per well in 384-well Poly-D-lysine coated plates (Becton Dickinson, cat#354663) and cultured overnight at 37° C. On the day of an experiment, two fluorescence dye loading buffers are prepared. Fluo-4 AM dye loading buffer consists of 5 μM Fluo-4 AM dye (Molecular Probes, cat# F-14202) in Hank's Balanced Salt Solution (HBSS) containing 20 mM HEPES (pH 7.4), 2.5 mM probenecid (Sigma, cat# P8761, inhibits cellular transporters from pumping the dye out), and 5 nM Pluronic® F-127 (Molecular probes, cat# P3000MP). Fluo-4 NW dye loading buffer is prepared by adding 100 ml of HBSS containing 20 mM HEPES (pH 7.4) and 2.5 mM probenecid to one bottle of Fluo-4 NW dye (Molecular Probes, high throughput pack, cat# F36205). Cultured GluA1-γ8 and GluA1-γ2 CHO-S cells are loaded with Fluo-4 AM dye loading buffer and incubated at 22° C. for 2 hr. GluA1 flip CHO-S cells are loaded with Fluo-4 NW dye loading buffer and incubated at 37° C. for 30 mM followed by an additional 90 min incubation at 22° C. Prior to initiation of exposure of cells to compounds, the dye loading buffer in the cell plate is removed and fresh assay buffer is added. Assay buffer consists of HBSS with 20 mM HEPES (pH 7.4), 2.5 mM probenecid and 4 mM $CaCl_2$. The assay is initiated by addition of compounds followed by stimulation of cells with glutamate (final concentration=45 μM) and cyclothiazide (CTZ, final concentration=20 μM) in assay buffer. Changes in intracellular lCa++l are kinetically recorded by a fluorescence imaging plate reader (FLIPR) Inhibition of the effect of glutamate by test compounds is expressed as a percentage of the responses stimulated by glutamate plus CTZ in the presence of test compounds to the effect seen in the absence of compounds. Relative $IC_{50}$s are calculated using a 4-parameter nonlinear logistic equation. Compounds are similarly evaluated using CHO-S cells expressing GluA lflip alone or GluA1 flop-γ2 to confirm TARP— dependent and TARP-selective activity.

The exemplified compounds are assayed essentially as described above and are found to inhibit glutamate plus CTZ activation of TARP γ8 dependent GluA1 flop receptors with relative $IC_{50's}$ of less than about 350 nM, but did not inhibit flip isoform devoid of TARP, nor TARP γ2 dependent GluA1 flop receptors ($IC_{50}$'s>assay limit) The compounds of Examples 3, 27, 53, and 54 are assayed essentially as described above and are found to inhibit glutamate plus CTZ activation of TARP γ8 dependent GluA1 flop receptors with $IC_{50}$'s of 91.1±48.1 nM, 61.6±23.5 nM, 65.6±14.9 nM, and 82.6±56.2 nM, respectively, but did not inhibit flip isoform devoid of TARP, nor TARP γ2 dependent GluA1 flop receptors ($IC_{50}$'s>assay limit of 9260 nM).

Therefore, physiologically relevant doses of the compounds of the invention, particularly the more active isomers or each enantiomeric pair, are expected to provide inhibition of TARP γ8 AMPA receptors in vivo, while not substantially interacting with other physiologically relevant receptors, as for example TARP independent receptors or TARP γ2 dependent receptors, and thus may be useful in the treatment of seizure while avoiding undesired effects associated with non-TARP γ8-dependent AMPA receptor antagonists.

Rat Pentylenetetrazole (PTZ)-Induced Seizure Model:

Male Sprague Dawley rats (from Harlan Sprague Dawley. Indianapolis, Ind.), weighing 90-110 grams at time of test, are housed 5 per cage with ad libitum food and water in a large colony room with a standard light cycle (lights on 6 am, lights off 6 pm). Animals are maintained in the colony room for at least 3 days before testing Animals are moved to a quiet room 1 hr. prior to the start of the test. Animals are used only once.

Animals are removed and dosed with test compound or vehicle (5% DMSO, 10% acacia and 0.05% Dow Corning® 1510-US antifoam), p.o., 10 mL/Kg, and returned to their home cage. Twenty five min after dosing, animals are placed onto a screen and the screen is inverted 180 degrees to test for motor impairment. The animals are scored 60 sec. after inversion as follows: 0 if the animal climbs over the screen; 1 if the animal is hanging onto the bottom of the screen; 2 if the animal has fallen off the screen. After completing the screen test, animals are dosed S.C. with 35 mg/kg PTZ in saline in a volume of 1 ml/kg. The animals are then placed in an observation cage and observed for 30 min post PTZ. Clonus is defined as clonic seizure of fore- and/or hindlimbs during which the rat demonstrates loss of righting. Tonic seizure is defined as loss of righting with tonic hindlimb extension. Lethality during the observation period is also recorded. Animals are scored according to the presence of a specific seizure type at any time during the observation period. Data are reported as the number of animals having a given seizure type (ex. 4/5 clonic seizures means 4 out of 5 animals exhibited at least one clonic seizure of any duration at any time during the observation period).

The compounds of the Examples are tested essentially as described above in the dose range of 1-10 mg/Kg and are found to protect rats against PTZ induced seizures with an estimated $ED_{50}$ of at least better than 10 mg/Kg, without any observed motor impairment as measured by the inverted screen test. This data indicates that the compounds of the Examples are efficacious in a rat seizure model and, therefore, that compounds of the invention may be useful in the treatment of seizure while avoiding undesired effects associated with non-TARP-dependent AMPA receptor antagonists.

Manual Formalin Induced Pain Model

The manual formalin induced pain model is well known for screening compounds for analgesic properties (Mogil J. S. et al., Heritability of nociception I: Responses of 11 inbred mouse strains on 12 measures of nociception. Pain 80 (1999) 67-82). The assay is performed in Plexiglas® boxes approx. 10 cm×10 cm×10 cm in size. A minor placed at the back of the cage allows the unhindered observation of the formalin injected paw. Non-fasted male mice (Harlan (HSD) CD1-Icr) are placed individually in the cubicles at least 60 min. prior to the experiment. All testing is conducted between 08:00 and 16:00 hr. and the testing room temperature is maintained at 21-23° C. Multiple doses of test compound (3, 10 and 30 mg/kg), vehicle (5% DMSO in 10% Acacia, 0.05% antifoam), and a positive control (tramadol 80 mg/kg in 1% HEC, 0.25% Tween 80, 0.05% antifoam) are peripherally administered (p.o.) at varying times before the formalin challenge. Formalin (20 uL of a 5% solution in 0.9% saline) is injected subcutaneously into the plantar surface of the left hind paw with a 27 gauge needle. Observation starts immediately after the formalin injection. Formalin induced pain is quantified by recording the number of seconds each licking event lasts in 5 min intervals. The pain scoring is measured for 60 min. after the formalin injection. Two phases of pain behavior are observed as previously described (Wheeler-Aceto, H., Porreca, F. and Cowan, A., The rat paw formalin test: comparison of noxious agents, Pain 40 (1990) 229-238). The early phase starts immediately after the formalin injection and lasts approximately 5 min., followed by the late phase that starts between minutes 10-15 with a maximum response typically observed around 25-40 min after the formalin injection. After the 60 min. observation period, animals are sacrificed with $CO_2$ followed by cervical dislocation. Of the different scoring parameters reported for the formalin test, the total time spent licking and biting the injected paw is considered to be most relevant. (Abbott et al., *The formalin test: scoring properties of the first and second phases of the pain response in rats*, Pain 60 (1995) 91-102; Coderre et al., *The formalin test: a validation of the weighted-scores method of the behavioral pain rating*, Pain 54 (1993) 43-50).) The early phase score is the sum of time spent licking (seconds) from time 0 to 5 min. The late phase score is obtained by adding the total number of seconds spent licking from minute 15 to min 55 of the observation period. Data are presented as means with standard errors of means (±SEM). Data are evaluated by one-way analysis of variance (ANOVA) and the appropriate contrasts analyzed by Dunnett "t" test for two sided comparisons. Differences are considered to be significant if the P-value is less than 0.05. (Abbott, supra.; Coderre, supra.; and Wheeler-Aceto, supra.)

The compounds of Examples 3, 27, 30, and 55 are tested essentially as described above and are found to reduce pain behavior with the dose responses presented in table 1.

TABLE 1

Percent reversal of Late Phase Licking

| Dose (mg/Kg) | Example: $EC_{50}$ (mg/Kg) | | | | | | | |
|---|---|---|---|---|---|---|---|---|
| | 3 | S.E.M. | 27 | S.E.M. | 30 | S.E.M. | 55 | S.E.M. |
| Vehicle | 0.00 | | 0.00 | 11.99 | 0.00 | 10.29 | 0.00 | 10.80 |
| 1 (mg/Kg) | 32.3 | 5.1 | | | | | | |
| 3 (mg/Kg) | 43.8 | 5.3 | — | — | 8.88 | 8.92 | 25.64 | 8.96 |
| 10 (mg/Kg) | 66.2 | | 24.27 | 10.28 | 11.77 | 6.93 | 31.08 | 6.19 |
| 30 (mg/Kg) | — | — | 57.15 | 7.41 | 47.77 | 4.00 | 63.47 | 8.36 |

TABLE 1-continued

| | Percent reversal of Late Phase Licking | | | | | | | |
|---|---|---|---|---|---|---|---|---|
| Dose | Example: EC$_{50}$ (mg/Kg) | | | | | | | |
| (mg/Kg) | 3 | S.E.M. | 27 | S.E.M. | 30 | S.E.M. | 55 | S.E.M. |
| 60 (mg/Kg) | — | — | 62.14 | 6.02 | 62.14 | 2.92 | — | — |
| Positive Control (80 mg/Kg Tramadol) | 94.7 | 1.5 | 86.97 | 4.61 | 57.96 | 5.59 | 81.84 | 8.65 |

Therefore, compounds of the invention may be useful in the treatment of pain.

While it is possible to administer compounds employed in the methods of this invention directly without any formulation, the compounds are usually administered in the form of pharmaceutical compositions comprising the compound of Formula I, or a pharmaceutically acceptable salt thereof, as an active ingredient and at least one pharmaceutically acceptable carrier, diluent and/or excipient. These compositions can be administered by a variety of routes including oral, sublingual, nasal, subcutaneous, intravenous, and intramuscular. Such pharmaceutical compositions and processes for preparing them are well known in the art. See, e.g., Remington: The Science and Practice of Pharmacy (University of the Sciences in Philadelphia, ed., 20 ed., Lippincott Williams & Wilkins Co., 2005).

The compositions are preferably formulated in a unit dosage form, each dosage containing from about 25 to about 1000 mg, more usually about 50 to about 500 mg, as for example about 100 mg of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient.

The compounds of Formula I are generally effective over a wide dosage range. For example, dosages per day normally fall within the range of about 0.3 mg/kg to about 15 mg/kg, more usually from about 0.7 mg/kg to about 7.5 mg/kg, and as for example about 1.5 mg/kg of body weight. In some instances dosage levels below the lower limit of the aforesaid range may be more than adequate, while in other cases still larger doses may be employed without causing any harmful side effect, and therefore the above dosage ranges are not intended to limit the scope of the invention in any way. It may also be advantageous to administer the daily dose in parts over the course of each day (e.g. ½ dose twice a day or ⅓ dose three times a day). It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

It is contemplated that the compound of the invention, or a pharmaceutically acceptable salt thereof, as for example in a pharmaceutical composition of the invention, will be used to treat seizures by chronic administration to prevent such seizures and/or by acute administration to control or stop ongoing seizures.

We claim:
1. A compound of the formula

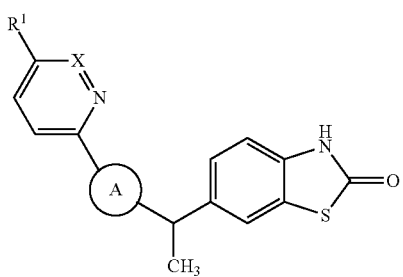

or a pharmaceutically acceptable salt thereof,
wherein X is CH or N;
A is

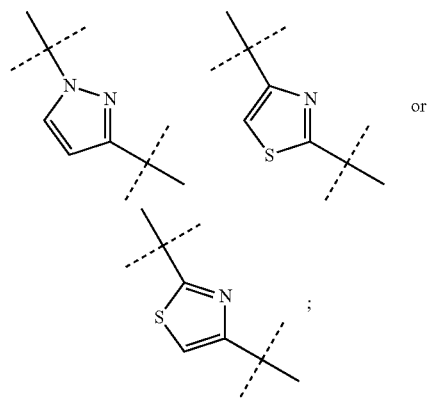

and
$R^1$ is selected from the group consisting of
hydrogen,
deuterium,
fluoro,
methyl,
HO—($C_1$-$C_4$)-alkyl, optionally substituted with with one or two methyl or deuterium groups,
HO—($C_1$-$C_3$)-alkoxy, optionally substituted with one or two methyl or deuterium groups,
fluoro-($C_1$-$C_3$)-alkyl,
HO—($C_1$-$C_3$)-alkoxy-methyl, optionally substituted with with one or two methyl groups,
cyano-($C_1$-$C_3$)-alkoxy,
HO—($C_1$-$C_3$)-alkylthio, optionally substituted with with one or two methyl groups,
HO—($C_1$-$C_3$)-alkyl-NH—,
HO—($C_1$-$C_3$)-alkyl-N(CH$_3$)—, methylsulfinyl,
acyl,
aminocarbonyl,
methylcarbonylmethoxymethyl,
aminomethylcarbonyloxyethoxy,
triazolylmethyl,
1-methyl-imidizol-2-ylthio,
5-hydroxymethyl-tetrahydrofuran-2-yl,
3-hydroxy-3-methylazetidin-1-yl,
3-methoxy-azetidin-1-yl
3-methoxy-3-methylazetidin-1-yl
4-hydroxypiperidin-1-yl,
4-hydroxy-4-methyl-piperidin-1-yl,
4-hydroxy-4-vinyl-piperidin-1-yl,
4-hydroxymethyl-piperidin-1-yl,
4-(2-hydroxyethyl)-piperindin-1-yl,
morpholin-4-yl,
2-hydroxymethyl-morpholin-4-yl,
morpholin-4-yl-ethoxy, and
tetrahydropyran-4-yl,
provided that when A is

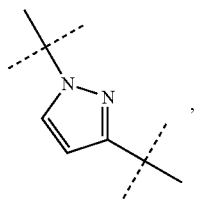

then $R^1$ is not unsubstituted HO—$(C_1$-$C_3)$-alkoxy, deuterium substituted HO—$(C_1$-$C_3)$-alkoxy, or HO—$(C_1$-$C_3)$-alkythio.

2. The compound according to claim 1, or a pharmaceutically acceptable salt thereof, having the following stereochemistry:

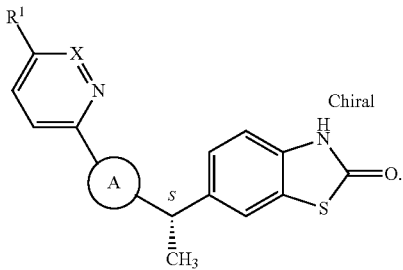

3. The compound according to claim 1, or a pharmaceutically acceptable salt thereof,
wherein
X is CH;
A is

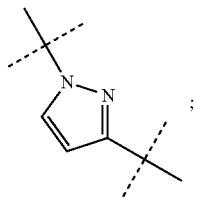

and
$R^1$ is selected from the group consisting of
deuterium,
fluoro,
2-hydroxyethyl,
1-hydroxyethyl,
2-hydroxy-2,2-dideutero-ethyl,
1-hydroxy-1-methylethyl,
2-hydroxy-propyl,
2-hydroxy-2-methylpropyl,
3-hydroxy-3-methylbutyl,
2-hydroxy-2-methyl-propoxy,
3-hydroxy-2,2-dimethyl-propoxy,
2-fluoroethyl,
2-hydroxyethoxymethyl,
2-hydroxy-2-methylpropoxymethyl,
2-hydroxypropoxymethyl,
1-(2-hydroxyethoxy)-ethyl,
1-(2-hydroxypropoxy)-ethyl,
cyanomethoxy,
2-hydroxy-1-methyl-ethylthio,
2-hydroxyethylamino,
N-(2-hydroxyethyl)-N-(methyl)amino,
methylsulfinyl,
methylcarbonylmethoxymethyl,
aminomethylcarbonyloxyethoxy,
1,2,3-triazol-1-ylmethyl,
1-methyl-imidizol-2-ylthio,
5-hydroxymethyl-tetrahydrofuran-2-yl,
3-hydroxy-3-methylazetidin-1-yl,
3-methoxy-azetidin-1-yl
3-methoxy-3-methylazetidin-1-yl
4-hydroxypiperidin-1-yl,
4-hydroxy-4-methyl-piperidin-1-yl,
4-hydroxy-4-vinyl-piperidin-1-yl,
4-(2-hydroxyethyl)-piperindin-1-yl,
morpholin-4-yl,
2-hydroxymethyl-morpholin-4-yl,
morpholin-4-yl-ethoxy, and
tetrahydropyran-4-yl.

4. The compound according to claim 1, or a pharmaceutically acceptable salt thereof,
wherein X is N;
A is

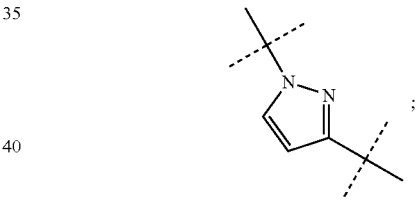

and
$R^1$ is selected from the group consisting of
hydrogen,
methyl,
hydroxymethyl, and
aminocarbonyl.

5. The compound according to claim 1, or a pharmaceutically acceptable salt thereof
wherein X is CH;
A is

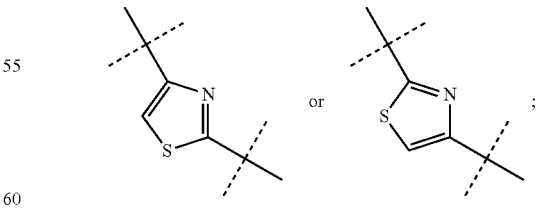

and
$R^1$ is selected from the group consisting of
hydrogen,
2-hydroxyethyl,
3-hydroxy-3-methylbutyl,
2-hydroxyethoxy, and
acyl.

6. The compound according to claim 2, or a pharmaceutically acceptable salt thereof,
wherein
X is CH;
A is

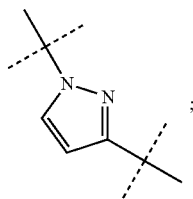

and
R¹ is selected from the group consisting of
deuterium,
fluoro,
2-hydroxyethyl,
1-hydroxyethyl,
2-hydroxy-2,2-dideutero-ethyl,
1-hydroxy-1-methylethyl,
2-hydroxy-propyl,
2-hydroxy-2-methylpropyl,
3-hydroxy-3-methylbutyl,
2-hydroxy-2-methyl-propoxy,
3-hydroxy-2,2-dimethyl-propoxy,
2-fluoroethyl,
2-hydroxyethoxymethyl,
2-hydroxy-2-methylpropoxymethyl,
2-hydroxypropoxymethyl,
1-(2-hydroxyethoxy)-ethyl,
1-(2-hydroxypropoxy)-ethyl,
cyanomethoxy,
2-hydroxy-1-methyl-ethylthio,
2-hydroxyethylamino,
N-(2-hydroxyethyl)-N-(methyl)amino,
methylsulfinyl,
methylcarbonylmethoxymethyl,
aminomethylcarbonyloxyethoxy,
1,2,3-triazol-1-ylmethyl,
1-methyl-imidizol-2-ylthio,
5-hydroxymethyl-tetrahydrofuran-2-yl,
3-hydroxy-3-methylazetidin-1-yl,
3-methoxy-azetidin-1-yl
3-methoxy-3-methylazetidin-1-yl
4-hydroxypiperidin-1-yl,
4-hydroxy-4-methyl-piperidin-1-yl,
4-hydroxy-4-vinyl-piperidin-1-yl,
4-(2-hydroxyethyl)-piperindin-1-yl,
morpholin-4-yl,
2-hydroxymethyl-morpholin-4-yl,
morpholin-4-yl-ethoxy, and
tetrahydropyran-4-yl.

7. The compound according to claim 2, or a pharmaceutically acceptable salt thereof,
wherein X is N;
A is

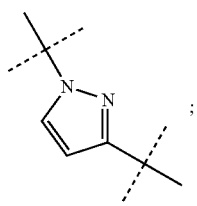

and
R¹ is selected from the group consisting of
hydrogen,
methyl,
hydroxymethyl, and
aminocarbonyl.

8. The compound according to claim 2, or a pharmaceutically acceptable salt thereof
wherein X is CH;
A is

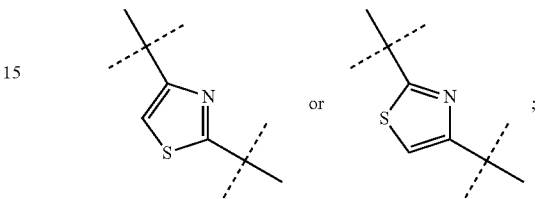

and
R¹ is selected from the group consisting of
hydrogen,
2-hydroxyethyl,
3-hydroxy-3-methylbutyl,
2-hydroxyethoxy, and
acyl.

9. The compound according to claim 1 which is selected from:
6-[1-[1-[5-(2-hydroxyethoxymethyl)-2-pyridyl]pyrazol-3-yl]ethyl]-3H-1,3-benzothiazol-2-one, Isomer 2;
6-[1-[1-[5-(acetonyloxymethyl)-2-pyridyl]pyrazol-3-yl]ethyl]-3H-1,3-benzothiazol-2-one, isomer 2;
6-(1-(1-(5-(4-hydroxypiperidin-1-yl)pyridin-2-yl)-1H-pyrazol-3-yl)ethyl)benzo[d]thiazol-2(3H)-one, isomer 1;
6-{1-[1-(5-Methanesulfinyl-pyridin-2-yl)-1H-pyrazol-3-yl]-ethyl}-3H-benzothiazol-2-one, isomer 4;
6-[1-[1-[5-[2-(hydroxymethyl)morpholin-4-yl]-2-pyridyl]pyrazol-3-yl]ethyl]-3H-1,3-benzothiazol-2-one, isomer 2;
6-[1-[1-[5-(1-hydroxyethyl)-2-pyridyl]pyrazol-3-yl]ethyl]-3H-1,3-benzothiazol-2-one, isomer 1;
6-[1-[1-[5-(1-hydroxyethyl)-2-pyridyl]pyrazol-3-yl]ethyl]-3H-1,3-benzothiazol-2-one, isomer 2;
6-[1-[1-[5-(fluoro-2-pyridyl)pyrazol-3-yl]ethyl]-3H-1,3-benzothiazol-2-one, isomer 1;
6-[1-[1-[5-(2,2-dideuterio-2-hydroxy-ethyl)-2-pyridyl]pyrazol-3-yl]ethyl]-3H-1,3-benzothiazol-2-one, isomer 2;
6-[1-[1-(5-morpholino-2-pyridyl)pyrazol-3-yl]ethyl]-3H-1,3-benzothiazol-2-one, Isomer 1;
6-[1-[1-[5-(2-hydroxy-2-methyl-propoxy)-2-pyridyl]pyrazol-3-yl]ethyl]-3H-1,3-benzothiazol-2-one, isomer 1;
6-[1-[1-[5-(2-Hydroxyethylamino)-2-pyridyl]pyrazol-3-yl]ethyl]-3H-1,3-benzothiazol-2-one, isomer 2;
6-[1-[1-[5-[2-Hydroxyethyl(methyl)amino]-2-pyridyl]pyrazol-3-yl]ethyl]-3H-1,3-benzothiazol-2-one, isomer 2;
6-[1-[1-[5-[(2-hydroxy-2-methyl-propoxy)methyl]-2-pyridyl]pyrazol-3-yl]ethyl]-3H-1,3-benzothiazol-2-one, isomer 1; and
6-(1-(1-(5-((1-hydroxypropan-2-yl)thio)pyridin-2-yl)-1H-pyrazol-3-yl)ethyl)benzo[d]thiazol-2(3H)-one, isomer 1; or a pharmaceutically acceptable salt thereof.

10. The compound according to claim 1 which is selected from:
- 6-(1-(1-(5-((1-hydroxypropan-2-yl)thio)pyridin-2-yl)-1H-pyrazol-3-yl)ethyl)benzo[d]thiazol-2(3H)-one, isomer 2;
- 6-(1-(1-(5-(4-hydroxy-4-vinylpiperidin-1-yl)pyridin-2-yl)-1H-pyrazol-3-yl)ethyl)benzo[d]thiazol-2(3H)-one, isomer 1;
- 6-(1-(1-(5-(3-hydroxy-3-methylazetidin-1-yl)pyridin-2-yl)-1H-pyrazol-3-yl)ethyl)benzo[d]thiazol-2(3H)-one, isomer 1;
- 6-(1-(1-(5-(3-methoxyazetidin-1-yl)pyridin-2-yl)-1H-pyrazol-3-yl)ethyl)benzo[d]thiazol-2(3H)-one, isomer 2;
- 6-(1-(1-(5-(3-methoxy-3-methylazetidin-1-yl)pyridin-2-yl)-1H-pyrazol-3-yl)ethyl)benzo[d]thiazol-2(3H)-one isomer 2;
- 6-((S)-1-{1-[5-(2-Hydroxy-propyl)-pyridin-2-yl]-1H-pyrazol-3-yl}-ethyl)-3H-benzothiazol-2-one, isomer 2;
- 6-[1-[1-(5-tetrahydropyran-4-yl-2-pyridyl)pyrazol-3-yl]ethyl]-3H-1,3-benzothiazol-2-one, isomer 1;
- 6-[(S)-1-[1-[5-(2-hydroxyethyl)-2-pyridyl]pyrazol-3-yl]ethyl]-3H-1,3-benzothiazol-2-one, isomer;
- 6-[1-[1-(5-deuterio-2-pyridyl)pyrazol-3-yl]ethyl]-3H-1,3-benzothiazol-2-one, isomer 2;
- 6-[1-[1-[5-(1-hydroxy-1-methyl-ethyl)-2-pyridyl]pyrazol-3-yl]ethyl]-3H-1,3-benzothiazol-2-one, isomer 1;
- 6-[(1S)-1-[1-[5-(3-hydroxy-3-methyl-butyl)-2-pyridyl]pyrazol-3-yl]ethyl]-3H-1,3-benzothiazol-2-one, isomer 1;
- 6-[1-[1-[5-(3-hydroxy-2,2-dimethyl-propoxy)-2-pyridyl]pyrazol-3-yl]ethyl]-3H-1,3-benzothiazol-2-one, isomer 1;
- 6-[1-[1-[5-(2-hydroxy-2-methyl-propyl)-2-pyridyl]pyrazol-3-yl]ethyl]-3H-1,3-benzothiazol-2-one, isomer 1;
- 6-[1-[1-[5-(1-methylimidazol-2-yl)sulfanyl-2-pyridyl]pyrazol-3-yl]ethyl]-3H-1,3-benzothiazol-2-one hydrochloride, isomer 1;
- 6-[1-[1-[5-(Triazol-1-ylmethyl)-2-pyridyl]pyrazol-3-yl]ethyl]-3H-1,3-benzothiazol-2-one hydrochloride, isomer 1; or a pharmaceutically acceptable salt thereof.

11. A compound according to claim 1 which is:
- 2-[[6-[3-[1-(2-Oxo-3H-1,3-benzothiazol-6-yl)ethyl]pyrazol-1-yl]-3-pyridyl]oxy]acetonitrile, isomer 2;
- 2-[[6-[3-[(1S)-1-(2-oxo-3H-1,3-benzothiazol-6-yl)ethyl]pyrazol-1-yl]-3-pyridyl]oxy]ethyl 2-aminoacetate;
- 6-[(1S)-1-[1-[5-(2-morpholinoethoxy)-2-pyridyl]pyrazol-3-yl]ethyl]-3H-1,3-benzothiazol-2-one;
- 6-[1-[1-[5-[1-(2-hydroxyethoxyl)ethyl]-2-pyridyl]pyrazol-3-yl]ethyl]-3H-1,3-benzothiazol-2-one, isomer 1;
- 6-[1-[1-[5-[1-(2-hydroxyethoxyl)ethyl]-2-pyridyl]pyrazol-3-yl]ethyl]-3H-1,3-benzothiazol-2-one, isomer 2;
- 6-[1-[1-[5-[1-(2-hydroxypropoxyl)ethyl]-2-pyridyl]pyrazol-3-yl]ethyl]-3H-1,3-benzothiazol-2-one, isomer 1;
- 6-(1-(1-(5-(4-hydroxy-4-methylpiperidin-1-yl)pyridin-2-yl)-1H-pyrazol-3-yl)ethyl)benzo[d]thiazol-2(3H)-one, isomer 1;
- 6-(1-(1-(5-(4-(2-hydroxyethyl)piperidin-1-yl)pyridin-2-yl)-1H-pyrazol-3-yl)ethyl)benzo[d]thiazol-2(3H)-one, isomer 1;
- 6-(1-(1-(5-((2-hydroxypropyl)thio)pyridin-2-yl)-1H-pyrazol-3-yl)ethyl)benzo[d]thiazol-2(3H)-one, isomer 3;
- 6-(1-(1-(5-((2-hydroxypropyl)thio)pyridin-2-yl)-1H-pyrazol-3-yl)ethyl)benzo[d]thiazol-2(3H)-one, isomer 4;
- 6-[1-[1-[5-(2-hydroxypropoxymethyl)-2-pyridyl]pyrazol-3-yl]ethyl]-3H-1,3-benzothiazol-2-one, Isomer 3;
- 6-[1-[1-[5-(2-hydroxypropoxymethyl)-2-pyridyl]pyrazol-3-yl]ethyl]-3H-1,3-benzothiazol-2-one, Isomer 4; and
- 6-[1-[1-[5-(2-fluoroethyl)-2-pyridyl]pyrazol-3-yl]ethyl]-3H-1,3-benzothiazol-2-one, isomer 2; or a pharmaceutically acceptable salt thereof.

12. The compound according to claim 1 which is selected from:
- 6-[1-[1-(6-methylpyridazin-3-yl)pyrazol-3-yl]ethyl]-3H-1,3-benzothiazol-2-one, isomer 2;
- 6-[1-[1-[6-(hydroxymethyl)pyridazin-3-yl]pyrazol-3-yl]ethyl]-3H-1,3-benzothiazol-2-one, isomer 2;
- 6-(1-{1-[6-(2-Hydroxy-ethylsulfanyl)-pyridazin-3-yl]-1H-pyrazol-3-yl}-ethyl)-3H-benzothiazol-2-one, isomer 2;
- 6-[1-(1-Pyridazin-3-yl-1H-pyrazol-3-yl)-ethyl]-3H-benzothiazol-2-one, isomer 2; and
- 6-[3-[1-(2-oxo-3H-1,3-benzothiazol-6-yl)ethyl]pyrazol-1-yl]pyridazine-3-carboxamide, isomer 1; or a pharmaceutically acceptable salt thereof.

13. The compound according to claim 1 which is selected from:
- 6-[1-[1-[5-[5-(Hydroxymethyl)tetrahydrofuran-2-yl]-2-pyridyl]pyrazol-3-yl]ethyl]-3H-1,3-benzothiazol-2-one, Isomer 1 Cis;
- 6-[1-[1-[5-[5-(Hydroxymethyl)tetrahydrofuran-2-yl]-2-pyridyl]pyrazol-3-yl]ethyl]-3H-1,3-benzothiazol-2-one, Isomer 2 Cis;
- 6-[1-[1-[5-[5-(hydroxymethyl)tetrahydrofuran-2-yl]-2-pyridyl]pyrazol-3-yl]ethyl]-3H-1,3-benzothiazol-2-one, Isomer 3 Trans; and
- 6-[1-[1-[5-[5-(hydroxymethyl)tetrahydrofuran-2-yl]-2-pyridyl]pyrazol-3-yl]ethyl]-3H-1,3-benzothiazol-2-one, Isomer 4 Trans; or a pharmaceutically acceptable salt thereof.

14. The compound according to claim 1 which is selected from:
- 6-[1-[4-[5-(2-hydroxyethoxy)-2-pyridyl]thiazol-2-yl]ethyl]-3H-1,3-benzothiazol-2-one, isomer 2;
- 6-[1-[4-[5-(2-hydroxyethyl)-2-pyridyl]thiazol-2-yl]ethyl]-3H-1,3-benzothiazol-2-one, isomer 2;
- 6-[1-[4-[5-(3-hydroxy-3-methyl-butyl)-2-pyridyl]thiazol-2-yl]ethyl]-3H-1,3-benzothiazol-2-one, isomer 1;
- 6-[1-(4-pyridazin-3-ylthiazol-2-yl)ethyl]-3H-1,3-benzothiazol-2-one, isomer 2; and
- 6-[1-[4-(5-acetyl-2-pyridyl)thiazol-2-yl]ethyl]-3H-1,3-benzothiazol-2-one, isomer 2; or a pharmaceutically acceptable salt thereof.

15. The compound according to claim 1 which is selected from:
- 6-(1-{2-[5-(2-hydroxy-ethyl)-pyridin-2-yl]-thiazol-4-yl}-ethyl)-3H-benzothiazol-2-one, isomer 2; and
- 6-[1-(2-pyridin-2-yl-thiazol-4-yl)-ethyl]-3H-benzothiazol-2-one, isomer 2; or a pharmaceutically acceptable salt thereof.

16. A pharmaceutical composition comprising a compound according to claim 1, or a pharmaceutically acceptable salt thereof, and one or more pharmaceutically acceptable carriers, diluents, or excipients.

17. A method of treating seizures in a mammal with epilepsy comprising administering to a mammal in need of such treatment an effective amount of a compound of the formula

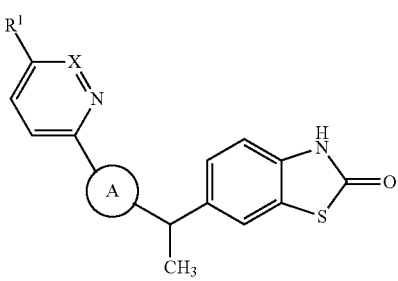

or a pharmaceutically acceptable salt thereof,
wherein X is CH or N;
A is

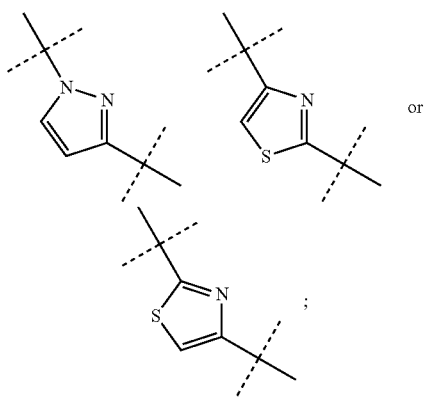

and
R¹ is selected from the group consisting of
  hydrogen,
  deuterium,
  fluoro,
  methyl,
  HO—($C_1$-$C_4$)-alkyl, optionally substituted with with one or two methyl or deuterium groups,
  HO—($C_1$-$C_3$)-alkoxy, optionally substituted with one or two methyl or deuterium groups,
  fluoro-($C_1$-$C_3$)-alkyl,
  HO—($C_1$-$C_3$)-alkoxy-methyl, optionally substituted with with one or two methyl groups,
  cyano-($C_1$-$C_3$)-alkoxy,
  HO—($C_1$-$C_3$)-alkylthio, optionally substituted with with one or two methyl groups,
  HO—($C_1$-$C_3$)-alkyl-NH—,
  HO—($C_1$-$C_3$)-alkyl-N($CH_3$)—,
  methylsulfinyl,
  acyl,
  aminocarbonyl,
  methylcarbonylmethoxymethyl,
  aminomethylcarbonyloxyethoxy,
  triazolylmethyl,
  1-methyl-imidizol-2-ylthio,
  5-hydroxymethyl-tetrahydrofuran-2-yl,
  3-hydroxy-3-methylazetidin-1-yl,
  3-methoxy-azetidin-1-yl
  3-methoxy-3-methylazetidin-1-yl
  4-hydroxypiperidin-1-yl,
  4-hydroxy-4-methyl-piperidin-1-yl,
  4-hydroxy-4-vinyl-piperidin-1-yl,
  4-hydroxymethyl-piperidin-1-yl,
  4-(2-hydroxyethyl)-piperindin-1-yl,
  morpholin-4-yl,
  2-hydroxymethyl-morpholin-4-yl,
  morpholin-4-yl-ethoxy, and
  tetrahydropyran-4-yl,
provided that when A is

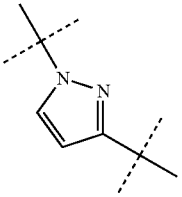

then R¹ is not unsubstituted HO—($C_1$-$C_3$)-alkoxy, deuterium substituted HO—($C_1$-$C_3$)-alkoxy, or HO—($C_1$-$C_3$)-alkythio.

18. The method according to claim 17 wherein the mammal is a human.

19. The method according to claim 17 wherein the seizures are simple or complex partial onset seizures.

20. The method according to claim 19 wherein the mammal is a human.

21. The method according to claim 17 wherein the seizures are primary or secondary generalized seizures.

22. The method according to claim 21 wherein the mammal is a human.

23. A method of treating pain in a mammal comprising administering to a mammal in need of such treatment an effective amount of a compound of the formula

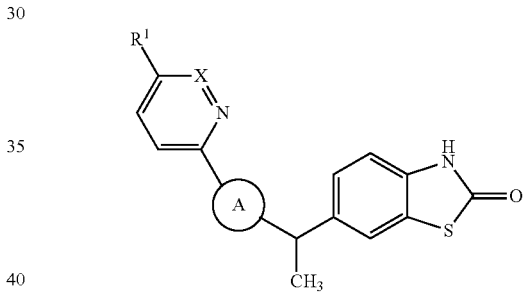

or a pharmaceutically acceptable salt thereof,
wherein X is CH or N;
A is

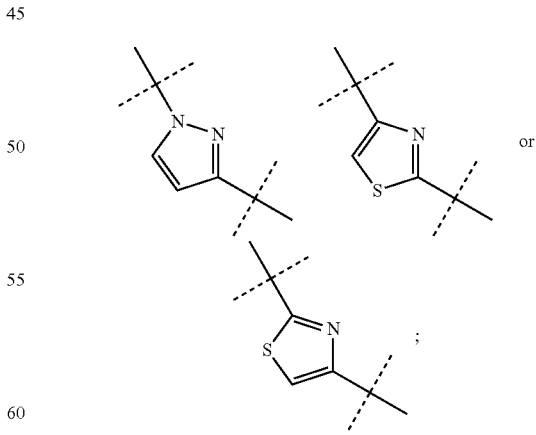

and
R¹ is selected from the group consisting of
  hydrogen,
  deuterium,
  fluoro,
  methyl, HO—(C$_1$-C$_4$)-alkyl, optionally substituted with with one or two methyl or deuterium groups,
HO—(C$_1$-C$_3$)-alkoxy, optionally substituted with one or two methyl or deuterium groups,
fluoro-(C$_1$-C$_3$)-alkyl,
HO—(C$_1$-C$_3$)-alkoxy-methyl, optionally substituted with with one or two methyl groups,
cyano-(C$_1$-C$_3$)-alkoxy,
HO—(C$_1$-C$_3$)-alkylthio, optionally substituted with with one or two methyl groups,
HO—(C$_1$-C$_3$)-alkyl-NH—,
HO—(C$_1$-C$_3$)-alkyl-N(CH$_3$)—,
methylsulfinyl,
acyl,
aminocarbonyl,
methylcarbonylmethoxymethyl,
aminomethylcarbonyloxyethoxy,
triazolylmethyl,
1-methyl-imidizol-2-ylthio,
5-hydroxymethyl-tetrahydrofuran-2-yl,
3-hydroxy-3-methylazetidin-1-yl,
3-methoxy-azetidin-1-yl
3-methoxy-3-methylazetidin-1-yl
4-hydroxypiperidin-1-yl,
4-hydroxy-4-methyl-piperidin-1-yl,
4-hydroxy-4-vinyl-piperidin-1-yl,
4-hydroxymethyl-piperidin-1-yl,
4-(2-hydroxyethyl)-piperindin-1-yl,
morpholin-4-yl,
2-hydroxymethyl-morpholin-4-yl,
morpholin-4-yl-ethoxy, and
tetrahydropyran-4-yl,
provided that when A is

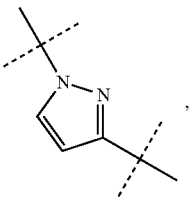

then R$^1$ is not unsubstituted HO—(C$_1$-C$_3$)-alkoxy, deuterium substituted HO—(C$_1$-C$_3$)-alkoxy, or HO—(C$_1$-C$_3$)-alkythio.

24. The method according to claim 23 where the mammal is a human.

25. The method according to claim 23 where the pain is nociceptive pain.

26. The method according to claim 25 where the mammal is a human.

* * * * *